US007521455B2

(12) United States Patent
Nagase et al.

(10) Patent No.: US 7,521,455 B2
(45) Date of Patent: Apr. 21, 2009

(54) FUSED RING 4-OXOPYRIMIDINE DERIVATIVE

(75) Inventors: Tsuyoshi Nagase, Tsukuba (JP); Nagaaki Sato, Tsukkuba (JP); Akio Kanatani, Tsukkuba (JP); Shigeru Tokita, Tsukkuba (JP)

(73) Assignee: Banyu Pharmaceutical Co. Ltd., Chuo-ku Tokyo (JP)

( * ) Notice: Subject to any disclaimer, the term of this patent is extended or adjusted under 35 U.S.C. 154(b) by 635 days.

(21) Appl. No.: 11/058,444

(22) Filed: Feb. 14, 2005

(65) Prior Publication Data
US 2005/0182045 A1 Aug. 18, 2005

(30) Foreign Application Priority Data
Feb. 13, 2004 (JP) ............. P2004-037190

(51) Int. Cl.
*A61K 31/517* (2006.01)
*C07D 239/91* (2006.01)
*A61K 31/519* (2006.01)
*A61K 31/47* (2006.01)
*C07D 487/04* (2006.01)
*C07D 471/04* (2006.01)

(52) U.S. Cl. ................... 514/266.31; 544/287
(58) Field of Classification Search ............ 514/266.31; 544/287
See application file for complete search history.

(56) References Cited

U.S. PATENT DOCUMENTS

| 4,166,117 A | 8/1979 | Vincent et al. |
| 4,247,555 A | 1/1981 | Sircar et al. |
| 4,261,996 A | 4/1981 | Sircar et al. |
| 4,261,997 A | 4/1981 | Sircar et al. |
| 4,276,295 A | 6/1981 | Ishikawa et al. |
| 4,451,467 A | 5/1984 | Ishikawa et al. |
| 5,948,775 A | 9/1999 | Koko et al. |
| 6,518,277 B1 | 2/2003 | Sadhu et al. |
| 6,667,300 B2 | 12/2003 | Sadhu et al. |
| 6,949,535 B2 | 9/2005 | Sadhu et al. |
| 7,220,777 B2 | 5/2007 | Armstrong et al. |
| 7,285,557 B2 | 10/2007 | Carpenter et al. |
| 2005/0261317 A1 | 11/2005 | Sadhu et al. |
| 2006/0287321 A1 | 12/2006 | Armstrong et al. |
| 2008/0139589 A1 | 6/2008 | Kanatani et al. |

FOREIGN PATENT DOCUMENTS

| DE | 1 939 109 | 3/1970 |
| EP | 1 903 040 A1 | 7/2006 |
| WO | WO-03/035075 A1 | 5/2003 |

OTHER PUBLICATIONS

L. Daleva et al., "Pharmocological Study of a Group of Quinazolinone Derivatives, II," Trudove na Nauchnoizsledovatelskiya Khimikofarmatsevtichen Institut, vol. 7, pp. 241-252, 1972.
S. Saxena et al., "Anti-Inflammatory Quinazolinones", Indian J. Pharm. Sci., vol. 53, No. 2, pp. 48-52, 1991.
Histamine as a Transmitter in Brain, J.C. Schwartz, Life Sciences vol. 17, pp. 503-518.
Organization of Histaminergic Fibers in the Rat Brain, Naoyuki Inagaki et al, The Journal of Comparative Neurology 273:283-300 (1988).
The Physiology of Brain Histamine, Ritchie E. Brown et al, Progress in Neurobiology vol. 63, pp. 637-672 (2001).
Airway Neuropeptides and Asthma, Peter J. Barnes, TIPS vol. 8, pp. 24-27 (Jan. 1987).
Cloning and Functional Expression of the Human Histamine $H_3$ Receptor, T. W. Lovenberg, Molecular Pharmacology 55, pp. 1101-1107 (1999).

(Continued)

*Primary Examiner*—James O Wilson
*Assistant Examiner*—Tamthom N Truong
(74) *Attorney, Agent, or Firm*—William Krovatin; J. Eric Thies

(57) ABSTRACT

The present invention provides a compound represented by formula (I) below, or a pharmaceutically acceptable salt thereof, which, having histamine H3 receptor antagonist or inverse agonist activity, is useful in the prophylaxis or therapy of metabolic diseases, circulatory diseases, or nervous system diseases.

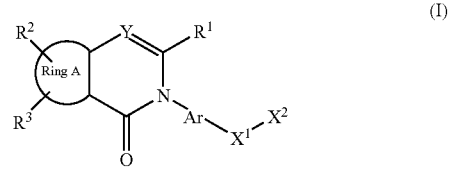

(I)

[where, for example, Ar is a divalent group formed by eliminating two hydrogen atoms from benzene, $X^1$ is a nitrogen atom, sulfur atom or oxygen atom, $R^1$ is a 5- to 6-membered heteroaryl group, Ring A is a 5- to 6-membered heteroaryl ring, $R^2$ and $R^3$ are amino groups or alkylamino groups, and $X^2$ is represented by formula (II):

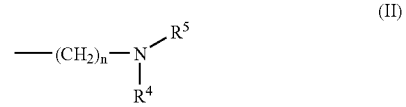

(II)

(where $R^4$ and $R^5$ are lower alkyl groups, and n is an integer from 2 to 4).]

26 Claims, No Drawings

OTHER PUBLICATIONS

Therapeutic Potential of Histamine $H_3$ Receptor Agonists and Antagonists, Rob Leurs et al, TIPS Vo. 19, pp. 177-183 (May 1998).

High Constitutive Activity of Native $H_3$ Receptors Regulates Histamine Neurons in Brain, S. Morisset et al, Nature vol. 408, pp. 860-864 (Dec. 14, 2000).

Involvement of Histaminergic Neurons in Arousal Mechanisms Demonstrated with $H_3$-Receptor Ligands in the Cat, J.S. Lin et al, Brain Research, 523, pp. 325-330 (Apr. 1990).

Effects of Thioperamide, a Histamine $H_3$ Receptor Antagonist, on Locomotor Activity and Brain Histamine Content in Mast Cell-Deficient W/WX Mice, Naruhiko Sakai et al, Life Sciences, vol. 48, pp. 2397-2404 (Apr. 11, 1991).

Effects of Intracerebroventricularly Infused Histamine and Selective $H_1$, $H_2$ and $H_3$ Agonists on Food and Water Intake and Urine Flow in Wistar Rats, Anne Lecklin et al, Brain Research 793, pp. 279-288 (Feb. 10, 1998).

The $H_3$ Receptor is Involved in Cholecystokinin Inhibition of Food Intake in Rats, Samir Attoub et al, Life Sciences 69, pp. 469-478 (2001).

Histamine and Selective $H_3$-Receptor Ligands: a Possible Role in the Mechanism and Management of Epilepsy, Divya Vohora et al, Pharmacology and Behavior 68, pp. 735-741 (Jan. 5, 2001).

Histamine $H_3$ Receptors—General Characterization and Their Function in the Cardiovascular System, B. Malinowska et al, Journal of Physiology and Pharmacology 49, 2, pp. 191-211 (1998).

Effects of Histamine $H_3$ Receptor Agonists and Antagonists on Cognitive Performance and Scopolamine-induced Amnesia, Maria G. Giovannini et al, Behavioural Brain Research 104, pp. 147-155 (Apr. 21, 1999).

Effect of Thioperamide, a Histamine $H_3$ Receptor Antagonist, on Electrically Induced Convulsions in Mice, Hiroyuki Yokoyama et al, European Journal of Pharmacology, 234, pp. 129-133 (Feb. 2, 1993).

Translation of German Patent No. 1 939 109 published on Mar. 5, 1970.

Daleva, L., "Pharmacological study of a group of quinazolinone derivatives, II", Trudove na Nauchnoizsledovatelskiya Khimikofarmatsevtichen Institut, 1972, vol. 7, pp. 241-252, Abstract.

Cai, Y.C., et al., "Synthesis of 3-[4-[(3-alkylamino-2-hydroxy)propoxy]phenyl(benzyl)]-substituted-4(3H)-quinazolinones as antimyocardial Ischemic agents" Yaoxue Xuebao, 1990, vol. 25, No. 11, pp. 862-865, Abstract.

U.S. Appl. No. 11/922,479, filed Dec. 18, 2007, Ahao et al.

S. K. Singh et al., "Synthesis of 5-Trifuloromethyl-5,8-dideazafolic Acid and 5-Trifuluoromethyl-5,8-dideazaisofolic Acid", *J. Heterocyclic Chem.*, vol. 27, p. 2101-2104, 1990.

FUSED RING 4-OXOPYRIMIDINE DERIVATIVE

BACKGROUND OF THE INVENTION

1. Field of the Invention

The present invention relates to fused ring 4-oxopyrimidine derivatives.

2. Related Background Art

In living creatures including mammals, histamine, an endogenous factor with physiological activity, functions as a neurotransmitter and has far-reaching pharmacological effects (e.g., Life science, Vol. 17, p. 503 (1975)).

From immunohistochemical research, it has become clear that histaminergic (production) soma are present in the tubercle mammillary nuclei of the posterior hypothalmic region, and histaminergic nerve fibers extend over a very large area within the brain, which suggests that histamine has many different pharmacological actions (e.g., Journal of Comprehensive Neurology, Vol. 273, p. 283).

The presence of a histaminergic nerve in the tubercle mammillary nuclei of the posterior hypothalamic region suggests that histamine plays a particularly important role in cerebral function in controlling the physiology of the hypothalamus, i.e., in waking rhythms, internal secretions, food/water intake and sexual behavior (e.g., Progress in Neurobiology, Vol. 63, p. 637 (2001)).

The fact that there are projections of histaminergic nerve fibers to regions of the brain related to maintenance of the waking state (e.g., the cerebral cortex) suggests that histamine has a role in maintaining the waking state or the waking-sleep cycle. Also, the fact that there are projections of histaminergic nerve fibers to many peripheral structures such as the hippocampus or tonsil-like complex suggest that it has a role in regulating the autonomic nervous system and emotions, control of motivation, learning and memory.

After histamine is released from cells producing histamine, it interacts with specific polymers called receptors on the cell membrane surface or in target cells, which account for its pharmacological effects and regulation of body functions. Four types of histamine receptors have so far been discovered. Histamine H3 receptors have been shown by various pharmacological and physiological studies to participate in the function of central and peripheral nerves (e.g., Trends in Pharmacological Science, Vol. 8, p. 24 (1986)), and in recent years, man and rodent histamine H3 receptor genes have been identified (e.g., Molecular Pharmacology, Vol. 55, p. 1101 (1999)).

It has been shown that histamine H3 receptors are present in the center or the presynaptic membrane of peripheral nerve cells, functioning as autoreceptors, controlling the release of histamine and also controlling the release of other neurotransmitters. Specifically, it has been reported that histamine H3 receptor agonists, antagonists or inverse-agonists regulate the release of histamine, noradrenalin, serotonine, acetylcholine or dopamine from synaptic endings. For example, release of neurotransmitters such as (R)-(α)-methylhistamine is suppressed by agonists, and is promoted by antagonists or inverse-agonists like thioperamide (e.g., Trends in Pharmacological Science, Vol. 19, p. 177 (1998)).

SUMMARY OF THE INVENTION

It is therefore an object of the present invention to provide novel substances which have histamine H3 receptor antagonism (action of inhibiting the binding of histamine to histamine H3 receptors) or inverse agonism (action of suppressing the constant activity of histamine H3 receptors), i.e. novel substances which act as histamine H3 receptor antagonists or inverse-agonists.

The inventors discovered that specific fused ring 4-oxopyrimidine derivatives act as histamine H3 receptor antagonists or inverse-agonists, and on the basis of the discoveries, they arrived at the present invention.

In order to acieve the object described above, the present invention provides:

(1) A compound represented by formula (I):

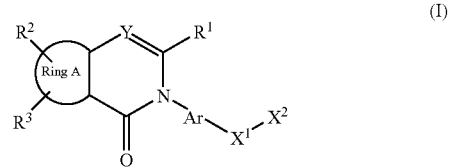

[where is phenyl, pyrimidinyl, pyridyl, thiazolyl, oxazolyl, pyrazolyl, thiadiazolyl or thienyl, i.e. a divalent group formed by eliminating two hydrogen atoms from benzene, pyrimidine, pyridine, thiazole, oxazole, pyrazole, thiadiazole or thiophene (this divalent group may be further substituted by a halogen atom, lower alkoxy (this lower alkoxy group may be further substituted by halogen), hydroxy or lower alkyl); $X^1$ is a nitrogen atom, sulfur atom or oxygen atom; $R^1$ is a 5- or 6-membered heteroaryl group having 1 to 4 heteroatoms selected from among nitrogen, sulfur and oxygen, heteroarylalkyl group (heteroaryl in this group has the same meaning as the above), straight chain or branched lower alkyl (this lower alkyl group may be further substituted by hydroxy, halogen, alkoxy, allyloxy or aralkyloxy), phenyl, aralkyl, alkoxy, alkylthio or lower alkylamino; Ring A is a 5- or 6-membered heteroaryl ring having 1 or 2 nitrogen atoms or sulfur atoms in the ring, or a benzene ring; $R^2$ and $R^3$ may be the same or different, and each represents hydrogen, amino, alkylamino, dialkylamino, nitro, cyano, hydroxy, lower alkylsulfonyl, halogen, lower alkyl (this lower alkyl group may be further substituted by halogen), lower cycloalkyl (this lower cycloalkyl group may be further substituted by halogen), lower alkoxy (this lower alkoxy group may be further substituted by halogen or hydroxy), lower cycloalkoxy (this lower cycloalkoxy group may be further substituted by halogen), aryloxy, aralkyloxy, heteroaryloxy, heteroarylalkyloxy, aryl, heteroaryl, arylcarbamoyl, heteroarylcarbamoyl, arylalkylcarbamoyl, heteroarylalkylcarbamoyl, mono-lower alkylcarbamoyl, di-lower alkylcarbamoyl, lower alkylcarboxamide, arylcarboxamide, heteroarylcarboxamide, arylalkylcarboxamide, heteroarylalkylcarboxamide, alkanoyl, arylcarbonyl, arylalkylcarbonyl, formyl, hydroxy, alkylthio, alkoxycarbonylamino, lower alkylsulfonylamino, arylsulfonylamino, alkylaminosulfonyl, arylaminosulfonyl, aralkyl, alkanoylamino or alkanoylalkylamino; Y is CH or a nitrogen atom; —$X^2$ is a group represented by formula (II):

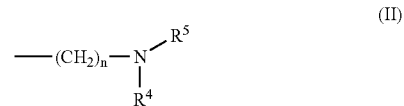

(where $R^4$ and $R^5$ may be the same or different, and each is a lower alkyl group (this lower alkyl group may be further substituted by halogen) or a cycloalkyl group, or $R^4$, $R^5$ and a nitrogen atom together form a 5- to 8-membered monocyclic ring (this monocyclic ring may be substituted by a halogen atom, an oxo group, or a lower alkyl group which itself may be substituted by halogen), or a 6- to 10-membered bicyclo ring, n is an integer of 2 to 4, and $(CH_2)_n$ may be substituted by a lower alkyl group having 1 to 3 carbon atoms), formula (III):

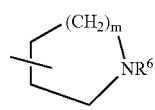

(III)

(where m is an integer from 0 to 4, and $R^6$ is a lower alkyl or cycloalkyl group), or formula (IV):

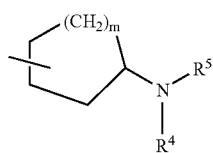

(IV)

(where the symbols have the same meaning as the above), with the proviso that formula (I) excludes 3-[4-(2-diethylaminoethoxy)-phenyl]-2-methyl-3H-quinazolin-4-one, 3-[4-(2-dimethylaminoethoxy)-phenyl]-2-methyl-3H-quinazolin-4-one, 2-methyl-3-[4-(2-piperidin-1-yl-ethoxy)-phenyl]-3H-quinazolin-4-one, 3-[4-(3-dimethylaminopropoxy)-phenyl]-2-methyl-3H-quinazolin-4-one, 3-[4-(3-diethylaminopropoxy)-phenyl]-2-methyl-3H-quinazolin-4-one and 3-[2-(2-diethylaminoethoxy)-phenyl]-2-methyl-3H-quinazolin-4-one], or a pharmaceutically acceptable salt thereof;

(2) The compound according to (1), wherein Ring A is a benzene ring, a pyridine ring, a pyrimidine ring or a thiophene ring, or a pharmaceutically acceptable salt thereof;

(3) The compound according to (1), wherein Ring A is a benzene ring or a pyridine ring, or a pharmaceutically acceptable salt thereof;

(4) The compound according to (1), (2) or (3), wherein at least one of $R^2$ and $R^3$ is a hydrogen atom, or a pharmaceutically acceptable salt thereof;

(5) The compound according to (1), (2) or (3), wherein one of $R^2$ and $R^3$ is a hydrogen atom, and the other is a hydrogen atom, a halogen atom, hydroxy, lower alkyl (this lower alkyl group may be further substituted by halogen), lower alkoxy (this lower alkoxy group may be further substituted by a halogen atom or hydroxy), aryl (this aryl group may be further substituted by lower alkyl), heteroaryl, lower alkylcarboxamide, arylcarboxamide, arylalkylcarboxamide or lower alkylsulfonylamino, or a pharmaceutically acceptable salt thereof;

(6) The compound according to (1), (2) or (3), wherein one of $R^2$ and $R^3$ is a hydrogen atom, and the other is a hydrogen atom, a halogen atom, lower alkyl (this lower alkyl group may be further substituted by halogen), or lower alkoxy (this lower alkoxy group may be further substituted by halogen), or a pharmaceutically acceptable salt thereof;

(7) The compound according to any one of (1) to (6), wherein Ar is phenyl or pyrimidinyl, i.e. a divalent group formed by eliminating two hydrogen atoms from benzene or pyrimidine (this divalent group may be further substituted by a halogen atom, lower alkoxy (this lower alkoxy group may be further substituted by halogen), hydroxy or lower alkyl), and n is 3 or 4, or a pharmaceutically acceptable salt thereof;

(8) The compound according to any one of (1) to (7), wherein —$X^2$ is represented by formula (II):

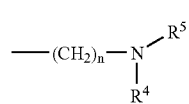

(II)

[where symbols have the same meaning as the above], or a pharmaceutically acceptable salt-thereof;

(9) The compound according to (8), wherein n is 3 or 4, and R4, R5 and a nitrogen atom together form a 5- to 8-membered monocyclic ring (this monocyclic ring may have as a substituent group a halogen atom, or a lower alkyl group which may be substituted by halogen), or a pharmaceutically acceptable salt thereof;

(10) The compound according to (8), wherein n is 3 or 4, and R4, R5 and a nitrogen atom together form a 6- to 10-membered bicyclo ring, or a pharmaceutically acceptable salt thereof;

(11) The compound according to (8), wherein n is 3, and R4, R5 and a nitrogen atom together form a 5- to 8-membered monocyclic ring (this monocyclic ring may have as a substituent group a halogen atom, or a lower alkyl group which may be substituted by halogen), or a pharmaceutically acceptable salt thereof;

(12) The compound according to (8), wherein n is 3, and R4, R5 and a nitrogen atom together form a 6- to 10-membered bicyclo ring, or a pharmaceutically acceptable salt thereof;

(13) The compound according to any one of (1) to (7), wherein —$X^2$ is represented by formula (III):

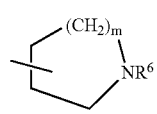

(III)

[where symbols have the same meaning as the above], or a pharmaceutically acceptable salt thereof;

(14) The compound according to any one of (1) to (7), wherein —$X^2$ is represented by formula (IV):

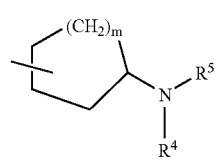

(IV)

[where symbols have the same meaning as the above], or a pharmaceutically acceptable salt thereof;

(15) The compound according to any one of (1) to (14), wherein $R^1$ is a lower alkyl group having 1 to 3 carbon atoms (this lower alkyl group may be further substituted by halogen), or a phenyl group, or a pharmaceutically acceptable salt thereof;

(16) The compound according to any one of (1) to (14), wherein $R^1$ is methyl, ethyl, n-propyl, isopropyl or trifluoromethyl, or a pharmaceutically acceptable salt thereof;

(17) The compound according to (1), wherein the compound represented by formula (I) is:

2-ethyl-3-{4-[3-(1-pyrrolidinyl)propoxy]phenyl}-4(3H)-quinazolinone,
2-methyl-3-{4-[3-(1-piperidinyl)propoxy]phenyl}-4(3H)-quinazolinone,
2-methyl-3-{4-[3-(1-pyrrolidinyl)propoxy]phenyl}-4(3H)-quinazolinone,
3-{4-[3-(diethylamino)propoxy]phenyl}-2-methyl-4-(3H)-quinazolinone,
2-methyl-3-{4-[3-(2-methyl-1-pyrrolidinyl)-propoxy]phenyl}-4(3H)-quinazolinone,
3-{4-[3-(2,5-dimethyl-1-pyrrolidinyl)propoxy]phenyl}-2-methyl-4(3H)-quinazolinone,
2-methyl-3-{4-[4-(1-piperidinyl)butoxy]phenyl}-4(3H)-quinazolinone,
3-{4-[3-(1-azepanyl)propoxy]phenyl}-2-methyl-4(3H)-quinazolinone,
3-{4-[3-(1-azocanyl)propoxy]-phenyl}-2-methyl 4(3H)-quinazolinone,
2-methyl-3-{4-[3-(2-methyl-1-piperidinyl)propoxy]phenyl}-4(3H)-quinazolinone,
2-methyl-3-{4-[3-(4-methyl-1-piperidinyl)propoxy]phenyl}-4(3H)-quinazolinone,
3-(4-{3-[(2R,6S)-2,6-dimethyl-1-piperidinyl]propoxy}phenyl)-2-methyl-4(3H)-quinazolinone,
2-methyl-3-{4-[3-(3-methyl-1-piperidinyl)propoxy]phenyl}-4(3H)-quinazolinone,
3-{4-[3-(3,5-dimethyl-1-piperidinyl)propoxy]phenyl}-2-methyl-4(3H)-quinazolinone,
2-methyl-3-{3-[3-(1-piperidinyl)propoxy]phenyl}-4(3H)-quinazolinone,
3-{3-bromo-4-[3-(1-piperidinyl)propoxy]phenyl}-2-ethyl-4(3H)-quinazolinone,
2-methyl-3-{4-[2-(1-piperidinyl)ethoxy]phenyl)}-4(3H)-quinazolinone,
2,5-dimethyl-3-{4-[3-(1-piperidinyl)propoxy]phenyl}-4(3H)-quinazolinone,
3-{4-[3-(1-piperidinyl)propoxy]phenyl}-2-propyl-4(3H)-quinazolinone,
3-{4-[3-(1-piperidinyl)propoxy]phenyl}-2-trifluoromethyl-4(3H)-quinazolinone,
2-isopropyl-3-{4-[3-(1-piperidinyl)propoxy]phenyl}-4(3H)-quinazolinone,
2,6-dimethyl-3-{4-[3-(1-piperidinyl)propoxy]phenyl}-4(3H)-quinazolinone,
7-chloro-2-methyl-3-{4-[3-(1-piperidinyl)propoxy]phenyl}-4(3H)-quinazolinone,
2,8-dimethyl-3-{4-[3-(1-piperidinyl)propoxy]phenyl}-4(3H)-quinazolinone,
2-ethyl-5-methyl-3-{4-[3-(1-piperidinyl)propoxy]phenyl}-4(3H)-quinazolinone,
5-fluoro-2-methyl-3-{4-[3-(1-piperidinyl)propoxy]phenyl}-4(3H)-quinazolinone,
5-chloro-2-methyl-3-{4-[3-(1-piperidinyl)propoxy]phenyl}-4(3H)-quinazolinone,
5-methoxy-2-methyl-3-{4-[3-(1-piperidinyl)propoxy]phenyl}-4(3H)-quinazolinone,
5-hydroxy-2-methyl-3-{4-[3-(1-piperidinyl)propoxy]phenyl}-4(3H)-quinazolinone trifluoroacetate,
2-methyl-3-{4-[3-(1-piperidinyl)propoxy]phenyl}-5-trifluoromethyl-4(3H)-quinazolinone,
7-fluoro-2-methyl-3-{4-[3-(1-piperidinyl)propoxy]phenyl}-4(3H)-quinazolinone,
6-fluoro-2-methyl-3-{4-[3-(1-piperidinyl)propoxy]phenyl}-4(3H)-quinazolinone,
6,7-difluoro-2-methyl-3-{4-[3-(1-piperidinyl)propoxy]phenyl}-4(3H)-quinazolinone,
6-bromo-2-methyl-3-{4-[3-(1-piperidinyl)propoxy]phenyl}-4(3H)-quinazolinone,
6-chloro-2-methyl-3-{4-[3-(1-piperidinyl)propoxy]phenyl}-4(3H)-quinazolinone,
6-methoxy-2-methyl-3-{4-[3-(1-piperidinyl)propoxy]phenyl}-4(3H)-quinazolinone,
6,7-dimethoxy-2-methyl-3-{4-[3-(1-piperidinyl)propoxy]phenyl}-4(3H)-quinazolinone,
8-chloro-2-methyl-3-{4-[3-(1-piperidinyl)propoxy]phenyl}-4(3H)-quinazolinone,
8-methoxy-2-methyl-3-{4-[3-(1-piperidinyl)propoxy]phenyl}-4(3H)-quinazolinone,
2,6-dimethyl-3-{4-[3-(1-pyrrolidinyl)propoxy]phenyl}-4(3H)-quinazolinone,
2-ethyl-5-methyl-3-{4-[3-(1-pyrrolidinyl)propoxy]phenyl}-4(3H)-quinazolinone,
5-fluoro-2-methyl-3-{4-[3-(1-pyrrolidinyl)propoxy]phenyl}-4(3H)-quinazolinone,
2-methyl-3-{4-[3-(1-pyrrolidinyl)propoxy]phenyl}-5-trifluoromethyl-4(3H)-quinazolinone,
5-chloro-2-methyl-3-{4-[3-(1-pyrrolidinyl)propoxy]phenyl}-4(3H)-quinazolinone,
2-ethyl-3-{4-[3-(1-pyrrolidinyl)propoxy]phenyl}-4(3H)-quinazolinone,
2,5-dimethyl-3-{4-[3-(1-pyrrolidinyl)propoxy]phenyl}-4(3H)-quinazolinone,
2-methyl-3-{4-[3-(1-piperidinyl)propoxy]phenyl}pyrido[2,3-d]pyrimidin-4(3H)-one,
2-methyl-3-{4-[3-(1-pyrrolidinyl)propoxy]phenyl}pyrido[2,3-d]pyrimidin-4(3H)-one,
6-chloro-2-methyl-3-{4-[3-(1-pyrrolidinyl)propoxy]phenyl}pyrido[3,4-d]pyrimidin-4(3H)-one,
2-methyl-3-{4-[3-(1-piperidinyl)propoxy]phenyl}pyrido[3,4-d]pyrimidin-4(3H)-one,
2-methyl-3-{4-[3-(1-pyrrolidinyl)propoxy]phenyl}-pyrido[4,3-d]pyrimidin-4(3H)-one,
2-methyl-3-{4-[3-(1-piperidinyl)propoxy]phenyl}-pyrido[4,3-d]pyrimidin-4(3H)-one,
2-methyl-3-{2-[3-(1-piperidinyl)propoxy]-5-pyrimidinyl}-4(3H)-quinazolinone,
2,5-dimethyl-3-{2-[3-(1-piperidinyl)propoxy]-5-pyrimidinyl}-4(3H)-quinazolinone,
2-ethyl-3-{4-[3-(1-piperidinyl)propoxy]phenyl}-pyrido[2,3-d]pyrimidin-4(3H)-one,
6-chloro-2-ethyl-3-{4-[3-(1-piperidinyl)propoxy]phenyl}-pyrido[3,4-d]pyrimidin-4(3H)-one,
6-chloro-2-ethyl-3-{4-[3-(1-pyrrolidinyl)propoxy]phenyl}-pyrido[3,4-d]pyrimidin-4(3H)-one,
2-ethyl-3-{4-[3-(1-piperidinyl)propoxy]phenyl}-pyrido[3,4-d]pyrimidin-4(3H)-one,
2-ethyl-3-{4-[3-(1-pyrrolidinyl)propoxy]phenyl}-pyrido[3,4-d]pyrimidin-4(3H)-one,
2-ethyl-3-{4-[3-(1-piperidinyl)propoxy]phenyl}-pyrido[4,3-d]pyrimidin-4(3H)-one,
2-ethyl-3-{4-[3-(1-pyrrolidinyl)propoxy]phenyl}-pyrido[4,3-d]pyrimidin-4(3H)-one,
6-chloro-2-methyl-3-{4-[3-(1-piperidinyl)propoxy]phenyl}pyrido-[3,4-d]pyrimidin-4(3H)-one, 3-{4-[3-(1-piperidinyl)propoxy]phenyl}-4(3H)-quinazolinone,
6-(acetylamino)-2-methyl-3-{4-[3-(1-piperidinyl)propoxy]phenyl}-4(3H)-quinazolinone,
6-(butyrylamino)-2-methyl-3-{4-[3-(1-piperidinyl)propoxy]phenyl}-4(3H)-quinazolinone,
6-(hexanoylamino)-2-methyl-3-{4-[3-(1-piperidinyl)propoxy]phenyl}-4(3H)-quinazolinone,
6-(benzoylamino)-2-methyl-3-{4-[3-(1-piperidinyl)propoxy]phenyl}-4(3H)-quinazolinone,
6-[(2-phenylacetyl)amino]2-methyl-3-{4-[3-(1-piperidinyl)propoxy]phenyl}-4(3H)-quinazolinone,
6-(2-naphthoylamino)-2-methyl-3-{4-[3-(1-piperidinyl)propoxy]phenyl}-4(3H)-quinazolinone,
2-methyl-6-[(methylsulfonyl)amino]-3-{4-[3-(1-piperidinyl)propoxy]phenyl}-4(3H)-quinazolinone,
2-methyl-6-[(methylsulfonyl)amino]-3-{4-[3-(1-pyrrolidinyl)propoxy]phenyl}-4(3H)-quinazolinone,
7-(acetylamino)-2-methyl-3-{4-[3-(1-piperidinyl)propoxy]phenyl}-4(3H)-quinazolinone,
7-(butyrylamino)-2-methyl-3-{4-[3-(1-piperidinyl)propoxy]phenyl}-4(3H)-quinazolinone,
7-(hexanoylamino)-2-methyl-3-{4-[3-(1-piperidinyl)propoxy]phenyl}-4(3H)-quinazolinone,
7-(benzoylamino)-2-methyl-3-{4-[3-(1-piperidinyl)propoxy]phenyl}-4(3H)-quinazolinone,
7-[(2-phenylacetyl)amino]2-methyl-3-{4-[3-(1-piperidinyl)propoxy]phenyl}-4(3H)-quinazolinone,
7-(2-naphthoylamino)-2-methyl-3-{4-[3-(1-piperidinyl)propoxy]phenyl}-4(3H)-quinazolinone
6-[acetyl(methyl)amino]2-methyl-3-{4-[3-(1-piperidinyl)propoxy]phenyl}-4(3H)-quinazolinone,
2-methyl-6-phenyl-3-{4-[3-(1-piperidinyl)propoxy]phenyl}-4(3H)-quinazolinone,
2-methyl-6-(4-methylphenyl)-3-{4-[3-(1-piperidinyl)propoxy]phenyl}-4(3H)-quinazolinone,
2-methyl-6-(3-methylphenyl)-3-{4-[3-(1-piperidinyl)propoxy]phenyl}-4(3H)-quinazolinone,
2-methyl-6-(2-methylphenyl)-3-{4-[3-(1-piperidinyl)propoxy]phenyl}-4(3H)-quinazolinone,
2-methyl-3-{4-[3-(1-piperidinyl)propoxy]phenyl}-6-(3-pyridyl)-4(3H)-quinazolinone,
2-methyl-3-{4-[3-(1-piperidinyl)propoxy]phenyl}-6-(4-pyridyl)-4(3H)-quinazolinone,
2-methyl-5-phenyl-3-{4-[3-(1-piperidinyl)propoxy]phenyl}-4(3H)-quinazolinone,
2-methyl-3-{4-[3-(1-piperidinyl)propoxy]phenyl}-6-(2-pyridyl)-4(3H)-quinazolinone,
3-{4-[(1-cyclobutyl-4-piperidinyl)oxy]phenyl}-2-methyl-4(3H)-quinazolinone,
3-{4-[(1-cyclopentyl-4-piperidinyl)oxy]phenyl}-2-methyl-4(3H)-quinazolinone,
3-{4-(1-cyclohexyl-4-piperidinyloxy)phenyl}-2-methyl-4(3H)-quinazolinone,
3-{4-(1-isopropyl-4-piperidinyloxy)phenyl}-2-methyl-4(3H)-quinazolinone,
3-{4-(1-ethyl-4-piperidinyloxy)phenyl}-2-methyl-4(3H)-quinazolinone,
3-{4-(1-butyl-4-piperidinyloxy)phenyl}-2-methyl-4(3H)-quinazolinone,
3-{4-[(1-cyclopentyl-4-piperidinyl)oxy]phenyl}-2-methyl-5-trifluoromethyl-4(3H)-quinazolinone,
3-{4-(1-cyclopentyl-4-piperidinyloxy)phenyl}-2,5-dimethyl-4(3H)-quinazolinone,
7-chloro-3-{4-[(1-cyclopentyl-4-piperidinyl)oxy]phenyl}-2-methyl-4(3H)-quinazolinone,
3-{4-[(1-cyclopentyl-4-piperidinyl)oxy]phenyl}-2,6-dimethyl-4(3H)-quinazolinone,
6-chloro-3-{4-[(1-cyclopentyl-4-piperidinyl)oxy]phenyl}-2-methyl-4(3H)-quinazolinone,
3-{4-[(1-cyclopentyl-4-piperidinyl)oxy]phenyl}-6-methoxy-2-methyl-4(3H)-quinazolinone,
3-{4-[(1-cyclopentyl-4-piperidinyl)oxy]phenyl}-2-methylpyrido[2,3-d]pyrimidin-4(3H)-one,
3-{4-[(1-cyclopentyl-4-piperidinyl)oxy]phenyl}-2-methylpyrido[4,3-d]pyrimidin-4(3H)-one,
6-chloro-3-{4-[(1-cyclopentyl-4-piperidinyl)oxy]phenyl}-2-methylpyrido[3,4-d]pyrimidin-4(3H)-one,
3-{4-[(1-cyclopentyl-4-piperidinyl)oxy]phenyl}-2-methylpyrido[3,4-d]pyrimidin-4(3H)-one,
3-{4-[(1-cyclobutyl-4-piperidinyl)oxy]phenyl}-2,5-dimethyl-4(3H)-quinazolinone,
3-{4-[(1-cyclobutyl-4-piperidinyl)oxy]phenyl}-5-methoxy-2-methyl-4(3H)-quinazolinone,
3-{4-[(1-cyclobutyl-4-piperidinyl)oxy]phenyl}-2-methyl-5-trifluoromethyl-4(3H)-quinazolinone,
5-chloro-3-{4-[(1-cyclobutyl-4-piperidinyl)oxy]phenyl}-2-methyl-4(3H)-quinazolinone,
3-{4-[(1-cyclobutyl-4-piperidinyl)oxy]phenyl}-2-methylpyrido[4,3-d]pyrimidin-4(3H)-one,
3-{4-[(1-cyclobutyl-4-piperidinyl)oxy]phenyl}-2-ethylpyrido[4,3-d]pyrimidin-4(3H)-one,
3-{4-[(1-cyclobutyl-4-piperidinyl)oxy]phenyl}-2-methylpyrido[2,3-d]pyrimidin-4(3H)-one,
3-{4-[(1-cyclobutyl-4-piperidinyl)oxy]phenyl}-2-ethylpyrido[2,3-d]-pyrimidin-4(3H)-one,
6-chloro-3-{4-[(1-cyclobutyl-4-piperidinyl)oxy]phenyl}-2-methylpyrido[3,4-d]pyrimidin-4(3H)-one,
6-chloro-3-{4-[(1-cyclobutyl-4-piperidinyl)oxy]phenyl}-2-ethylpyrido[3,4-d]pyrimidin-4(3H)-one,
3-{4-[(1-cyclobutyl-4-piperidinyl)oxy]phenyl}-2-methylpyrido[3,4-d]pyrimidin-4(3H)-one,
2-phenyl-3-{4-[3-(1-piperidinyl)propoxy]phenyl}-4(3H)-quinazolinone,
cis-2-methyl-3-(4-{[4-(1-pyrrolidinyl)cyclohexyl]oxy}phenyl)-4(3H)-quinazolinone,
trans-2-methyl-3-(4-{[4-(1-pyrrolidinyl)cyclohexyl]oxy}phenyl)-4(3H)-quinazolinone,
3-{4-[(1-cyclopentyl-3-pyrrolidinyl)oxy]phenyl}-2-methyl-4(3H)-quinazolinone,
3-{4-[(1-cyclobutyl-3-pyrrolidinyl)oxy]phenyl}-2-methyl-4(3H)-quinazolinone
3-{4-[(1-cyclopentyl-4-azepanyl)oxy]phenyl}-2-methyl-4(3H)-quinazolinone,
3-{4-[(1-cyclobutyl-4-azepanyl)oxy]phenyl}-2-methyl-4(3H)-quinazolinone,
3-methyl-2-{4-[3-(1-piperidinyl)propoxy]phenyl}-1(2H)-isoquinolinone,
2-{4-[(1-cyclobutyl-4-piperidinyl)oxy]phenyl}-3-methyl-1(2H)-isoquinolinone,
2-methyl-3-[4-{[3-(1-pyrrolidinyl)-cyclopentyl]oxy}phenyl]-4(3H)-quinazolinone,
2-ethyl-3-(4-{3-[(3S)-3-methylpiperidin-1-yl]propoxy}phenyl)pyrido[2,3-d]pyrimidin-4(3H)-one,
2-methyl-3-(4-{3-[(3S)-3-methylpiperidin-1-yl]propoxy}phenyl) pyrido[4,3-d]pyrimidin-4(3H)-one,
3-{4-[(1-cyclobutylpiperidin-4-yl)oxy]phenyl}-5-fluoro-2-methyl-4(3H)-quinazolinone,
3-{4-[(1-cyclobutylpiperidin-4-yl)oxy]phenyl}-7-fluoro-2-methyl-4(3H)-quinazolinone,
3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone,
3-{4-[(1-cyclobutylpiperidin-4-yl)oxy]phenyl}-8-fluoro-2-methyl-4(3H)-quinazolinone,
3-{4-[(1-cyclobutylpiperidin-4-yl)oxy]phenyl}-6-fluoro-2-methylpyrido[3,4-d]pyrimidin-4(3H)-one,
6-methoxy-2-methyl-3-{4-[3-(1-piperidinyl)propoxy]phenyl}pyrido[3,4-d]pyrimidin-4(3H)-one,
6-methoxy-2-methyl-3-{4-[3-(1-pyrrolidinyl)propoxy]phenyl}pyrido[3,4-d]pyrimidin-4(3H)-one,
5-methoxy-2-methyl-3-(4-{3-[(3S)-3-methylpiperidin-1-yl]propoxy}phenyl)-4(3H)-quinazolinone,
7-methoxy-2-methyl-3-(4-{3-[(3S)-3-methylpiperidin-1-yl]propoxy}phenyl)-4(3H)-quinazolinone,
2-methyl-3-(4-{3-[(3S)-3-methylpiperidin-1-yl]propoxy}phenyl)pyrido[2,3-d]pyrimidin-4(3H)-one,
5-fluoro-2-methyl-3-(4-{3-[(2R)-2-methylpyrrolidin-1-yl]propoxy}phenyl)-4(3H)-quinazolinone,
2-methyl-3-(4-{3-[(2R)-2-methylpyrrolidin-1-yl]propoxy}phenyl)pyrido[4,3-d]pyrimidin-4(3H)-one,
6-methoxy-2-methyl-3-(4-{3-[(2R)-2-methylpyrrolidin-1-yl]propoxy}phenyl)-4(3H)-quinazolinone, or
6-methoxy-2-methyl-3-(4-{3-[(2S)-2-methylpyrrolidin-1-yl]propoxy}phenyl)-4(3H)-quinazolinone, or a pharmaceutically acceptable salt thereof;

(18) The compound according to (1), wherein the compound represented by formula (I) is 3-{4-[(1-cyclobutyl-4-piperidinyl)oxy]phenyl}-2-ethylpyrido[2,3-d]-pyrimidin-4(3H)-one, or a pharmaceutically acceptable salt thereof;

(19) The compound according to (1), wherein the compound represented by formula (I) is 3-{4-[(1-cyclobutyl-4-piperidinyl)oxy]phenyl}-2-methylpyrido[4,3-d]-pyrimidin-4(3H)-one, or a pharmaceutically acceptable salt thereof;

(20) The compound according to (1), wherein the compound represented by formula (I) is 2-ethyl-3-(4-{3-[(3S)-3-methylpiperidin-1-yl]propoxy}phenyl)pyrido[2,3-d]pyrimidin-4(3H)-one, or a pharmaceutically acceptable salt thereof;

(21) The compound according to (1), wherein the compound represented by formula (I) is 2-methyl-3-(4-{3-[(3S)-3-methylpiperidin-1-yl]propoxy}phenyl)pyrido[4,3-d]pyrimidin-4(3H)-one, or a pharmaceutically acceptable salt thereof;

(22) The compound according to (1), wherein the compound represented by formula (I) is 3-{4-[(1-cyclobutyl-4-piperidinyl)oxy]phenyl}-2,5-dimethyl-4(3H)-quinazolinone, or a pharmaceutically acceptable salt thereof;

(23) The compound according to (1), wherein the compound represented by formula (I) is 3-{4-[(1-cyclobutyl-4-piperidinyl)oxy]phenyl}-2-methyl-5-trifluoromethyl-4(3H)-quinazolinone, or a pharmaceutically acceptable salt thereof;

(24) The compound according to (1), wherein the compound represented by formula (I) is 3-{4-[(1-cyclobutyl-4-piperidinyl)oxy]phenyl}-5-methoxy-2-methyl-4(3H)-quinazolinone, or a pharmaceutically acceptable salt thereof;

(25) The compound according to (1), wherein the compound represented by formula (I) is 3-{4-[(1-cyclobutylpiperidin-4-yl)oxy]phenyl}-5-fluoro-2-methyl-4(3H)-quinazolinone, or a pharmaceutically acceptable salt thereof;

(26) The compound according to (1), wherein the compound represented by formula (I) is 3-{4-[(1-cyclobutylpiperidin-4-yl)oxy]phenyl}-7-fluoro-2-methyl-4(3H)-quinazolinone, or a pharmaceutically acceptable salt thereof;

(27) The compound according to (1), wherein the compound represented by formula (I) is 3-{4-[(1-cyclobutylpiperidin-4-yl)oxy]phenyl}-6-methoxy-2-methyl-4(3H)-quinazolinone, or a pharmaceutically acceptable salt thereof;

(28) The compound according to (1), wherein the compound represented by formula (I) is 3-{4-[(1-cyclobutylpiperidin-4-yl)oxy]phenyl}-6-fluoro-2-methyl-4(3H)-quinazolinone, or a pharmaceutically acceptable salt thereof;

(29) The compound according to (1), wherein the compound represented by formula (I) is 3-{4-[(1-cyclobutylpiperidin-4-yl)oxy]phenyl}-8-fluoro-2-methyl-4(3H)-quinazolinone, or a pharmaceutically acceptable salt thereof;

(30) The compound according to (1), wherein the compound represented by formula (I) is 3-{4-[(1-cyclopentyl-4-piperidinyl)oxy]phenyl}-2-methylpyrido[4,3-d]pyrimidin-4(3H)-one, or a pharmaceutically acceptable salt thereof;

(31) The compound according to (1), wherein the compound represented by formula (I) is 3-{4-[(1-cyclobutylpiperidin-4-yl)oxy]phenyl}-6-fluoro-2-methylpyrido[3,4-d]pyrimidin-4(3H)-one, or a pharmaceutically acceptable salt thereof;

(32) The compound according to (1), wherein the compound represented by formula (I) is 3-{4-[(1-cyclobutyl-4-piperidinyl)oxy]phenyl}-2-ethylpyrido[4,3-d]pyrimidin-4(3H)-one, or a pharmaceutically acceptable salt thereof;

(33) The compound according to (1), wherein the compound represented by formula (I) is 6-methoxy-2-methyl-3-{4-[3-(1-piperidinyl)propoxy]phenyl}pyrido[3,4-d]pyrimidin-4(3H)-one, or a pharmaceutically acceptable salt thereof;

(34) The compound according to (1), wherein the compound represented by formula (I) is 6-methoxy-2-methyl-3-{4-[3-(1-pyrrolidinyl)propoxy]phenyl}pyrido[3,4-d]pyrimidin-4(3H)-one, or a pharmaceutically acceptable salt thereof;

(35) The compound according to (1), wherein the compound represented by formula (I) is 2,5-dimethyl-3-{4-[3-(1-pyrrolidinyl)propoxy]phenyl}-4(3H)-quinazolinone, or a pharmaceutically acceptable salt thereof;

(36) The compound according to (1), wherein the compound represented by formula (I) is 2-methyl-3-{4-[3-(1-pyrrolidinyl)propoxy]phenyl}-5-trifluoromethyl-4(3H)-quinazolinone, or a pharmaceutically acceptable salt thereof;

(37) The compound according to (1), wherein the compound represented by formula (I) is 5-fluoro-2-methyl-3-{4-[3-(1-piperidinyl)propoxy]phenyl}-4(3H)-quinazolinone, or a pharmaceutically acceptable salt thereof;

(38) The compound according to (1), wherein the compound represented by formula (I) is 6-methoxy-2-methyl-3-{4-[3-(1-piperidinyl)propoxy]phenyl}-4(3H)-quinazolinone, or a pharmaceutically acceptable salt thereof;

(39) The compound according to (1), wherein the compound represented by formula (I) is 5-methoxy-2-methyl-3-(4-{3-[(3S)-3-methylpiperidin-1-yl]propoxy}phenyl)-4(3H)-quinazolinone, or a pharmaceutically acceptable salt thereof;

(40) The compound according to (1), wherein the compound represented by formula (I) is 7-methoxy-2-methyl-3-(4-{3-[(3S)-3-methylpiperidin-1-yl]propoxy}phenyl)-4(3H)-quinazolinone, or a pharmaceutically acceptable salt thereof;

(41) The compound according to (1), wherein the compound represented by formula (I) is 2-methyl-3-(4-{3-[(3S)-3-methylpiperidin-1-yl]propoxy}phenyl)pyrido[2,3-d]pyrimidin-4(3H)-one, or a pharmaceutically acceptable salt thereof;

(42) The compound according to (1), wherein the compound represented by formula (I) is 5-fluoro-2-methyl-3-(4-{3-[(2R)-2-methylpyrrolidin-1-yl]propoxy}phenyl)-4(3H)-quinazolinone, or a pharmaceutically acceptable salt thereof;

(43) The compound according to (1), wherein the compound represented by formula (I) is 2-methyl-3-(4-{3-[(2R)-

2-methylpyrrolidin-1-yl]propoxy}phenyl)pyrido[4,3-d]pyrimidin-4(3H)-one, or a pharmaceutically acceptable salt thereof;

(44) The compound according to (1), wherein the compound represented by formula (I) is 6-methoxy-2-methyl-3-(4-{3-[(2R)-2-methylpyrrolidin-1-yl]propoxy}phenyl)-4(3H)-quinazolinone, or a pharmaceutically acceptable salt thereof; and

(45) The compound according to (1), wherein the compound represented by formula (I) is 6-methoxy-2-methyl-3-(4-{3-[(2S)-2-methylpyrrolidin-1-yl]propoxy}phenyl)-4(3H)-quinazolinone, or a pharmaceutically acceptable salt thereof.

The compound or salt according to any one of (1) to (45) acts as a histamine H3 receptor antagonist or inverse agonist. In other words, the present invention also provides a histamine H3 receptor antagonist or inverse agonist consisting of the compound according to any one of (1) to (45), or a pharmaceutically acceptable salt thereof.

According to the most recent research, histamine H3 receptors are very active in receptor cells and tissues, or the membrane fractions derived from receptor cells and tissues, and in the living body, they are constantly active (endogenous factors, e.g., the activity observed when histamine is absent) (e.g., Nature, Vol. 408, p. 860). It has been reported that this constant activity is suppressed by inverse-agonists. For example, constant autoreceptor activity is suppressed by thioperamide or ciproxifan and, as a result, release of neurotransmitters from synaptic endings, e.g., release and separation of histamine, is promoted.

In the rat, from the fact that a high-level selective inhibitor of histamine synthetic enzyme (histidine decarboxylase) interferes with waking, it was shown that histamine functions to regulate motivated waking. In the cat, administration of (R)-(α)-methylhistamine which is a histamine H3 receptor agonist increases deep slow wave sleep (e.g., Brain Research, Vol. 523, p. 325 (1990)).

On the other hand, thioperamide which is a histamine H3 receptor antagonist or inverse-agonist increases wakefulness in a dose-dependent manner. Also, thioperamide decreases slow wave and REM sleep (e.g., Life Science, Vol. 48, p. 2397 (1991)). In addition, thioperamide or GT-2331, which is a histamine H3 antagonist or inverse agonist, decreases emotive cataplexy and sleep in the dog (e.g., Brain Research, Vol. 793, p. 279 (1998)).

These findings suggest that H3 receptors participates in waking-sleep adjustment and sleep disorders, and suggest that selective histamine H3 agonists, antagonists or inverse agonists may be useful for prevention or treatment of sleep disorders and conditions accompanied by sleep disorders (e.g., idiopathic hypersomnia, recurrent hypersomnia, genuine hypersomnia, narcolepsy, periodic limb motor deficits at sleep time, sleep apnea syndrome, circadian rhythm barrier, chronic fatigue syndrome, REM sleep disorder, sleeplessness in the elderly, lack of sleep in night shift workers, idiopathic insomnia, repeatability insomnia, inborn character insomnia, depression and integration dysfunction syndrome).

Therefore, the compound or salt according to any one of (1) to (45) which acts as a histamine H3 receptor antagonist or inverse agonist is presumably useful in the prophylaxis or therapy of sleep disorders, and conditions accompanied by sleep disorders.

In the rat, administration of histamine H3 antagonists, thioperamide or GT-2331, which is an inverse agonist, improves learning disability (LD) attention defect hyperkinesia disorder (ADHD) (e.g., Life Science, Vol. 69, p. 469 (2001)). In the rat, administration of (R)-(α)-methylhistamine, which is a histamine H3 receptor agonist, decreases recognition ability and learning in an object recognition test and passive obstacle test.

On the other hand, thioperamide, which is a histamine H3 antagonist or inverse agonist, improves poor memory induced by the drug scopolamine in an amnesia induction test in a dose-dependent manner (e.g., Pharmacology, Biochemistry and Behavior, Vol. 68, p. 735 (2001)).

These findings suggest that histamine H3 receptor antagonists or inverse agonists may be useful in the prevention and therapy of memory/learning disability and diseases accompanied by memory/learning disability, such as Alzheimer's disease, Parkinson's disease or attention defect/hyperkinesia disorder.

Therefore, the compound or salt according to any one of (1) to (45) is presumably useful in the prophylaxis or therapy of memory/learning disability and diseases accompanied by memory/learning disability In the rat, intraventricular administration of histamine suppresses feeding behavior, which suggests that histamine participates in feeding behavior adjustment (e.g., Journal of Physiology and Pharmacology Vol. 49, p. 191 (1998)). Actually, thioperamide, which is a histamine H3 antagonist or inverse agonist, suppresses feeding behavior in a dose-dependent manner, and also promotes release of intracerebral histamine (e.g., Behavioral Brain Research, Vol. 104, p. 147 (1999)).

These findings suggests that histamine H3 receptors participates in feeding behavior adjustment, and that histamine H3 antagonists or inverse agonists may be useful for prevention or treatment of metabolic diseases such as eating disorder, obesity, diabetes mellitus, emaciation and hyperlipemia.

Therefore, the compound or salt according to any one of (1) to (45) is presumably useful in the prophylaxis or therapy of such metabolic diseases.

In the rat, administration of (R)-(α)-methylhistamine, which is a histamine H3 receptor agonist, decreases basics diastolic pressure in a dose-dependent manner. These effects are antagonized by thioperamide, which is a histamine H3 antagonist or inverse agonist (e.g., European Journal of Pharmacology, Vol. 234, p. 129 (1993)).

These findings suggest that histamine H3 receptors participate in adjustment of blood pressure, heartbeat and cardiovascular output, and that histamine H3 receptor agonists, antagonists or inverse agonists may be useful in prevention or therapy of circulatory diseases such as hypertension and various heart troubles.

Therefore, the compound or salt according to any one of (1) to (45) is presumably useful in the prophylaxis or therapy of such circulatory diseases.

In the mouse, thioperamide, which is a histamine H3 antagonist or inverse agonist, suppressed convulsion uided induced by electric shock stimuli or epileptoid strokes induced by pentylenetetrazol (PTZ) in a dose-dependent manner, (e.g., European Journal of Pharmacology, Vol. 234, p. 129 (1993), and Pharmacology, Biochemistry and Behavior, Vol. 68, p. 735 (2001)).

These findings suggest that histamine H3 antagonists or inverse agonists may be useful for the prevention or treatment of epilepsy or central convulsions.

Therefore, the compound or salt according to any one of (1) to (45) is presumably useful in the prophylaxis or therapy of such epilepsy or central convulsions.

In other words, the present invention further provides a prophylactic or therapeutic agent for a metabolic disease, a circulatory disease or a nervous system disease containing as an active ingredient the compound according to any one of (1) to (45), or a pharmaceutically acceptable salt thereof.

As the metabolic disease, there may be mentioned at least one selected from the group consisting of obesity, diabetes mellitus, hormone secretion disorders, hyperlipidemia, gout and fatty liver.

As the circulatory disease, there may be mentioned at least one selected from the group consisting of angina pectoris, acute or congestive heart failure, myocardial infarction, annular arteriosclerosis, hypertension, kidney disease and electrolyte imbalance.

As the nervous system disease, there may be mentioned at least one selected from the group consisting of sleep disorder, disease accompanied by sleep disorder, bulimia, emotional disorder, epilepsy, delirium, dementia, attention deficit/hyperactivity disorder, memory impairment, Alzheimer's disease, Parkinson's disease, cognitive disorder, movement disorder, dysesthesia, dysosmia, morphine resistance, narcotics dependence, alcohol dependence and tremor.

As the nervous system disease, there may also be mentioned at least one selected from the group consisting of idiopathic hypersomnia, repeatability hypersomnia, intrinsic hypersomnia, narcolepsy, periodic limb movement during sleep, sleep apnea syndrome, circadian rhythm hindrance, chronic fatigue syndrome, REM sleep hindrance, sleep loss in the elderly, night shift worker sleep insanitation, idiopathic insomnia, repeatability insomnia, intrinsic insomnia, depression, insecurity, schizophrenia.

The compound or salt according to any one of (1) to (45) may be used in combination with concomitant drugs. In other words, the present invention further provides a prophylactic or therapeutic agent for a metabolic disease, a circulatory disease or a nervous system disease containing as active ingredients the compound according to any one of (1) to (45), or a pharmaceutically acceptable salt thereof, and a concomitant drug. Here, examples of the concomitant drug are antidiabetic agents, lipid lowering agents, anti-hypertensive agents and anti-obesity agents. Two or more of these concomitant drugs may be combined.

As such prophylactic or therapeutic agent, a prophylactic or therapeutic agent for a metabolic disease, a circulatory disease or a nervous system disease comprising the following (i) to (iii) is further provided.
- (i) the compound according to any one of (1) to (45), or a pharmaceutically acceptable salt thereof;
- (ii) one or more compound(s) selected from the group consisting of the following (a) to (g):
  - (a) Histamine H3 antagonist or inverse agonist other than (i),
  - (b) a biguanide,
  - (c) a PPAR agonist,
  - (d) insulin,
  - (e) somatostatin,
  - (f) an α-glucosidase inhibitor, and
  - (g) insulin secretagogues; and
- (iii) a pharmaceutically acceptable carrier.

DESCRIPTION OF THE PREFERRED EMBODIMENTS

The terminology used in this specification will now be described, and then the compound relating to the present invention will be described in further detail.

"Aryl group" means a hydrocarbon ring aryl group having 6 to 14 carbon atoms, such as phenyl, naphthyl, biphenyl or anthryl.

"Lower alkyl group" means a straight-chain or branched alkyl group having 1 to 6 carbon atoms, e.g., methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl or 1-ethyl-2-methylpropyl.

"Cycloalkyl group having 3 to 9 carbon atoms" means for example cyclopropyl, cyclobutyl, cyclopentyl, a cyclohexyl, cycloheptyl, cyclooctyl or cyclononyl.

"Alkoxy group" means a group wherein the hydrogen atom of a hydroxy group is substituted by the aforesaid lower alkyl group, e.g., methoxy, ethoxy, propoxy, isopropoxy, butoxy, sec-butoxy, tert-butoxy, pentyloxy, isopentyloxy, hexyloxy or isohexyloxy.

"Alkylsulfonyl group" means a group wherein the aforesaid alkyl group is combined with sulfonyl, e.g., methylsulfonyl, ethylsulfonyl, propylsulfonyl, isopropylsulfonyl or butylsulfonyl.

"Alkylsulfonylamino group" means a group wherein one of the hydrogen atoms of an amino group is substituted by the aforesaid alkylsulfonyl group, e.g., methylsulfonylamino, ethylsulfonylamino, propylsulfonylamino, isopropylsulfonylamino, butylsulfonylamino, sec-butylsulfonylamino, tert-butylsulfonylamino, N-methyl-methylsulfonylamino, N-methyl-ethylsulfonylamino, N-methyl-propylsulfonylamino, N-methyl-isopropylsulfonylamino, N-methyl-butylsulfonylamino, N-methyl-sec-butylsulfonylamino, N-methyl-tert-butylsulfonylamino, N-ethyl-methylsulfonylamino, N-ethyl-ethylsulfonylamino, N-ethyl-propylsulfonylamino, N-ethyl-isopropylsulfonylamino, N-ethyl-butylsulfonylamino, N-ethyl-sec-butylsulfonylamino or N-ethyl-tert-butylsulfonylamino.

"Cyclo lower alkylsulfonyl group" means a group wherein the aforesaid "cycloalkyl group having 3 to 9 carbon atoms" is combined with sulfonyl, e.g., cyclopropylulfonyl, cyclobutylulfonyl, cyclopentylulfonyl, cyclohexylulfonyl, cycloheptylulfonyl, cyclooctylulfonyi or cyclononylulfonyl.

"Aralkyl group" means a group wherein the aforesaid lower alkyl group has one of the aforesaid aryl groups, i.e., benzyl, 1-phenylethyl, 2-phenylethyl, 1-naphthylmethyl or 2-naphthylmethyl.

"Heteroaryl group" means a 5- to 7-membered monocylic ring having 1 to 3 hetero atoms selected from the group consisting of oxygen, sulfur and nitrogen, or a bicyclic ring wherein the monocyclic ring is fused with a benzene ring or pyridine ring, e.g., furyl, thienyl, pyrrolyl, imidazolyl, triazolyl, thiazolyl, thiadiazolyl, isothiazolyl, oxazolyl, isoxazolyl, pyridyl, pyrimidinyl, pyridinyl, pyrazolyl, pyradinyl, quinolyl, isoquinolyl, quinazolinyl, quinolidinyl, quinoxanyl, cinnolinyl, benzoimidazolyl, imidazopyridyl, benzofuranyl, naphthylidenyl, 1,2-benzoisoxazolyl, benzoxazolyl, benzothiazolyl, oxazolopyridyl, pyridothiazolyl, isothiazolopyridyl or benzothienyl.

"Halogen atom" means fluorine, chlorine, bromine or iodine.

"Alkoxycarbonylamino group" is a group wherein one of the hydrogen atoms in an amino group is substituted by the aforesaid alkoxycarbonyl group, e.g., methoxycarbonylamino, ethoxycarbonylamino, propoxycarbonylamino, isopropoxycarbonylamino, butoxycarbonylamino, sec-butoxycarbonylamino, tert-butoxycarbonylamino, pentyloxycarbonylamino, N-methylmethoxycarbonylamino, N-methylethoxycarbonylamino, N-methylpropoxycarbonylamino, N-methylisopropoxycarbonylamino, N-methylbutoxycarbonylamino, N-methyl-sec-butoxycarbonylamino, N-methyl-tert-butoxycarbonylamino, N-ethylmethoxycarbonylamino, N-ethylethoxycarbonylamino, N-ethylpropoxycarbonylamino, N-ethylisopropoxycarbonylamino, N-ethylbutoxycarbonylamino, N-ethyl-sec-butoxycarbonyl amino or N-ethyl-tert-butoxycarbonylamino.

"Hydroxyalkyl group" means a group wherein one of the hydrogen atoms in the aforesaid lower alkyl group is substituted by hydroxy, e.g., hydroxymethyl, hydroxyethyl, 1-hydroxypropyl, 1-hydroxyethyl, 2-hydroxypropyl or 2-hydroxy-1-methylethyl.

"Mono-lower alkylcarbamoyl group" means a group wherein a carbamoyl group is mono-substituted by the aforesaid lower alkyl group, e.g., methylcarbamoyl, ethylcarbamoyl, propylcarbamoyl, isopropy carbamoyl, butylcarbamoyl, sec-butylcarbamoyl or tert-butylcarbamoyl.

"Di-lower alkylcarbamoyl group" means a carbamoyl which is disubstituted by the same or different lower alkyl groups. Examples of "di-lower alkylcarbamoyl groups" are dimethylcarbamoyl, diethylcarbamoyl, ethylmethylcarbamoyl, dipropylcarbamoyl, methylpropylcarbamoyl and diisopropylcarbamoyl.

"Di-lower alkylcarbamoyl group" also includes a 5 to 8-membered monocyclic ring which the nitrogen atom forming the carbamoyl group, and the same or different lower alkyl groups combined with the nitrogen atom, together form, or a bicyclic ring which the monocyclic ring is fused with a benzene ring or a pyridine ring to form. Specific examples are groups represented by the following formulae.

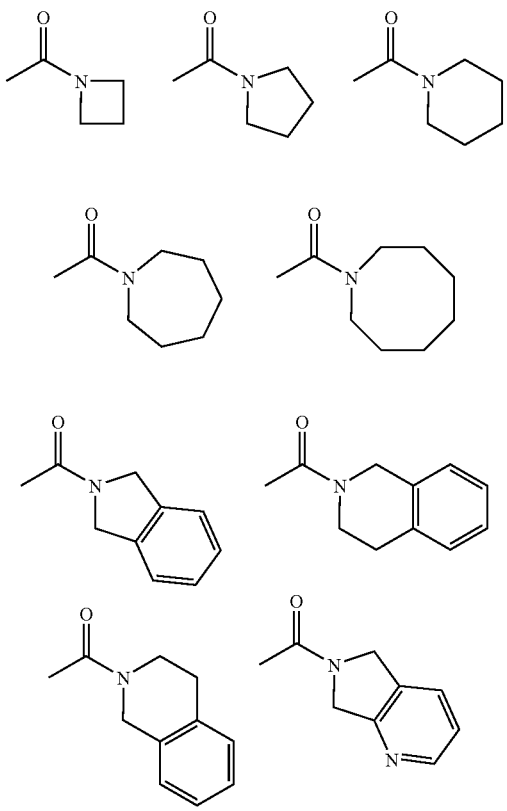

-continued

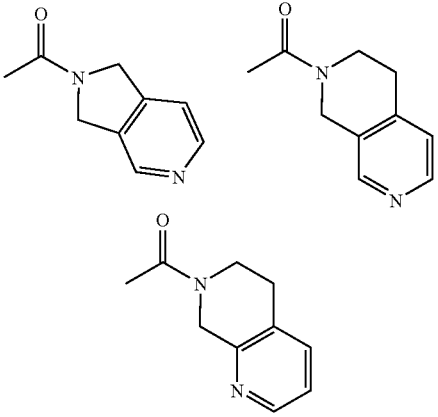

"Alkylamino group" means a group wherein an amino group is mono-substituted by the aforesaid lower alkyl group, e.g., methylamino, ethylamino, propylamino, isopropylamino, butylamino, sec-butylamino or tert-butylamino.

"Dialkylamino group" means a group wherein an amino group is disubstituted by the same or different lower alkyl groups, e.g., dimethylamino, diethylamino, dipropylamino, methylpropylamino or diisopropylamino.

"Aminoalkyl group" means a group wherein one of the hydrogen atoms forming the aforesaid alkyl group is substituted by amino, e.g., aminomethyl, aminoethyl or aminopropyl.

"Alkanoyl group" means a group wherein the aforesaid alkyl group is combined with a carbonyl group, e.g., methylcarbonyl, ethylcarbonyl, propylcarbonyl or isopropylcarbonyl.

"Alkanoylamino group" means a group wherein the aforesaid alkanoyl group is combined with an amino group, e.g., acetylamino, propanoylamino, butanoylamino, pentanoylamino, N-methylacetylamino, N-methylpropanoylamino, N-methylbutanoylamino, N-methylpentanoylamino, N-ethylacetylamino, N-ethylpropanoylamino, N-ethylbutanoylamino or N-ethylpentanoylamino.

"Mono-lower alkylaminocarbonyloxy group" means a carbonyloxy group mono-substituted by the aforesaid lower alkyl group, e.g., methylaminocarbonyloxy, ethylaminocarbonyloxy, propylaminocarbonyloxy or isopropylaminocarbonyloxy.

"Di-lower alkylaminocarbonyloxy group" means a carbonyloxy group disubstituted by the aforesaid lower alkyl groups, e.g., dimethylaminocarbonyloxy, diethylaminocarbonyloxy, diisopropylaminocarbonyloxy or ethylmethylaminocarbonyloxy.

"Alkylthio group" means a group wherein the aforesaid alkyl group is combined with a sulfur atom, e.g., methylthio, ethylthio, propylthio or isopropylthio.

"Cycloalkoxy group" means a group wherein the hydrogen atom of the hydroxy group is substituted by a cycloalkyl group having 3 to 9 carbon atoms, e.g., cyclopropoxy, cyclobutoxy, cyclopentyloxy, cyclohexyloxy or cycloheptyloxy.

"Aryloxy group" means a group wherein an oxygen atom is combined with the aforesaid aryl group, e.g., phenoxy, naphthalen-1-yl-oxy or naphthalen-2-yl-oxy.

"Heteroaryloxy group" means a group wherein the aforesaid heteroaryl group is combined with an oxy group, e.g., furan-2-yl-oxy, furan-3-yl-oxy, thiophen-2-yl-oxy, thiophen- 3-yl-oxy, 1H-pyrrol-2-yl-oxy, 1H-pyrrol-3-yl-oxy, 1H-imidazol-2-yl-oxy, 1H-imidazol-4-yl-oxy, 3H-imidazol-4-yl-oxy, 4H-[1,3,4]triazol-3-yl-oxy, 2H-[1,2,4]triazol-3-yl-oxy, 1H-[1,2,4]triazol-3-yl-oxy, thiazol-2-yl-oxy, thiazol-4-yl-oxy, thiazol-5-yl-oxy, pyridin-2-yl-oxy, pyridin-3-yl-oxy, pyridin-4-yl-oxy, pyrimidin-2-yl-oxy, pyrimidin-4-yl-oxy, pyrimidin-5-yl-oxy, pyridazin-3-yl-oxy, pyridazin-4-yl-oxy, 2H-pyrazol-3-yl-oxy, 1H-pyrazol-4-yl-oxy, 1H-pyrazolyl-3-oxy, pyrazin-3-yl-oxy, pyrazin-4-yl-oxy, quinolin-2-yl-oxy, quinolin-3-yl-oxy, quinolin-4-yl-oxy, isoquinolin-1-yl-oxy, isoquinolin-3-yl-oxy, isoquinolin-4-yl-oxy, quinazolin-2-yl-oxy, quinazolinyl-3-yl-oxy, quinoxalin-2-yl-oxy, quinoxalin-3-yl-oxy, cinnolin-3-yl-oxy, cinnolin-4-yl-oxy, 1H-benzimidazol-2-yl-oxy, 1H-imidazo[4,5-b]pyridin-5-yl-oxy, 1H-imidazo[4,5-b]pyridin-6-yl-oxy, 1H-imidazo[4,5-b]pyridin-7-yl-oxy, benzo[d]isoxazol-4-yl-oxy, benzo[d]isoxazol-5-yl-oxy, benzo[d]isoxazol-6-yl-oxy, benzoxazol-4-yl-oxy, benzoxazol-5-yl-oxy or benzoxazol-6-yl-oxy group.

"Heteroarylalkyl group" means a group wherein the aforesaid heteroaryl group is combined with the aforesaid alkyl group, e.g., furan-3-yl-methyl, furan-2-yl-methyl, furan-3-yl-ethyl, furan-2-yl-ethyl, furan-3-yl-propyl, furan-2-yl-propyl, thiophen-3-yl-methyl, thiophen-2-yl-methyl, thiophen-3-yl-ethyl, thiophen-2-yl-ethyl, thiophen-3-yl-propyl, thiophen-2-yl-propyl, 1H-pyrrol-3-yl-methyl, 1H-pyrrol-2-yl-methyl, 1H-pyrrol-3-yl-ethyl, 1H-pyrrol-2-yl-ethyl, 1H-pyrrol-3-yl-propyl, 1H-pyrrol-2-yl-propyl, 1H-imidazol-4-yl-methyl, 1H-imidazol-2-yl-methyl, 1H-imidazol-5-yl-methyl, 1H-imidazol-4-yl-ethyl, 1H-imidazol-2-yl-ethyl, 1H-imidazol-5-yl-ethyl, 1H-imidazol-4-yl-propyl, 1H-imidazol-2-yl-propyl, 1H-imidazol-5-yl-propyl, 1H-[1,2,3]triazol-4-yl-methyl, 1H-[1,2,3]triazol-5-yl-methyl, 1H-[1,2,3]triazol-4-yl-ethyl, 1H-[1,2,3]triazol-5-yl-ethyl, 1H-[1,2,3]triazol-4-yl-propyl, 1H-[1,2,3]triazol-5-yl-propyl, 1H-[1,2,4]triazol-3-yl-methyl, 1H-[1,2,4]triazol-5-yl-methyl, 1H-[1,2,4]triazol-3-yl-ethyl, 1H-[1,2,4]triazol-5-yl-ethyl, 1H-[1,2,4]triazol-3-yl-propyl, 1H-[1,2,4]triazol-5-yl-propyl, thiazol-4-yl-methyl, thiazole-3-yl-methyl, thiazol-2-yl-methyl, thiazol-4-yl-ethyl, thiazol-3-yl-ethyl, thiazol-2-yl-ethyl, thiazol-4-yl-propyl, thiazol-3-yl-propyl, thiazol-2-yl-propyl, [1,2,4]thiadiazol-3-yl-methyl, [1,2,4]thiadiazol-3-yl-ethyl, [1,2,4]thiadiazol-3-yl-propyl, [1,2,4]thiadiazol-5-yl-methyl, [1,2,4]thiadiazol-5-yl-ethyl, [1,2,4]thiadiazol-5-yl-propyl, [1,3,4]thiadiazol-2-yl-methyl, [1,3,4]thiadiazol-2-yl-ethyl or [1,3,4]thiadiazol-2-yl-propyl.

"Monoarylcarbamoyl group" means a carbamoyl group mono-substituted by the aforesaid aryl group, e.g., phenylcarbamoyl.

Next, the compound represented by the aforesaid formula (I) relating to the present invention will be described in further detail.

The symbols used in formula (I) will first be described.

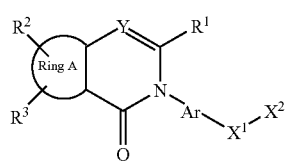

[where the symbols have the same meaning as the above.]

Ar is phenyl, pyrimidinyl, pyridyl, thiazolyl, oxazolyl, pyrazolyl, thiadiazolyl or thienyl, i.e. a divalent group formed by eliminating two hydrogen atoms from benzene, pyrimidine, pyridine, thiazole, oxazole, pyrazole, thiadiazole or thiophene, but among these, phenyl or pyrimidinyl, i.e a divalent group formed by eliminating two hydrogen atoms from benzene or pyrimidine, is preferred.

Ar may be substituted by halogen, lower alkoxy, hydroxy and lower alkyl. Examples of this halogen are fluorine, bromine and chlorine. As the lower alkoxy there may be mentioned methoxy and ethoxy. This lower alkoxy group may be further substituted by halogen. As the lower alkyl there may be mentioned methyl and ethyl.

$X^1$ is a nitrogen atom, a sulfur atom or an oxygen atom, but among these, an oxygen atom is preferred.

$X^2$ is represented by formula (II):

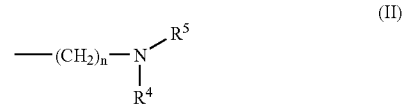

[where the symbols have the same meaning as the above], formula (III):

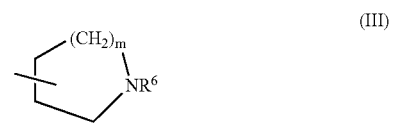

[where the symbols have the same meaning as the above], or formula (IV):

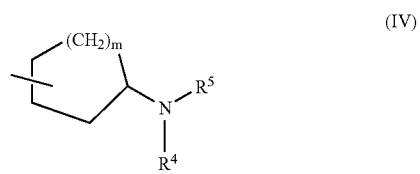

[where the symbols have the same meaning as the above].

The case where —$X^2$ is represented by formula (II) will first be described.

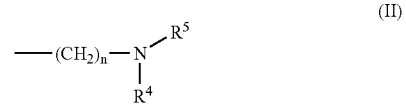

[where the symbols have the same meaning as the above.]

n is an integer from 2 to 4, preferably 3 or 4, but more preferably 3.

The "lower alkyl groups" represented by $R^4$ and $R^5$ are identical to the above. More specifically, this lower alkyl group may for example be methyl, ethyl, propyl or isopropyl.

The "lower alkyl groups" represented by $R^4$ and $R^5$ may be the same or different.

The "cycloalkyl groups" represented by $R^4$ and $R^5$ are identical to the above. This cycloalkyl group may for example be cyclopropyl, cyclobutyl or the like.

$R^4$, $R^5$ and a nitrogen atom in the aforesaid formula (II) may form a 5- to 8-membered monocyclic ring (in addition to the nitrogen atom adjoining $R^4$ and $R^5$, this ring may further have a hetero atom selected from among a nitrogen atom, a sulfur atom and an oxygen atom) Examples of this 5- to 8-membered monocyclic ring are a pyrrolidine ring, a piperidine ring, a homopiperidine ring, a heptamethyleneimine ring, a piperazine ring, a morpholine ring and a homomorpholine ring.

$R^4$, $R^5$ and the nitrogen atom in the aforesaid formula (II) may also form a bicyclo ring. This bicyclo ring is an azabicyclic ring, and is a non-aromatic ring containing the nitrogen atom adjoining $R^4$ and $R^5$ in the aforesaid formula (II) as the only hetero atom forming the ring. This ring preferably has 6 to 10 ring-forming atoms, but more preferably 7 to 9 ring-forming atoms.

Examples of this bicyclo ring are groups represented by formulae (V).

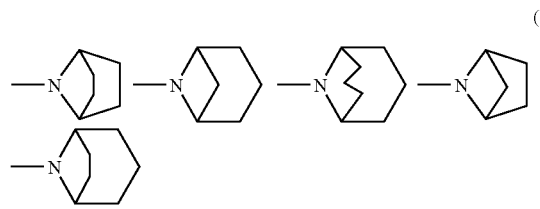

(V)

$(CH_2)_n$ in the aforesaid formula (II) may be substituted by a lower alkyl group having 1 to 3 carbon atoms. Examples of this lower alkyl group are methyl, ethyl, n-propyl and isopropyl.

When $X^2$ is a group represented by the aforesaid formula (II), it is preferred that n is 3 or 4, and R4, R5 and a nitrogen atom together form a 5- to 8-membered monocyclic ring (this monocyclic ring may have as a substituent group a halogen atom, or a lower alkyl group which may be substituted by halogen), or form a 6- to 10-membered bicyclo ring, and more preferred that n is 3, and R4, R5 and a nitrogen atom together form a 5- to 8-membered monocyclic ring (this monocyclic ring may have as a substituent group a halogen atom, or a lower alkyl group which may be substituted by halogen), or form a 6- to 10-membered bicyclo ring.

The case where —$X^2$ is represented by formula (III) will now be described.

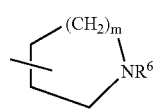

(III)

[where the symbols have the same meaning as the above.]

m is an integer from 0 to 4, among which, 2 or 3 is preferred.

$R^6$ is a lower alkyl group or a cycloalkyl group.

The "lower alkyl group" represented by $R^6$ is identical to the above. More specifically, this lower alkyl group may for example be alkyl, methyl, ethyl, propyl, butyl or pentyl.

The "cycloalkyl group" represented by $R^6$ is identical to the aforesaid lower alkyl group, for example, methyl, ethyl, propyl, butyl, isopropyl, isobutyl, tert-butylpentyl, isoamyl, neopentyl, 1,1-dimethylpropyl, 1-methylbutyl, 2-methylbutyl, hexyl, isohexyl, 1-methylpentyl or 1,1-dimethylbutyl.

When —$X^2$ is represented by formula (III), two different carbon atoms of the carbon atoms forming $X^2$ may be joined together via —$(CH_2)m11$- (m11 is an integer from 1 to 3) to form a bicyclo ring. Examples of this bicyclo ring are groups represented by formulae (III-2)

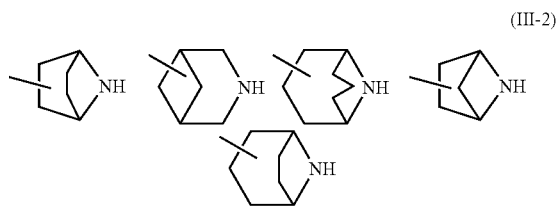

(III-2)

[where the symbols have the same meaning as the above.]

The case where —$X^2$ is represented by formula (IV) will now be described.

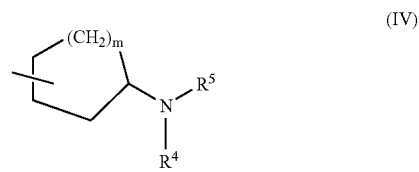

(IV)

[where the symbols have the same meaning as the above.]

m is an integer from 0 to 4, among which, 2 or 3 is preferred.

$R^4$ and $R^5$ have the same meanings as the above, and the preferred and more preferred aspects are identical to the aforesaid aspects of $R^4$ and $R^5$.

When —$X^2$ is represented by formula (IV), two different carbon atoms of the carbon atoms forming $X^2$ (except the carbon atoms in $R^4$ and $R^5$) may be joined together via a single bond or —$(CH_2)m11$- (m11 is an integer from 1 to 3) to form a bicyclo ring. Examples of this bicyclo ring are groups represented by formulae (IV-2)

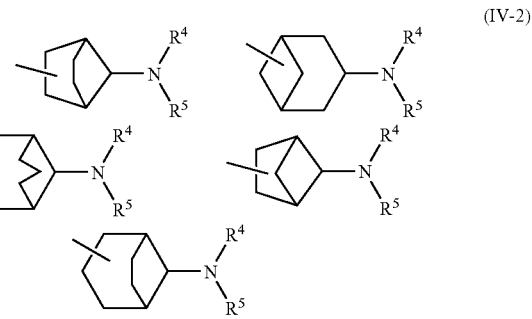

(IV-2)

[where the symbols have the same meaning as the above.]

When —$X^2$ is one of the bicyclo rings represented by formulae (IV-2), the preferred aspects of $R^4$ and $R^5$ are identical to the above.

From the above, more specifically, $X^2$ may for example be 2-dimethylaminoethyl, 2-diethylaminoethyl, 2-di-n-propylaminoethyl, 2-diisopropylaminoethyl, 3-dimethylaminopropyl, 3-diethylaminopropyl, 3-di-n-propylaminopropyl, 3-diisopropylaminopropyl, 4-dimethylaminobutyl, 4-diethylaminobutyl, 4-di-n-propylaminobutyl, 4-diisopropylaminobutyl, 2-(ethylmethylamino)ethyl, 2-(ethylpropylamino)ethyl, 2-(ethylisopropylamino)ethyl, 2-(methylisopropylamino)ethyl, 2-(ethyl-n-propylamino)ethyl, 3-(ethylmethylamino)propyl, 3-(ethylpropylamino)propyl, 3-(ethylisopropylamino)propyl, 3-(methylisopropylamino)propyl, 2-(ethyl-n-propylamino)propyl, 4-(ethylmethylamino)butyl, 4-(ethylpropylamino)butyl, 4-(ethylisopropylamino)butyl, 2-(ethyl-n-propylamino)butyl, 2-dicyclopropylaminoethyl, 2-dicyclobutylaminoethyl, 2-dicyclopentylaminoethyl, 2-dicyclohexylaminoethyl, 3-dicyclopropylaminopropyl, 3-dicyclobutylaminopropyl, 3-dicyclopentylaminopropyl, 3-dicyclohexylaminopropyl, 4-dicyclopropylaminobutyl, 4-dicyclobutylaminobutyl, 4-dicyclopentylaminobutyl, 4-dicyclohexylaminobutyl, 2-(cyclobutyl-cyclopropylamino)ethyl, 2-(cyclobutyl-cyclopentylamino)ethyl, 2-(cyclohexyl-cyclopentyl)ethyl, 3-(cyclobutyl-cyclopropylamino)propyl, 3-(cyclobutyl-cyclopentylamino)propyl, 3-(cyclohexyl-cyclopentylamino)propyl, 4-(cyclobutyl)-cyclopropylaminobutyl, 4-(cyclobutyl-cyclopentylamino)butyl, 4-(cyclohexyl-cyclopentylamino)butyl, 2-(cyclopropylmethylamino)ethyl, 2-(cyclopropylethylamino)ethyl, 2-(cyclopropyl-n-propylamino)ethyl, 2-(cyclopropylisopropylamino)ethyl, 2-(cyclobutylmethylamino)ethyl, 2-(cyclobutylethylamino)ethyl, 2-(cyclobutyl-n-propylamino)ethyl, 2-(cyclobutylisopropylamino)ethyl, 2-(cyclopentylmethylamino)ethyl, 2-(cyclopentylethylamino)ethyl, 2-(cyclopentyl-n-propylamino)ethyl, 2-(cyclopentylisopropylamino)ethyl, 2-(cyclohexylmethylamino)ethyl, 2-(cyclohexylethylamino)ethyl, 2-(cyclohexyl-n-propyl) aminoethyl,2-(cyclohexylisopropylamino)ethyl, 3-(cyclopropylmethylamino)propyl, 3-(cyclopropylethylamino)propyl, 3-(cyclopropyl-n-propylamino)propyl, 3-(cyclopropylisopropylamino)propyl, 3-(cyclobutylmethylamino)propyl, 3-(cyclobutylethylamino)propyl, 3-(cyclobutyl-n-propylamino)propyl, 3-(cyclobutylisopropylamino)propyl, 3-(cyclopentylmethylamino)propyl, 3-(cyclopentyl)-ethylaminopropyl, 3-(cyclopentyl-n-propylamino) propyl, 3-(cyclopentylisopropylamino)propyl, 3-(cyclohexylmethylamino)propyl, 3-(cyclohexylethylamino)propyl, 3-(cyclohexyl-n-propylamino)propyl, 3-(cyclohexylisopropylamino)propyl, 4-(cyclopropylmethylamino)butyl, 4-(cyclopropylethylamino)butyl, 4-(cyclopropyl-n-propylamino)butyl, 4-(cyclopropylisopropylamino)butyl, 4-(cyclobutylmethylamino)butyl, 4-(cyclobutylethylamino)butyl, 4-(cyclobutyl-n-propylamino)butyl, 4-(cyclobutylisopropylamino)butyl, 4-(cyclopentylmethylamino)butyl, 4-(cyclopentylethylamino)butyl, 4-(cyclopentyl-n-propylamino)butyl, 4-(cyclopentylisopropylamino) butyl, 4-(cyclohexylmethylamino)butyl, 4-(cyclohexylethylamino)butyl, 4-(cyclohexyl-n-propylamino)butyl, 4-(cyclohexylisopropylamino)butyl, 2-pyrrolidin-1-yl-ethyl, 2-piperidin-1-yl-ethyl, 2-homopiperidin-1-yl-ethyl, 2-hepta-methyleneimin-1-yl-ethyl, 2-morpholin-4-yl-ethyl, 2-homomorpholin-4-yl-ethyl, 3-pyrrolidin-1-yl-propyl, 3-piperidin-1-yl-propyl, 3-homopiperidin-1-yl-propyl, 3-hepta-methyleneimin-1-yl-propyl, 3-morpholin-4-yl-propyl, 3-homomorpholin-4-yl-propyl, 4-pyrrolidin-1-yl-butyl, 4-piperidin-1-yl-butyl, 4-homopiperidin-1-yl-butyl, 4-hepta-methyleneimin-1-yl-butyl, 4-morpholin-4-yl-butyl, 4-homomorpholin-4-yl-butyl, 2-(5-aza-bicyclo[2.1.1]hexan-5-yl-ethyl, 2-(6-aza)-bicyclo[3.1.1]heptan-6-yl-ethyl, 2-(7-aza-bicyclo[2.1.1]heptan-7-yl-ethyl), 2-(8-aza-bicyclo[3.2.1]octan-8-yl-ethyl), 2-(9-aza-bicyclo[3.3.1]nonan-9-yl-ethyl), 3-(5-aza-bicyclo[2.1.1]hexan-5-yl-propyl), 3-(6-aza-bicyclo[3.1.1]heptan-6-yl-propyl), 3-(7-aza-bicyclo[2.1.1]heptan-7-yl-propyl), 3-(8-aza-bicyclo[3.2.1]octan-8-yl-propyl), 3-(9-aza-bicyclo[3.3.1]nonan-9-yl-propyl), 4-(5-aza-bicyclo[2.1.1]hexan-5-yl-butyl), 4-(6-aza-bicyclo[3.1.1]heptan-6-yl-butyl), 4-(7-aza-bicyclo[2.1.1]heptan-7-yl-butyl), 4-(8-aza-bicyclo[3.2.1]octan-8-yl-butyl, 4-(9-aza-bicyclo[3.3.1]nonan-9-yl-butyl, 1-methylazetidin-3-yl, 1-methyl-azetidin-2-yl), 1-ethylazetidin-3-yl, 1-ethyl-azetidin-2-yl, 1-isopropylazetidin-3-yl, 1-isopropylazetidin-2-yl, 1-cyclopropylazetidin-3-yl, 1-cyclobutylazetidin-2-yl, 1-cyclobutylazetidin-3-yl, 1-cyclobutylazetidin-2-yl, 1-cyclopentylazetidin-3-yl, 1-cyclopentylazetidin-2-yl, 1-cyclohexylazetidin-3-yl, 1-cyclohexylazetidin-2-yl, 1-methylpyrrolidin-3-yl, 1-methylpyrrolidin-2-yl, 1-ethylpyrrolidin-3-yl, 1-ethylpyrrolidin-3-yl, 1-isopropylpyrrolidin-3-yl, 1-isopropylpyrrolidin-2-yl, 1-cyclopropylpyrrolidin-3-yl, 1-cyclopropylpyrrolidin-2-yl, 1-cyclobutylpyrrolidin-3-yl, 1-cyclobutylpyrrolidin-2-yl, 1-cyclopentylpyrrolidin-3-yl, 1-cyclopentylpyrrolidin-2-yl, 1-cyclohexylpyrrolidin-3-yl, 1-cyclohexylpyrrolidin-2-yl, 1-methylpiperidin-4-yl, 1-methylpiperidin-3-yl, 1-methylpiperidin-2-yl, 1-ethylpiperidin-4-yl, 1-ethylpiperidin-3-yl, 1-ethylpiperidin-2-yl, 1-isopropylpiperidin-4-yl, 1-isopropylpiperidin-3-yl, 1-isopropylpiperidin-2-yl, 1-cyclopropylpiperidin-4-yl, 1-cyclopropylpiperidin-3-yl, 1-cyclopropylpiperidin-2-yl, 1-cyclobutylpiperidin-4-yl, 1-cyclobutylpiperidyl-3-yl, 1-cyclobutylpiperidin-2-yl, 1-cyclopentylpiperidin-4-yl, 1-cyclopentylpiperidin-3-yl, 1-cyclopentylpiperidin-2-yl, 1-cyclohexylpiperidin-4-yl, 1-cyclohexylpiperidin-3-yl, 1-cyclohexylpiperidin-2-yl, 3-dimethylaminocyclobutyl, 3-diethylaminocyclobutyl, 3-diisopropylaminocyclobutyl, 3-dicyclopropylaminobutyl, 3-dicyclobutylaminobutyl, 3-dicyclopentylaminobutyl, 3-dicyclohexylaminobutyl, 2-dimethylaminocyclobutyl, 2-diethylaminocyclobutyl, 2-diisopropylaminocyclobutyl, 2-dicyclopropylaminobutyl, 2-dicyclobutylaminobutyl, 2-dicyclopentylaminobutyl, 2-dicyclohexylaminobutyl, 3-(cyclopropylmethylamino)cyclobutyl, 3-(cyclopropylethylamino)cyclobutyl, 3-(cyclobutylmethylamino)cyclobutyl, 3-(cyclobutylethylamino)cyclobutyl, 3-(cyclopentylmethylamino)cyclobutyl, 3-(cyclopentylethylamino) cyclobutyl, 3-(cyclohexylmethylamino)cyclobutyl, 2-(cyclopropylmethylamino)cyclobutyl, 2-(cyclopropylethylamino)cyclobutyl, 2-(cyclobutylmethylamino)cyclobutyl, 2-(cyclobutylethylamino)cyclobutyl, 2-(cyclopentylmethylamino)cyclobutyl, 2-(cyclopentylethylamino) cyclobutyl, 2-(cyclohexylmethylamino)cyclobutyl, 3-pyrrolidin-1-yl-cyclobutyl, 2-pyrrolidin-1-yl-cyclobutyl, 3-pyrrolidin-1-yl-cyclopentyl, 2-pyrrolidin-1-yl-cyclopentyl, 4-pyrrolidin-1-yl-cyclohexyl, 3-pyrrolidin-1-yl-cyclohexyl, 2-pyrrolidin-1-yl-cyclohexyl, 3-piperidin-1-yl-cyclobutyl, 2-piperidin-1-yl-cyclobutyl, 3-piperidin-1-yl-cyclopentyl, 2-piperidin-1-yl-cyclopentyl, 4-piperidin-1-yl-cyclohexyl, 3-piperidin-1-yl-cyclohexyl, 2-piperidin-1-yl-cyclohexyl, 3-homopiperidin-1-yl-cyclobutyl, 2-homopiperidin-1-yl-cyclobutyl, 3-homopiperidin-1-yl-cyclopentyl, 2-homopiperidin-1-yl-cyclopentyl, 4-homopiperidin-1-yl-cyclohexyl, 3-homopiperidin-1-yl-cyclohexyl, 2-homopiperidin-1-yl-cyclohexyl, 3-hepta-methyleneimin-1-yl-cyclobutyl, 2-hepta-methyleneimin-1-yl-cyclobutyl, 3-hepta-methyleneimin-1-yl-cyclopentyl, 2-hepta-methyleneimin-1-yl-cyclopentyl, 4-hepta-methyleneimin-1-yl-cyclohexyl, 3-hepta-methyleneimin-1-yl-cyclohexyl, 2-hepta-methyleneimin-1-yl-cyclohexyl, 2-morpholin-4-yl-cyclobutyl, 3-morpholin-4-yl-cyclobutyl, 2-morpholin-4-yl-cyclopentyl, 3-morpholin-4-yl-cyclopentyl, 2-morpholin-4-yl-cyclohexyl, 3-morpholin-4-yl-cyclohexyl, 4-morpholin-4-yl-cyclohexyl, 2-homomorpholin-4-yl-cyclobutyl, 3-homomorpholin-4-yl-cyclobutyl, 4-homomorpholin-4-ylcyclobutyl, 2-homomorpholin-4-yl-cyclopentyl, 3-homomorpholin-4-yl-cyclopentyl, 4-homomorpholin-4-yl-cyclopentyl, 2-homomorpholin-4-yl-cyclohexyl, 3-homomorpholin-4-yl-cyclohexyl, 4-homomorpholin-4-yl-cyclohexyl, 2-(5-aza-bicyclo[2.1.1]hexan-5-yl)cyclobutyl, 2-(6-aza-bicyclo[3.1.1]heptan-6-yl)cyclobutyl, 2-(7-aza-bicyclo[2.1.1]heptan-7-yl)cyclobutyl, 2-(8-aza-bicyclo[3.2.1]octan-8-yl)cyclobutyl, 2-(9-aza-bicyclo[3.3.1]nonan-9-yl)cyclobutyl, 3-(5-aza-bicyclo[2.1.1]hexan-5-yl)cyclobutyl, 3-(6-aza-bicyclo[3.1.1]heptan-6-yl)cyclobutyl, 3-(7-aza-bicyclo[2.1.1]heptane)-7-yl-cyclobutyl, 3-(8-aza-bicyclo[3.2.1]octan-8-yl)cyclobutyl, 3-(9-aza-bicyclo[3.3.1]nonan-9-yl)cyclobutyl, 2-(5-aza-bicyclo[2.1.1]hexan-5-yl)cyclopentyl, 2-(6-aza-bicyclo[3.1.1]heptan-6-yl)cyclopentyl, 2-(7-aza-bicyclo[2.1.1]heptan-7-yl)cyclopentyl, 2-(8-aza-bicyclo[3.2.1]octan-8-yl)cyclopentyl, 2-(9-aza-bicyclo[3.3.1]nonan-9-yl)cyclopentyl, 3-(5-aza-bicyclo[2.1.1]hexan-5-yl)cyclopentyl, 3-(6-aza)-bicyclo[3.1.1]heptan-6-yl-cyclopentyl, 3-(7-aza-bicyclo[2.1.1]heptan-7-yl)cyclopentyl, 3-(8-aza-bicyclo[3.2.1]octan-8-yl)cyclopentyl, 3-(9-aza-bicyclo[3.3.1]nonan-9-yl)cyclopentyl, 2-(5-aza-bicyclo[2.1.1]hexan-5-yl)cyclohexyl, 2-(6-aza-bicyclo[3.1.1]heptan-6-yl)cyclohexyl, 2-(7-aza-bicyclo[2.1.1]heptan-7-yl)cyclohexyl, 2-(8-aza-bicyclo[3.2.1]octan-8-yl)cyclohexyl, 2-(9-aza-bicyclo[3.3.1]nonan-9)-yl-cyclohexyl, 3-(5-aza-bicyclo[2.1.1]hexan-5-yl)cyclohexyl, 3-(6-aza-bicyclo[3.1.1]heptan-6-yl)cyclohexyl, 3-(7-aza-bicyclo[2.1.1]heptan-7-yl)cyclohexyl, 3-(8-aza-bicyclo[3.2.1]octan-8-yl)cyclohexyl, 3-(9-aza-bicyclo[3.3.1]nonan-9-yl)cyclohexyl, 3-(7-aza-bicyclo[2.2.1]hepto-7-yl)propyl, 3-(8-aza-bicyclo[3.2.1]octo-8-yl)propyl, 3-(3,3-difluoropyrrolidin-1-yl)propyl, 3-(3-fluoropiperidin-1-yl)propyl, 3-[(3R)-3-fluoropyrrolidin-1-yl]propyl, 3-(4,4-difluoropiperidin-1-yl)propyl, 3-(4-fluoropiperidin-1-yl)propyl, 3-(3,3-difluoropiperidin-1-yl)propyl, 3-[(3R)-3-methylpiperidin-1-yl]propyl, 3-[(2R, 5R)-2,5-dimethylpyrrolidin-1-yl]propyl, 3-[3-methylpyrrolidin-1-yl-propyl, 3-[(2S)-2-methylpyrrolidin-1-yl]propyl, 3-[(2R)-2-methylpyrrolidin-1-yl]propyl, 3-[(3S)-3-methylpiperidin-1-yl]propyl, 3-(azepan-1-yl)propyl, 3-[(2-oxopyrrolidin-1-yl)]propyl. Among these, 3-piperidin-1-yl-propyl, 1-cyclobutylpiperidin-4-yl, 1-cyclopentylpiperidin-4-yl, 3-[(3S)-3-methylpiperidin-1-yl]propyl, 3-[(2R)-2-methylpyrrolidin-1-yl]propyl, 3-[(2S)-2-methylpyrrolidin-1-yl]propyl, 1-cyclopentylpiperidin-4-yl, 3-(pyrrolidin-1-yl)propyl, 3-(piperidin-1-yl)propyl are preferred.

$R^1$ is a 5- to 6-membered heteroaryl group having 1 to 4 hetero atoms selected from among nitrogen, sulfur and oxygen in the ring, a heteroarylalkyl group, a straight-chain or branched lower alkyl group (this lower alkyl group may further be substituted by hydroxy, halogen, alkoxy, allyloxy or aralkyloxy), a phenyl group, an aralkyl group, an alkoxy group, an alkylthio group or a lower alkylamino group.

In the "5- to 6-membered heteroaryl group having 1 to 4 hetero atoms selected from among nitrogen, sulfur and oxygen in the ring" represented by $R^1$, when the ring contains 2 to 4 heteroatoms, these hetero atoms may be the same or different. Examples of 5- to 6-membered heteroaryl groups are furyl, thienyl, pyrrolyl, imidazolyl, triazolyl, thiazolyl, thiadiazolyl, isothiazolyl, oxazolyl, isoxazolyl, pyridyl, pyrimidinyl, pyridinyl, pyrazolyl and pyradinyl.

The "heteroarylalkyl group" represented by $R^1$ has the same meaning as the above.

$R^1$ is preferably a lower alkyl group having 1 to 3 carbon atoms (this lower alkyl group may be further substituted by halogen), or phenyl, but more prefarably, methyl, ethyl, n-propyl, isopropyl or trifluoromethyl.

$R^2$ and $R^3$ may be the same or different, and each represents a hydrogen atom, amino, nitro, cyano, hydroxy, lower alkylsulfonyl, a halogen atom, lower alkyl (this lower alkyl group may be further substituted by hydroxy or a halogen atom), lower cycloalkyl (this lower cycloalkyl group may be further substituted by a halogen atom), lower alkoxy (this lower alkoxy group may be further substituted by a halogen atom), lower cycloalkoxy (this lower cycloalkoxy group may be further substituted by a halogen atom), aryloxy, aralkyloxy, aryl, heteroaryl, mono-lower alkylcarbamoyl, di-lower alkylcarbamoyl, lower alkylcarboxamide, arylcarboxamide, heteroarylcarboxamide, alkanoyl, alkylthio, alkoxycarbonylamino, alkyl, arylsulfonylamino, alkylaminosulfonyl, arylaminosulfonyl, aralkyl, alkanoylamino or alkanoylalkylamino.

The "lower alkylsulfonyl group" represented by $R^2$ or $R^3$ has the same meaning as the above.

The "lower alkyl group" represented by $R^2$ or $R^3$ has the same meaning as the above. This lower alkyl group may be further substituted by a hydroxy group, or a halogen atom such as chlorine or fluorine.

The "lower alkoxy group" represented by $R^2$ or $R^3$ has the same meaning as the above.

The "cyclo lower alkoxy group" represented by $R^2$ or $R^3$ means a group wherein the aforesaid cyclo lower alkyl group is combined with an oxygen atom. This cyclo lower alkoxy group may be further substituted by a halogen atom such as chlorine or fluorine.

The "aryloxy group" represented by $R^2$ or $R^3$ has the same meaning as the above.

The "aralkyloxy group" represented by $R^2$ or $R^3$ means a group wherein the aforesaid aralkyl group is combined with an oxygen atom.

The "aryl group" represented by $R^2$ or $R^3$ has the same meaning as the above.

The "heteroaryl group" represented by $R^2$ or $R^3$ has the same meaning as the above.

The "mono-lower alkylcarbamoyl group" represented by $R^2$ or $R^3$ has the same meaning as the above.

The "di-lower alkylcarbamoyl group" represented by $R^2$ or $R^3$ has the same meaning as the above.

The "lower alkylcarboxamide group" represented by $R^2$ or $R^3$ means a group wherein the aforesaid branched or straight-chain alkyl group having 1 to 6 carbon atoms is combined with carboxamide, e.g., methylcarboxamide, ethyl carboxamide or isopropylcarboxamide.

The "alkanoyl group" represented by $R^2$ or $R^3$ means a group wherein the aforesaid alkyl group is combined with carbonyl, e.g., methylcarbonyl, ethylcarbonyl, propylcarbonyl or isopropylcarbonyl.

The "alkylthio group" represented by $R^2$ or $R^3$ means a group wherein the aforesaid alkyl group is combined with sulfur, e.g., methylthio, ethylthio, propylthio or isopropylthio.

The "alkoxycarboxamide group" represented by $R^2$ or $R^3$ means a group wherein the aforesaid alkoxy group is combined with carboxamide, e.g., methoxycarboxamide, ethoxycarboxamide or isopropoxycarboxamide.

The "arylcarboxamid group" represented by $R^2$ or $R^3$ means a group wherein the aforesaid aryl group is combined with carboxamide, e.g., phenylcarboxamide or naphthylcarboxamide.

The "heteroarylcarboxamide group" represented by R2 or $R^3$ means a group wherein the aforesaid heteroaryl group is combined with carboxamide, e.g., furylcarboxamide, thienylcarboxamide or pyrrolylcarboxamide.

The "arylsulfonylamino group" represented by $R^2$ or $R^3$ means a group wherein the aforesaid aryl group is combined with sulfonylamino, e.g., phenylsulfonylamino or naphthylsulfonylamino.

The "alkylaminosulfonyl group" represented by $R^2$ or $R^3$ means a group wherein the aforesaid alkyl group is combined with aminosulfonyl, e.g., methylaminosulfonyl, ethylaminosulfonyl or isopropylaminosulfonyl.

The "arylaminosulfonyl group" represented by $R^2$ or $R^3$ means a group wherein the aforesaid aryl group is combined with aminosulfonyl, e.g., phenylaminosulfonylamino or naphthylaminosulfonylamino.

The "aralkyl group" represented by $R^2$ or $R^3$ has the same meaning as the above.

The "alkanoylalkylamino group" represented by $R^2$ or $R^3$ means a group wherein the aforesaid alkanoyl group is combined with the aforesaid alkylamino, e.g., acetylmethylamino or acetylethylamino.

Ring A is a 5- to 6-membered heteroaryl ring having 1 or 2 hetero atoms selected from among nitrogen or sulfur in the ring, or a benzene ring. This Ring A may for example be a benzene ring, thiophene ring, pyridine ring, pyrimidine ring or pyrazine ring, among which, a benzene ring, pyridine ring and pyrimidine ring are preferred, and a benzene ring and pyridine ring are more preferred.

When the 5- to 6-membered heteroaryl ring represented by Ring A has two hetero atoms, the hetero atoms may be the same or different.

The aforesaid substituent groups $R^2$ or $R^3$ on this Ring A may be the same or different.

From the above, groups represented by formula (VI):

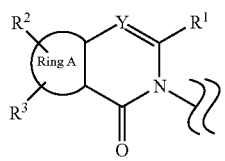

(VI)

[where the symbols have the same meaning as the above, and formula (VI-0):

(VI-0)

shows the bonding site] may for example be groups represented by formulae (VI-1):

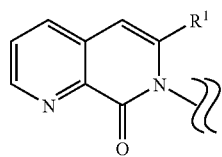 

-continued

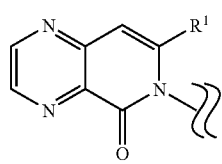 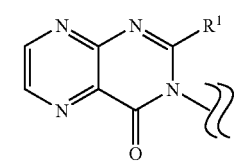

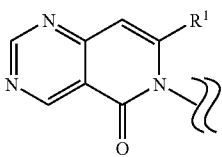 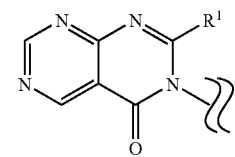

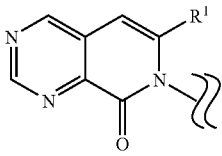 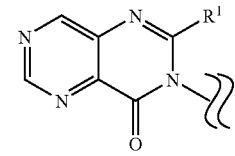

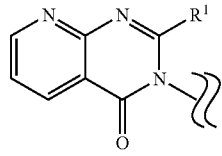 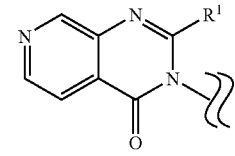

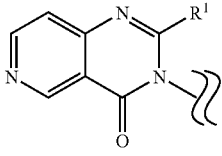 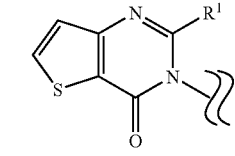

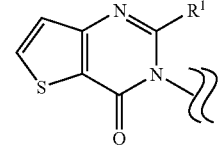 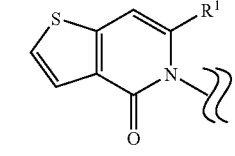

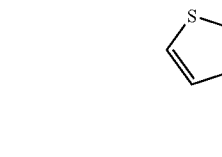 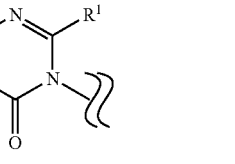

[where the symbols have the same meaning as the above], among which, groups represented by formulae (VI-2):

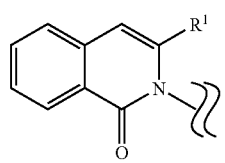 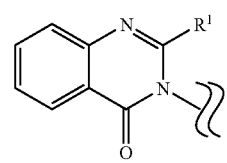

(VI-1)

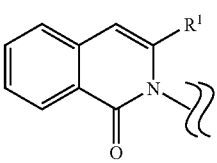 

(VI-2)

-continued

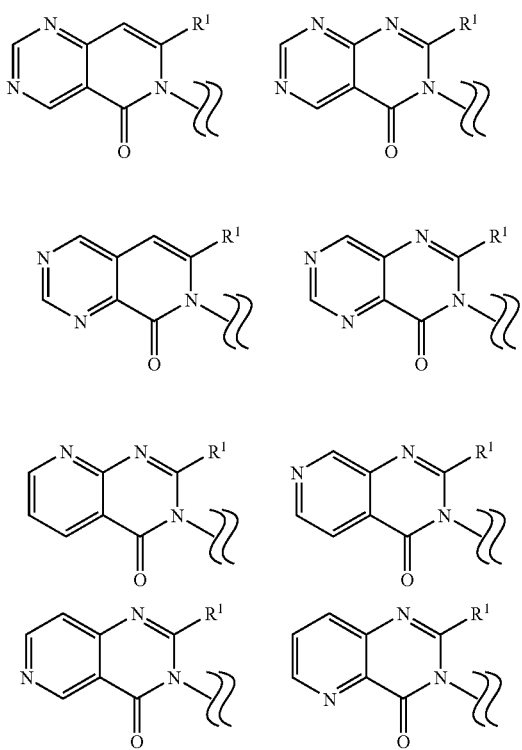

[where the symbols have the same meaning as the above] are preferred, and among these, groups represented by formulae (VI-3):

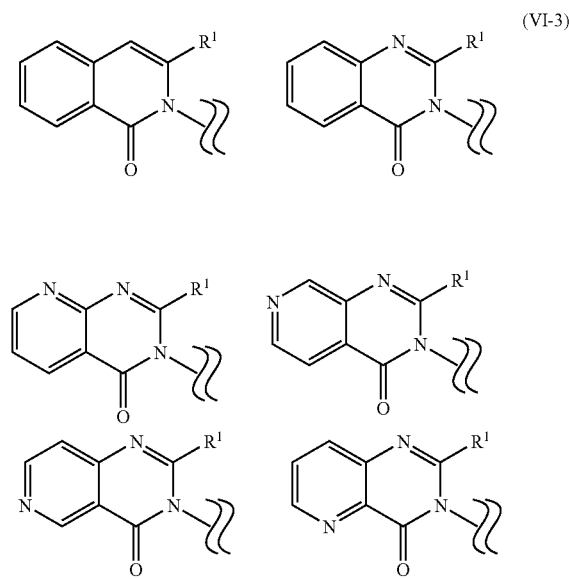

[where the symbols have the same meaning as the above] are more preferred.

Any of the preferred aspects of Ar, $X^1$, $X^2$, Y, $R^1$, $R^2$, $R^3$, $R^4$, $R^5$, $R^6$, n, m and Ring A, which are described above, may be combined.

More specifically, the compound represented by formula (I):

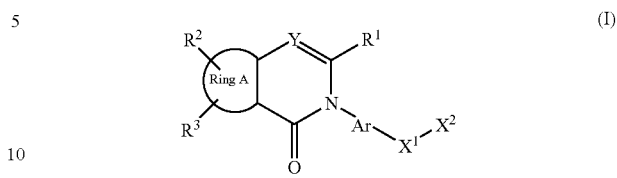

[where the symbols have the same meaning as the above] are preferably 2-ethyl-3-{4-[3-(1-pyrrolidinyl)propoxy]phenyl}-4(3H)-quinazolinone, 2-methyl-3-{4-[3-(1-piperidinyl)propoxy]phenyl}-4(3H)-quinazolinone, 2-methyl-3-{4-[3-(1-pyrrolidinyl)propoxy]phenyl}-4(3H)-quinazolinone, 3-{4-[3-(diethylamino)propoxy]phenyl}-2-methyl-4-(3H)-quinazolinone, 2-methyl-3-{4-[3-(2-methyl-1-pyrrolidinyl)propoxy]phenyl}-4(3H)-quinazolinone, 3-{4-[3-(2,5-dimethyl-1-pyrrolidinyl)propoxy]phenyl}-2-methyl-4(3H)-quinazolinone, 2-methyl-3-{4-[4-(1-piperidinyl)butoxy]phenyl}-4(3H)-quinazolinone, 3-{4-[3-(1-azepanyl)propoxy]phenyl}-2-methyl-4(3H)-quinazolinone, 3-{4-[3-(1-azocanyl)propoxy]phenyl}-2-methyl 4(3H)-quinazolinone, 2-methyl-3-{4-[3-(2-methyl-1-piperidinyl)propoxy]phenyl}-4(3H)-quinazolinone, 2-methyl-3-{4-[3-(4-methyl-1-piperidinyl)propoxy]phenyl}-4(3H)-quinazolinone, 3-(4-{3-[(2R,6S)-2,6-dimethyl-1-piperidinyl]propoxy}phenyl)-2-methyl-4(3H)-quinazolinone, 2-methyl-3-{4-[3-(3-methyl-1-piperidinyl)propoxy]phenyl}-4(3H)-quinazolinone, 3-{4-[3-(3,5-dimethyl-1-piperidinyl)propoxy]phenyl}-2-methyl-4(3H)-quinazolinone, 2-methyl-3-{3-[3-(1-piperidinyl)propoxy]phenyl}-4(3H)-quinazolinone, 3-{3-bromo-4-[3-(1-piperidinyl)propoxy]phenyl}-2-ethyl-4(3H)-quinazolinone, 2-methyl-3-{4-[2-(1-piperidinyl)ethoxy]phenyl}-4(3H)-quinazolinone, 2,5-dimethyl-3-{4-[3-(1-piperidinyl)propoxy]phenyl}-4(3H)-quinazolinone, 3-{4-[3-(1-piperidinyl)propoxy]phenyl}-2-propyl-4(3H)-quinazolinone, 3-{4-[3-(1-piperidinyl)propoxy]phenyl}-2-trifluoromethyl-4(3H)-quinazolinone, 2-isopropyl-3-{4-[3-(1-piperidinyl)propoxy]phenyl}-4(3H)-quinazolinone, 2,6-dimethyl-3-{4-[3-(1-piperidinyl)propoxy]phenyl}-4(3H)-quinazolinone, 7-chloro-2-methyl-3-{4-[3-(1-piperidinyl)propoxy]phenyl}-4(3H)-quinazolinone, 2,8-dimethyl-3-{4-[3-(1-piperidinyl)propoxy}phenyl]-4(3H)-quinazolinone, 2-ethyl-5-methyl-3-{4-[3-(1-piperidinyl)propoxy]phenyl}-4(3H)-quinazolinone, 5-fluoro-2-methyl-3-{4-[3-(1-piperidinyl)propoxy]phenyl}-4(3H)-quinazolinone, 5-chloro-2-methyl-3-{4-[3-(1-piperidinyl)propoxy]phenyl}-4(3H)-quinazolinone, 5-methoxy-2-methyl-3-{4-[3-(1-piperidinyl)propoxy]phenyl}-4(3H)-quinazolinone, 5-hydroxy-2-methyl-3-{4-[3-(1-piperidinyl)propoxy]phenyl}-4(3H)-quinazolinone trifluoroacetate, 2-methyl-3-{4-[3-(1-piperidinyl)propoxy]phenyl}-5-trifluoromethyl-4(3H)-quinazolinone, 7-fluoro-2-methyl-3-{4-[3-(1-piperidinyl)propoxy]phenyl}-4(3H)-quinazolinone, 6-fluoro-2-methyl-3-{4-[3-(1-piperidinyl)propoxy]phenyl}-4(3H)-quinazolinone, 6,7-difluoro-2-methyl-3-{4-[3-(1-piperidinyl)propoxy]phenyl}-4(3H)-quinazolinone, 6-bromo-2-methyl-3-{4-[3-(1-piperidinyl)propoxy]phenyl}-4(3H)-quinazolinone, 6-chloro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 6,7-dimethoxy-2-methyl-3-{4-[3-(1- piperidinyl)propoxy]phenyl}-4(3H)-quinazolinone, 8-chloro-2-methyl-3-{4-[3-(1-piperidinyl)propoxy]phenyl}-4(3H)-quinazolinone, 8-methoxy-2-methyl-3-{4-[3-(1-piperidinyl)propoxy]phenyl}-4(3H)-quinazolinone, 2,6-dimethyl-3-{4-[3-(1-pyrrolidinyl)propoxy]phenyl}-4(3H)-quinazolinone, 2-ethyl-5-methyl-3-{4-[3-(1-pyrrolidinyl)propoxy]phenyl}-4(3H)-quinazolinone, 5-fluoro-2-methyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-chloro-2-methyl-3-{4-[3-(1-pyrrolidinyl)propoxy]phenyl}-4(3H)-quinazolinone, 2-ethyl-3-{4-[3-(1-pyrrolidinyl)propoxy]phenyl}-4(3H)-quinazolinone, 2,5-dimethyl-3-{4-[3-(1-pyrrolidinyl)propoxy]phenyl}-4(3H)-quinazolinone, 2-methyl-3-{4-[3-(1-piperidinyl)propoxy]phenyl}pyrido[2,3-d]pyrimidin-4(3H)-one, 2-methyl-3-{4-[3-(1-pyrrolidinyl)propoxy]phenyl}pyrido[2,3-d]pyrimidin-4(3H)-one, 6-chloro-2-methyl-3-{4-[3-(1-pyrrolidinyl)propoxy]phenyl}pyrido[3,4-d]pyrimidin-4(3H)-one, 2-methyl-3-{4-[3-(1-piperidinyl)propoxy]phenyl}pyrido[3,4-d]pyrimidin-4(3H)-one, 2-methyl-3-{4-[3-(1-pyrrolidinyl)propoxy]phenyl}pyrido[4,3-d]pyrimidin-4 (3H)-one, 2-methyl-3-{4-[3-(1-piperidinyl)propoxy]phenyl}pyrido[4,3-d]pyrimidin-4(3H)-one, 2-methyl-3-{2-[3-(1-piperidinyl)propoxy]-5-pyrimidinyl}-4(3H)-quinazolinone, 2,5-dimethyl-3-{2-[3-(1-piperidinyl)propoxy]-5-pyrimidinyl}-4(3H)-quinazolinone, 2-ethyl-3-{4-[3-(1-piperidinyl)propoxy]phenyl}pyrido[2,3-d]pyrimidin-4(3H)-one, 6-chloro-2-ethyl-3-{4-[3-(1-piperidinyl)propoxy]phenyl}pyrido[3,4-d]pyrimidin-4(3H)-one, 6-chloro-2-ethyl-3-{4-[3-(1-pyrrolidinyl)propoxy]phenyl}pyrido[3,4-d]pyrimidin-4 (3H)-one, 2-ethyl-3-{4-[3-(1-piperidinyl)propoxy]phenyl}pyrido[3,4-d]pyrimidin-4(3H)-one, 2-ethyl-3-{4-[3-(1-pyrrolidinyl)propoxy]phenyl}pyrido[3,4-d]pyrimidin-4 (3H)-one, 2-ethyl-3-{4-[3-(1-piperidinyl)propoxy]phenyl}pyrido[4,3-d]pyrimidin-4(3H)-one, 2-ethyl-3-{4-[3-(1-pyrrolidinyl)propoxy]phenyl}pyrido[4,3-d]pyrimidin-4 (3H)-one, 6-chloro-2-methyl-3-{4-[3-(1-piperidinyl)propoxy]phenyl}pyrido[3,4-d]pyrimidin-4(3H)-one, 3-{4-[3-(1-piperidinyl)propoxy]phenyl}-4(3H)-quinazolinone, 6-(acetylamino)-2-methyl-3-{4-[3-(1-piperidinyl)propoxy]phenyl}-4(3H)-quinazolinone, 6-(butyrylamino)-2-methyl-3-{4-[3-(1-piperidinyl)propoxy]phenyl}-4(3H)-quinazolinone, 6-(hexanoylamino)-2-methyl-3-{4-[3-(1-piperidinyl)propoxy]phenyl}-4(3H)-quinazolinone, 6-(benzoylamino)-2-methyl-3-{4-[3-(1-piperidinyl)propoxy]phenyl}-4(3H)-quinazolinone, 6-[(2-phenylacetyl)amino]-2-methyl-3-{4-[3-(1-piperidinyl)propoxy]phenyl}-4(3H)-quinazolinone, 6-(2-naphthoylamino)-2-methyl-3-{4-[3-(1-piperidinyl)propoxy]phenyl}-4(3H)-quinazolinone, 2-methyl-6-[(methylsulfonyl)amino]-3-{3-[3-(1-piperidinyl)propoxy]phenyl}-4(3H)-quinazolinone, 2-methyl-6-[(methylsulfonyl)amino]-3-{3-[3-(1-pyrrolidinyl)propoxy]phenyl}-4(3H)-quinazolinone, 7-(acetylamino)-2-methyl-3-{4-[3-(1-piperidinyl)propoxy]phenyl}-4(3H)-quinazolinone, 7-(butyrylamino)-2-methyl-3-{4-[3-(1-piperidinyl)propoxy]phenyl}-4(3H)-quinazolinone, 7-(hexanoylamino)-2-methyl-3-{4-[3-(1-piperidinyl)propoxy]phenyl}-4(3H)-quinazolinone, 7-(benzoylamino)-2-methyl-3-{4-[3-(1-piperidinyl)propoxy]phenyl}-4(3H)-quinazolinone, 7-[(2-phenylacetyl)amino]-2-methyl-3-{4-[3-(1-piperidinyl)propoxy]phenyl}-4(3H)-quinazolinone, 7-(2-naphthoylamino)-2-methyl-3-{4-[3-(1-piperidinyl)propoxy]phenyl}-4(3H)-quinazolinone, 6-[acetyl-(methyl)amino]-2-methyl-3-{4-[3-(1-piperidinyl)propoxy]phenyl}-4(3H)-quinazolinone, 2-methyl-6-phenyl-3-{4-[3-(1-piperidinyl)propoxy]phenyl}-4(3H)-quinazolinone, 2-methyl-6-(4-methylphenyl)-3-{4-[3-(1-piperidinyl)propoxy]phenyl}-4(3H)-quinazolinone, 2-methyl-6-(3-methylphenyl)-3-{4-[3-(1-piperidinyl)propoxy]phenyl}-4(3H)-quinazolinone, 2-methyl-6-(2-methylphenyl)-3-{4-[3-(1-piperidinyl)propoxy]phenyl}-4(3H)-quinazolinone, 2-methyl-3-{4-[3-(1-piperidinyl)propoxy]phenyl}-6-(3-pyridyl)-4(3H)-quinazolinone, 2-methyl-3-{4-[3-(1-piperidinyl)propoxy]phenyl}-6-(4-pyridyl)-4(3H)-quinazolinone, 2-methyl-5-phenyl-3-{4-[3-(1-piperidinyl)propoxy]phenyl}-4(3H)-quinazolinone, 2-methyl-3-{4-[3-(1-piperidinyl)propoxy]phenyl}-6-(2-pyridyl)-4(3H)-quinazolinone, 3-{4-[(1-cyclobutyl-4-piperidinyl)oxy]phenyl}-2-methyl-4(3H)-quinazolinone, 3-{4-[(1-cyclopentyl-4-piperidinyl)oxy]phenyl}-2-methyl-4(3H)-quinazolinone, 3-{4-(1-cyclohexyl-4-piperidinyloxy)phenyl}-2-methyl-4(3H)-quinazolinone, 3-{4-(1-isopropyl-4-piperidinyloxy)phenyl}-2-methyl-4(3H)-quinazolinone, 3-{4-(1-ethyl-4-piperidinyloxy)phenyl}-2-methyl-4(3H)-quinazolinone, 3-{4-(1-butyl-4-piperidinyloxy)phenyl}-2-methyl-4(3H)-quinazolinone, 3-{4-[(1-cyclopentyl-4-piperidinyl)oxy]phenyl}-2-methyl-5-trifluoromethyl-4(3H)-quinazolinone, 3-{4-(1-cyclopentyl-4-piperidinyloxy)phenyl}-2,5-dimethyl-4(3H)-quinazolinone, 7-chloro-3-{4-[(1-cyclopentyl-4-piperidinyl)oxy]phenyl}-2-methyl-4(3H)-quinazolinone, 3-{4-[(1-cyclopentyl-4-piperidinyl)oxy]phenyl}-2,6-dimethyl-4(3H)-quinazolinone, 6-chloro-3-{4-[(1-cyclopentyl-4-piperidinyl)oxy]phenyl}-2-methyl-4(3H)-quinazolinone, 3-{4-[(1-cyclopentyl-4-piperidinyl)oxy]phenyl}-6-methoxy-2-methyl-4(3H)-quinazolinone, 3-{4-[(1-cyclopentyl-4-piperidinyl)oxy]phenyl}-2-methylpyrido[2,3-d]pyrimidin-4(3H)-one, 3-{4-[(1-cyclopentyl-4-piperidinyl)oxy]phenyl}-2-methylpyrido[4,3-d]pyrimidin-4(3H)-one, 6-chloro-3-{4-[(1-cyclopentyl-4-piperidinyl)oxy]phenyl}-2-methylpyrido[3,4-d]pyrimidin-4(3H)-one, 3-{4-[(1-cyclopentyl-4-piperidinyl)oxy]phenyl}-2-methylpyrido[3,4-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutyl-4-piperidinyl)oxy]phenyl}-2-methyl-5-trifluoromethyl-4(3H)-quinazolinone, 5-chloro-3-{4-[(1-cyclobutyl-4-piperidinyl)oxy]phenyl}-2-methyl-4(3H)-quinazolinone, 3-{4-[(1-cyclobutyl-4-piperidinyl)oxy]phenyl}-2-methylpyrido[4,3-d]pyrimidin-4(3H)-one, 3-{4-[(1-cyclobutyl-4-piperidinyl)oxy]phenyl}-2-ethylpyrido[4,3-d]pyrimidin-4(3H)-one, 3-{4-[(1-cyclobutyl-4-piperidinyl)oxy]phenyl}-2-methylpyrido[2,3-d]pyrimidin-4(3H)-one, 3-{4-[(1-cyclobutyl-4-piperidinyl)oxy]phenyl}-2-ethylpyrido[2,3-d]pyrimidin-4(3H)-one, 6-chloro-3-{4-[(1-cyclobutyl-4-piperidinyl)oxy]phenyl}-2-methylpyrido[3,4-d]pyrimidin-4(3H)-one, 6-chloro-3-{4-[(1-cyclobutyl-4-piperidinyl)oxy]phenyl}-2-ethylpyriddo[3,4-d]pyrimidin-4(3H)-one, 3-{4-[(1-cyclobutyl-4-piperidinyl)oxy]phenyl}-2-methylpyrido[3,4-d]pyrimidin-4(3H)-one, 3-{4-[(1-cyclobutyl-4-piperidinyl)oxy]phenyl}-2-ethylpyrido[3,4-d]pyrimidin-4(3H)-one, 2-phenyl-3-{4-[3-(1-piperidinyl)propoxy]phenyl}-4(3H)-quinazolinone, cis-2-methyl-3-(4-{[4-(1-pyrrolidinyl)cyclohexyl]oxy}phenyl)-4(3H)-quinazolinone, trans-2-methyl-3-(4-{[4-(1-pyrrolidinyl)cyclohexyl]oxy}phenyl)-4(3H)-quinazolinone, 3-{4-[(1-cyclopentyl-3-pyrrolidinyl)oxy]phenyl}-2-methyl-4(3H)-quinazolinone, 3-{4-[(1-cyclobutyl-3-pyrrolidinyl)oxy]phenyl}-2-methyl-4(3H)-quinazolinone, 3-{4-[(1-cyclopentyl-4-azepanyl)oxy]phenyl}-2-methyl-4(3H)-quinazolinone, 3-{4-[(1-cyclobutyl-4-azepanyl)oxy]phenyl}-2-methyl-4(3H)-quinazolinone, 3-methyl-2-{4-[3-(1-piperidinyl)propoxy]phenyl}-1(2H)-isoquinoline, 2-{4-[(1-cyclobutyl-4- piperidinyl)oxy]phenyl}-3-methyl-1 (2H)-isoquinoline, or 2-methyl-3-[4-{[3-(1-pyrrolidinyl)cyclopentyl]oxy}phenyl]-4(3H)-quinazolinone.

As the compound (I) relating to the present invention functions as a histamine H3 receptor antagonist or inverse agonist, it is useful as a prophylactic or therapeutic agent for metabolic diseases such as obesity, diabetes mellitus, hormone secretion disorders, hyperlipidemia, gout and fatty liver; circulatory diseases such as angina pectoris, acute or congestive heart failure, myocardial infarction, annular arteriosclerosis, hypertension, kidney disease and electrolyte imbalance; and/or central or peripheral nervous system diseases such as sleep disorders or diseases accompanied by sleep disorders (e.g., idiopathic hypersomnia, repeatability hypersomnia, intrinsic hypersomnia, narcolepsy, periodic limb movement during sleep, sleep apnea syndrome, circadian rhythm hindrance, chronic fatigue syndrome, REM sleep hindrance, sleep loss in the elderly, night shift worker sleep insanitation, idiopathic insomnia, repeatability insomnia, intrinsic insomnia, depression, insecurity and schizophrenia), bulimia, emotional disorders, epilepsy, delirium, dementia, attention deficit/hyperactivity disorder, memory impairment, Alzheimer's disease, Parkinson's disease, cognitive disorder, movement disorder, dysesthesia, dysosmia, morphine resistance, narcotics dependence and alcohol dependence.

Among the compounds having the formula (I) relating to the present invention, the compound represented by formula (I-1):

(I-1)

[where the symbols have the same meaning as the above] may for example be manufactured by the following method.

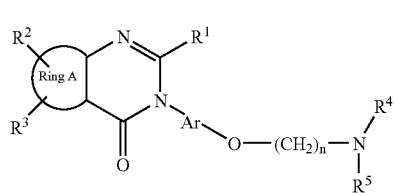

(1)    (2)    Step 1

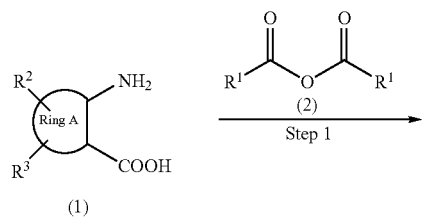

(3)    Step 2

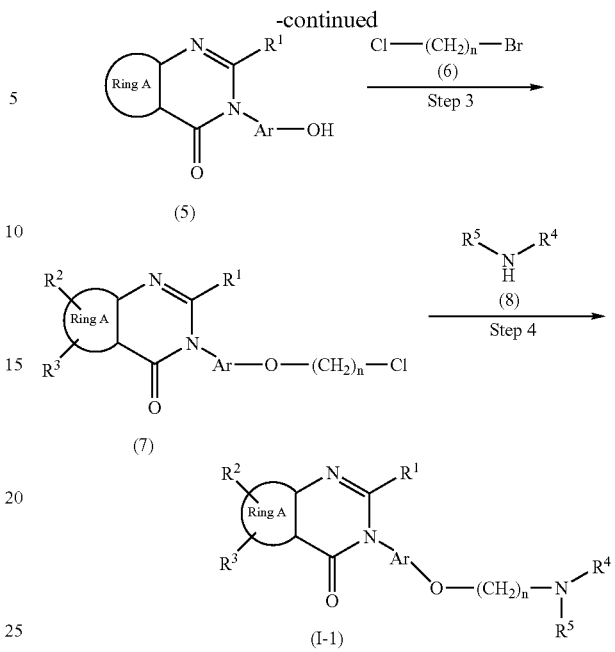

[where the symbols have the same meaning as the above.]

(Step 1)

This step is a method of manufacturing compound (3) by reacting an aminocarboxylic acid derivative (1) with an acid anhydride (2).

The amount of acid anhydride (2) used is usually 1 to 10 Eq, but preferably 2 to 5 Eq, relative to 1 Eq of compound (1).

The reaction temperature is from room temperature to 150° C., but preferably 100 to 130° C.

The reaction time is usually 1 to 24 hours, but preferably 1 to 6 hours.

The reaction solvent is not particularly limited provided it does not interfere with the reaction, for example dimethylformamide, dimethylsulfoxide, 1,4-dioxane or toluene, but among these, dimethylformamide and 1,4-dioxane are preferred.

Alternatively, in this step, compound (3) can be manufactured by reacting the aforesaid aminocarboxylic acid derivative (1) and acid anhydride (2) under the aforesaid reaction conditions, without using a reaction solvent.

Compound (3) thus obtained can then be passed on to the next step by isolation/purification using a means known in the art, e.g., concentration, concentration under reduced pressure, crystallization, solvent extraction, reprecipitation or chromatography, or without isolation and purification.

Compound (3) obtained in this step can be manufactured also by the following method.

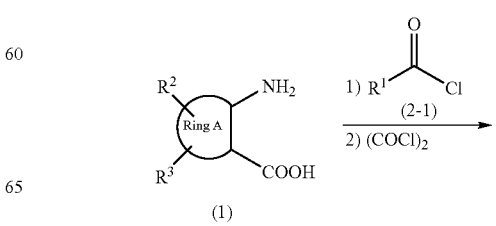

(1)

-continued

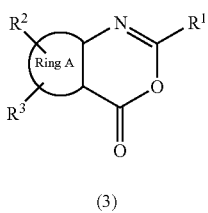

(3)

[where the symbols have the same meaning as the above.]

Step 1) is a method of manufacturing an amido compound represented by formula (1-2) by reacting compound (1) and an acid chloride (2-1) in the presence of a base.

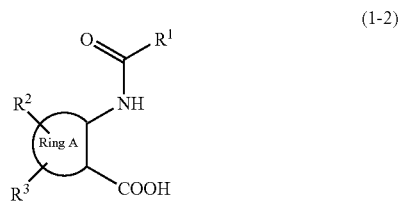

(1-2)

[where the symbols have the same meaning as the above.]

The acid chloride used in this step may for example be phenylacetyl chloride, 1-naphthoyl chloride, 2-naphthoyl chloride, cyclopropane carbonyl chloride, cyclobutane carbonyl chloride, cyclopentane carbonyl chloride or cyclohexane carbonyl chloride.

The amount of compound (2-1) used is usually 1 to 10 Eq, but preferably 1 to 1.5 Eq, relative to 1 Eq of compound (1).

The base used may for example be triethylamine, diisopropylamine, pyridine or the like, but preferably diisopropylamine, ethylamine or pyridine.

The reaction temperature is usually 0 to 100° C., but preferably 0 to 80° C.

The reaction time is usually 1 to 48 hours, but preferably 3 to 12 hours.

The reaction solvent is not particularly limited provided that it does not interfere with the reaction, but an inert solvent is preferred. Examples of this inert solvent are pyridine, methylene chloride, chloroform, tetrahydrofuran, 1,4-dioxane, diethyl ether and toluene, but among these, tetrahydrofuran or pyridine is preferred.

The amide compound (1-2) produced after the reaction is used for the reaction of Step 2) without isolation/purification, after distilling off the reaction solvent to obtain a residue.

Step 2) is a method of manufacturing compound (4) by reacting the residue containing the amide compound (1-2) obtained in the aforesaid Step 1) with oxalyl chloride.

In this step, the reaction may be performed by adding a catalytic amount of dimethylformamide to the reaction system.

The amount of oxalyl chloride used is generally 1 to 10 Eq, but preferably 1 to 3 Eq, relative to 1 Eq of compound (1).

The reaction time is usually 1 to 48 hours, but preferably 1 to 12 hours.

The reaction temperature is usually 0 to 100° C., but preferably 0 to 50° C.

The reaction solvent is not particularly limited provided that it does not interfere with the reaction of Step 2), but an inert solvent is preferred. Examples of this inert solvent are methylene chloride, chloroform, tetrahydrofuran, 1,4-dioxane, dimethylformamide, dimethylsulfoxide and toluene, but among these, methylene chloride, chloroform, tetrahydrofuran and toluene are preferred.

The catalytic amount of dimethylformamide is usually 0.01 to 0.5 Eq, but preferably 0.01 to 0.2 Eq, relative to 1 Eq of compound (1).

Compound (3) thus obtained can then be passed on to the next step by isolation/purification using a means known in the art, e.g., concentration, concentration under reduced pressure, crystallization, solvent extraction, reprecipitation or chromatography, or without isolation/purification.

(Step 2)

This step is a method of manufacturing compound (5) by reacting compound (3) and compound (4) which were obtained by the aforesaid Step 1.

The amount of compound (4) used is usually 0.5 to 10 Eq, but preferably 1 to 3 Eq, relative to 1 Eq of compound (4).

The reaction temperature is usually 60° C. to 160° C., but preferably 80° C. to 130° C.

The reaction time is usually 2 to 48 hours, but preferably 5 to 10 hours.

The reaction solvent used is not particularly limited provided that it does not interfere with the reaction, but an inert solvent such as toluene, 1,4-dioxane, dimethylformamide and dimethylsulfoxide is preferred.

Specific examples of compound (4) used in this step are 4-aminophenol, 5-amino-2-naphthol, 6-amino-2-naphthol, 2-amino-5-hydroxypyrimidine, 2-amino-5-hydroxypyridine, 3-amino-6-hydroxypyridine, 5-amino-3-hydroxy-1H-1,2,4-triazole, 2-amino-4-hydroxythiazole, 3-amino-6-hydroxypyridazine, 2-amino-4-hydroxyoxazole, 2-amino-5-hydroxypyrazine, 5-amino-3-hydroxyisothiazole, 2-amino-5-hydroxy-1,3,4-thiadiazole, 3-amino-5-hydroxy-1,2,4-thiadiazole, 5-amino-3-hydroxy-1,3,4-thiadiazole, 5-amino-3-hydroxyisoxazole, 2-amino-6-hydroxyquinoline, 2-amino-5-hydroxy-1H-benzimidazol-5-amino-2-hydroxy-1H-benzimidazole, 2-amino-5-hydroxythiazole[5,4-b]pyridine, 2-amino-5-hydroxybenzothiazole, 2-amino-5-hydroxybenzoxazole and 3-amino-6-hydroxybenzoxazole.

Compound (5) thus obtained can then be passed on to the next step by isolation/purification using means known in the art, e.g., concentration, concentration under reduced pressure, crystallization, solvent extraction, reprecipitation or chromatography, or without isolation/purification.

(Step 3)

This step is a method of manufacturing compound (7) by reacting compound (5) obtained in the aforesaid Step 2 with the halogenated compound (6).

The base used may for example be sodium hydrogen carbonate, potassium carbonate or sodium hydride, but preferably, potassium carbonate and sodium carbonate.

The amount of base used is usually 1 to 10 Eq, but preferably 1.5 to 5 Eq, relative to 1 Eq of compound (5).

The reaction time is usually 1 to 48 hours, but preferably 5 to 12 hours.

The reaction temperature is usually 0 to 150° C., but preferably 50° C. to 100° C.

The halogenated compound may for example be 1,3-bromochloropropane or 1,4-bromochlorobutane.

Compound (7) thus obtained can then be passed on to the next step by isolation/purification using a means known in the art, e.g., concentration, concentration under reduced pressure, solvent extraction, crystallization, reprecipitation or chromatography, or without isolation/purification.

(Step 4)

This step is a method of manufacturing compound (I-1) according to the present invention by reacting compound (7) obtained in the aforesaid Step 3 with the amino compound (8) in the presence of a base.

The base used in this step may for example be sodium hydrogen carbonate, sodium carbonate, potassium carbonate or sodium hydride, but among these, sodium carbonate and potassium carbonate are preferred.

The amount of base used is usually 1 to 10 Eq, but preferably 1 to 5 Eq.

The amount of compound (7) used is usually 1 to 10 Eq, but preferably 2 to 5 Eq, relative to 1 Eq of compound (5).

In this step, to increase the reactivity of compound (7), potassium iodide, tetra-n-butylammonium iodide and the like are preferably co-present in the reaction system. The amount of potassium iodide used is usually 0.1 to 10 Eq, but preferably 0.1 to 3 Eq.

The reaction temperature is usually 0 to 150° C., but preferably 50° C. to 100° C.

The reaction time is usually 1 to 48 hours, but preferably 1 to 12 hours.

The reaction solvent is not particularly limited provided that it does not interfere with the reaction, but an inert solvent such as dimethylformamide, tetrahydrofuran, 1,4-dioxane, acetone or methyl ethyl ketone is preferred.

Compound (I-1) according to the present invention thus obtained can then be isolated/purified using a means known in the art, e.g., concentration, concentration under reduced pressure, solvent extraction, crystallization, reprecipitation or chromatography.

Compound (I-1) relating to the present invention can be manufactured also by the following method:

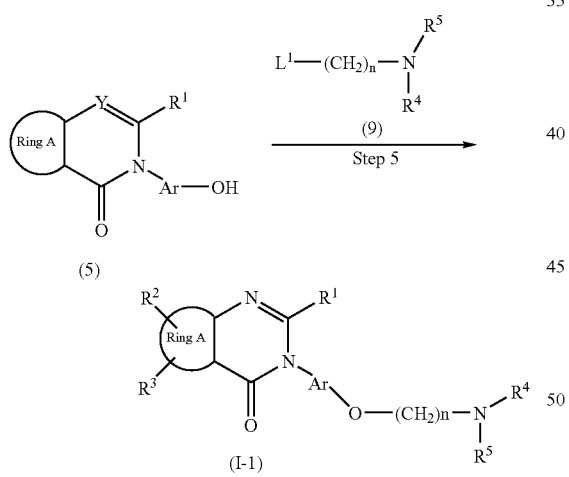

[where $L^1$ is a leaving group, and the remaining symbols have the same meaning as the above].

(Step 5)

This step is a method of manufacturing compound (I-1) by reacting compound (5) obtained by the aforesaid Step 2 with the amino compound (9).

The amino compound (9) used has a leaving group in the molecule. The leaving group is not particularly limited provided that it detaches to produce compound (I-1) in the reaction with compound (5). Examples are halogen atoms such as chlorine and bromine, tosyl and mesyl, but among these, bromine and tosyl are preferred.

The amount of the amino compound used is usually 1 to 10 Eq, but preferably 1 to 3 Eq, relative to 1 Eq of compound (5).

The base used in this step may for example be sodium hydrogen carbonate, sodium carbonate, potassium carbonate or sodium hydride, but among these, potassium carbonate and sodium carbonate are preferred.

The reaction temperature is usually 0 to 150° C., but preferably 25° C. to 100° C.

The reaction time is usually 1 to 72 hours, but preferably 3 to 12 hours.

The reaction solvent is not particularly limited provided that it does not interfere with the reaction, but an inert solvent such as dimethylformamide, tetrahydrofuran, 1,4-dioxane, acetone or methyl ethyl ketone is preferred.

Compound (I-1) according to the present invention thus obtained can then be isolated/purified using a means known in the art, e.g., concentration, concentration under reduced pressure, solvent extraction, crystallization, reprecipitation or chromatography.

The compound relating to the present invention can be manufactured also by the following method using compound (3) obtained in Step 1.

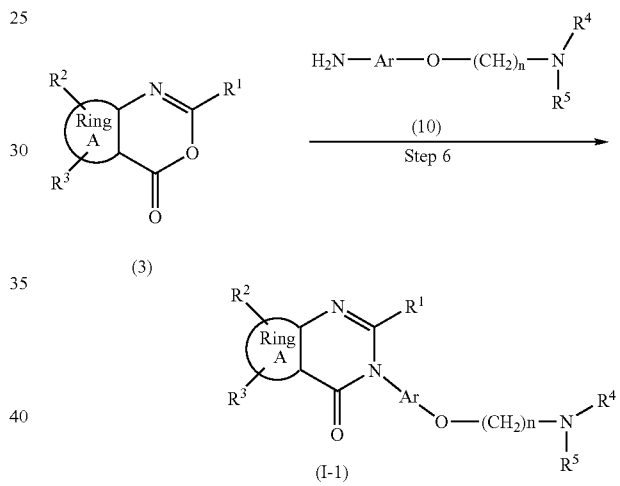

[where the symbols have the same meaning as the above.]

(Step 6)

This step is a method of manufacturing compound (I-1) relating to the present invention by reacting compound (3) obtained by the aforesaid Step 1 with the amino compound (10).

In this step, the amount of compound (10) used is 1 to 10 Eq, but preferably 1 to 5 Eq, relative to 1 Eq of compound (3).

The reaction temperature is usually −20° C. to 180° C., but preferably 0° C. to 130° C.

The reaction time is usually 1 to 72 hours, but preferably 3 to 12 hours.

The reaction solvent is not particularly limited provided that it does not interfere with the reaction, e.g., an inert solvent such as dimethylformamide, dimethylsulfoxide, acetic acid, 1,4-dioxane or toluene, but among these, dimethylformamide or acetic acid is preferred.

Compound (I-1) of the present invention which is thus obtained can then be passed on to the next step by isolation/purification using a means known in the art, e.g., concentration, concentration under reduced pressure, solvent extraction, crystallization, reprecipitation or chromatography.

Compound (10) is not limited to the free amine, but an acid addition salt may also be used. This acid addition salt may for example be the hydrochloride, tosylate or trifluoroacetate.

Among the compounds (10), the compound represented by formula (10-1):

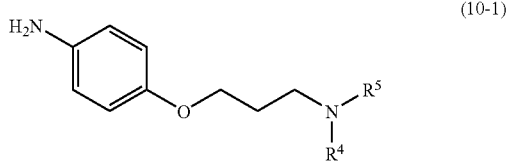

[where the symbols have the same meaning as the above] can be manufactured by the following method.

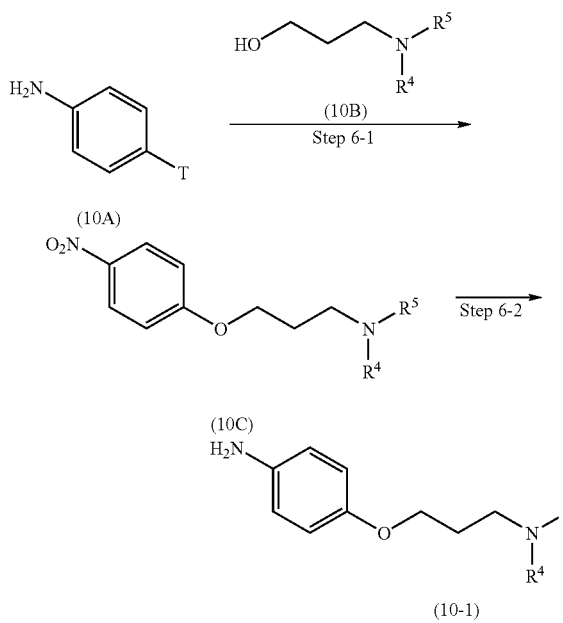

[where T is a hydroxy group or fluorine atom, and the other the symbols have the same meaning as the above.]

(Step 6-1)

This step is a method of reacting compound (10A) with compound (10B) to manufacture compound (10C).

In formula (10A), when T is a hydroxy group (this compound will be referred to as (10A-1)), the compound (10C) can be manufactured by using compound (10A-1) and compound (10B) in a Mitsunobu reaction. The Mitsunobu reaction can be performed by the method described in the literature (e.g., "The Use of Diethylazodicarboxylate and Triphenylphosphine in Synthesis and Transformation of Natural Products", Synthesis, Vol. 1, 1981, p. 1-28, by O. Mitsunobu et al.) in the presence of phosphine and an azo compound, a method based thereon, or a combination of these methods with conventional methods.

The amount of the compound (10B) used is usually 0.5 to 10 Eq, but preferably 1 to 3 Eq, relative to 1 Eq of compound (10A-1).

The phosphine compound used in this step is usually, for example, triphenylphosphine, triethylphosphine or the like.

The amount of the phosphine compound used is usually 0.5 to 10 Eq, but preferably 1 to 3 Eq, relative to 1 Eq of compound (10B).

The azo compound used may for example be diethylazodicarboxylate or diisopropyl azodicarboxylate.

The amount of the azo compound used is usually 0.5 to 10 Eq, but preferably 1 to 3 Eq, relative to 1 Eq of compound (10B).

The reaction time in this step is usually 1 to 48 hours, but preferably 4 to 12 hours.

The reaction temperature in this step is usually from room temperature to the boiling point of the reaction solvent, but preferably 15° C. to 30° C.

The reaction solvent used in this step is not particularly limited provided that it does not interfere with the reaction, but specific examples are tetrahydrofuran and toluene.

In formula (10A), when T is a fluorine atom (this compound will be referred to as (10A-2)), compound (10C) can be manufactured by reacting compound (10A-2) with compound (10B) in the presence of a base. The base used in this step may for example be sodium hydroxide.

The amount of base used is usually 1 to 10 Eq, but preferably 1 to 5 Eq, relative to 1 Eq of compound (10B).

The amount of compound (10B) used is usually 1 to 10 Eq, but preferably 2 to 5 Eq, relative to 1 Eq of compound (10A-2).

In this step, to increase the reactivity of compound (10A-2), potassium iodide and tetra-n-butylammonium iodide are preferably co-present in the reaction system.

The amount of potassium iodide used is usually 0.1-10 Eq, but preferably 0.1 to 3 Eq. The reaction temperature is usually from 0° C. to 150° C., but preferably 50° C. to 100° C.

The reaction time is usually 1 to 48 hours, but preferably 1 to 12 hours.

The reaction solvent used in this step is not particularly limited provided that it does not interfere with the reaction, but specific examples are inert solvents such as dimethyl formamide, tetrahydrofuran, 1,4-dioxane, acetone and methylethyl ketone.

The compound (10C) thus obtained in this step can then be isolated/purified using a means known in the art, e.g., concentration, concentration under reduced pressure, solvent extraction, crystallization, reprecipitation or chromatography.

The compound (10B) used in this step may for example have the formula given below.

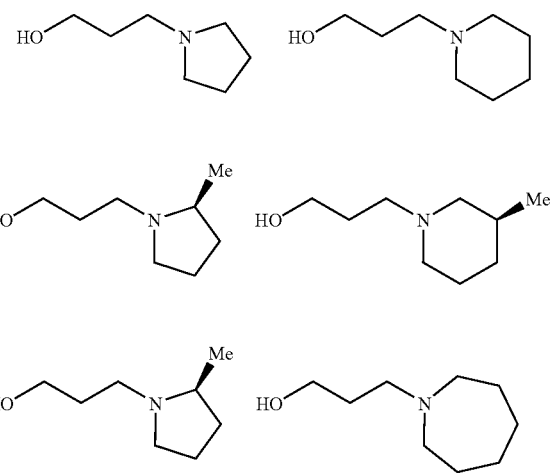

(Step 6-2)

This step is a method of manufacturing compound (10-1) by catalytic reduction of compound (10C) obtained in the above-mentioned step 6-1, using palladium charcoal as catalyst.

The amount of palladium charcoal used is usually 0.01 to 1 Eq, but preferably 0.05 to 0.5 Eq, relative to 1 Eq of compound (10C).

The reaction temperature is usually from 0° C. to 80° C.

The reaction time is usually 1 to 48 hours, but preferably 1 to 12 hours.

The compound (10-1) thus obtained in this step can then be isolated/purified using a means known in the art, e.g., concentration, concentration under reduced pressure, solvent extraction, crystallization, reprecipitation or chromatography, or passed to the next step without isolation/purification.

Among the compounds (10), the compound represented by the formula (10-2):

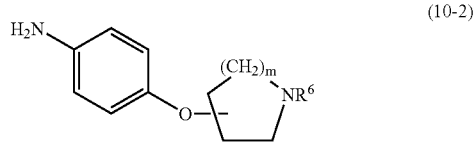

[where the symbols have the same meaning as the above] can be manufactured by the following method.

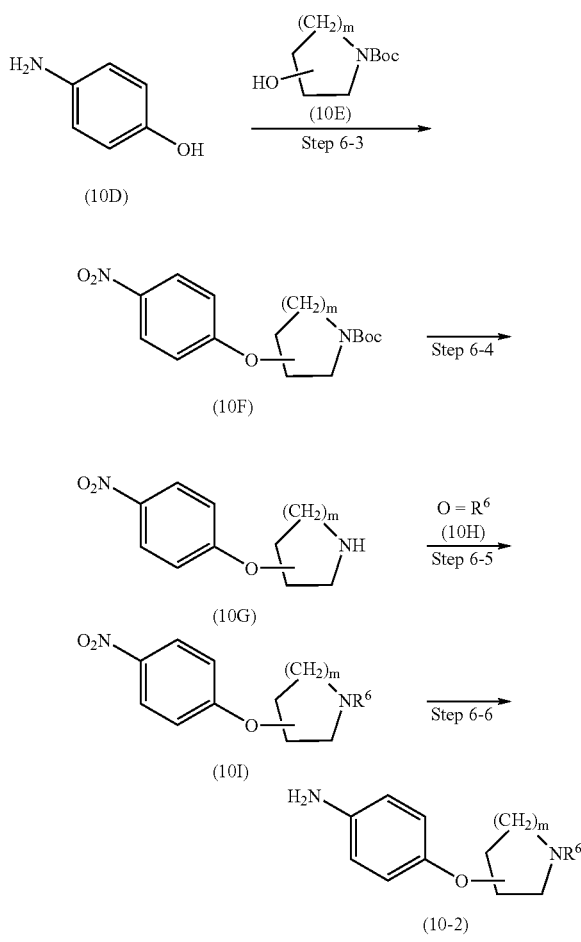

(Step 6-3)

In this step, compound (10F) can be manufactured by reacting 4-aminophenol (10D) with compound (10E). The reaction used in this step is the aforesaid Mitsunobu reaction.

The amount of the alcohol compound (10E) used is usually 0.5 to 10 Eq, but preferably 1 to 3 Eq, relative to 1 Eq of compound (10D).

The protective group for the amino group in compound (10E) is not limited to Boc, and may be any protective group for amino groups described in the aforesaid "Protective Groups in Organic Synthesis", by T. W. Green, Vol. 2, John Wiley & Sons, 1991, which acts as a protective group for the amino group in Step 6-3 and can be removed in Step 6-4.

The phosphine compound used in this step is usually, for example, triphenylphosphine or triethylphosphine.

The amount of the phosphine compound used is usually 0.5 to 10 Eq, but preferably 1 to 3 Eq, relative to 1 Eq of compound (10E).

The azo compound used may for example be diethylazodicarboxylate or diisopropyl azodicarboxylate. The amount of the azo compound used is usually 0.5 to 10 Eq, but preferably 1 to 3 Eq, relative to 1 Eq of compound (10E).

The compound (10E) used in this step may for example be 1-Boc-4-piperidinol.

The reaction time is usually 1 to 48 hours, but preferably 4 to 24 hours.

The reaction temperature in this step is usually from room temperature to the boiling point of the reaction solvent, but is preferably 15° C. to 30° C.

The reaction solvent used in this step is not particularly limited provided that it does not interfere with the reaction, but specific examples are tetrahydrofuran and toluene.

The compound (10F) thus obtained can then be isolated/purified using a means known in the art, e.g., concentration, concentration under reduced pressure, crystallization, solvent extraction, reprecipitation or chromatography, or passed to the next step without isolation/purification.

(Step 6-4)

This step is a method of manufacturing compound (10G) by removing the protective group of the amino group in compound (10F) obtained in the aforesaid Step 6-3.

The protective group can be removed by the method described in the literature (e.g., "Protective Groups in Organic Synthesis", by T. W. Green, Vol. 2, John Wiley & Sons, 1991), a method based thereon, or a combination of these methods with conventional methods. When the protective group of the amino group is a Boc group, the Boc group can be removed by for example using trifluoroacetic acid.

The compound (10G) thus obtained can then be isolated/purified using a means known in the art, e.g., concentration, concentration under reduced pressure, crystallization, solvent extraction, reprecipitation or chromatography, or passed to the next step without isolation/purification.

(Step 6-5)

This step is a method of manufacturing compound (10I) by reacting compound (10G) obtained in the Step 6-4 with compound (10H). The reaction of this step is a so-called reductive amination.

The amount of compound (10H) used in this step is usually 1 to 10 Eq, but preferably 2 to 4 Eq, relative to 1 Eq of compound (10G).

Compound (10H) used in this step may for example be cyclobutanone or cyclopentanone.

The reducing agent used may be an organometallic reagent such as sodium borohydride, sodium cyanoborohydride or sodium triacetoxyborohydride.

The amount of this reducing agent is usually 1 to 5 Eq, but preferably 1 to 3 Eq, relative to 1 Eq of the compound (10G).

A catalytic amount of ZnCl$_2$ may also be included in the reaction system.

The reaction is usually performed in an inert solvent, such as for example methanol, ethanol, benzene, toluene, xylene, methylene chloride, chloroform, dimethoxyethane, tetrahydrofuran, dioxane, dimethylformamide, or a mixture thereof.

The reaction temperature is usually from room temperature to the boiling point of the solvent used for the reaction, but preferably 20° C. to 100° C.

The reaction time is usually 30 minutes to 7 days, but preferably 3 hours to 2 days.

The compound (10I) thus obtained in this step can then be isolated/purified using a means known in the art, e.g., concentration, concentration under reduced pressure, solvent extraction, crystallization, reprecipitation or chromatography, or passed to the next step without isolation/purification.

In the reaction of this step, when R$^6$ is a cyclopropyl group, compound (10I) can be manufactured by using (1-methoxycyclopropoxy)-trimethylsilane instead of compound (10H).

(Step 6-6)

This step is a method of manufacturing compound (10-2) by catalytic reduction of compound (10I), using palladium charcoal as catalyst.

The amount of palladium charcoal used is usually 0.01 to 1 Eq, but preferably 0.05 to 0.5 Eq, relative to 1 Eq of compound (10I).

The reaction temperature is usually 0 to 80° C.

The reaction time is usually 1 to 48 hours, but preferably 1 to 12 hours.

Compound (10-2) thus obtained can then be isolated/purified using a means known in the art, e.g., concentration, concentration under reduced pressure, solvent extraction, crystallization, reprecipitation or chromatography, or passed to the next step without isolation/purification.

Other examples of compound (10) are compounds or their acid addition salts represented by the following formulae.

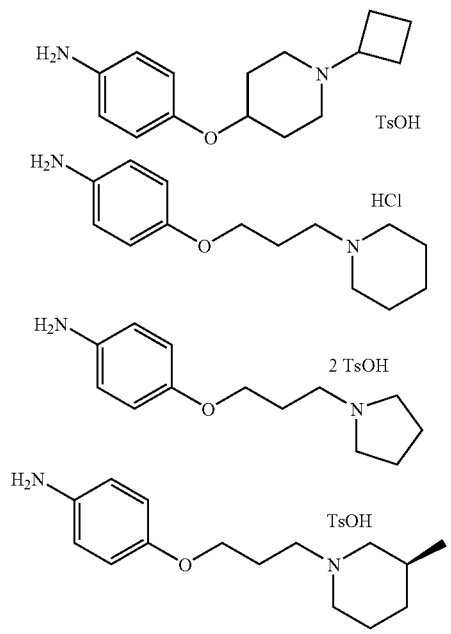

-continued

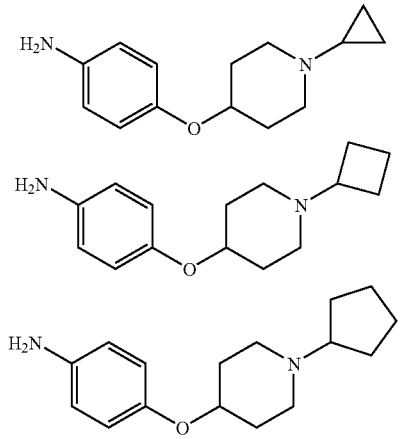

When it has a substituent group on Ring A, the compound relating to the present invention included in formula (I) can be manufactured using a starting material which already has the corresponding substituent. When introduction or deprotection of a protective group in the substituent group is required, a method described in the literature, e.g., "Protective Groups in Organic Synthesis", T. W. Green, 2nd Edition, John Wiley & Sons, Ltd., 1991, a method based thereon or a combination of these methods with a conventional method, may be used.

The compound relating to the present invention can be manufactured also by changing the functional group on Ring A, and introducing/removing a protective group if required. A protective group in the substituent group may be introduced or removed by the method described in "Protective Groups in Organic Synthesis", T. W. Green, 2nd Edition, John Wiley & Sons, Ltd., 1991, a method based thereon or a combination of these methods with a conventional method. The functional group can be changed by a method described in the literature, e.g., "Comprehensive Organic Synthesis", Vol. 6, Pergamon Press, 1991, or "Comprehensive Organic Transformations", Richard L et al, VCH Publishers, 1988, a method based thereon or a combination of these methods with a conventional method.

When Ring A is a benzene ring, Ar is phenyl, i.e. a divalent group formed by eliminating two hydrogen atoms from benzene, and Ring A has a nitro group, the substituent on Ring A can be further modified by the following methods, for example.

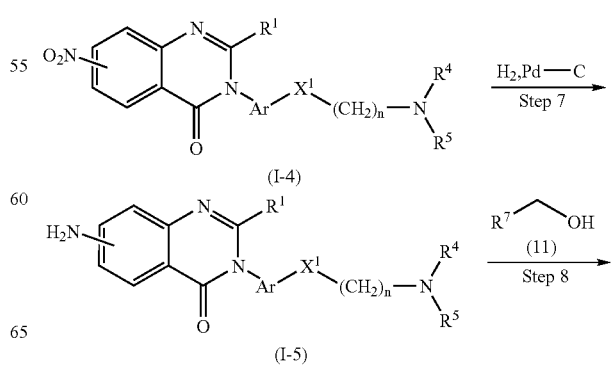

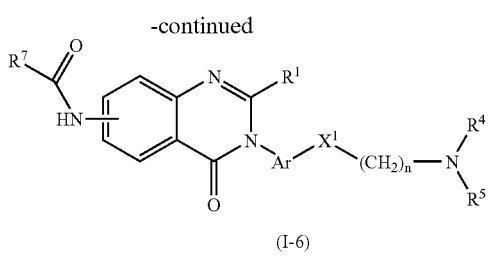

(I-6)

[where R⁷ has the same meaning as R¹, and the other symbols have the same meaning as the above.]

(Step 7)

In this step, compound (I-4) relating to the present invention which has a nitro group as substituent, is catalytically reduced using palladium charcoal as a catalyst so that the nitro group is converted to amino.

The amount of palladium charcoal used in this step is usually 0.01 to 1 Eq, but preferably 0.05 to 0.5 Eq, relative to 1 Eq of compound (I-4).

The reaction temperature is usually 0 to 80° C.

The reaction time is usually 1 Hour to 48 hours, or preferably 1 to 12 hours.

Compound (I-5) thus obtained can then be passed on to the next step by isolation/purification using a means known in the art, e.g., concentration, concentration under reduced pressure, solvent extraction, crystallization, reprecipitation or chromatography, or without isolation/purification.

(Step 8)

This step is a method of manufacturing compound (I-6) by reacting compound (I-5) obtained in Step 7 with a carboxylic acid compound (11).

This reaction is an amide bonding reaction, and may be the usual amide forming reaction described in the literature, e.g., "Theory and Experiment in Peptide Synthesis", Nobuo Izumiya; Maruzen, 1983, or "Comprehensive Organic Synthesis", Vol. 6, Pergamon Press, 1991, a method based thereon, or a combination of these with a conventional method. Specifically, this can be carried out by those skilled in the art using a known condensation agent, or alternatively, it may be achieved by an ester activation method, mixed acid anhydride method, acid chloride method or carbodiimide method familiar to those skilled in the art.

Examples of this amide-forming agent are thionyl chloride, oxazalyl chloride, N,N-dicyclohexylcarbodiimide, 1-methyl 2-bromopyridinium iodide, N,N'-carbonyl diimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl) carbodiimide hydrochloride, ethyl chloroformate, isobutyl chlorformate and benzotriazo-1-yl-oxy-tris(dimethylamino)phosphonium hexafluorophosphate, but among these, thionyl chloride, 1-ethyl-3-(3-dimethylaminopropyl) carbodiimide hydrochloride, N,N-dicyclohexylcarbodiimide and benzotriazo-1-yl-oxy-tris(dimethylamino)phosphonium hexafluorophosphate are preferred.

In the amide-forming reaction, a base and a condensation agent may be used together with the aforesaid amide-forming agent.

The base used may be a tertiary aliphatic amine such as trimethylamine, triethylamine, N,N-diisopropylethylamine, N-methyl morpholine, N-methyl pyrrolidine, N-methylpiperidine, N,N-dimethylaniline, 1,8-diazabicyclo[5.4.0]undeca-7-ene (DBU) and 1,5-azabicyclo[4.3.0]nona-5-ene (DBN), or an aromatic amine, e.g., pyridine, 4-dimethylaminopyridine, picoline, lutidine, quinoline or isoquinoline, but among these, tertiary aliphatic amines are preferred, and triethylamine or N,N-diisopropylethylamine is particularly preferred.

The condensation agent used may for example be N-hydroxybenzotriazole hydrate, N-hydroxysuccinimide, N-hydroxy-5-norbornene-2,3-dicarboxyimide or 3-hydroxy-3,4-dihydro-4-oxo-1,2,3-benzotriazol, but among these, N-hydroxybenzotriazole is particularly preferred.

The amount of compound (I-5) used varies with the type of compound and solvent used, and other reaction conditions, but it is usually 0.1 to 10 Eq and preferably 0.5 to 3 Eq relative to 1 Eq of the carboxylic acid derivative (11) or its reactive derivative.

The amount of the amide-forming agent used varies with the type of compound and solvent used, and other reaction conditions, but it is usually 1 to 10 Eq and preferably 1 to 3 Eq relative to 1 Eq of the carboxylic acid derivative (11) or its reactive derivative.

The amount of the condensation agent used varies with the type of compound and solvent used, and other reaction conditions, but it is usually 1 to 10 Eq and preferably 1 to 3 Eq relative to 1 Eq of the carboxylic acid derivative (11) or its reactive derivative.

The amount of base used varies with the type of compound and solvent used, and other reaction conditions, but it is usually 1 to 10 Eq and preferably 1 to 5 Eq.

The reaction solvent in this step may for example be an inert solvent, and is not particularly limited provided that it does not interfere with the reaction, specific examples being methylene chloride, chloroform, 1,2-dichloroethane, N,N-dimethylformamide, ethyl acetate ester, acetic acid methyl ester, acetonitrile, benzene, xylene, toluene, 1,4-dioxane, tetrahydrofuran, dimethoxyethane or mixed solvents thereof, but from the viewpoint of suitable reaction temperature maintenance, methylene chloride, chloroform, 1,2-dichloroethane, acetonitrile or N,N-dimethylformamide are for example preferred.

The reaction temperature in this step is usually from −78° C. to the boiling point of the solvent, but it is preferably 0 to 30° C.

The reaction time in this step is usually 0.5 to 96 hours, but preferably 3 to 24 hours.

The base, amide-forming agent and condensation agent used in this step can be combined together.

Compound (I-6) according to the present invention thus obtained can then be isolated/purified using a means known in the art, e.g., concentration, concentration under reduced pressure, solvent extraction, crystallization, reprecipitation or chromatography.

When the substituent group on Ring A is an aryl group or a heteroaryl group, it can be manufactured by the following method using compound (I-7) of the present invention having a halogen atom on Ring A.

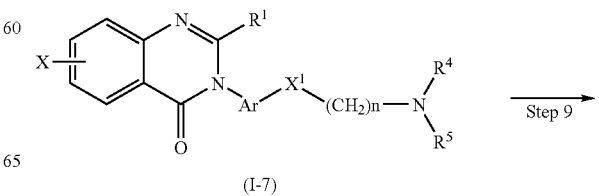

(I-7)

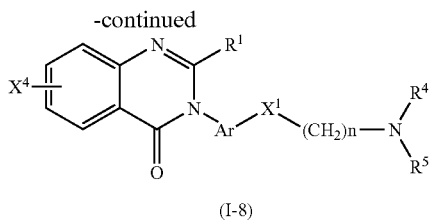

(I-8)

[where X is a halogen atom, $X^4$ is an aryl or a heteroaryl group, and the other symbols have the same meaning as the above.]

(Step 9)

This step is a method of manufacturing compound (I-8) of the present invention having an aryl or a heteroaryl substituent group on Ring A by preparing another derivative of compound (I-7) relating to the present invention which has a halogen atom such as chlorine, bromine or iodine on Ring A.

To convert compound (I-7) to compound (I-8), a Suzuki coupling can be performed.

More specifically, compound (I-8) according to the present invention having an aryl or a heteroaryl substituent group on Ring A can be manufactured by reacting compound (I-7) having a halogen atom on Ring A with $X^4$—$B(OH)_2$ in the presence of a base, a palladium catalyst and, if required, a phosphine ligand.

This step may be performed by the method described in "Angew. Chem., Int. Ed. Eng.", 1999, 38(16), pp. 2413-2416, by J. P. Wolfe, S. L. Buchwald et al., by a method based thereon, or by a combination of these with a conventional method.

The base used may for example be sodium carbonate, potassium carbonate, cesium carbonate, cesium fluoride, potassium fluoride or sodium fluoride.

The amount of base used is usually 1 to 10 Eq, but preferably 1 to 3 Eq, relative to 1 Eq of compound (I-7).

The palladium catalyst used may for example be $Pd(PPh_3)_4$, $Pd(OAc)_3$, $Pd_3(dba)_3$ or $PdCl_3(PPh_3)_3$.

The amount of palladium catalyst used is usually 0.01 to 0.5 Eq, but preferably 0.05 to 0.2 Eq, relative to 1 Eq of compound (I-7).

The phosphine ligand used may for example be $PPh_3$, $P(o\text{-tol})_3$, $P(tBu)_3$, 2-[di(t-butyl)phosphino]-1,1'-biphenyl, 2-[di(t-butyl)phosphino]-2'-dimethylamino-1,1'-biphenyl, 2-[dicyclohexylphosphino]-1,1'-biphenyl, or 2-[dicyclohexylphosphino]-2'-dimethylamino-1,1'-biphenyl.

The borane compound used may be a commercial aryl boron derivative or heteroaryl boron derivative such as phenyl boric acid, a phenylboric acid ester or dialkylphenyl borane, or the target boron derivative can be manufactured by a known method, a method based thereon or a combination of these with a conventional method.

The amount of boron compound used is usually 1 to 10 Eq, but preferably 2 to 5 Eq.

The amount of the boric acid compound $X^4$—$B(OH)_2$ ($X^4$ is the same as the above) is usually 1 to 10 Eq, but preferably 2 to 5 Eq.

Compound (I-9) relating to the present invention can be manufactured by the following method.

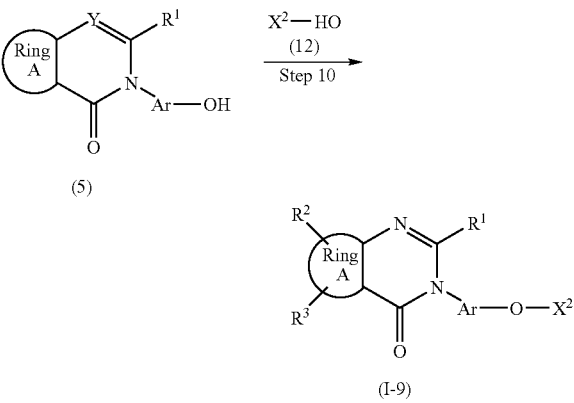

[where the symbols have the same meaning as the above.]

The reaction in this step is known as the Mitsunobu reaction, and is a method described in the literature, e.g., Mitsunobu. O, "Use of diethylazodicarboxylate and triphenylphosphine in synthesis and transformation of natural products", Synthesis, Vol. 1, 1981, p. 1-28, a method based thereon, or a combination of these with a conventional method, in the presence of a phoshine compound and an azo compound.

The amount of the alcohol compound (12) $X^2OH$ used in this step is usually 0.5 to 10 Eq, but preferably 1 to 3 Eq, relative to 1 Eq of compound (5).

The phosphine compound used in this step is usually for example triphenylphosphine or triethylphosphine.

The amount of phosphine compound used is usually 0.5 to 10 Eq, but preferably 1 to 3 Eq, relative to 1 Eq of (5).

The azo compound used may for example be diethylazodicarboxylate or diisopropyl azodicarboxylate.

The amount of azo compound used is usually 0.5 to 10 Eq, but preferably 1 to 3 Eq, relative to 1 Eq of compound (5).

The reaction time in this step is usually 1 to 48 hours, but preferably 4 to 12 hours.

The reaction temperature in this step is usually from room temperature to the boiling point of the reaction solvent, but preferably 15° C. to 30° C.

The reaction solvent in this step is not particularly limited if it does not interfere with the reaction, but specific examples are tetrahydrofuran or toluene.

Compound (I-9) thus obtained can then be isolated/purified using a means known in the art, e.g., concentration, concentration under reduced pressure, solvent extraction, crystallization, reprecipitation or chromatography.

The compound relating to the present invention represented by formula (I) can easily be isolated/purified by the usual isolation/purification means. This means may for example be solvent extraction, recrystallization, reprecipitation, column chromatography or fractionation thin layer chromatography.

These compounds can be made into salts or esters which are pharmaceutically acceptable by conventional methods, or conversely, the free compounds may be prepared from salts or esters by conventional methods.

The fused ring 4-oxopyrimidine derivative of the present invention can exist as a pharmaceutically acceptable salt, and this salt can be manufactured according to conventional methods using the compound represented by the aforesaid formula (I). Examples of this acid addition salt are halide acid salts such as the hydrochloride, hydrofluoride, hydrobromide and hydroiodide; inorganic acid salts such as the nitrate, perchlorate, sulfate, phosphate and carbonate; lower alkylsulfonic acid salts such as the methane sulfonic acid salt, trifluoromethane sulfonic acid salt and ethane sulfonic acid salt; arylsulfonates, such as the benzenesulfonic acid salt and p-toluenesulfonic acid salt; salts of organic acids, such as the fumarate, succinate, citrate, tartrate, oxalate and maleate; and salts of aminoacids such as the glutamate and aspartate.

Examples of a base addition salt are salts of alkali metals such as sodium and potassium, salts of alkaline earth metals such as calcium, and magnesium, and salts of organic bases such as ammonium, guanidine, triethylamine and dicyclohexylamine. The compound of the present invention may further exist as a free compound, a hydrate of a salt, or a solvate.

The compound represented by formula (I) may be administered orally or non-orally may be used.

When the compound of the present invention is used clinically, it may also be combined with other pharmaceutically acceptable additives in various pharmaceutical preparations depending on the mode of administration. These additives may be those usually used as additives in pharmaceutical preparations, such as gelatin, lactose, white soft sugar, titanium oxide, starch, crystalline cellulose, hydroxypropyl methylcellulose, carboxymethylcellulose, amylum maydis, microcrystalline wax, white vaseline, magnesium aluminometasilicate, anhydrous calcium phosphate, citric acid, sodium tricitrate, hydroxypropylcellulose, sorbitol, sorbitan fatty acid ester, polysorbate, sucrose fatty acid ester, polyoxyethylene, hydrogenated castor oil, polyvinyl pyrrolidone, magnesium stearate, light anhydrous silicic acid, talc, vegetable oil, benzyl alcohol, gum arabic, propylene glycol, polyalkylene glycol, cyclodextrin or hydroxypropyl cyclodextrin.

The form of administration of this pharmaceutical preparation as a mixture with these additives may be a solid preparation, such as tablets, capsules, granules, powders or suppositories, or a liquid preparation such as syrups, elixirs or injections, and these can be prepared according to the methods usually used for pharmaceutical preparations. In the case of a liquid preparation, it may be dissolved or suspended in water or other suitable media. In particular, in the case of an injection, it may be dissolved or suspended in physiological saline or grape sugar, and buffers and preservatives may be added if required. These pharmaceutical preparations may contain 1.0 to 100 wt %, but preferably 1.0 to 60 wt %, of the compound of the present invention relative to the total preparation.

Pharmaceutical preparations containing the compound of the present invention can be made, for example, according to the following pharmaceutical examples.

Pharmaceutical Example 1

10 parts of the compound of Example 1, 15 parts of heavy magnesium oxide and 75 parts of lactose are mixed uniformly to manufacture a powder or particulate of 350 µm or less. This powder is inserted into a capsule container to manufacture a capsule.

Pharmaceutical Example 2

45 parts of the compound of Example 1, 15 parts of starch, 16 parts of lactose, 21 parts of crystalline celluloses, 3 parts of polyvinyl alcohol and 30 parts of distilled water is mixed uniformly, crushed, dried and graded to obtain granules of diameter 1410 to 177 µm.

Pharmaceutical Example 3

After producing granules by the same method as that of Pharmaceutical Example 2, 3 parts of calcium stearate is added to 96 parts of these granules and compressed into tablets of 10 mm diameter.

PharmaceuticaL Example 4

10 parts of crystalline cellulose and 3 parts of calcium stearate are added to 90 parts of the granules obtained in Pharmaceutical Example 2, compressed into tablets of diameter 8 mm and sirup gelatin/precipitated calcium carbonate mixed suspension is added to produced sugar-coated tablets.

These pharmaceutical preparations may also contain other therapeutically useful compounds.

The compound of the present invention may be used in conjunction with other agents useful for the treatment of metabolic disorders and/or eating disorders. These ingredients in these combinations may be administered at different times or simultaneously during the treatment, or may be administered as different medications or as a single pharmaceutical preparation. The present invention should therefore be understood to include simultaneous administration or administration at different times, and "administration" in the context of the present invention should be interpreted as such. The range of combinations between the compound of the present invention and other agents useful in metabolic disorders and/or eating disorders, in principle covers combinations with all pharmaceutical preparations useful in the treatment of metabolic disorders and/or eating disorders.

The compound of the present invention can be used in combination with other drugs effective in the treatment, prevention, or control of disorders, such as hypertension, hypertension associated with obesity, hypertension-related disorders, cardiac hypertrophy, left ventricular hypertrophy, and metabolic syndrome, obesity and obesity-related disorders. In the prophylaxis or therapy of these disorders, such other drugs (concomitant drugs) can be administered simultaneously, separately or successively. When used simultaneously with one, two or more other drugs, it can be administered as a single dose. However, in combination therapy, the composition containing the compound of the present invention and concomitant drugs may be administered simultaneously, separately or successively as different packages. These may also be administered with a time lag.

The dosage amount of concomitant drugs may be based on the dosage used in clinical practice, and may be selected as appropriate, depending on the patient, the route of administration, the disease or the combination. The administration modality of the concomitant drug is not particularly limited, it being sufficient that the compound of the present invention and the concomitant drug are combined in some way. Examples of the administration modality are: 1) administration of a single pharmaceutical preparation obtained by simultaneously blending the compound of the present invention with another drug; 2) simultaneous administration of two types of pharmaceutical preparation, obtained by separately preparing the compound of the present invention and another drug, by the same route of administration; 3) administration of two types of pharmaceutical preparation, obtained by separately preparing the compound of the present invention and another drug by the same route of administration, with a time lag; 4) simultaneous administration of two types of pharmaceutical preparation, obtained by separately preparing the compound of the present invention and another drug, by a different route of administration, and 5) administration of two types of pharmaceutical preparation, obtained by separately preparing the compound of the present invention and another drug, by a different route of administration with a time lag (e.g., administration of the compound of the present invention followed by the other drug, or in the reverse order).

The blending ratio of the compound of the present invention and the other drug may be suitably selected depending on the drugs being administered, route of administration and disease.

Examples of concomitant drugs used in the present invention are anti-diabetic agents, lipid lowering agents, anti-hypertensive agents and anti-obesity agents. Two or more of these concomitant drugs may be combined in a suitable proportion.

Examples of anti-diabetic agents are:
1) PPARγ agonists such as glitazones (e.g. ciglitazone; darglitazone; englitazone; isaglitazone (MCC-555); pioglitazone; rosiglitazone; troglitazone; BRL49653; CLX-0921; 5-BTZD, and the like), and GW-0207, LG-100641, and LY-300512, and the like;
2) biguanides such as buformin; metformin; and phenformin, and the like;
3) protein tyrosine phosphatase-1B (PTP-1B) inhibitors;
4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like;
5) meglitinides such as repaglinide, and nateglinide, and the like;
6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like;
7) alpha-amylase inhibitors such as tendamistat, trestatin, and Al-3688, and the like;
8) insulin secreatagogues such as linogliride; and A-4166, and the like;
9) fatty acid oxidation inhibitors, such as clomoxir, and etomoxir, and the like;
10) A2 antagonists, such as midaglizole; isaglidole; deriglidole; idazoxan; earoxan; and fluparoxan, and the like;
11) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36) —$NH_2$), and the like;
12) non-thiazolidinediones such as JT-501, and farglitazar (GW-2570/GI-262579), and the like;
13) PPARα/γ dual agonists such as CLX-0940, GW-1536, GW1929, GW-2433, KRP-297, L-796449, LR-90, and SB 219994, and the like;
14) other insulin sensitizing drugs; and
15) VPAC2 receptor agonists.

Examples of lipid lowering agents are:
1) bile acid sequestrants such as, cholestyramine, colesevelem, colestipol, dialkylaminoalkyl derivatives of a cross-linked dextran; Colestid®; LoCholest®; and Questran®, and the like;
2) HMG-CoA reductase inhibitors such as atorvastatin, itavastatin, fluvastatin, lovastatin, pravastatin, rivastatin, rosuvastatin, simvastatin, and ZD-4522, and the like;
3) HMG-CoA synthase inhibitors;
4) cholesterol absorption inhibitors such as stanol esters, beta-sitosterol, sterol glycosides such as tiqueside; and azetidinones such as ezetimibe, and the like;
5) acyl coenzyme A-cholesterol acyl transferase (ACAT) inhibitors such as avasimibe, eflucimibe, KY505, SMP 797, and the like;
6) CETP inhibitors such as JTT 705, torcetrapib, CP 532,632, BAY63-2149, SC 591, SC 795, and the like;
7) squalene synthetase inhibitors;
8) anti-oxidants such as probucol, and the like;
9) PPARα agonists such as beclofibrate, benzafibrate, ciprofibrate, clofibrate, etofibrate, fenofibrate, gemcabene, and gemfibrozil, GW 7647, BM 170744, LY518674; and other fibric acid derivatives, such as Atromid®, Lopid® and Tricor®, and the like;
10) FXR receptor modulators such as GW 4064, SR 103912, and the like;
11) LXR receptor such as GW 3965, T9013137, and XTCO179628, and the like;
12) lipoprotein synthesis inhibitors such as niacin;
13) renin angiotensin system inhibitors;
14) PPARδ partial agonists;
15) bile acid reabsorption inhibitors, such as BARI 1453, SC435, PHA384640, S8921, AZD7706, and the like;
16) PPARδ agonists such as GW 501516, and GW 590735, and the like;
17) triglyceride synthesis inhibitors;
18) microsomal triglyceride transport (MTTP) inhibitors, such as inplitapide, LAB687, and CP346086, and the like;
19) transcription modulators;
20) squalene epoxidase inhibitors;
21) low density lipoprotein (LDL) receptor inducers;
22) platelet aggregation inhibitors;
23) 5-LO or FLAP inhibitors; and
24) niacin receptor agonists.

Examples of anti-hypertensive agents are:
1) diuretics, such as thiazides, including chlorthalidone, chlorthiazide, dichlorophenamide, hydroflumethiazide, indapamide, and hydrochlorothiazide; loop diuretics, such as bumetamide, ethacrynic acid, furosemide, and torsemide; potassium sparing agents, such as amiloride, and triamterene; and aldosterone antagonists, such as spironolactone, epirenone, and the like;
2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like;
4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like;
5) neutral endopeptidase inhibitors such as omapatrilat, cadoxatril and ecadotril, fosidotril, sampatrilat, AVE7688, ER4030, and the like;
6) endothelin antagonists such as tezosentan, A308165, and YM62899, and the like;
7) vasodilators such as hydralazine, clonidine, minoxidil, and nicotinyl alcohol, and the like;

8) angiotensin II receptor antagonists such as candesartan, eprosartan, irbesartan, losartan, pratosartan, tasosartan, telmisartan, valsartan, and EXP-3137, FI6828K, and RNH6270, and the like;
9) α/β adrenergic blockers as nipradilol, arotinolol and amosulalol, and the like;
10) alpha 1 blockers, such as terazosin, urapidil, prazosin, bunazosin, trimazosin, doxazosin, naftopidil, indoramin, WHIP 164, and XEN010, and the like;
11) alpha 2 agonists such as lofexidine, tiamenidine, moxonidine, rilmenidine and guanobenz, and the like; and
12) aldosterone inhibitors, and the like.

Examples of anti-obesity agents are:
1) 5HT (serotonin) transporter inhibitors, such as paroxetine, fluoxetine, fenfluramine, fluvoxamine, sertraline, and imipramine;
2) NE (norepinephrine) transporter inhibitors, such as GW 320659, despiramine, talsupram, and nomifensine;
3) CB-1 (cannabinoind-1 receptor) antagonist/inverse agonists, such as rimonabant (Sanofi Synthelabo), SR-147778 (Sanofi Synthelabo), BAY 65-2520 (Bayer), and SLV 319 (Solvay), and those disclosed in U.S. Pat. Nos. 5,532,237, 4,973,587, 5,013,837, 5,081,122, 5,112,820, 5,292,736, 5,624,941 and 6,028,084; and PCT Patent Application Nos. WO 96/33159, WO 98/33765, WO 98/43636, WO 98/43635, WO 01/09120, WO 01.96330, WO 98/31227, WO 98/41519, WO 98/37061, WO 00/10967, WO 00/10968, WO 97/29079, WO 99/02499, WO 01/58869, WO 02/076949, WO 01/64632, WO 01/64633, WO 01/64634, WO 03/006007 and WO 03/007887; and EPO Application No. EP-658546;
4) ghrelin antagonists, such as those disclosed in WO 01/87335, and WO 02/08250;
5) H3 (histamine H3) antagonist/inverse agonists, such as thioperamide, 3-(1H-imidazol-4-yl)propyl N-(4-pentenyl) carbamate, clobenpropit, iodophenpropit, imoproxifan, GT2394 (Gliatech), and A331440, and those disclosed in WO02/15905; and O-[3-(1H-imidazol-4-yl)propanol]carbamates (Kiec-Kononowicz, K. et al., Pharmazie, 55: 349-55 (2000)), piperidine-containing histamine H3-receptor antagonists (Lazewska, D. et al., Pharmazie, 56: 927-32 (2001), benzophenone derivatives and related compounds (Sasse, A. et al., Arch. Pharm. (Weinheim) 334: 45-52 (2001)), substituted N-phenylcarbamates (Reidemeister, S. et al., Pharmazie, 55: 83-6 (2000)), and proxifan derivatives (Sasse, A. et al., J. Med. Chem., 43: 3335-43 (2000));
6) melanin-concentrating hormone 1 receptor (MCH1R) antagonists, such as T-226296 (Takeda), SNP-7941 (Synaptic), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799 and WO 03/004027, and Japanese Patent Application No. JP 13226269;
7) MCH2R (melanin concentrating hormone 2R) agonist/antagonists;
8) NPY1 (neuropeptide Y Y1) antagonists, such as BIBP3226, J-115814, BIBO 3304, LY-357897, CP-671906, and GI-264879A; and those disclosed in U.S. Pat. No. 6,001,836; and PCT Patent Application Nos. WO 96/14307, WO 01/23387, WO 99/51600, WO 01/85690, WO 01/85098, WO 01/85173 and WO 01/89528;
9) NPY5 (neuropeptide Y Y5) antagonists, such as 152,804, GW-569180A, GW-594884A, GW-587081X, GW-548118X FR235,208; FR226928, FR240662, FR252384; 1229U91, GI-264879A, CGP71683A, LY-377897, LY-366377, PD-160170, SR-120562A, SR-120819A, JCF-104, and H409/22; and those compounds disclosed in U.S. Pat. Nos. 6,140,354, 6,191,160, 6,258,837, 6,313,298, 6,337,332, 6,329,395 and 6,340,683; U.S. Pat. Nos. 6,326,375; 6,329,395; 6,337,332; 6,335,345; European Patent Nos. EP-01010691, and EP-01044970; and PCT Patent Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648 and WO 02/094789; and Norman et al., J. Med. Chem. 43: 4288-4312 (2000);
10) leptin, such as recombinant human leptin (PEG-OB, Hoffman La Roche) and recombinant methionyl human leptin (Amgen);
11) leptin derivatives, such as those disclosed in U.S. Pat. Nos. 5,552,524, 5,552,523, 5,552,522 and 5,521,283; and PCT Patent Publication Nos. WO 96/23513, WO 96/23514, WO 96/23515, WO 96/23516, WO 96/23517, WO 96/23518, WO 96/23519 and WO 96/23520;
12) opioid antagonists, such as nalmefene (Revex®), 3-methoxynaltrexone, naloxone, and naltrexone; and those disclosed in WO 00/21509;
13) orexin antagonists, such as SB-334867-A; and those disclosed in WO 01/96302, WO 01/68609, WO 02/51232, WO 02/51838 and WO 03/023561;
14) BRS3 (bombesin receptor subtype 3) agonists;
15) CCK-A (cholecystokinin-A) agonists, such as AR-R 15849, GI 181771, JMV-180, A-71378, A-71623 and SR146131, and those disclosed in U.S. Pat. No. 5,739,106;
16) CNTF (ciliary neurotrophic factors), such as GI-181771 (Glaxo-SmithKline); SR146131 (Sanofi Synthelabo); butabindide; and PD170,292, PD149164 (Pfizer);
17) CNTF derivatives, such as axokine (Regeneron); and PCT Application Nos. WO 94/09134, WO 98/22128, and WO 99/43813;
18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and PCT Patent Application Nos. WO 01/56592 and WO 02/32888;
19) 5HT2c (serotonin receptor 2c) agonists, such as BVT933, DPCA37215, IK264; PNU22394; WAY161503, R-1065, and YM348; and those disclosed in U.S. Pat. No. 3,914, 250; and PCT Patent Application Nos. WO 02/36596, WO 02/48124, WO 02/10169, WO 01/66548, WO 02/44152; WO 02/51844, WO 02/40456 and WO 02/40457;
20) Mc3r (melanocortin 3 receptor) agonists;
21) Mc4r (melanocortin 4 receptor) agonists, such as CHIR86036 (Chiron); ME-10142, and ME-10145 (Melacure), and those disclosed in WO 99/64002, WO 00/74679, WO 01/991752, WO 01/74844, WO 01/70708, WO 01/70337, WO 01/91752, WO 02/059095, WO 02/059107, WO 02/059108, WO 02/059117, WO 02/12166, WO 02/11715, WO 02/12178, WO 02/15909, WO 02/068387, WO 02/068388, WO 02/067869, WO 03/007949 and WO 03/009847;
22) monoamine reuptake inhibitors, such as sibutratmine (Meridia®/Reductil®) and a salt thereof, and those compounds disclosed in U.S. Pat. Nos. 4,746,680, 4,806,570, and 5,436,272, and U.S. Patent Publication No. 2002/0006964, and PCT Patent Application Nos. WO 01/27068 and WO 01/62341;
23) serotonin reuptake inhibitors, such as dexfenfluramine, fluoxetine, and those in U.S. Pat. No. 6,365,633, and PCT Patent Application Nos. WO 01/27060, and WO 01/162341;
24) GLP-1 (glucagon-like peptide 1) agonists;
25) Topiramate (Topimax®);
26) phytopharm compound 57 (CP 644,673);
27) ACC2 (acetyl-CoA carboxylase-2) inhibitors;
28) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, and SR 59119A, and those disclosed in U.S. patent application No. 5,705,515, U.S. Pat. No. 5,451,677; and PCT Patent Application Nos. WO 01/74782 and WO 02/32897;
29) DGAT1 (diacylglycerol acyltransferase 1) inhibitors;
30) DGAT2 (diacylglycerol acyltransferase 2) inhibitors;
31) FAS (fatty acid synthase) inhibitors, such as Cerulenin and C75;
32) PDE (phosphodiesterase) inhibitors, such as theophylline, pentoxifylline, zaprinast, sildenafil, amrinone, milrinone, cilostamide, rolipram, and cilomilast;
33) thyroid hormone β agonists, such as KB-2611 (KaroBioBMS), and those disclosed in PCT Application No. WO 02/15845, and Japanese Patent Application No. JP 2000256190;
34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123;
35) acyl-estrogens, such as oleoyl-estrone, disclosed in del Mar-Grasa, M. et al., Obesity Research, 9: 202-9 (2001);
36) glucocorticoid antagonists;
37) 11β HSD-1 (11-beta-hydroxy-steroid dehydrogenase type 1) inhibitors, such as BVT-3498, BVT 2733, and those compounds disclosed in WO 01/90091, WO 01/90090 and WO 01/90092;
38) SCD-1 (stearoyl-CoA desaturase-1) inhibitors;
39) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444; and the compounds disclosed in WO 03/004498, WO 03/004496, EP 1 258 476 WO 02/083128, WO 02/062764, WO 03/000250, WO 03/002530, WO 03/002531, WO 03/002553, WO 03/002593, WO 03/000180, and WO 03/000181;
40) lipase inhibitors, such as tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in PCT Application No. WO 01/77094, and U.S. Pat. Nos. 4,598,089. 4,452,813, 5,512,565, 5,391,571, 5,602,151, 5,405,644, 4,189,438 and 4,242,453;
41) fatty acid transporter inhibitors;
42) dicarboxylate transporter inhibitors;
43) glucose transporter inhibitors;
44) phosphate transporter inhibitors;
45) melanocortin agonists, such as Melanotan II or those described in WO 99/64002 and WO 00/746799;
46) melanin concentrating hormone antagonists;
47) galanin antagonists;
48) CCK agonists;
49) corticotropin-releasing hormone agonists; and
50) phosphodiesterase-3B (PDE3B) inhibitors; and the like.

The above combinations include combinations of a composition of the present invention not only with one other active compound, but also with two or more other active compounds. Non-limiting examples include combinations of the compositions of the present invention with one, two or more active compounds (concomitant drugs) selected from lipid-lowering agents, and anti-hypertensive agents. Combinations of the compositions of the present invention with one, two or more active compounds (concomitant drugs) selected from lipid lowering agents, and anti-diabetic agents are useful to treat, control or prevent metabolic syndrome. In particular, compositions comprising an anti-obesity agent, an anti-hypertensive agent, in addition to an anti-diabetic agent and/or a lipid lowering agent will be useful to synergistically treat, control or prevent metabolic syndrome.

When the compound of the present invention is used in a clinical setting, the dose and frequency of administration depend on the patient's sex, age, weight, condition, and the type and extent of the effect it is desired to obtain. However, in oral administration to an adult, it is 0.01-100 mg/kg but preferably 0.3-1 mg/kg per day administered in one or several doses, and in non-oral administration to an adult, it is 0.001-10 mg/kg but preferably 0.001-0.1 mg/kg per day administered in one or several doses.

The physician, veterinarian or clinician can easily determine an effective pharmacological amount of the drug to prevent, suppress or stop a disease process.

EXAMPLES

The present invention will now be described by means of examples, but it will be understood that the present invention is not limited in any way thereby.

For the thin layer chromatography of the examples, Silicagel 60F245 (Merck) was used for the plates and a UV detector was used as the detection method. Wakogel™ C-300 (Wako Pure Chem.) was used as silica gel for columns and LC-SORBTM SP-B-ODS (Chemco) or YMC-GEL™ ODS-AQ120-S50 (Yamamura Chemical Research Institute) was used as silica gel for reverse phase columns. The mass spectrum was measured by the electrospray ionizing method (ESI) using QuattroII (product of Micromass Co.)

When measuring the NMR spectrum in heavy dimethylsulfoxide solution, measurements were performed using a Gemini-200 (200 MHz, Varian), Gemini-300 (300 MHz, Varian), Mercury 400 (400 MHz, Varian) or Inova 400 (400 MHz, Varian) spectrometer with dimethylsulfoxide as internal reference, and all δ values were expressed as ppm.

The meanings of the abbreviations in the following examples are as follows:
i-Bu: isobutyl-group
n-Bu: n-butyl
t-Bu: t-butyl
Me: methyl-group
Et: ethyl-group
Ph: phenyl-group
i-Pr: isopropyl group
n-Pr: n-propyl group
CDCl$_3$: heavy-chloroform
CD$_3$OD: heavy-methanol
DMSO-d6: heavy-dimethylsulfoxide.

The meanings of the abbreviations on the nuclear magnetic resonance spectrum are as follows:
s: singlet
d: doublet
dd: double-doublet
t: triplet
m: multiplet
br: broad
q: quartet
J: coupling-constant
Hz: a hertz Example 1

2-ethyl-3-{4-[3-(1-piperidinyl)propoxy]phenyl}-4(3H)-quinazolinone (1) Manufacture of 2-ethyl-4H-3,1-benzoxazin-4-one Anthranilic acid (10 g, 72.9 mmol) and propionic anhydride (20.9 g, 160 mmol) were mixed and stirred at 130° C. for 2 hours. The reaction solution was concentrated under reduced pressure, the residue was dissolved in methylene chloride, the organic phase was washed with saturated sodium hydrogen carbonate aqueous solution and then distilled water and dried with anhydrous sodium sulfate. The target compound (12.5 g, 98%) was obtained as a colorless solid by filtering off the sodium sulfate and concentrating to dryness.

(2) Manufacture of 2-ethyl-3-(4-hydroxyphenyl)-4-(3H)-quinazolinone 2-ethyl-4H-3,1-benzoxazin-4-one (6.5 g, 37.1 mmol) and 4-aminophenol (4.05 g, 37.1 mmol) were dissolved in dimethylformamide (18 mL) and stirred at 140° C. for 10 hours. After leaving to cool to room temperature, distilled water (94 mL) was added, and the solid precipitate was filtered off. The product was recrystallized (ethanol) and the target compound (6.52 g, 66%) was obtained as light brown crystals.

(3) Manufacture of 2-ethyl-3-[4-(3-chloropropoxy)phenyl]-4(3H)-quinazolinone 2-ethyl-3-(4-hydroxyphenyl)-4(3H)-quinazolinone (17.9 g, 67.5 mmol), 1,3-bromochloropropane (12.1 g, 70.3 mmol) and potassium carbonate (19.7 g, 143 mmol) were mixed in dimethylformamide (180 mL) and stirred at 80° C. for 2 hours.

After evaporating the solvent under reduced pressure, ethyl acetate and distilled water were added. After extracting with ethyl acetate, the organic phase was washed with distilled water and dried with anhydrous sodium sulfate.

The sodium sulfate was filtered off, the filtrate was evaporated under reduced pressure and the obtained solid was washed by ethanol to obtain the target compound (19.1 g, 82%) as a light brown solid.

(4) Manufacture of 2-ethyl-3-{4-[3-(1-piperidinyl)propoxy]phenyl}-4(3H)-quinazolinone 2-ethyl-3-[4-(3-chloropropoxy)phenyl]-4(3H)-quinazolinone (19 g, 55.6 mmol), piperidine (23.7 g, 278 mmol), potassium carbonate (11.5 g, 83.4 mmol) and potassium iodide (13.8 g, 83.4 mmol) were mixed in dimethylformamide (400 mL) and stirred at 80° C. for 24 hours.

The solvent was evaporated under reduced pressure, the residue was dissolved in ethyl acetate and the organic phase was washed with distilled water and dried with anhydrous sodium sulfate.

After purifying with silica gel column chromatography (chloroform/methanol=30/1), the title compound (10.1 g, 47%) was obtained as colorless crystals by recrystallizing from diethyl ether/heptane.

$^1$HNMR (400 MHz,CDCl$_3$,δppm): 1.22 (3H, t, J=7.2 Hz), 1.41-1.47 (2H, m), 1.57-1.64 (4H, m), 1.97-2.05 (2H, m), 2.36-2.58 (8H, m), 4.06 (2H, t, J=6.4 Hz), 7.02 (2H, d, J=8.4 Hz), 7.12 (2H, d, J=8.4 Hz), 7.43 (1H, t, J=7.6 Hz), 7.67-7.78 (2H, m), 8.25 (1H, d, J=8.4 Hz)

The compound of Example 2-16 can be manufactured by the same method as that of Example 1, a method based thereon or a combination of these and a conventional method, using the corresponding anthranilic acid, acid anhydride, aminophenol, 1,3-bromochloroalkane and amine as starting materials.

Example 2

2-methyl-3-{4-[3-(1-piperidinyl)propoxy]phenyl}-4(3H)-quinazolinone

The title compound was obtained by the method according to Example 1, using anthranilic acid, acetic anhydride, 4-aminophenol, 1,3-bromochloropropane and piperidine as starting materials.

$^1$HNMR (400 MHz,CDCl$_3$,δppm): 1.41-1.55 (2H, m), 1.50-1.64 (4H, m), 1.97-2.04 (2H, m), 2.25 (3H, s), 2.37-2.46 (4H, brs), 2.49 (2H, t, J=6.8 Hz), 4.06 (2H, t, J=6.8 Hz), 7.03 (2H, d, J=8.4 Hz), 7.12 (2H, d, J=8.4 Hz), 7.44 (1H, t, J=8.0 Hz), 7.65 (1H, d, J=8.8 Hz), 7.74 (1H, t, J=8.0 Hz), 8.25 (1H, d, J=8.0 Hz)

Example 3

2-methyl-3-{4-[3-(1-pyrrolidinyl)propoxy]phenyl}-4(3H)-quinazolinone

The title compound was obtained by the method according to Example 1, using anthranilic acid, acetic anhydride, 4-aminophenol, 1,3-bromochloropropane and pyrrolidine as starting materials.

$^1$HNMR (400 MHz,CDCl$_3$,δppm): 1.41-1.49 (2H, m), 1.58-1.66 (4H, m), 2.25 (3H, s), 2.48-2.58 (4H, brs), 2.81 (2H, t, J=6.0 Hz), 4.15 (2H, t, J=5.6 Hz), 7.03 (2H, d, J=9.2 Hz), 7.13 (2H, d, J=9.2 Hz), 7.44 (1H, t, J=8.0 Hz), 7.65 (1H, d, J=8.0 Hz), 7.72 (1H, t, J=7.2 Hz), 8.25 (1H, d, J=8.0 Hz)

Example 4

3-{4-[3-(diethylamino)propoxy]phenyl}-2-methyl-4(3H)-quinazolinone

The title compound was obtained by the method according to Example 1, using anthranilic acid, acetic anhydride, 4-aminophenol, 1,3-bromochloropropane and diethylamine as starting materials.

$^1$HNMR (400 MHz,CDCl$_3$,δppm): 1.04 (6H, t, J=7.2 Hz), 1.91-2.00 (2H, m), 2.25 (3H, s), 2.55 (4H, q, J=6.8 Hz), 2.63 (2H, t, J=6.8 Hz), 4.06 (2H, t, J=6.4 Hz), 7.03 (2H, d, J=8.8 Hz), 7.13 (2H, d, J=8.8 Hz), 7.44 (1H, t, J=8.4 Hz), 7.65 (1H, d, J=8.0 Hz), 7.74 (1H, t, J=8.0 Hz), 8.25 (1H, d, J=8.0 Hz)

Example 5

2-methyl-3-{4-[3-(2-methyl-1-pyrrolidinyl)propoxy]phenyl}-4(3H)-quinazolinone (Racemic Mixture)

The title compound was obtained by the method according to Example 1, using anthranilic acid, acetic anhydride, 4-aminophenol, 1,3-bromochloropropane and 2-methylpyrrolidine as starting materials.

$^1$HNMR (400 MHz,CDCl$_3$,δppm): 1.10 (3H, d, J=6.4 Hz), 1.37-1.46 (1H, m), 1.65-1.72 (2H, m), 1.86-1.97 (1H, m), 1.99-2.17 (3H, m), 2.17-2.24 (1H, m), 2.25 (3H, s), 2.26-2.33 (1H, m), 2.96-3.03 (1H, m), 3.16-3.23 (1H, m), 4.05-4.10 (2H, m), 7.03 (2H, d, J=8.8 Hz), 7.13 (2H, d, J=8.8 Hz), 7.44 (1H, t, J=8.0 Hz), 7.65 (1H, d, J=8.8 Hz), 7.74 (1H, t, J=8.0 Hz), 8.25 (1H, d, J=8.0 Hz)

Example 6

3-{4-[3-(2,5-dimethyl-1-pyrrolidinyl)propoxy]phenyl}-2-methyl-4(3H)-quinazolinone (Mixture of cis- and trans-isomers)

The title compound was obtained by the method according to Example 1, using anthranilic acid, acetic anhydride, 4-aminophenol, 1,3-bromochloropropane and 2,5-dimethylpyrrolidine as starting materials.

$^1$HNMR (400 MHz,CDCl$_3$,δppm): 1.12 (6H, d, J=6.0 Hz), 1.35-1.40 (2H, m), 1.80-1.86 (2H, m), 1.94-2.00 (2H, m), 2.57-2.66 (2H, m), 2.76 (2H, t, J=7.2 Hz), 4.06 (2H, t, J=6.0 Hz), 7.02 (2H, d, J=8.8 Hz), 7.12 (2H, d, J=8.8 Hz), 7.44 (1H, t, J=7.2 Hz), 7.65 (1H, d, J=8.0 Hz), 7.74 (1H, t, J=8.4 Hz), 8.25 (1H, d, J=8.0 Hz)

Example 7

2-methyl-3-{4-[4-(1-piperidinyl)butoxy]phenyl}-4(3H)-quinazolinone

The title compound was obtained by the method according to Example 1, using anthranilic acid, acetic anhydride, 1,4-bromochlorobutane and piperidine as starting materials.

$^1$HNMR (400 MHz,CDCl$_3$,δppm): 1.41-1.53 (2H, m), 1.57-1.65 (4H, m), 1.66-1.75 (2H, m), 1.97-2.06 (2H, m), 2.25 (3H, s), 2.36-2.50 (6H, m), 4.03 (2H, t, J=6.4 Hz), 7.01 (2H, d, J=8.8 Hz), 7.12 (2H, d, J=8.8 Hz), 7.44 (1H, t, J=8.0 Hz), 7.65 (1H, d, J=7.6 Hz), 7.74 (1H, t, J=8.0 Hz), 8.25 (1H, d, J=8.0 Hz)

Example 8

3-{4-[3-(1-azepanyl)propoxy]phenyl}-2-methyl-4(3H)-quinazolinone

The title compound was obtained by the method according to Example 1, using anthranilic acid, acetic anhydride, 4-aminophenol, 1,3-bromochloropropane and azepan as starting materials.

$^1$HNMR (400 MHz,CDCl$_3$,δppm): 1.62-1.70 (8H, m), 2.25 (3H, s), 2.73 (4H, brs), 4.08 (2H, t, J=6.2 Hz), 7.03 (2H, d, J=8.4 Hz), 7.12 (2H, d, J=8.4 Hz), 7.44 (1H, t, J=8.0 Hz), 7.65 (1H, d, J=8.8 Hz), 7.74 (1H, t, J=8.0 Hz), 8.25 (1H, d, J=8.0 Hz)

Example 9

3-{4-[3-(1-azocanyl)propoxy]phenyl}-2-methyl-4(3H)-quinazolinone

The title compound was obtained by the method according to Example 1, using anthranilic acid, acetic anhydride, 4-aminophenol, 1,3-bromochlQropropane and azocan as starting materials.

$^1$HNMR (400 MHz,CDCl$_3$,δppm): 1.57-1.63 (8H, m), 2.26 (3H, s), 2.56 (4H, brs), 4.08 (2H, t, J=6.2 Hz), 7.03 (2H, d, J=8.4 Hz), 7.12 (2H, d, J=8.4 Hz), 7.44 (1H, t, J=8.0 Hz), 7.65 (1H, d, J=8.8 Hz), 7.74 (1H, t, J=8.0 Hz), 8.25 (1H, d, J=8.0 Hz)

Example 10

2-methyl-3-{4-[3-(2-methyl-1-piperidinyl)propoxy]phenyl}-4(3H)-quinazolinone (Racemic Mixture)

The title compound was obtained by the method according to Example 1, using anthranilic acid, acetic anhydride, 4-aminophenol, 1,3-bromochloropropane and 2-methylpiperidine as starting materials.

$^1$HNMR (400 MHz,CDCl$_3$,δppm): 1.14 (3H, d, J=5.5 Hz), 1.36 (1H, brs), 1.36 (1H, brs), 2.03 (1H, brs), 2.26 (3H, s), 2.42 (1H, brs), 2.60 (1H, brs), 2.93 (1H, brs), 4.08 (2H, t, J=6.2 Hz), 7.03 (2H, d, J=8.4 Hz), 7.12 (2H, d, J=8.4 Hz), 7.44 (1H, t, J=8.0 Hz), 7.65 (1H, d, J=8.8 Hz), 7.74 (1H, t, J=8.0 Hz), 8.25 (1H, d, J=8.0 Hz)

Example 11

2-methyl-3-{4-[3-(4-methyl-1-piperidinyl)propoxy]phenyl}-4(3H)-quinazolinone

The title compound was obtained by the method according to Example 1, using anthranilic acid, acetic anhydride, 4-aminophenol, 1,3-bromochloropropane and 4-methylpiperidine as starting materials.

$^1$HNMR (400 MHz,CDCl$_3$,δppm): 0.93 (3H, d, J=6.6 Hz), 1.25-1.30 (1H, m), 1.36 (1H, brs), 1.62-1.65 (1H, m), 1.92-2.03 (1H, m), 2.25 (3H, s), 2.49-2.51 (1H, m), 2.90-2.93 (1H, m), 4.06 (2H, t, J=6.2 Hz), 7.02 (2H, d, J=6.6 Hz), 7.12 (2H, d, J=6.6 Hz), 7.46 (1H, t, J=6.5 Hz), 7.65 (1H, d, J=7.7 Hz), 7.76 (1H, t, J=8.4 Hz), 8.26 (1H, d, J=8.4 Hz)

Example 12

3-(4-{3-[([2R,6S)-2,6-dimethyl-1-piperidinyl]propoxy}phenyl)-2-methyl-4(3H)-quinazolinone The title compound was obtained by the method according to Example 1, using anthranilic acid, acetic anhydride, 4-aminophenol, 1,3-bromochloropropane and (2R,6S)-2,6-dimethylpiperidine as starting materials.

$^1$HNMR (400 MHz,CDCl$_3$,δppm): 1.18 (6H, d, J=6.6 Hz), 1.36 (2H, brs), 1.58-1.68 (2H, m), 1.943 (1H, brs), 2.25 (3H, s), 2.54 (2H, brs), 3.00 (2H, m), 3.99 (2H, t, J=5.8 Hz), 7.00 (2H, d, J=5.9 Hz), 7.12 (2H, d, J=5.9 Hz), 7.43 (1H, t, J=6.6 Hz), 7.64 (1H, d, J=8.0 Hz), 7.76 (1H, t, J=8.4 Hz), 8.23 (1H, d, J=8.0 Hz)

Example 13

2-methyl-3-{4-[3-(3-methyl-1-piperidinyl)propoxy]phenyl}-4(3H)-quinazolinone (Racemic Mixture)

The title compound was obtained by the method according to Example 1, using anthranilic acid, acetic anhydride, 4-aminophenol, 1,3-bromochloropropane and 3-methylpiperidine as starting materials.

$^1$HNMR (400 MHz, CDCl$_3$, δppm): 0.87 (3H, d, J=6.6 Hz), 1.57-1.72 (2H, m), 1.88 (1H, td, J=11.0, 2.9 Hz), 1.98-2.06 (2H, m), 2.24 (3H, s), 2.52 (2H, t, J=7.3 Hz), 2.85-2.92 (2H, m), 7.02 (2H, d, J=8.8 Hz), 7.12 (2H, d, J=8.8 Hz), 7.43 (1H, t, J=7.3 Hz), 7.64 (1H, d, J=8.0 Hz), 7.73 (1H, t, J=8.0 Hz), 8.23 (1H, d, J=8.6 Hz)

Example 14

3-{4-[3-(3,5-dimethyl-1-piperidinyl)propoxy]phenyl}-2-methyl-4(3H)-quinazolinone The title compound was obtained by the method according to Example 1, using anthranilic-acid, acetic anhydride, 4-aminophenol, 1,3-bromochloropropane and 3,5-dimethylpiperidine as starting materials.

$^1$HNMR (400 MHz, CDCl$_3$, δppm): 0.86 (6H, d, J=6.8 Hz), 1.49 (2H, t, J=10.8), 1.70-1.72 (2H, m), 2.24 (3H, s), 2.53 (2H, t, J=7.2 Hz), 2.88-2.90 (2H, m), 4.04 (2H, t, J=6.8 Hz), 7.00 (2H, d, J=8.8 Hz), 7.12 (2H, d, J=8.8 Hz), 7.42 (1H, t, J=7.2 Hz), 7.63 (1H, d, J=7.2 Hz), 7.72 (1H, t, J=8.0 Hz), 8.23 (1H, d, J=8.0 Hz)

Example 15

2-methyl-3-{3-[3-(1-piperidinyl)propoxy]phenyl}-4(3H)-quinazolinone

The title compound was obtained by the method according to Example 1, using anthranilic acid, acetic anhydride, 3-aminophenol, 1,3-bromochloropropane and piperidine as starting materials.

$^1$HNMR (400 MHz, CDCl$_3$, δppm): 1.39-1.47 (2H, m), 1.54-1.62 (4H, m), 1.94-2.02 (2H, m), 2.28 (3H, s), 2.36-2.43 (4H, brs), 2.46 (2H, t, J=7.2 Hz), 3.98-4.06 (2H, m), 6.77 (1H, s), 6.81 (1H, d, J=8.0 Hz), 7.01 (1H, d, J=8.4 Hz), 7.39.7.47 (2H, m), 7.65 (1H, d, J=8.0 Hz), 7.75 (1H, t, J=8.0 Hz), 8.25 (1H, d, J=8.4 Hz)

Example 16

3-{3-bromo-4-[3-(1-piperidinyl)propoxy]phenyl}-2-ethyl-4(3H)-quinazolinone (1) Manufacture of 2-bromo-1-(3-chloropropoxy)-4-nitrobenzene 4-amino-2-bromophenol (2.0 g, 9.17 mmol), 1,3-bromochloropropane (907 μL, 9.17 mmol) and potassium carbonate (1.90 g, 13.8 mmol) were mixed in dimethylformamide (8 mL), and stirred at 80° C. for 17 hours. Ethyl acetate was added, the mixture washed with 1N sodium hydroxide aqueous solution and distilled water in that order, and the organic phase was dried with anhydrous sodium sulfate. The product was purified by silica gel column chromatography (hexane/ethyl acetate=9/1-7/3), and the target substance (1.3 g, 48%) was thus obtained. 4-amino-2-bromophenol was manufactured by the method described in the literature (J. Org. Chem., Vol. 62, 1997, p. 4504).

(2) Manufacture of 3-bromo-4-(3-chloropropoxy)aniline 2-bromo-1-(3-chloropropoxy)-4-nitrobenzene (1.3 g), ammonium chloride (1.3 g) and iron (1.3 g) were added to a mixed solvent of methanol (8 mL) and distilled water (4 mL), and the mixture was heated under reflux for 2 hours. The reaction mixture was filtered through cerite, and the filtrate was concentrated. The residue was dissolved in ethyl acetate, and washed with distilled water and saturated brine. The organic phase was dried with anhydrous sodium sulfate, concentrated and dried to obtain the target substance (0.92 g).

(3) Manufacture of 3-[3-bromo-4-(3-chloropropoxy)phenyl]-2-ethyl-4(3H)-quinazolinone 3-bromo-4-(3-chloropropoxy)aniline (0.92 g, 4.92 mmol) and 2-ethyl-4H-3,1-benzoxadin-4-one (0.87 g, 4.92 mmol) were dissolved in dimethylformamide (3 mL), and stirred at 140° C. for 5 hours. Ethyl acetate and distilled water were added, and the mixture extracted with ethyl acetate and dried with anhydrous sodium sulfate. Methanol was added to the residue, and insoluble matter was filtered off. The filtrate was concentrated, the product purified by silica gel column chromatography, (hexane/ethyl acetate=80/20-75/25), and the target substance (416 mg, 20%) was thus obtained.

(4) Manufacture of 3-{3-bromo-4-[3-(1-piperidinyl)propoxy]phenyl}-2-ethyl-4(3H)-quinazolinone 3-[3-bromo-4-(3-chloropropoxy)phenyl]-2-ethyl-4(3H)-quinazolinone (70 mg) was dissolved in piperidine (1 mL), and stirred at 80° C. for 5 hours. The reaction solution was diluted with diethyl ether, and insoluble matter was filtered off. The filtrate was concentrated, dried under vacuum, and the title compound (80 mg, 99%) was thus obtained as a light yellow solid.

$^1$HNMR (400 MHz, CDCl$_3$, δppm): 1.23 (3H, t, J=7.6 Hz), 1.43-1.53 (2H, m), 1.54-1.66 (4H, m), 2.03-2.12 (2H, m), 2.39-2.52 (6H, m), 2.54-2.60 (2H, m), 4.13-4.18 (2H, m), 7.04 (1H, d, J=8.4 Hz), 7.15 (1H, dd, J=2.8, 8.4 Hz), 7.44-7.48 (2H, m), 7.71 (1H, d, J=8.0 Hz), 7.77 (1H, t, J=7.2 Hz), 8.26 (1H, d, zJ=8.0 Hz

Example 17

2-methyl-3-{4-[2-(1-piperidinyl)ethoxy]phenyl}-4(3H)-quinazolinone 2-methyl-3-(4-hydroxyphenyl)-4-(3H)quinazolinone synthesized according to Example 1-(1) and -(2) (100 mg, 0.40 mmol), 2-(1-piperidinyl)ethanol (89 mg, 0.50 mmol) and triphenylphosphine (125 mg, 0.50 mmol) were dissolved in dry tetrahydrofuran (2 mL) and cooled on an ice bath. Diethylazodicarboxylate (75 uL, 0.50 mmol) was dripped in at 0° C. and stirred at room temperature for 48 hours. The solvent was distilled off under reduced pressure, ether was added, the solid precipitate was filtered off and the filtrate was concentrated. The residue was purified by silica gel column chromatography (chloroform/methanol=30/1) and the title compound (124 mg, 0.86%) was obtained as a light brown oily substance.

$^1$HNMR (400 MHz, CDCl$_3$, δppm): 1.77-1.83 (4H, m), 2.01-2.08 (2H, m), 2.25 (3H, s), 2.51-2.59 (4H, m), 2.64 (2H, t, J=7.2 Hz), 4.08 (2H, t, J=6.4 Hz), 7.03 (2H, d, J=9.2 Hz), 7.13 (2H, d, J=9.2 Hz), 7.44 (1H, t, J=8.0 Hz), 7.65 (1H, d, J=8.0 Hz), 7.74 (1H, t, J=6.8 Hz), 8.25 (1H, d, J=8.0 Hz)

Example 18

2,5-dimethyl-3-{4-[3-(1-piperidinyl)propoxy]phenyl}-4(3H)-quinazolinone

(1) Manufacture of 1-[3-(4-nitrophenoxy)propyl]piperidine 3-piperidin-1-yl-propan-1-ol (3.66 g, 25.6 mmol), 4-nitrophenol (2.96 g, 21.3 mmol) and triphenylphosphine (6.71 g, 25.6 mmol) were dissolved in dry tetrahydrofuran in a current of nitrogen, and cooled on the ice bath. Diisopropyl azodicarboxylate (5.0 mL, 25.6 mmol) was dripped in, and stirred at room temperature for 40 hours. The reaction liquid was concentrated, diethyl ether was added, and the solid precipitate was filtered off. The filtrate was concentrated, the product purified by silica gel column chromatography (chloroform/methanol=100/0-95/5), and the target substance (3.49 g, 62%) was thus obtained as a light yellow oily residue.

1-[3-(4-nitrophenoxy)propyl]piperidine was also manufactured by the following method.

Sodium hydride (2.8 g) was precipitated in dimethylformamide (20 mL) in a current of nitrogen, and 3-piperidin-1-yl-propan-1-ol (5.0 g, 34.9 mmol) was slowly added on the ice bath. After 1 hour stirring at room temperature, 1-fluoro-4-nitrobenzene (4.92 g, 34.9 mmol) was added, and the mixture stirred at room temperature for 15 hours. Distilled water and ethyl acetate were added, the mixture extracted with ethyl acetate, and dried with anhydrous sodium sulfate. After concentration, the residue was purified by silica gel column chromatography (chloroform/methanol=10/0-9/1), and the target substance (7.56 g, 82%) was thus obtained as a light yellow oily residue.

(2) Manufacture of 4-[(3-(1-piperidinyl)propoxy]aniline

1-[3-(4-nitrophenoxy)propyl]piperidine was dissolved in methanol, and the target compound was obtained by catalytic reduction using a palladium charcoal catalyst in a current of hydrogen.

(3) Manufacture of 2,5-dimethyl-3-{4-[3-(1-piperidinyl)propoxy]phenyl}-4(3H)-quinazolinone 2,5-dimethyl-4H-3,1-benzoxadin-4-one (100 mg, 0.57 mmol) and 4-[(3-(1-piperidinyl)propoxy]aniline (134 mg, 0.57 mmol) were dissolved in acetic acid (3 mL), and stirred at 130° C. for 10 hours. The solvent was distilled off under reduced pressure, and ethyl acetate and 1N sodium hydroxide aqueous solution were added. The mixture was extracted with ethyl acetate, and the organic phase was dried with anhydrous sodium sulfate. After purification by silica gel column chromatography (chloroform/methanol=20/1), the title compound (76 mg, 34%) was obtained as colorless crystals by recrystallization (ether/heptane). 2,5-dimethyl-4H-3,1-benzoxadin-4-one was manufactured according to the method of Example 1-(1), using 2-amino-6-methylbenzoic acid and acetic anhydride as starting materials.

$^1$HNMR (400 MHZ,CDCl$_3$,δppm): 1.41-1.50 (2H, m), 1.57-1.64 (4H, m), 1.97-2.04 (2H, m), 2.22 (3H, s), 2.37-2.45 (4H, brs), 2.50 (2H, t, J=7.2 Hz), 2.81 (3H, s), 4.05 (2H, t, J=6.4 Hz), 7.02 (2H, d, J=9.2 Hz), 7.12 (2H, d, J=9.2 Hz), 7.19 (1H, d, J=7.6 Hz), 7.48 (1H, d, J=7.6 Hz), 7.57 (1H, t, J=8.0 Hz)

NMR data for 4-[3-(1-piperidinyl)propoxy]aniline hydrochloride used for manufacturing the compound of this example is shown below.

1HNMR (400 MHz,CDCl$_3$/CD$_3$OD=5/1,δppm): 1.40-1.49 (1H, m), 1.86-1.95 (3H, m), 2.14-2.24 (2H, m), 2.32-2.38 (2H, m), 2.68-2.75 (2H, m), 3.17-3.21 (2H, m), 3.62-3.57 (2H, m), 4.01 (2H, t, J=5.6 Hz), 6.76 (2H, d, J=8.8 Hz), 6.85 (2H, d, J=8.8 Hz)

The compound of Example 19-62 can be manufactured by same method as that of Example 18, a method based thereon or a combination of these with a conventional method, using the corresponding anthranilic acid, acid anhydride and 4-[3-(1-piperidinyl)propoxy]aniline, 4-[3-(1-pyrrolidinyl)propoxy]aniline or 5-amino-2-[3-(1-piperidinyl)propoxy]pyrimidine as starting materials.

Example 19

3-{4-[3-(1-piperidinyl)propoxy]phenyl}-2-propyl-4(3H)-quinazolinone

The title compound was obtained by the method according to Example 18, using anthranilic acid, butyric anhydride and 4-[3-(1-piperidinyl)propoxy]aniline as starting materials.

$^1$HNMR (400 MHz,CDCl$_3$,δppm): 0.88 (3H, t, J=7.2 Hz), 1.41-1.52 (2H, m), 1.55-1.62 (4H, m), 1.65-1.78 (2H, m), 1.97-2.06 (2H, m), 2.37-2.46 (6H, m), 2.5.0 (2H, t, J=6.8 Hz), 4.06 (2H, t, J=6.8 Hz), 7.02 (2H, d, J=8.4 Hz), 7.12 (2H, d, J=8.4 Hz), 7.43 (1H, t, J=8.0 Hz), 7.67 (1H, d, J=8.4 Hz), 7.73 (1H, t, J=8.0 Hz), 8.24 (1H, d, J=8.0 Hz)

Example 20

3-{4-[3-(1-piperidinyl)propoxy]phenyl}-2-trifluoromethyl-4(3H)-quinazolinone The title compound was obtained by the method according to Example 18, using anthranilic acid, anhydrous trifluoroacetic acid and 4-[3-(1-piperidinyl)propoxy]aniline as starting materials.

$^1$HNMR (400 MHz,CDCl$_3$,δppm): 1.41-1.53 (2H, m), 1.59-1.64 (4H, m), 2.00-2.08 (2H, m), 2.38-2.49 (4H, brs), 2.52 (2H, t, J=7.2 Hz), 4.06 (2H, t, J=6.8 Hz), 7.00 (2H, d, J=8.8 Hz), 7.17 (2H, d, J=8.4 Hz), 7.60-7.65 (1H, m), 7.84-7.89 (2H, m), 8.31 (1H, d, J=7.2 Hz)

Example 21

2-isopropyl-3-{4-[3-(1-piperidinyl)propoxy]phenyl}-4(3H)-quinazolinone

The title compound was obtained by the method according to Example 18, using anthranilic acid, anhydrous isobutyl acid and 4-[3-(1-piperidinyl)propoxy]aniline as starting materials.

$^1$HNMR (400 MHz,CDCl$_3$,δppm): 1.21 (6H, d, J=6.4 Hz), 1.41-1.53 (2H, m), 1.57-1.64 (4H, m), 1.97-2.06 (2H, m), 2.38-2.49 (4H, brs), 2.51 (2H, t, J=7.2 Hz), 2.72-2.79 (1H, m), 4.06 (2H, t, J=6.4 Hz), 7.01 (2H, d, J=8.8 Hz), 7.12 (2H, d, J=8.8 Hz), 7.41 (1H, t, J=7.6 Hz), 7.67-7.75 (2H, m), 8.23 (1H, d, J=8.0 Hz)

Example 22

2,6-dimethyl-3-{4-[3-(1-piperidinyl)propoxy]phenyl}-4(3H)-quinazolinone

The title compound was obtained by the method according to Example 18, using 2-amino-5-methylbenzoic acid, acetic anhydride and 4-[3-(1-piperidinyl)propoxy]aniline as starting materials.

¹HNMR (400 MHz,CDCl₃,δppm): 1.41-1.53 (2H, m), 1.57-1.64 (4H, m), 1.97-2.06 (2H, m), 2.23 (3H, s),2.38-2.49 (4H, brs), 2.48 (3H, s), 2.49 (2H, t, J=7.2 Hz), 4.05 (2H, t, J=6.0 Hz), 7.01 (2H, d, J=9.2 Hz), 7.12 (2H, d, J=8.8 Hz), 7.55 (2H, s),8.03 (1H, s)

Example 23

7-chloro-2-methyl-3-{4-[3-(1-piperidinyl)propoxy]phenyl}-4(3H)-quinazolinone

The title compound was obtained by the method according to Example 18, using 2-amino-4-chlorobenzoic acid, acetic anhydride and 4-[3-(1-piperidinyl)propoxy]aniline as starting materials.

¹HNMR (400 MHz,CDCl₃,δppm): 1.41-1.53 (2H, m), 1.57-1.65 (4H, m), 1.97-2.06 (2H, m), 2.24 (3H, s), 2.37-2.48 (4H, brs), 2.50 (2H, t, J=7.2 Hz), 4.06 (2H, t, J=6.0 Hz), 7.01 (2H, d, J=9.2 Hz), 7.12 (2H, d, J=9.2 Hz), 7.38 (1H, dd, J=2.4, 8.4 Hz), 7.64 (1H, d, J=2.4 Hz), 8.16 (1H, d, J=8.8 Hz)

Example 24

2,8-dimethyl-3-{4-[3-(1-piperidinyl)propoxy]phenyl}-4(3H)-quinazolinone

The title compound was obtained by the method according to Example 18, using 2-amino-3-methylbenzoic acid, acetic anhydride and 4-[3-(1-piperidinyl)propoxy]aniline as starting materials.

¹HNMR (400 MHz,CDCl₃,δppm): 1.41-1.51 (2H, m), 1.56-1.65 (4H, m), 1.97-2.04 (2H, m), 2.26 (3H, s), 2.37-2.48 (4H, brs), 2.49 (2H, t, J=6.8 Hz), 2.63 (3H, s), 4.05 (2H, t, J=6.4 Hz), 7.01 (2H, d, J=8.8 Hz), 7.11 (2H, d, J=8.8 Hz), 7.31 (1H, t, J=8.0 Hz), 7.58 (1H, d, J=7.2 Hz), 8.09 (1H, d, J=8.4 Hz)

Example 25

2-ethyl-5-methyl-3-{4-[3-(1-piperidinyl)propoxy]phenyl}-4(3H)-quinazolinone

The title compound was obtained by the method according to Example 18, using 2-amino-6-methylbenzoic acid, propionic anhydride and 4-[3-(1-piperidinyl)propoxy]aniline as starting materials.

¹HNMR (400 MHz,CDCl₃,δppm): 1.20 (3H, t, J=7.6 Hz), 1.41-1.51 (2H, m), 1.57-1.65 (4H, m), 1.97-2.04 (2H, m), 2.38-2.53 (8H, m), 2.81 (3H, s), 4.05 (2H, t, J=6.4 Hz), 7.02 (2H, d, J=8.8 Hz), 7.11 (2H, d, J=8.8 Hz), 7.18 (1H, d, J=6.4 Hz) 7.50-7.60 (2H, m)

Example 26

5-fluoro-2-methyl-3-{4-[3-(1-piperidinyl)propoxy]phenyl}-4(3H)-quinazolinone

The title compound was synthesized as a white solid (m.p.: 141-145° C.) by the method according to Example 18, using 2-amino-6-fluorobenzoic acid, acetic anhydride and 4-(3-piperidinyl)propoxyaniline as starting materials, followed by recrystallization (ethyl acetate/n-heptane).

¹HNMR (400 MHz,CDCl₃,δppm): 1.41-1.51 (2H, m), 1.57-1.65 (4H, m), 1.97-2.04 (2H, m), 2.24 (3H, s), 2.37-2.48 (4H, brs), 2.50 (2H, t, J=7.2 Hz), 4.06 (2H, t, J=6.0 Hz), 7.01 (2H, d, J=8.8 Hz), 7.05-7.13 (1H, m), 7.11 (2H, d, J=8.8 Hz), 7.44 (1H, d, J=8.4 Hz), 7.63-7.69 (1H, m)

Example 27

5-chloro-2-methyl-3-{4-[3-(1-piperidinyl)propoxy]phenyl}-4(3H)-quinazolinone

The title compound was obtained by the method according to Example 18, using 2-amino-6-chlorobenzoic acid, acetic anhydride and 4-[3-(1-piperidinyl)propoxy]aniline as starting materials.

¹HNMR (400 MHz,CDCl₃,δppm): 1.41-1.50 (2H, m), 1.57-1.64 (4H, m), 1.97-2.04 (2H, m), 2.23 (3H, s), 2.37-2.45 (4H, brs), 2.48 (2H, t, J=7.2 Hz), 4.05 (2H, t, J=6.4 Hz), 7.01 (2H, d, J=8.8 Hz), 7.11 (2H, d, J=8.8 Hz), 7.43 (1H, dd, J=1.6, 8.0 Hz), 7.53-7.60 (2H, m)

Example 28

5-methoxy-2-methyl-3-{4-[3-(1-piperidinyl)propoxy]phenyl}-4(3H)-quinazolinone

The title compound was obtained by the method according to Example 3, using 2-amino-6-methoxybenzoic acid, acetic anhydride and 4-[3-(1-piperidinyl)propoxy]aniline as starting materials.

¹HNMR (400 MHz,CDCl₃,δppm): 1.41-1.50 (2H, m), 1.57-1.64 (4H, m), 1.97-2.04 (2H, m), 2.21 (3H, s), 2.37-2.45 (4H, brs), 2.49 (2H, t, J=7.2 Hz), 3.94 (3H, s), 4.04 (2H, t, J=6.4 Hz), 6.85 (1H, d, J=8.4 Hz), 6.99 (2H, d, J=8.8 Hz), 7.09 (2H, d, J=8.8 Hz), 7.21 (1H, d, J=8.4 Hz), 7.62 (1H, t, J=8.0 Hz)

Example 29

5-hydroxy-2-methyl-3-{4-[3-(1-piperidinyl)propoxy]phenyl}-4(3H)-quinazolinone trifluoroacetate The title compound was obtained by demethylating 5-methoxy-2-methyl-3-{4-[3-(1-piperidinyl)propoxy]phenyl}-4(3H)-quinazolinone synthesized in Example 28 using boron tribromide.

¹HNMR (400 MHz,CDCl₃,δppm): 1.90-2.04 (6H, m), 2.33 (3H, s), 2.85-3.00 (4H, m), 3.22-3.30 (2H, m), 3.71-3.79 (2H, m), 4.13 (2H, t, J=6.0 Hz), 6.94 (1H, d, J=8.4 Hz), 7.03 (2H, d, J=8.8 Hz), 7.17 (2H, d, J=8.8 Hz), 7.22 (1H, d, J=8.0 Hz), 7.68 (1H, t, J=8.0 Hz)

Example 30

2-methyl-3-{4-[3-(1-piperidinyl)propoxy]phenyl}-5-trifluoromethyl-4(3H)-quinazolinone The title compound was obtained by the method according to Example 18, using 2-amino-6-trifluoromethylbenzoic acid, acetic anhydride and 4-[3-(1-piperidinyl)propoxy]aniline as starting materials.

¹HNMR (400 MHz,CDCl₃,δppm): 1.41-1.50 (2H, m), 1.57-1.64 (4H, m), 1.97-2.04 (2H, m), 2.26 (3H, s), 2.37-2.45 (4H, brs), 2.48 (2H, t, J=7.2 Hz), 4.04 (2H, t, J=6.0 Hz), 7.01 (2H, d, J=8.4 Hz), 7.11 (2H, d, J=8.8 Hz), 7.77 (1H, t, J=8.0 Hz), 7.83-7.87 (2H, m)

Example 31

7-fluoro-2-methyl-3-{4-[3-(1-piperidinyl)propoxy]phenyl}-4(3H)-quinazolinone

The title compound was obtained by the method according to Example 18, using 2-amino-4-fluorobenzoic acid, acetic anhydride and 4-[3-(1-piperidinyl)propoxy]aniline as starting materials.

$^1$HNMR (400 MHz,CDCl$_3$,δppm) 1.42-1.49 (2H, m), 1.57-1.64 (4H, m), 1.96-2.06 (2H, m), 2.24 (3H, s), 2.37-2.46 (4H, brs), 2.49 (2H, t, J=7.2 Hz), 4.06 (2H, t, J=6.4 Hz), 7.03 (2H, d, J=8.8 Hz), 7.12 (2H, d, J=8.8 Hz), 7.16 (1H, dd, J=2.4, 8.4 Hz), 7.29 (1H, dd, J=2.4, 9.6 Hz), 8.25 (1H, dd, J=6.0, 8.8 Hz)

Example 32

6-fluoro-2-methyl-3-{4-[3-(1-piperidinyl)propoxy]phenyl}-4(3H)-quinazolinone

The title compound was obtained by the method according to Example 18, using 2-amino-5-fluorobenzoic acid, acetic anhydride and 4-[3-(1-piperidinyl)propoxy]aniline as starting materials.

$^1$HNMR (400 MHz,CDCl$_3$,δppm) 1.41-1.49 (2H, m), 1.56-1.65 (4H, m), 1.96-2.06 (2H, m), 2.24 (3H, s), 2.37-2.46 (4H, brs), 2.49 (2H, t, J=6.8 Hz), 4.06 (2H, t, J=6.4 Hz), 7.03 (2H, d, J=8.8 Hz), 7.12 (2H, d, J=8.8 Hz), 7.42-7.48 (1H, m), 7.65 (1H, dd, J=4.8, 9.2 Hz), 7.87 (1H, dd, J=2.8, 8.4 Hz)

Example 33

6,7-difluoro-2-methyl-3-{4-[3-(1-piperidinyl)propoxy]phenyl}-4(3H)-quinazolinone The title compound was obtained by the method according to Example 18, using 2-amino-4,5-difluorobenzoic acid, acetic anhydride and 4-[3-(1-piperidinyl)propoxy]aniline as starting materials.

$^1$HNMR (400 MHz,CDCl$_3$,δppm): 1.42-1.49 (2H, m), 1.57-1.63 (4H, m), 1.96-2.05 (2H, m), 2.23 (3H, s), 2.37-2.46 (4H, brs), 2.49 (2H, t, J=6.8 Hz), 4.06 (2H, t, J=6.4 Hz), 7.03 (2H, d, J=8.8 Hz), 7.11 (2H, d, J=8.8 Hz), 7.42 (1H, dd, J=7.2, 11.2 Hz), 7.99 (1H, dd, J=8.4, 10 Hz)

Example 34

6-bromo-2-methyl-3-{4-[3-(1-piperidinyl)propoxy]phenyl}-4(3H)-quinazolinone

The title compound was obtained by the method according to Example 18, using 2-amino-5-bromobenzoic acid, acetic anhydride and 4-[3-(1-piperidinyl)propoxy]aniline as starting materials.

$^1$HNMR (400 MHz,CDCl$_3$,δppm): 1.45 (2H, brs), 1.57-1.65 (4H, m), 1.98-2.03 (2H, m), 2.23 (3H, s), 2.41-2.51 (6H, m), 4.06 (2H, t, J=6.4 Hz), 7.03 (2H, d, J=8.8 Hz), 7.11 (2H, d, J=8.8 Hz), 7.52 (1H, d, J=8.8 Hz), 7.81 (1H, dd, J=2.4, 8.8 Hz), 8.36 (1H, s)

Example 35

6-chloro-2-methyl-3-{4-[3-(1-piperidinyl)propoxy]phenyl}-4(3H)-quinazolinone

The title compound was obtained by the method according to Example 18, using 2-amino-5-chlorobenzoic acid, acetic anhydride and 4-[3-(1-piperidinyl)propoxy]aniline as starting materials.

$^1$HNMR (400 MHz,CDCl$_3$,δppm): 1.41-1.49 (2H, m), 1.56-1.63 (4H, m), 1.97-2.05 (2H, m), 2.24 (3H, s), 2.37-2.45 (4H, brs), 2.49 (2H, t, J=6.8 Hz), 4.06 (2H, t, J=6.4 Hz), 7.02 (2H, d, J=8.8 Hz), 7.11 (2H, d, J=8.8 Hz), 7.59 (1H, d, J=9.2 Hz), 7.66 (1H, dd, J=2.8, 8.8 Hz), 8.20 (1H, d, J=2.4 Hz)

Example 36

6-methoxy-2-methyl-3-{4-[3-(1-piperidinyl)propoxy]phenyl}-4(3H)-quinazolinone

The title compound was synthesized as a white solid (m.p.: 136-138° C.) by the method according to Example 18, using 2-amino-5-methoxybenzoic acid, acetic anhydride and 4-(3-piperidinyl)propoxyaniline as starting materials, followed by recrystallization (ethyl acetate/diethyl ether/n-heptane).

$^1$HNMR (400 MHz,CDCl$_3$,δppm): 1.41-1.49 (2H, m), 1.56-1.63 (4H, m), 1.98-2.05 (2H, m), 2.22 (3H, s), 2.37-2.46 (4H, brs), 2.49 (2H, t, J=7.6 Hz), 3.89 (3H, s), 4.06 (2H, t, J=6.0 Hz), 7.02 (2H, d, J=8.8 Hz), 7.11 (2H, d, J=8.8 Hz), 7.33 (1H, dd, J=2.8, 8.8 Hz), 7.58 (1H, d, J=8.8 Hz), 7.61 (1H, d, J=3.2 Hz)

Example 37

6,7-dimethoxy-2-methyl-3-{4-[3-(1-piperidinyl)propoxy]phenyl}-4(3H)-quinazolinone The title compound was obtained by the method according to Example 18, using 2-amino-4,5-dimethoxybenzoic acid, acetic anhydride and 4-[3-(1-piperidinyl)propoxy]aniline as starting materials.

$^1$HNMR (400 MHz,CDCl$_3$,δppm): 1.41-1.49 (2H, m), 1.57-1.65 (4H, m), 1.98-2.05 (2H, m), 2.22 (3H, s), 2.37-2.46 (4H, brs), 2.49 (2H, t, J=7.6 Hz), 3.97 (3H, s), 4.00 (3H, s), 4.06 (2H, t, J=6.0 Hz), 7.02 (2H, d, J=8.8 Hz), 7.11 (2H, d, J=8.8 Hz), 7.24 (1H, s), 7.56 (1H, s)

Example 38

8-chloro-2-methyl-3-{4-[3-(1-piperidinyl)propoxy]phenyl}-4(3H)-quinazolinone

The title compound was obtained by the method according to Example 18, using 2-amino-3-chlorobenzoic acid, acetic anhydride and 4-[3-(1-piperidinyl)propoxy]aniline as starting materials.

$^1$HNMR (400 MHz,CDCl$_3$,δppm): 1.41-1.48 (2H, m), 1.57-1.63 (4H, m), 1.97-2.04 (2H, m), 2.32 (3H, s), 2.37-2.45 (4H, brs), 2.49 (2H, t, J=7.6 Hz), 4.06 (2H, t, J=6.4 Hz), 7.03 (2H, d, J=8.8 Hz), 7.11 (2H, d, J=8.8 Hz), 7.35 (1H, t, J=7.6 Hz), 7.81 (1H, dd, J=1.2, 8.0 Hz), 8.17 (1H, dd, J=1.2, 8.0 Hz)

Example 39

8-methoxy-2-methyl-3-{4-[3-(1-piperidinyl)propoxy]phenyl}-4(3H)-quinazolinone

The title compound was obtained by the method according to Example 18, using 2-amino-3-methoxybenzoic acid, acetic anhydride and 4-[3-(1-piperidinyl)propoxy]aniline as starting materials.

$^1$HNMR (400 MHz, CDCl$_3$, δppm): 1.41-1.48 (2H, m), 1.57-1.63 (4H, m), 1.97-2.04 (2H, m), 2.31 (3H, s), 2.37-2.45 (4H, brs), 2.49 (2H, t, J=7.2 Hz), 4.03 (3H, s), 4.05 (2H, t, J=6.4 Hz), 7.02 (2H, d, J=8.8 Hz), 7.11 (2H, d, J=8.8 Hz), 7.19 (1H, dd, J=1.2, 8.0 Hz), 7.38 (1H, t, J=8.0 Hz), 7.83 (1H, dd, J=1.2, 8.0 Hz)

Example 40

2-methyl-3-{4-[3-(1-piperidinyl)propoxy]phenyl}benzo[g]-quinazolin-4(3H)-one

The title compound was obtained by the method according to Example 18, using 3-amino-2-naphthoic acid, acetic anhydride and 4-[3-(1-pyrrolidinyl)propoxy]aniline as starting materials.

$^1$HNMR (400 MHz, CDCl$_3$, δppm): 1.41-1.52 (2H, m), 1.57-1.64 (4H, m), 1.98-2.06 (2H, m), 2.28 (3H, s), 2.38-2.46 (4H, brs), 2.50 (2H, t, J=7.2 Hz), 4.07 (2H, t, J=6.8 Hz), 7.04 (2H, d, J=8.8 Hz), 7.17 (2H, d, J=8.8 Hz), 7.51 (1H, t, J=7.6 Hz), 7.59 (1H, t, J=7.6 Hz), 7.97 (1H, d, J=8.4 Hz), 8.03 (1H, d, J=8.0 Hz), 8.12 (1H, s), 8.86 (1H, s)

Example 41

2,6-dimethyl-3-{4-[3-(1-pyrrolidinyl)propoxy]phenyl}-4(3H)-quinazolinone (1) Manufacture of 4-[3-(1-pyrrolidinyl)propoxy]aniline The target compound was obtained by the method according to Example 18, using 3-pyrrolidin-1-yl-propan-1-ol, and 4-nitrophenol or 1-fluoro-4-nitrobenzene as starting materials.

(2) Manufacture of 2,6-dimethyl-3-{4-[3-(1-pyrrolidinyl)propoxy]phenyl}-4(3H)-quinazolinone The title compound was obtained by the method according to Example 18, using 2-amino-5-methylbenzoic acid, acetic anhydride and 4-[3-(1-pyrrolidinyl)propoxy]aniline as starting materials.

$^1$HNMR (400 MHz, CDCl$_3$, δppm): 1.76-1.84 (4H, m), 2.00-2.09 (2H, m), 2.23 (3H, s), 2.47 (3H, s), 2.50-2.58 (4H, m), 2.64 (2H, t, J=7.2 Hz), 4.08 (2H, t, J=6.4 Hz), 7.02 (2H, d, J=8.8 Hz), 7.12 (2H, d, J=8.8 Hz), 7.55 (2H, s), 8.03 (1H, s)

NMR data for 4-[3-(1-pyrrolidinyl)propoxy]aniline used for manufacturing the compound of this example is shown below.

1HNMR (400 MHz, CDCl$_3$, δppm): 1.77-1.80 (4H, m), 1.93-2.00 (2H, m), 2.49-2.54 (4H, m), 2.60 (2H, t, J=7.6 Hz), 3.41 (2H, brs), 3.95 (2H, t, J=6.6 Hz), 6.63 (2H, d, J=8.8 Hz), 6.74 (2H, d, J=9.3 Hz)

4-[3-(1-pyrrolidinyl)propoxy]aniline can also be obtained as 4-[3-(1-pyrrolidinyl)propoxy]aniline ditosylate by treating with 2 Eq of p-toluenesulfonic acid. NMR data for this tosyl salt is shown below.

1HNMR (DMSO-d6)δ: 1.81-1.90 (2H, m), 1.96-2.05 (2H, m), 2.06-2.13 (2H, m), 2.29 (6H, s), 3.02-3.04 (2H, m), 3.28-3.30 (2H, m), 3.57-3.59 (2H, m), 4.05 (2H, t, J=6.1 Hz), 7.03 (2H, d, J=8.8 Hz), 7.12 (4H, d, J=7.8 Hz), 7.28 (2H, d, J=8.8 Hz), 7.49 (4H, d, J=7.8 Hz), 9.49 (1H, brs), 9.73 (2H, brs)

Example 42

2-ethyl-5-methyl-3-{(4-[3-(1-pyrrolidinyl)propoxy]phenyl}-4(3H)-quinazolinone

The title compound was obtained by the method according to Example 18, using 2-amino-6-methylbenzoic acid, propionic anhydride and 4-[3-(1-pyrrolidinyl)propoxy]aniline as starting materials.

$^1$HNMR (400 MHz, CDCl$_3$, δppm): 1.20 (3H, t, J=7.2 Hz), 1.76-1.85 (4H, m), 2.00-2.09 (2H, m), 2.43 (2H, q, J=7.6 Hz), 2.50-2.59 (4H, m), 2.65 (2H, t, J=7.2 Hz), 2.81 (3H, s), 4.07 (2H, t, J=6.0 Hz), 7.03 (2H, d, J=8.8 Hz), 7.12 (2H, d, J=8.8 Hz), 7.18 (1H, d, J=6.8 Hz), 7.51-7.59 (2H, m)

Example 43

5-fluoro-2-methyl-3-{4-[3-(1-pyrrolidinyl)propoxy]phenyl}-4(3H)-quinazolinone

The title compound was obtained by the method according to Example 18, using 2-amino-6-fluorobenzoic acid, acetic anhydride and 4-[3-(1-pyrrolidinyl)propoxy]aniline as starting materials.

$^1$HNMR (400 MHz, CDCl$_3$, δppm): 1.77-1.83 (4H, m), 2.00-2.08 (2H, m), 2.23 (3H, s), 2.51-2.56 (4H, m), 2.64 (2H, t, J=7.2 Hz), 4.08 (2H, t, J=6.4 Hz), 7.03 (2H, d, J=8.8 Hz), 7.02-7.11 (1H, m), 7.12 (2H, d, J=8.8 Hz), 7.43 (1H, d, J=8.0 Hz), 7.63-7.68 (1H, m)

Example 44

2-methyl-3-{4-[3-(1-pyrrolidinyl)propoxy]phenyl}-5-trifluoromethyl-4(3H)-quinazolinone The title compound was synthesized as a white solid (m.p.: 137-140° C.) by the method according to Example 18, using 2-amino-6-trifluoromethylbenzoic acid, acetic anhydride and 4-[(3-(1-pyrrolidinyl)propoxy]aniline as starting materials, followed by recrystallization (ethyl acetate/n-heptane).

$^1$HNMR (400 MHz, CDCl$_3$, δppm): 1.77-1.83 (4H, m), 2.00-2.08 (2H, m), 2.26 (3H, s), 2.51-2.57 (4H, m), 2.63 (2H, t, J=7.2 Hz), 4.07 (2H, t, J=6.8 Hz), 7.03 (2H, d, J=8.8 Hz), 7.12 (2H, d, J=8.8 Hz), 7.79 (1H, t, J=7.6 Hz), 7.82-7.88 (2H, m)

Example 45

5-chloro-2-methyl-3-{4-[3-(1-pyrrolidinyl)propoxy]phenyl}-4(3H)-quinazolinone

The title compound was obtained by the method according to Example 18, using 2-amino-6-chlorobenzoic acid, acetic anhydride and 4-[3-(1-pyrrolidinyl)propoxy]aniline as starting materials.

$^1$HNMR (400 MHz, CDCl$_3$, δppm): 1.77-1.84 (4H, m), 2.00-2.08 (2H, m), 2.22 (3H, s), 2.51-2.56 (4H, m), 2.64 (2H, t, J=6.8 Hz), 4.07 (2H, t, J=6.4 Hz), 7.03 (2H, d, J=8.8 Hz), 7.12 (2H, d, J=8.8 Hz), 7.43 (1H, dd, J=2.0, 7.6 Hz), 7.44-7.60 (2H, m)

Example 46

2-ethyl-3-{4-[3-(1-pyrrolidinyl)propoxy]phenyl}-4(3H)-quinazolinone

The title compound was obtained by the method according to Example 18, using anthranilic acid, propionic anhydride and 4-[3-(1-pyrrolidinyl)propoxy]aniline as starting materials.

$^1$HNMR (400 MHz,CDCl$_3$,δppm): 1.21 (3H, t, J=7.2 Hz), 1.77-1.84 (4H, m), 2.01-2.09 (2H, m), 2.46 (2H, q, J=7.2 Hz), 2.51-2.58 (4H, m), 2.65 (2H, t, J=6.8 Hz), 4.08 (2H, t, J=6.4 Hz), 7.03 (2H, d, J=8.8 Hz), 7.12 (2H, d, J=8.8 Hz), 7.43 (1H, t, J=8.0 Hz), 7.67-7.76 (2H, m), 8.24 (1H, d, J=8.4 Hz)

Example 47

2,5-dimethyl-3-{4-[3-(1-pyrrolidinyl)propoxy]phenyl}-4(3H)-quinazolinone

The title compound was synthesized as a white solid (m.p.: 112-113° C.) by the method according to Example 18, using 2-amino-6-methylbenzoic acid, acetic anhydride and 4-[(3-(1-pyrrolidinyl)propoxy]aniline as starting materials, followed by recrystallization (ethyl acetate/diethyl ether).

$^1$HNMR (400 MHz,CDCl$_3$,δppm): 1.77-1.84 (4H, m), 2.01-2.09 (2H, m), 2.22 (3H, s), 2.51-2.58 (4H, m), 2.63 (2H, t, J=7.2 Hz), 2.81 (3H, s), 4.07 (2H, t, J=6.4 Hz), 7.03 (2H, d, J=8.8 Hz), 7.12 (2H, d, J=8.8 Hz), 7.19 (1H, d, J=7.6 Hz), 7.48 (1H, d, J=8.0 Hz), 7.57 (1H, t, J=8.0 Hz)

Example 48

2-methyl-3-{4-[3-(1-piperidinyl)propoxy]phenyl}pyrido[2,3-d]pyrimidin-4(3H)-one

The title compound was obtained by the method according to Example 18, using 2-amino-nicotinic acid, acetic anhydride and 4-[3-(1-piperidinyl)propoxy]aniline as starting materials.

$^1$HNMR (400 MHz,CDCl$_3$:CD$_3$OD=6:1,δppm): 1.42-1.53 (2H, m), 1.59-1.67 (4H, m), 2.00-2.07 (2H, m), 2.33 (3H, s), 2.41-2.48 (4H, brs), 2.53 (2H, t, J=7.2 Hz), 4.06 (2H, t, J=6.4 Hz), 7.05 (2H, d, J=8.8 Hz), 7.13 (2H, d, J=8.8 Hz), 7.43 (1H, dd, J=4.4, 7.6 Hz), 8.58 (1H, dd, J=2.4, 7.6 Hz), 8.95 (1H, dd, J=2.0, 4.8 Hz)

Example 49

2-methyl-3-{4-[3-(1-pyrrolidinyl)propoxy]phenyl}pyrido[2,3-d]pyrimidin-4(3H)-one The title compound was obtained by the method according to Example 18, using 2-aminonicotinic acid, acetic anhydride and 4-[3-(1-pyrrolidinyl)propoxy]aniline as starting materials.

$^1$HNMR (400 MHz,CDCl$_3$,δppm): 1.76-1.84 (4H, m), 2.00-2.10 (2H, m), 2.34 (3H, s), 2.50-2.59 (4H, m), 2.65 (2H, t, J=6.8 Hz), 4.08 (2H, t, J=6.4 Hz), 7.03 (2H, d, J=8.8 Hz), 7.12 (2H, d, J=8.8 Hz), 7.39 (1H, dd, J=4.8, 8.8 Hz), 8.56 (1H, dd, J=2.4, 8.4 Hz), 8.96 (1H, dd, J=2.4, 4.4 Hz)

Example 50

6-chloro-2-methyl-3-{4-[3-(1-pyrrolidinyl)propoxy]phenyl}pyrido[3,4-d]pyrimidin-4(3H)-one The title compound was obtained by the method according to Example 18, using 5-amino-2-chloroisonicotinic acid, acetic anhydride and 4-[3-(1-pyrrolidinyl)propoxy]aniline as starting materials. 5-amino-2-chloroisonicotinic acid was manufactured according to the method described in the literature (J. Chem. Soc. Perkin Trans. 1, 1996, p. 2221).

$^1$HNMR (400 MHz,CD$_3$OD, δppm): 2.08-2.16 (4H, brs), 2.24-2.32 (5H, m), 3.37-3.48 (6H, m), 4.21 (2H, t, J=5.6 Hz), 7.16 (2H, d, J=9.2 Hz), 7.31 (2H, d, J=9.2 Hz), 8.03 (1H, s), 8.83 (1H, s)

Example 51

2-methyl-3-[4-[3-(1-piperidinyl)propoxy]phenylpyrido[3,4-d]pyrimidin-4(3H)-one

The title compound was obtained by catalytic reduction of 6-chloro-2-methyl-3-{4-[3-(1-piperidinyl)propoxy]phenyl}pyrido[3,4-d]pyrimidin-4(3H)-one synthesized in Example 63 in ethyl acetate using a palladium charcoal catalyst in the presence of triethylamine.

$^1$HNMR (400 MHZ,CDCl$_3$,δppm): 1.41-1.50 (2H, m), 1.57-1.64 (4H, m), 1.98-2.05 (2H, m), 2.29 (3H, s), 2.39-2.45 (4H, brs), 2.50 (2H, t, J=7.2 Hz), 4.06 (2H, t, J=6.4 Hz), 7.05 (2H, d, J=8.8 Hz), 7.12 (2H, d, J=8.8 Hz), 8.01 (1H, d, J=5.2 Hz), 8.65 (1H, d, J=5.2 Hz), 9.10 (1H, s)

Example 52

2-methyl-3-{4-[3-(1-pyrrolidinyl)propoxy]phenyl}pyrido[4,3-d]pyrimidin-4 (3H)-one The title compound was obtained by the method according to Example 18, using 4-aminonicotinic acid, acetic anhydride and 4-[3-(1-pyrrolidinyl)propoxy]aniline as starting materials.

$^1$HNMR (400 MHz,CD$_3$OD, δppm): 2.23-2.33 (4H, m), 2.23-2.33 (5H, m), 3.36-3.49 (6H, brt, J=8.0 Hz), 4.20 (2H, t, J=6.0 Hz), 7.14 (2H, d, J=8.8 Hz), 7.30 (2H, d, J=8.8 Hz), 7.57 (1H, dd, J=0.8, 6.0 Hz), 8.78 (1H, d, J=5.6 Hz), 9.28 (1H, d, J=0.8 Hz)

Example 53

2-methyl-3-{4-[3-(1-piperidinyl)propoxy]phenyl}pyrido[4,3-d]pyrimidin-4(3H)-one

The title compound was obtained by the method according to Example 18, using 4-aminonicotinic acid, acetic anhydride and 4-[3-(1-piperidinyl)propoxy]aniline as starting materials.

$^1$HNMR (400 MHz,CDCl$_3$,δppm): 1.40-1.49 (2H, m), 1.53-1.66 (4H, m), 1.97-2.05 (2H, m), 2.29 (3H, s), 2.35-2.45 (4H, brs), 2.50 (2H, t, J=6.8 Hz), 4.07 (2H, t, J=6.4 Hz), 7.04 (2H, d, J=8.8 Hz), 7.12 (2H, d, J=8.8 Hz), 7.47 (1H, dd, J=0.8, 5.2 Hz), 8.82 (1H, d, J=5.6 Hz), 9.45 (1H, d, J=0.8 Hz)

Example 54

2-methyl-3-{2-[3-(1-piperidinyl)propoxy]-5-pyrimidinyl}-4(3H)-quinazolinone (1) Manufacture of 5-nitro-2-(3-piperidin-1-yl-propoxy)pyrimidine 2-chloro-5-nitropyrimidine (300 mg, 1.88 mmol), 3-piperidin-1-yl-propan-1-ol (323 mg, 2.26 mmol) and cesium carbonate (725 mg, 3.76 mmol) were mixed in dry dimethylformamide (5 mL), and stirred for 2 days at room temperature. The solvent was distilled off under reduced pressure, ethyl acetate and 1N sodium hydroxide aqueous solution were added, and the mixture extracted with ethyl acetate. After drying with anhydrous sodium sulfate, the product was purified by silica gel column chromatography (chloroform/methanol=30/1), and the target compound (110 mg, 22%) was obtained as a light brown solid. 2-chloro-5-nitropyrimidine was manufactured by the method described in the literature (Heterocycles, 1984, Vol. 22, p. 79).

(2) Manufacture of 5-amino-2-(3-piperidin-1-yl-propoxy)pyrimidine 5-nitro-2-(3-piperidin-1-yl-propoxy)pyrimidine (100 mg, 0.38 mmol) was dissolved in a mixed solvent of methanol (2 mL) and distilled water (2 mL), sodium dithionite ($Na_2S_2O_4$) (655 mg) was added, and the mixture stirred for 30 minutes at room temperature. The solvent was distilled off under reduced pressure, methanol was added to the residue, and the precipitate was filtered off. The filtrate was concentrated, and the target compound (60 mg, 68%) was obtained as a yellow oily residue.

(3) Manufacture of 2-methyl-3-{2-[3-(1-piperidinyl)propoxy]-5-pyrimidinyl}-4(3H)-quinazolinone The title compound was obtained by the method according to Example 18, using anthranilic acid, acetic anhydride and 5-amino-2-[3-(1-piperidinyl)propoxy]pyrimidine as starting materials.

$^1$HNMR (400 MHz,CDCl$_3$,δppm) 1.41-1.47 (2H, m), 1.57-1.64 (4H, m), 2.02-2.10 (2H, m), 2.30 (3H, s),2.37-2.46 (4H, brs), 2.53 (2H, t, J=7.2 Hz), 4.49 (2H, t, J=6.4 Hz), 7.49 (1H, dt, J=0.8, 7.6 Hz), 7.67 (1H, d, J=7.6 Hz), 7.79 (1H, dt, J=1.6, 7.6 Hz), 8.24 (1H, dd, J=1.6, 8.0 Hz), 8.43 (2H, s)

Example 55

2,5-dimethyl-3-{2-[3-(1-piperidinyl)propoxy]-5-pyrimidinyl}-4(3H)-quinazolinone

The title compound was obtained by the method according to Example 18, using 2-amino-6-methylbenzoic acid, acetic anhydride and 5-amino-2-[3-(1-piperidinyl)propoxy]pyrimidine as starting materials.

$^1$HNMR (400 MHz,CDCl$_3$,δppm): 1.40-1.48 (2H, m), 1.57-1.64 (4H, m), 2.02-2.10 (2H, m), 2.27 (3H, s), 2.37-2.47 (4H, brs), 2.49 (3H, s), 2.53 (2H, t, J=7.2 Hz), 4.48 (2H, t, J=6.4 Hz), 7.55-7.62 (2H, m), 8.02 (1H, s), 8.42 (2H, s)

Example 56

2-ethyl-3-{4-[3-(1-piperidinyl)propoxy]phenyl}pyrido[2,3-d]pyrimidin-4 (3H)-one

The title compound was obtained by the method according to Example 18, using 2-aminonicotinic acid, propionic anhydride and 4-[3-(1-piperidinyl)propoxy]aniline as starting materials.

$^1$HNMR (400 MHz,CDCl$_3$,CD$_3$OD, δppm) 1.30 (3H, t, J=7.2 Hz), 1.42-1.52 (2H, brs), 1.59-1.67 (4H, m), 1.97-2.07 (2H, m), 2.47-2.58 (8H, m), 4.07 (2H, t, J=6.4 Hz), 7.03 (2H, d, J=8.8 Hz), 7.12 (2H, d, J=8.8 Hz), 7.39 (1H, dd, J=4.8, 8.0 Hz), 8.57 (1H, dd, J=2.0, 7.6 Hz), 8.96 (1H, dd, J=2.4, 4.8 Hz)

Example 57

6-chloro-2-ethyl-3-{4-[3-(1-piperidinyl)propoxy]phenyl}pyrido[3,4-d]pyrimidin-4(3H)-one The title compound was obtained by the method according to Example 18, using 5-amino-2-chloroisonicotinic acid, propionic anhydride and 4-[3-(1-piperidinyl)propoxy]aniline as starting materials.

$^1$HNMR (400 MHz,CDCl$_3$,δppm): 1.23 (3H, t, J=7.2 Hz), 1.41-1.50 (2H, m), 1.57-1.64 (4H, m), 1.98-2.05 (2H, m), 2.39-2.53 (8H, m), 4.07 (2H, t, J=6.4 Hz), 7.05 (2H, d, J=8.8 Hz), 7.12 (2H, d, J=8.8 Hz), 8.06 (1H, s), 8.94 (1H, s)

Example 58

6-chloro-2-ethyl-3-{4-[3-(1-pyrrolidinyl)propoxy]phenyl}pyrido[3,4-d]pyrimidin-4(3H)-one The title compound was obtained by the method according to Example 18, using 5-amino-2-chloroisonicotinic acid, propionic anhydride and 4-[3-(1-pyrrolidinyl)propoxy]aniline as starting materials.

$^1$HNMR (400 MHz, CDCl$_3$,δppm): 1.23 (3H, t, J=7.6 Hz), 1.79-1.86 (4H, m), 2.01-2.11 (2H, m), 2.46 (2H, q, J=7.6 Hz), 2.50-2.62 (4H, brs), 2.67 (2H, t, J=6.8 Hz), 4.09 (2H, t, J=6.4 Hz), 7.05 (2H, d, J=8.8 Hz), 7.10 (2H, d, J=8.8 Hz), 8.03 (1H, s), 8.91 (1H, s)

Example 59

2-ethyl-3-{4-[3-(1-piperidinyl)propoxy]phenyl}pyrido[3,4-d]pyrimidin-4(3H)-one

The title compound was obtained by catalytic reduction of 6-chloro-2-ethyl-3-{4-[3-(1-piperidinyl)propoxy]phenyl}pyrido[3,4-d]pyrimidin-4 (3H)-one synthesized in Example 57 using palladium charcoal as catalyst in the presence of triethylamine.

$^1$HNMR (400 MHz,CDCl$_3$,δppm): 1.24 (3H, t, J=7.2 Hz), 1.41-1.49 (2H, m), 1.57-1.65 (4H, m), 1.98-2.06 (2H, m), 2.39-2.56 (8H, m), 4.07 (2H, t, J=6.4 Hz), 7.03 (2H, d, J=8.8 Hz), 7.13 (2H, d, J=8.8 Hz), 8.00 (1H, dd, J=0.8, 4.8 Hz), 8.64 (1H, dd, J=4.8 Hz), 9.13 (1H, d, J=0.8 Hz)

Example 60

2-ethyl-3-{4-[3-(1-pyrrolidinyl)propoxy]phenyl}pyrido[3,4-d]pyrimidin-4(3H)-one

The title compound was obtained by catalytic reduction of 6-chloro-2-ethyl-3-{4-[3-(1-pyrrolidinyl)propoxy]

phenyl}pyrido[3,4-d]pyrimidin-4 (3H)-one synthesized in Example 58 using palladium charcoal as catalyst in the presence of triethylamine.

$^1$HNMR (400 MHz,CDCl$_3$,δppm): 1.24 (3H, t, J=7.2 Hz), 1.81-1.86 (4H, m), 2.05-2.13 (2H, m), 2.48 (2H, q, J=7.2 Hz), 2.59-2.67 (4H, brs), 2.72 (2H, t, J=7.2 Hz), 4.09 (2H, t, J=6.0 Hz), 7.03 (2H, d, J=8.8 Hz), 7.1 (2H, d, J=8.8 Hz), 8.00 (1H, dd, J=0.8, 5.2 Hz), 8.64 (1H, dd, J=4.8 Hz), 9.13 (1H, d, J=0.8 Hz)

Example 61

2-ethyl-3-{4-[3-(1-piperidinyl)propoxy]phenyl}pyrido[4,3-d]pyrimidin-4(3H)-one

The title compound was obtained by the method according to Example 18, using 4-aminonicotinic acid, propionic anhydride and 4-[3-(1-piperidinyl)propoxy]aniline as starting materials.

$^1$HNMR (400 MHz,CDCl$_3$,δ ppm): 1.23 (3H, t, J=7.6 Hz), 1.42-1.51 (2H, m), 1.59-1.67 (4H, m), 2.00-2.09 (2H, m), 2.42-2.58 (8H, m), 4.08 (2H, t, J=6.4 Hz), 7.05 (2H, d, J=8.8 Hz), 7.13 (2H, d, J=8.8 Hz), 7.53 (1H, d, J=6.0 Hz), 8.84 (1H, d, J=5.6 Hz), 9.47 (1H, s)

Example 62

2-ethyl-3-{4-[3-(1-pyrrolidinyl)propoxy]phenyl}pyrido[4,3-d]pyrimidin-4(3H)-one

The title compound was obtained by the method according to Example 18, using 4-aminonicotinic acid, propionic anhydride and 4-[3-(1-pyrrolidinyl)propoxy]aniline as starting materials.

$^1$HNMR (400 MHz,CDCl$_3$,δppm) 1.23 (3H, t, J=7.2 Hz), 1.99-2.07 (4H, m), 2.25-2.35 (2H, m), 2.48 (2H, q, J=7.6 Hz), 2.96-3.07 (4H, brs), 4.14 (2H, t, J=6.0 Hz), 7.05 (2H, d, J=8.8 Hz), 7.15 (2H, d, J=8.8 Hz), 7.53 (1H, d, J=5.6 Hz), 8.84 (1H, d, J=5.6 Hz), 9.47 (1H, s)

Example 63

6-chloro-2-methyl-3-{4-[3-(1-piperidinyl)propoxy]phenyl}pyrido[3,4-d]pyrimidin-4 (3H)-one Using 5-amino-4-carboxy-2-chloropyridine and acetic anhydride as starting materials, 6-chloro-2-methyl-3-(4-hydroxyphenyl)pyrido[3,4-d]pyrimidin-4(3H)-one synthesized according to Example 1-(1) and -(2) (52 mg, 0.18 mmol), 1-(3-bromopropyl)piperidine hydrobromide (78 mg, 0.27 mmol) and potassium carbonate (100 mg, 0.72 mmol) were mixed in dimethylformamide (1 mL) and stirred at 80° C. for 1 hour. The solvent was distilled off under reduced pressure, distilled water was added, and the mixture was extracted with ethyl acetate. The organic phase was washed with distilled water, and dried with anhydrous sodium sulfate. The title compound (45 mg, 60%) was obtained as colorless crystals by purifying with silica gel column chromatography (chloroform/methanol=30/1) and recrystallizing (ethanol).

$^1$HNMR (400 MHz,CDCl$_3$,δppm): 1.41-1.50 (2H, m), 1.57-1.64 (4H, m), 1.98-2.05 (2H, m), 2.28 (3H, s),2.39-2.46 (4H, brs), 2.50 (2H, t, J=7.2 Hz), 4.06 (2H, t, J=6.4 Hz), 7.04 (2H, d, J=8.8 Hz), 7.11 (2H, d, J=8.8 Hz), 8.04 (1H, s), 8.88 (1H, s)

Example 64

3-{4-[3-(1-piperidinyl)propoxy]phenyl}-4(3H)-quinazolinone

The title compound was obtained by alkylating 3-(4-hydroxyphenyl)-4(3H)quinazolinone and 1-(3-bromopropyl)piperidine hydrobromide according to Example 63. 3-(4-hydroxyphenyl)-4 (3H) quinazolinone was manufactured by the method described in the literature (Heterocycles, 1993, Vol. 35, p. 775).

$^1$HNMR (400 MHz,CDCl$_3$,δppm): 1.41-1.50 (2H, m), 1.56-1.63 (4H, m), 1.97-2.04 (2H, m), 2.38-2.45 (4H, brs), 2.49 (2H, t, J=7.2 Hz), 4.06 (2H, t, J=6.8 Hz), 7.02 (2H, d, J=8.8 Hz), 7.29 (2H, d, J=8.8 Hz), 7.52 (1H, t, J=8.0 Hz), 7.72-7.80 (2H, m), 8.09 (1H, s), 8.34 (1H, d, J=8.0 Hz)

Example 65

6-(acetylamino)-2-methyl-3-{4-[3-(1-piperidinyl)propoxy]phenyl}-4(3H)-quinazolinone (1) Manufacture of 6-amino-2-methyl-3-{4-[3-(1-piperidinyl)propoxy]phenyl}-4(3H)-quinazolinone 2-methyl-6-nitro-3-{4-[3-(1-piperidinyl)propoxy]phenyl}-4(3H)-quinazolinone synthesized according to Example 1 (110 mg, 0.26 mmol) was dissolved in methanol (3 mL), and the atmosphere in the system replaced by nitrogen. After adding 10% palladium charcoal (100 mg), the atmosphere was replaced by hydrogen, and the mixture stirred at room temperature for 1 Hour. The catalyst was filtered off, and the filtrate was concentrated to dryness to obtain the target compound (91 mg, 89%) as a light yellow solid.

(2) Manufacture of 6-(acetylamino)-2-methyl-3-{4-[3-(1-piperidinyl)propoxy]phenyl}-4(3H)-quinazolinone 6-amino-2-methyl-3-{4-[3-(1-piperidinyl)propoxy]phenyl}-4(3H)-quinazolinone (228 mg, 0.58 mmol) were dissolved in a mixed solvent of dry tetrahydrofuran (5 mL) and dry pyridine (1 mL), and coooled on an ice bath. Acetyl chloride (68 mg, 0.87 mmol) was dripped in, and the mixture stirred at room temperature overnight. Ethyl acetate and 1N sodium hydroxide aqueous solution were added, the mixture was extracted with ethyl acetate, and the organic phase was dried with anhydrous sodium sulfate. The product was purified by silica gel column chromatography (chloroform/methanol=20/1), and the title compound (156 mg, 62%) was obtained as colorless crystals by recrystallization from diethyl ether/heptane.

$^1$HNMR (400 MHz,CDCl$_3$,δppm): 1.40-1.49 (2H, m), 1.52-1.65 (4H, m), 1.97-2.07 (2H, m), 2.02 (3H, s), 2.23 (3H, s), 2.38-2.46 (4H, brs), 2.50 (2H, t, J=7.2 Hz), 4.05 (2H, t, J=6.0 Hz), 7.03 (2H, d, J=8.8 Hz), 7.12 (2H, d, J=8.8 Hz), 7.64 (1H, d, J=8.8 Hz), 7.86-7.92 (1H, brs), 7.99 (1H, d, J=2.8 Hz), 8.40 (1H, dd, J=2.0, 8.8 Hz)

The compound of Example 66-79 was obtained by condensation of amino-2-methyl-3-{4-[3-(1-piperidinyl)propoxy]phenyl}-4(3H)-quinazolinone with the corresponding acid chloride or carboxylic acid according to the method of Example 65.

Example 66

6-(butyrylamino)-2-methyl-3-{4-[3-(1-piperidinyl)propoxy]phenyl}-4(3H)-quinazolinone The title compound was obtained by condensing 6-amino-2-methyl-3-{4-[3-(1-piperidinyl)propoxy]phenyl}-4(3H)-quinazolinone with butanoyl chloride according to the method of Example 65.

$^1$HNMR (400 MHz,CDCl$_3$,δppm): 0.99 (3H, t, J=7.6 Hz), 1.42-1.50 (2H, m), 1.56-1.66 (4H, m), 1.68-1.78 (2H, m), 1.98-2.07 (2H, m), 2.23 (3H, s), 2.25 (2H, t, J=7.6 Hz), 2.38-2.46 (2H, brs), 2.49 (2H, t, J=7.2 Hz), 4.05 (2H, t, J=6.0 Hz), 7.03 (2H, d, J=8.8 Hz), 7.12 (2H, d, J=8.8 Hz), 7.63 (1H, d, J=8.8 Hz), 7.65 (1H, s), 7.97 (1H, d, J=2.4 Hz), 8.38 (1H, d, J=9.2 Hz)

Example 67

6-(hexanoylamino)-2-methyl-3-{4-[3-(1-piperidinyl)propoxy]phenyl}-4(3H)-quinazolinone The title compound was obtained by condensing 6-amino-2-methyl-3-{4-[3-(1-piperidinyl)propoxy]phenyl}-4(3H)-quinazolinone with hexanoyl chloride according to the method of Example 65.

$^1$HNMR (400 MHz,CDCl$_3$,δppm): 0.91 (3H, t, J=6.8 Hz), 1.29-1.40 (4H, m), 1.41-1.49 (2H, m), 1.58-1.65 (4H, m), 1.66-1.78 (2H, m), 1.97-2.06 (2H, m), 2.23 (3H, s), 2.28 (2H, t, J=7.6 Hz), 2.38-2.46 (4H, brs), 2.49 (2H, t, J=7.2 Hz), 4.05 (2H, t, J=6.0 Hz), 7.03 (2H, d, J=8.8 Hz), 7.12 (2H, d, J=8.8 Hz), 7.63 (1H, d, J=8.8 Hz), 7.64 (1H, s), 7.97 (1H, d, J=2.8 Hz), 8.38 (1H, dd, J=2.4, 8.4 Hz)

Example 68

6-(benzoylamino)-2-methyl-3-{4-[3-(1-piperidinyl)propoxy]phenyl}-4(3H)-quinazolinone The title compound was obtained by condensing 6-amino-2-methyl-3-{4-[3-(1-piperidinyl)propoxy]phenyl}-4(3H)-quinazolinone with benzoyl chloride according to the method of Example 65.

$^1$HNMR (400 MHz,CDCl$_3$,δppm): 1.40-1.49 (2H, m), 1.55-1.65 (4H, m), 1.95-2.05 (2H, m), 2.24 (3H, s), 2.37-2.46 (4H, brs), 2.48 (2H, t, J=7.2 Hz), 4.02 (2H, t, J=6.0 Hz), 7.03 (2H, d, J=8.8 Hz), 7.12 (2H, d, J=8.8 Hz), 7.48 (2H, t, J=7.6 Hz), 7.52-7.57 (1H, m), 7.70 (1H, d, J=8.8 Hz), 7.86 (2H, d, J=7.6 Hz), 8.09 (1H, d, J=2.4 Hz), 8.15 (1H, brs), 8.48 (1H, dd, J=2.8, 8.8 Hz)

Example 69

6-[(2-phenylacetyl)amino]2-methyl-3-{4-[3-(1-piperidinyl)propoxy]phenyl}-4(3H)-quinazolinone The title compound was obtained by condensation of 6-amino-2-methyl-3-{4-[3-(1-piperidinyl)propoxy]phenyl}-4(3H)-quinazolinone with benziloyl chloride according to the method of Example 65.

$^1$HNMR (400 MHz,CDCl$_3$,δppm): 1.40-1.49 (2H, brs), 1.50-1.65 (4H, m), 1.93-2.05 (2H, m), 2.21 (3H, s), 2.37-2.45 (4H, brs), 2.48 (2H, t, J=7.2 Hz), 3.60 (2H, s), 3.97 (2H, brt), 6.97 (2H, d, J=8.0 Hz), 7.10 (2H, d, J=8.0 Hz), 7.20-7.41 (5H, m), 7.61 (1H, d, J=9.2 Hz), 7.69 (1H, s), 7.89 (1H, s), 8.33 (1H, d, J=8.8 Hz)

Example 70

6-(2-naphthoylamino)-2-methyl-3-{4-[3-(1-piperidinyl)propoxy]phenyl}-4(3H)-quinazolinone The title compound was obtained by condensing 6-amino-2-methyl-3-{4-[3-(1-piperidinyl)propoxy]phenyl}-4(3H)-quinazolinone with 2-naphthoyl chloride according to the method of Example 65.

$^1$HNMR (400 MHz,CDCl$_3$, δppm): 1.40-1.49 (2H, m), 1.55-1.65 (4H, m), 1.92-2.00 (2H, m), 2.23 (3H, s), 2.37-2.50 (6H, m), 3.93 (2H, t, J=6.0 Hz), 6.93 (2H, d, J=8.8 Hz), 7.09 (2H, d, J=8.8 Hz), 7.53-7.62 (2H, m), 7.72 (1H, d, J=8.8 Hz), 7.86-7.95 (4H, m), 8.17 (1H, d, J=2.4 Hz), 8.39 (1H, s), 8.44 (1H, s), 8.55 (1H, dd, J=2.4, 9.2 Hz)

Example 71

2-methyl-6-[(methylsulfonyl)amino]-3-{3-[3-(1-piperidinyl)propoxy]phenyl}-4(3H)-quinazolinone The title compound was obtained by condensation of 6-amino-2-methyl-3-{4-[3-(1-piperidinyl)propoxy]phenyl}-4(3H)-quinazolinone with mesyl chloride according to the method of Example 65.

$^1$HNMR (400 MHz,CDCl$_3$,δppm): 1.49-1.60 (2H, m), 1.71-1.80 (4H, m), 2.12-2.20 (2H, m), 2.24 (3H, s),2.62-2.70 (4H, brs), 2.73 (2H, t, J=7.6 Hz), 2.97 (3H, s), 4.07 (2H, t, J=6.0 Hz), 7.01 (2H, d, J=8.8 Hz), 7.11 (2H, d, J=8.8 Hz), 7.63 (1H, d, J=8.4 Hz), 7.74 (1H, dd, J=2.4, 8.4 Hz), 8.02 (1H, d, J=2.4 Hz)

Example 72

2-methyl-6-[(methylsulfonyl)amino]-3-{3-[3-(1-pyrrolidinyl)propoxy]phenyl}-4(3H)-quinazolinone The title compound was obtained by condensation of 6-amino-2-methyl-3-{4-[3-(1-pyrrolidinyl)propoxy]phenyl}-4(3H)-quinazolinone with mesyl chloride according to the method of Example 65.

$^1$HNMR (400 MHz,CDCl$_3$,δppm): 2.01-2.09 (4H, m), 2.24 (3H, s), 2.25-2.34 (2H, m), 3.01 (3H, s), 3.05-3.18 (6H, m), 4.13 (2H, t, J=6.0 Hz), 7.03 (2H, d, J=8.8 Hz), 7.12 (2H, d, J=8.8 Hz), 7.65 (1H, d, J=8.8 Hz), 7.77 (1H, dd, J=2.4, 8.4 Hz), 7.91 (1H, d, J=2.4 Hz)

Example 73

7-(acetylamino)-2-methyl-3-{4-[3-(1-piperidinyl)propoxy]phenyl}-4(3H)-quinazolinone The title compound was obtained by condensing 7-amino-2-methyl-3-{4-[3-(1-piperidinyl)propoxy]phenyl}-4(3H)-quinazolinone with acetyl chloride according to the method of Example 65.

$^1$HNMR (400 MHz,CDCl$_3$,δppm): 1.53-1.40 (2H, m), 1.69-1.59 (4H, m), 2.10-2.00 (2H, m), 2.21 (3H, s), 2.22 (3H, s), 2.55-2.46 (4H, m), 2.58 (2H, t, J=7.3 Hz), 4.04 (2H, t, J=6.2 Hz), 6.99 (2H, d, J=8.8 Hz), 7.11 (2H, d, J=8.8 Hz), 7.58 (2H, m), 7.82 (1H, brs), 8.16 (1H, d, J=8.8 Hz)

Example 74

7-(butyrylamino)-2-methyl-3-{4-[3-(1-piperidinyl)propoxy]phenyl}-4(3H)-quinazolinone The title compound was obtained by condensation of 7-amino-2-methyl-3-{4-[3-(1-piperidinyl)propoxy]phenyl}-4(3H)-quinazolinone with butanoyl chloride according to the method of Example 65.

$^1$HNMR (400 MHZ,CDCl$_3$,δppm): 1.52-1.40 (2H, m), 1.66-1.58 (4H, m), 1.77 (2H, m), 2.00 (2H, t, J=10.0 Hz), 2.21 (3H, s), 2.38 (2H, t, J=6.6 Hz), 2.52 (2H, brs), 2.55 (2H, t, J=12.2 Hz), 4.03 (2H, t, J=6.2 Hz) 6.99 (2H, d, J=8.8 Hz), 7.11 (2H, d, J=8.8 Hz), 7.54 (1H, s), 7.61 (1H, dd, J=8.4, 1.8 Hz), 7.79 (1H, d, J=2.2 Hz), 1.01 (3H, t, J=7.3 Hz), 8.15 (1H, d, J=8.8 Hz)

Example 75

7-(hexanoylamino)-2-methyl-3-{4-[3-(1-piperidinyl)propoxy]phenyl}-4(3H)-quinazolinone The title compound was obtained by condensation of 7-amino-2-methyl-3-{4-[3-(1-piperidinyl)propoxy]phenyl}-4(3H)-quinazolinone with hexanoyl chloride according to the method of Example 65.

$^1$HNMR (400 MHz,CDCl$_3$,δppm): 0.91 (3H, t, J=7.0 Hz), 1.41-1.29 (4H, m), 1.53-1.41 (2H, m), 1.68-1.57 (4H, m), 1.81-1.68 (2H, m),2.08-1.97 (2H, m), 2.22 (3H, s), 2.39 (2H, t, J=10.0 Hz), 2.47 (4H, m), 2.56 (2H, t, J=10.0 Hz), 4.04 (2H, t, J=6.2 Hz), 7.00 (2H, d, J=8.8 Hz), 7.12 (2H, d, J=8.8 Hz), 7.63 (1H, d, J=8.8 Hz), 7.72 (1H, brs), 7.80 (1H, brs), 8.15 (1H, d, J=8.8 Hz)

Example 76

7-(benzoylamino)-2-methyl-3-{4-[3-(1-piperidinyl)propoxy]phenyl}-4(3H)-quinazolinone The title compound was obtained by condensation of 7-amino-2-methyl-3-{4-[3-(1-piperidinyl)propoxy]phenyl}-4(3H)-quinazolinone with benzoyl chloride according to the method of Example 65.

$^1$HNMR (400 MHz,CD$_3$OD, δppm): 1.57-1.47 (2H, m), 1.72-1.63 (4H, m), 2.12-2.02 (2H, m), 2.24 (3H, s),2.63-2.54 (2H, m), 2.66 (2H, t, J=10.8 Hz), 3.32-3.28 (8H, m), 4.11 (2H, t, J=5.9 Hz), 7.10 (2H, d, J=8.8 Hz), 7.25 (2H, d, J=8.8 Hz), 7.52 (2H, t, J=7.3 Hz), 7.60 (1H, t, J=7.3 Hz), 7.79 (1H, dd, J=8.8, 2.2 Hz), 7.96 (2H, d, J=7.3 Hz), 8.14 (1H, d, J=8.8 Hz), 8.27 (1H, d, J=2.2 Hz)

Example 77

7-[(2-phenylacetyl)amino]2-methyl-3-{4-[3-(1-piperidinyl)propoxy]phenyl}-4(3H)-quinazolinone The title compound was obtained by condensation of 7-amino-2-methyl-3-{4-[3-(1-piperidinyl)propoxy]phenyl}-4(3H)-quinazolinone with benziloyl chloride according to the method of Example 65.

$^1$HNMR (400 MHZ,CD$_3$OD, δppm) 1.62-1.47 (2H, m), 1.78-1.63 (4H, m), 2.16-2.02 (2H, m), 2.21 (3H, s), 2.67-2.56 (4H, m), 2.70 (2H, t, J=10.0 Hz), 3.74 (2H, s), 4.11 (2H, t, J=5.9 Hz), 7.09 (2H, d, J=8.8 Hz), 7.42-7.20 (8H, m), 7.63 (1H, d, J=8.8 Hz), 8.09 (2H, d, J=8.1 Hz)

Example 78

7-(2-naphthoylamino)-2-methyl-3-{4-[3-(1-piperidinyl)propoxy]phenyl}-4(3H)-quinazolinone The title compound was obtained by condensation of 7-amino-2-methyl-3-{4-[3-(1-piperidinyl)propoxy]phenyl}-4(3H)-quinazolinone with 2-naphthoyl chloride according to the method of Example 65.

$^1$HNMR (400 MHz,CD$_3$OD, δppm): 1.74-1.61 (2H, m), 1.90-1.77 (4H, m), 2.26 (3H, s), 3.24-3.05 (4H, m), 3.34-3.27 (2H, m), 4.19 (2H, t, J=5.5 Hz), 7.13 (2H, d, J=8.8 Hz), 7.30 (2H, d, J=8.8 Hz), 7.68-7.57 (2H, m),7.88-7.84 (2H, m), 7.96 (1H, d, J=8.8 Hz), 8.08-8.00 (3H, m), 8.17 (1H, d, J=8.8 Hz), 8.34 (1H, d, J=2.2 Hz), 8.56 (1H, s)

Example 79

6-[acetyl(methyl)amino]-2-methyl-3-{4-[3-(1-piperidinyl)propoxy]phenyl}-4(3H)-quinazolinone The title compound was obtained by treating 6-(acetylamino)-2-methyl-3-{4-[3-(1-piperidinyl)propoxy]phenyl}-4(3H)-quinazolinone synthesized in Example 65 with sodium hydride in dimethylformamide, and methylating with methyl iodide.

$^1$HNMR (400 MHz,CDCl$_3$,δppm): 1.42-1.50 (2H, m), 1.58-1.66 (4H, m), 1.98-2.08 (2H, m), 2.27 (3H, s),2.40-2.50 (4H, brs), 2.53 (2H, t, J=7.6 Hz), 3.31 (3H, s), 4.07 (2H, t, J=6.4 Hz), 7.02 (2H, d, J=8.4 Hz), 7.12 (2H, d, J=8.4 Hz), 7.55 (1H, d, J=8.4 Hz), 7.70 (1H, d, J=8.4 Hz), 8.05 (1H, s)

Example 80

2-methyl-6-phenyl-3-{4-[3-(1-piperidinyl)propoxy]phenyl}-4(3H)-quinazolinone 2-methyl-6-bromo-3-{4-[3-(1-piperidinyl)propoxy]phenyl}-4(3H)-quinazolinone synthesized in Example 34 (100 mg, 0.25 mmol) and phenylboronic acid (40 mg, 0.32 mmol) were dissolved in dimethoxyethane (1 mL), and the atmosphere in the system was replaced by nitrogen. 2M sodium carbonate aqueous solution (0.3 mL) and palladium tetrakis (triphenylphosphine) complex (10 mg, 0.012 mmol) were added, and stirred at 80° C. for 3 hours. Ethyl acetate and distilled water were added to the reaction mixture to perform an ethyl acetate extraction. The organic phase was washed with saturated brine and dried with anhydrous sodium sulfate. The product was purified by silica gel column chromatography (chloroform/methanol=20/1), and the target substance (61 mg, 61%) was obtained as a colorless solid. $^1$HNMR (400 MHz,CDCl$_3$,δppm): 1.45 (2H, brs), 1.58-1.63 (4H, m), 2.00-2.04 (2H, m), 2.27 (3H, s), 2.42 (4H, brs), 2.50 (2H, t, J=7.2 Hz), 4.07 (2H, t, J=6.4 Hz), 7.04 (2H, d, J=8.8 Hz), 7.15 (2H, d, J=8.8 Hz), 7.36 (1H, t, J=7.6 Hz), 7.46 (2H, t, J=7.6 Hz), 7.67 (2H, d, J=7.2 Hz), 7.72 (1H, d, J=8.4 Hz), 7.98 (1H, d, J=2.0 Hz), 8.46 (1H, s)

Example 81

2-methyl-6-(4-methylphenyl)-3-{4-[3-(1-piperidinyl)propoxy]phenyl}-4(3H)-quinazolinone The title compound was obtained by Suzuki coupling of 2-methyl-6-bromo-3-{4-[3-(1-piperidinyl)propoxy]phenyl}-4(3H)-quinazolinone with 4-methylphenylboronic acid according to the method of Example 80.

$^1$HNMR (400 MHz,CDCl$_3$,δppm): 1.46 (2H, brs), 1.59-1.63 (4H, m), 2.01-2.04 (2H, m), 2.28 (3H, s), 2.41 (7H, brs), 2.49-2.53 (2H, m), 4.08 (2H, t, J=6.0 Hz), 7.05 (2H, d, J=8.8 Hz), 7.16 (2H, d, J=8.8 Hz), 7.27 (2H, d, J=8.0 Hz), 7.58 (2H, d, J=8.0 HZ), 7.71 (1H, d, J=8.8 Hz), 7.97-8.00 (1H, m), 8.46 (1H, s)

Example 82

2-methyl-6-(3-methylphenyl)-3-{4-[3-(1-piperidinyl)propoxy]phenyl}-4(3H)-quinazolinone The title compound was obtained by Suzuki coupling of 2-methyl-6-bromo-3-{4-[3-(1-piperidinyl)propoxy]phenyl}-4(3H)-quinazolinone with 3-methylphenylboronic acid according to the method of Example 80.

$^1$HNMR (400 MHz,CDCl$_3$,δppm): 1.47 (2H, brs), 1.59-1.64 (4H, m), 2.02-2.06 (2H, m), 2.28 (3H, s), 2.44 (7H, m), 2.52 (2H, t, J=7.2 Hz), 4.08 (2H, t, J=6.4 Hz), 7.05 (2H, d, J=7.2 Hz), 7.15-7.20 (3H, m), 7.35 (1H, t, J=7.2 Hz), 7.47-7.50 (2H, m), 7.72 (1H, dd, J=2.0, 8.8 Hz), 7.98-8.01 (1H, m), 8.46 (1H, s)

Example 83

2-methyl-6-(2-methylphenyl)-3-{4-[3-(1-piperidinyl)propoxy]phenyl}-4(3H)-quinazolinone The title compound was obtained by Suzuki coupling of 2-methyl-6-bromo-3-{4-[3-(1-piperidinyl)propoxy]phenyl}-4(3H)-quinazolinone with 2-methylphenylboronic acid according to the method of Example 80.

$^1$HNMR (400 MHz,CDCl$_3$,δppm): 1.46 (2H, brs), 1.59-1.64 (4H, m), 2.01-2.05 (2H, m), 2.29 (3H, s), 2.30 (3H, s), 2.43 (4H, brs), 2.51 (2H, t, J=7.2 Hz), 4.07 (2H, t, J=6.8 Hz), 7.04 (2H, d, J=8.8 Hz), 7.16 (2H, d, J=8.8 Hz), 7.24-7.30 (4H, m), 7.71 (2H, brs), 8.21 (1H, brs)

Example 84

2-methyl-3-{4-[3-(1-piperidinyl)propoxy]phenyl}-6-(3-pyridyl)-4(3H)-quinazolinone The title compound was obtained by Suzuki coupling of 2-methyl-6-bromo-3-{4-[3-(1-piperidinyl)propoxy]phenyl}-4(3H)-quinazolinone with 3-pyridylboronic acid according to the method of Example 80.

$^1$HNMR (400 MHz,CD$_3$OD, δppm): 1.51-1.53 (2H, m), 1.63-1.67 (4H, m), 2.04-2.08 (2H, m), 2.28 (3H, s), 2.59 (4H, brs), 2.61-2.63 (2H, m), 4.11 (2H, t, J=6.4 Hz), 7.11 (2H, d, J=9.2 Hz), 7.28 (2H, d, J=8.8 Hz), 7.53-7.757 (1H, m), 7.79 (1H, d, J=8.4 Hz), 8.14-8.21 (4H, m), 8.45 (1H, d, J=2.4 Hz), 8.55 (1H, dd, J=1.8, 5.0 Hz), 8.89 (1H, dd, J=0.6, 2.2 Hz)

Example 85

2-methyl-3-{4-[3-(1-piperidinyl)propoxy]phenyl}-6-(4-pyridyl)-4(3H)-quinazolinone The title compound was obtained by Suzuki coupling of 2-methyl-6-bromo-3-{4-[3-(1-piperidinyl)propoxy]phenyl}-4(3H)-quinazolinone with 4-pyridylboronic acid according to the method of Example 80.

$^1$HNMR (400 MHz,CD$_3$OD, δppm): 1.51-1.52 (2H, m), 1.63-1.68 (4H, m) 2.04-2.08 (2H, m), 2.28 (3H, s) 2.54 (4H, brs), 2.58-2.62 (2H, m), 4.11 (2H, t, J=6.0 Hz), 7.11 (2H, d, J=8.4 Hz), 7.28 (2H, d, J=8.8 Hz), 7.78-7.81 (3H, m), 8.23 (1H, dd, J=2.4, 8.4 Hz), 8.54 (1H, s), 8.61 (2H, d, J=6.4 Hz)

Example 86

2-methyl-5-phenyl-3-{4-[3-(1-piperidinyl)propoxy]phenyl}-4(3H)-quinazolinone 5-chloro-2-methyl-3-{4-[3-(1-piperidinyl)propoxy]phenyl}-4(3H)-quinazolinone synthesized in Example 27 (100 mg, 0.24 mmol), phenylboric acid (90 mg, 0.73 mmol) and cesium carbonate (480 mg, 1.45 mmol) were mixed in 1,4-dioxane (1 mL), and the atmosphere in the system was replaced by nitrogen. Pd$_2$(dba)$_3$ (15 mg, 0.012 mmol) and tri-t-butylphosphine (10 mg, 0.036 mmol) were added, and stirred at 100° C. for 12 hours. Distilled water was added to the reaction mixture, and the mixture extracted with chloroform. The organic phase was washed by saturated brine, and dried with anhydrous sodium sulfate. The product was purified by thin layer silica gel chromatography, and the title compound (20 mg, 18%) was obtained as a colorless solid.

$^1$HNMR (400 MHz,CDCl$_3$,δppm): 1.44 (2H, brs), 1.56-1.62 (4H, m), 1.95-1.99 (2H, m), 2.23 (3H, s), 2.40 (4H, brs), 2.46 (2H, t, J=6.8 Hz), 3.99 (2H, t, J=6.8 Hz), 6.94 (2H, d, J=8.8 Hz), 7.06 (2H, d, J=8.8 Hz), 7.23-7.33 (6H, m), 7.66-7.73 (2H, m)

Example 87

2-methyl-3-{4-[3-(1-piperidinyl)propoxy]phenyl}-6-(2-pyridyl)-4(3H)-quinazolinone 6-bromo-2-methyl-3-{4-[3-(1-piperidinyl)propoxy]phenyl}-4(3H)-quinazolinone synthesized in Example 34 (100 mg, 0.25 mmol) and 2-(tributylstannyl)pyridine (90 mg, 0.25 mmol) were dissolved in toluene (1 mL), and the atmosphere in the system was replaced by nitrogen. Palladium tetrakis (triphenylphosphine) complex (30 mg, 0.025 mmol) was added, and stirred at 120° C. for 12 hours. Insoluble matter was filtered off through cerite, chloroform was added to the filtrate, the organic phase was washed with distilled water, and dried with anhydrous sodium sulfate. The product was purified by silica gel column chromatography (chloroform/methanol=9/1), and the target substance (20 mg, 20%) was obtained as a colorless solid.

$^1$HNMR (400 MHz,CD$_3$OD, δppm): 1.50-1.51 (2H, m), 1.62-1.67 (4H, m), 2.03-2.08 (2H, m), 2.28 (3H, s), 2.51 (4H, brs), 2.56-2.60 (2H, m), 4.11 (2H, t, J=5.6 Hz), 7.11 (2H, d, J=9.2 Hz), 7.28 (2H, d, J=9.2 Hz), 7.37-7.40 (1H, m), 7.76 (1H, d, J=8.8 Hz), 7.89-7.98 (4H, m), 8.45 (1H, dd, J=2.0, 8.4 Hz), 8.63-8.65 (2H, m)

Example 88

3-{4-[(1-cyclobutyl-4-piperidinyl)oxy]phenyl}-2-methyl-4 (3H)-quinazolinone (1) Manufacture of 3-{4-[(1-t-butoxycarbonyl-4-piperidinyl)oxy]phenyl}-2-methyl-4(3H)-quinazolinone 2-methyl-3-(4-hydroxyphenyl)-4 (3H)quinazolinone synthesized according to Example 1-(1) and -(2) (1.0 g, 3.96 mmol), N-(t-butoxycarbonyl)-4-piperidinol (956 mg, 4.75 mmol) and triphenylphosphine (1.56 g, 5.94 mmol) were dissolved in dry tetrahydrofuran (2 mL) in a current of nitrogen, and cooled on an ice bath. Diethylazodicarboxylate (1.17 mL, 5.94 mmol) was dripped in at 0° C., and stirred at room temperature for 48 hours. The solvent was distilled off under reduced pressure, ether was added, the solid precipitate was filtered off, and the filtrate was concentrated. The residue was purified by silica gel column chromatography (hexane/ethyl acetate=7/3), and the target substance (1.1 g, 64%) was obtained as a light brown solid.

(2) Manufacture of 2-methyl-3-[4-(4-piperidinyloxy) phenyl]-4(3H)-quinazolinone

3-{4-[(1-t-butoxycarbonyl-4-piperidinyl)oxy]phenyl}-2-methyl-4(3H)-quinazolinone (1.1 g, 2.53 mmol) was dissolved in chloroform (10 mL), trifluoroacetic acid (10 mL) was added and the mixture stirred at room temperature for 30 minutes. The solvent was distilled off under reduced pressure, ethyl acetate and 2N sodium hydroxide aqueous solution were added, the mixture was extracted with ethyl acetate, and the organic phase was dried with anhydrous sodium sulfate. The sodium sulfate was filtered off, and the filtrate was concentrated and dried to obtain the target substance (0.83 g, 98%) as a lavender-colored solid.

$^1$HNMR (400 MHz,CDCl$_3$,δppm): 1.67-1.81 (2H, m), 2.01-2.10 (2H, m), 2.26 (3H, s),2.72-2.80 (2H, m),3.13-3.20 (2H, m), 4.40-4.47 (1H, m), 7.03 (2H, d, J=8.8 Hz), 7.13 (2H, d, J=8.8 Hz), 7.44 (1H, t, J=8.0 Hz), 7.65 (1H, d, J=7.6 Hz), 7.74 (1H, t, J=7.6 Hz), 8.25 (1H, d, J=8.0 Hz)

(3) Manufacture of 3-{4-[(1-cyclobutyl-4-piperidinyl)oxy]phenyl}-2-methyl-4(3H)-quinazolinone 2-methyl-3-{4-(4-piperidinyloxy-)phenyl}-4(3H)-quinazolinone (370 mg, 1.10 mmol) and cyclobutanone (155 mg, 2.20 mmol) were dissolved in a 0.5M methanol solution (6 mL) of zinc(II) chloride and sodium cyanoborohydride, and stirred at room temperature for 1 Hour. The solvent was distilled off under reduced pressure, ethyl acetate and distilled water were added, the mixture was extracted with ethyl acetate, and the organic phase washed with distilled water. After drying with anhydrous sodium sulfate, the product was purified by silica gel column chromatography (chloroform/methanol=30/1), and the title compound (165 mg, 39%) was obtained as a colorless solid.

$^1$HNMR (400 MHz,CDCl$_3$,δppm) 1.63-1.76 (2H, m), 1.84-1.95 (4H, m), 1.99-2.10 (4H, m), 2.14-2.23 (2H, m), 2.26 (3H, s), 2.59-2.67 (2H, m), 2.70-2.79 (1H, m), 4.33-4.41 (1H, m), 7.01 (2H, d, J=8.8 Hz), 7.44 (1H, t, J=8.0 Hz), 7.65 (1H, d, J=8.4 Hz), 7.74 (1H, t, J=7.6 Hz), 8.24 (1H, d, J=7.6 Hz)

Example 89

3-{4-[(1-cyclopentyl-4-piperidinyl)oxy]phenyl}-2-methyl-4(3H)-quinazolinone

The title compound was obtained by performing a reductive amination according to the method of Example 88-(3), using 2-methyl-3-[4-(4-piperidinyloxy)phenyl]-4(3H)-quinazolinone, N-Boc-4-piperidinol and cyclopentanone as starting materials.

$^1$HNMR (400 MHz,CDCl$_3$,δppm): 1.25-1.48 (2H, m), 1.52-1.61 (2H, m), 1.66-1.73 (2H, m), 1.83-1.93 (4H, m), 2.01-2.12 (2H, m), 2.25 (3H, s), 2.32-2.40 (2H, m), 2.49-2.58 (1H, m), 2.79-2.95 (2H, m), 4.33-4.41 (1H, m), 7.03 (2H, d, J=8.8 Hz), 7.13 (2H, d, J=8.8 Hz), 7.44 (1H, t, J=7.2 Hz), 7.65 (1H, d, J=7.6 Hz), 7.74 (1H, t, J=7.2 Hz), 8.25 (1H, d, J=7.6 Hz)

Example 90

3-{4-(1-cyclohexyl-4-piperidinyloxy)phenyl}-2-methyl-4(3H)-quinazolinone

The title compound was obtained by performing a reductive amination according to the method of Example 88-(3), using 2-methyl-3-[4-(4-piperidinyloxy)phenyl]-4(3H)-quinazolinone, N-Boc-4-piperidinol and cyclohexanone as starting materials.

$^1$HNMR (400 MHz,CDCl$_3$,δppm): 1.18-1.30 (6H, m), 1.78-1.90 (6H, m), 2.01-2.08 (2H, m), 2.26 (3H, s), 2.27-2.36 (1H, m), 2.42-2.51 (2H, m), 2.81-2.89 (2H, m), 4.30-4.38 (1H, m), 7.03 (2H, d, J=8.8 Hz), 7.13 (2H, d, J=8.8 Hz), 7.44 (1H, t, J=8.0 Hz), 7.65 (1H, d, J=8.0 Hz), 7.74 (1H, t, J=8.0 Hz), 8.25 (1H, d, J=8.0 Hz)

Example 91

3-{4-(1-isopropyl-4-piperidinyloxy)phenyl}-2-methyl-4 (3H)-quinazolinone

The title compound was obtained by performing a reductive amination according to the method of Example 88-(3), using 2-methyl-3-[4-(4-piperidinyloxy)phenyl]-4(3H)-quinazolinone, N-Boc-4-piperidinol and acetone as starting materials.

$^1$HNMR (400 MHz,CDCl$_3$,δppm): 1.07 (6H, d, J=6.4 Hz), 1.82-1.92 (2H, m), 2.02-2.11 (2H, m), 2.26 (3H, s),2.37-2.46 (2H, m), 2.72-2.84 (3H, m), 4.31-4.40 (1H, m), 7.03 (2H, d, J=8.8 Hz), 7.13 (2H, d, J=8.8 Hz), 7.44 (1H, t, J=8.0 Hz), 7.65 (1H, d, J=8.0 Hz), 7.74 (1H, t, J=8.0 Hz), 8.25 (1H, d, J=8.0 Hz)

Example 92

3-{4-(1-ethyl-4-piperidinyloxy)phenyl}-2-methyl-4 (3H)-quinazolinone 2-methyl-3-[4-(4-piperidinyloxy)phenyl]-4(3H)-quinazolinone (50 mg, 0.15 mmol), ethyl iodide (23 mg, 0.15 mmol) and potassium carbonate (0.30 mmol) were mixed in dimethylformamide (1 mL), and stirred at room temperature for 1 hour. The solvent was distilled off under reduced pressure, ethyl acetate and 1N sodium hydroxide aqueous solution was added, and the mixture was extracted with ethyl acetate. The organic phase was washed with distilled water, dried with anhydrous sodium sulfate, and the product was purified by silica gel column chromatography (chloroform/methanol=30/1) to obtain the title compound (25 mg, 46%) as a colorless solid.

¹HNMR (400 MHz,CDCl₃,δppm): 1.12 (3H, t, J=6.8 Hz), 1.83-1.95 (2H, m), 2.02-2.10 (2H, m), 2.26 (3H, s),2.26-2.39 (2H, m), 2.45 (2H, q, J=7.2 Hz), 2.72-2.81 (2H, m), 4.35-4.43 (1H, m), 7.03 (2H, d, J=8.8 Hz), 7.13 (2H, d, J=8.8 Hz), 7.44 (1H, t, J=8.0 Hz), 7.65 (1H, d, J=8.0 Hz), 7.74 (1H, t, J=8.0 Hz), 8.25 (1H, d, J=8.0 Hz)

Example 93

3-{4-(1-butyl-4-piperidinyloxy)phenyl}-2-methyl-4 (3H)-quinazolinone

The title compound was obtained by N-alkylation, using 2-methyl-3-[4-(4-piperidinyloxy-)phenyl}-4(3H)-quinazolinone and butyl iodide according to Example 92.

¹HNMR (400 MHz,CDCl₃,δppm): 0.93 (3H, t, J=7.2 Hz), 1.28-1.39 (2H, m), 1.46-1.54 (2H, m), 1.83-1.93 (2H, m), 2.01-2.10 (2H,m), 2.26 (3H, s), 2.26-2.39 (4H, m), 2.72-2.81 (2H, m), 4.33-4.41 (1H, m), 7.03 (2H, d, J=8.8 Hz), 7.13 (2H, d, J=8.8 Hz), 7.44 (1H, t, J=8.0 Hz), 7.65 (1H, d, J=8.0 Hz), 7.74 (1H, t, J=8.0 Hz), 8.25 (1H, d, J=8.0 Hz)

Example 94

3-{4-[(1-cyclopentyl-4-piperidinyl)oxy]phenyl}-2-methyl-5-trifluoro methyl-4(3H)-quinazolinone (1) Manufacture of 4-(4-nitrophenoxy)piperidine N-Boc-4-piperidinol (10 g, 50 mmol), 4-nitrophenol (7.0 g, 50 mmol) and triphenylphosphine (15.7 g, 60 mmol) were dissolved in dry tetrahydrofuran (150 mL), and cooled on the ice bath. Diisopropyl azodicarboxylate (11.8 mL, 60 mmol) was added slowly, and stirred for 2 days at room temperature. The solvent was distilled off under reduced pressure, diethyl ether was added, and the solid precipitate was filtered off. The filtrate was concentrated and the product was purified by silica gel column chromatography (hexane/ethyl acetate=6/1). Trifluoroacetic acid was added to the obtained residue and stirred at room temperature for 1 hour. After distillation under reduced pressure, 1N sodium hydroxide aqueous solution was added, and the mixture extracted with ethyl acetate. After drying with anhydrous sodium sulfate, the product was concentrated and dried to obtain the target substance (6.75 g, 61%).

(2) Manufacture of 1-cyclopentyl-4-(4-nitrophenoxy)piperidine 4-(4-nitrophenoxy)piperidine (1.03 g, 4.65 mmol) and cyclopentanone (783 mg, 9.31 mmol) were dissolved in a 0.5M methanol solution (20 mL) of zinc(II) chloride and sodium cyanoborohydride, and stirred at room temperature for 10 hours. The solvent was distilled off under reduced pressure, ethyl acetate and 1N sodium hydroxide aqueous solution were added, the mixture was extracted with ethyl acetate, and the organic phase washed with distilled water. After drying with anhydrous sodium sulfate, the product was concentrated, and the target compound (1.31 g, 96%) was thereby obtained as a light brown solid.

(3) Manufacture of 4-[(1-cyclopentylpiperidin-4-yl)oxy]aniline 1-cyclopentyl-4-(4-nitrophenoxy)piperidine (1.30 g) was dissolved in methanol, and the target compound (1.0 g, 86%) was obtained as a light brown solid by catalytic reduction using a palladium charcoal catalyst.

(4) Manufacture of 3-{4-[(1-cyclopentyl-4-piperidinyl)oxy]phenyl}-2-methyl-5-trifluoromethyl-4(3H)-quinazolinone 2-methyl-5-trifluoromethyl-4H-3,1-benzoxadin-4-one (71 mg, 0.31 mmol) and 4-[(1-cyclopentyl-4-piperidinyl)oxy] aniline (80 mg, 0.31 mmol) were dissolved in acetic acid (0.5 mL), and stirred at 130 degrees for 6 hours. The solvent was distilled off under reduced pressure, and ethyl acetate and 1N sodium hydroxide-aqueous solution were added. The mixture was extracted with ethyl acetate, and the organic phase was dried with anhydrous sodium sulfate. The product was purified by silica gel column chromatography (chloroform/methanol=20/1), and the title compound (88 mg, 61%) was thus obtained as a light brown solid. 2-methyl-5-trifluoromethyl-4H-3,1-benzoxadin-4-one was manufactured by the method according to Example 1-(1), using 2-amino-6-trifluoromethylbenzoic acid and acetic anhydride as starting materials.

¹HNMR (400 MHz,CDCl₃,δppm): 1.38-1.49 (2H, m), 1.51-1.62 (2H, m), 1.65-1.76 (2H, m), 1.82-1.94 (4H, m), 2.00-2.09 (2H, m), 2.26 (3H, s), 2.32-2.42 (2H, m), 2.48-2.58 (1H, m), 2.76-2.86 (2H, m), 4.32-4.40 (1H, m), 7.02 (2H, d, J=8.8 Hz), 7.13 (2H, d, J=8.8 Hz), 7.78 (1H, t, J=8.0 Hz), 7.83-7.88 (2H, m)

NMR data for 4-[(1-cyclopentylpiperidin-4-yl)oxy]aniline used for manufacturing the compound of this example is shown below.

¹HNMR (400 MHz,CDCl₃,δppm): 1.36-1.45 (2H, m), 1.49-1.58 (2H, m), 1.64-1.99 (10H, m), 2.24-2.31 (2H, m), 2.45-2.54 (1H, m), 2.80 (2H, brs), 3.43 (2H, brs), 4.12 (1H, s), 6.63 (2H, d, J=8.8 Hz), 6.76 (2H, d, J=8.8 HZ)

The product of Example 95-115 can be manufactured by an identical method to that of Example 94, a method based thereon or a combination of these with a conventional method, using the corresponding anthranilic acid, acid anhydride and 4-[(1-cyclopentyl-4-piperidinyl)oxy]aniline or 4-[(1-cyclobutyl-4-piperidinyl)oxy]aniline as starting materials.

Example 95

3-{4-(1-cyclopentyl-4-piperidinyloxy-)phenyl}-2,5-dimethyl-4(3H)-quinazolinone

The title compound was obtained by cyclizing, using 2,5-dimethyl-4H-3,1-benzoxazin-4-one and 4-[(1-cyclopentyl-4-piperidinyl)oxy]aniline, according to the method of Example 94.

¹HNMR (400 MHz,CDCl₃,δppm): 1.37-1.50 (2H, m), 1.54-1.61 (2H, m), 1.64-1.78 (4H, m), 1.82-1.96 (4H, m), 2.00-2.10 (2H, m), 2.22 (3H, s), 2.32-2.42 (2H, m), 2.49-2.59 (1H, m), 2.81 (3H, s), 4.32-4.41 (1H, m), 7.03 (2H, d, J=8.8 Hz), 7.13 (2H, d, J=8.8 Hz), 7.19 (1H, d, J=7.2 Hz), 7.48 (1H, d, J=7.6 Hz), 7.57 (1H, t, J=8.0 Hz)

Example 96

7-chloro-3-{4-[(1-cyclopentyl-4-piperidinyl)oxy] phenyl}-2-methyl-4(3H)-quinazolinone The title compound was obtained by cyclizing, using 7-chloro-2-methyl-4H-3,1-benzoxazin-4-one and 4-[(1-cyclopentyl-4-piperidinyl)oxy]aniline according to the method of Example 94.

¹HNMR (400 MHz,CDCl₃,δppm): 1.37-1.49 (2H, m), 1.50-1.63 (2H, m), 1.65-1.76 (2H, m), 1.82-1.94 (4H, m), 2.00-2.10 (2H, m), 2.25 (3H, s), 2.30-2.41 (2H, m), 2.48-2.58 (1H, m), 2.77-2.87 (2H, m), 4.33-4.41 (1H, m), 7.02 (2H, d, J=8.8 Hz), 7.11 (2H, d, J=8.8 Hz), 7.38 (1H, dd, J=2.4, 8.4 Hz), 7.64 (1H, d, J=2.4 Hz), 8.16 (1H, d, J=8.4 Hz)

Example 97

3-{4-[(1-cyclopentyl-4-piperidinyl)oxy]phenyl}-2,6-dimethyl-4(3H)-quinazolinone

The title compound was obtained by cyclizing, using 2,6-dimethyl-4H-3,1-benzoxazin-4-one and 4-[(1-cyclopentyl-4-piperidinyl) oxy] aniline according to the method of Example 94.
¹HNMR (400 MHz,CDCl₃,δppm): 1.38-1.49 (2H, m), 1.50-1.63 (2H, m), 1.65-1.76 (2H, m), 1.84-1.95 (4H, m),2.00-2.11 (2H, m), 2.23 (3H, s), 2.31-2.42 (2H, m), 2.48 (3H, s), 2.48-2.58 (1H, m), 2.78-2.86 (2H, m), 4.33-4.41 (1H, m), 7.02 (2H, d, J=8.8 Hz), 7.11 (2H, d, J=8.8 Hz), 7.55 (2H, s),8.02 (1H, s)

Example 98

6-chloro-3-{4-[(1-cyclopentyl-4-piperidinyl)oxy-one]phenyl}-2-methyl-4(3H)-quinazolinone The title compound was obtained by cyclizing, using 6-chloro-2-methyl-4H-3,1-benzoxazin-4-one and 4-[(1-cyclopentyl-4-piperidinyl)oxy]aniline according to the method of Example 94.
¹HNMR (400 MHz,CDCl₃,δppm): 1.37-1.48 (2H, m), 1.50-1.62 (2H, m), 1.65-1.77 (2H, m), 1.84-1.94 (4H, m),2.00-2.10 (2H, m), 2.24 (3H, s), 2.30-2.41 (2H, m), 2.48-2.59 (1H, m), 2.78-2.87 (2H, m), 4.33-4.41 (1H, m), 7.02 (2H, d, J=8.8 Hz), 7.11 (2H, d, J=8.8 Hz), 7.58 (1H, d, J=8.8 Hz), 7.68 (1H, dd, J=2.4, 8.8 Hz), 8.19 (1H, d, J=2.8 Hz)

Example 99

3-{4-[(1-cyclopentyl-4-piperidinyl)oxy-one]phenyl}-6-methoxy-2-methyl-4(3H)-quinazolinone The title compound was obtained by cyclizing, using 6-methoxy-2-methyl-4H-3,1-benzoxazin-4-one and 4-[(1-cyclopentyl-4-piperidinyl)oxy]aniline according to the method of Example 94.
¹HNMR (400 MHz,CDCl₃,δppm): 1.37-1.48 (2H, m), 1.50-1.62 (2H, m), 1.65-1.77 (2H, m), 1.84-1.94 (4H, m),2.00-2.10 (2H, m), 2.23 (3H, s), 2.30-2.41 (2H, m), 2.49-2.58 (1H, m), 2.78-2.87 (2H, m), 3.89 (3H, s), 4.33-4.41 (1H, m), 7.02 (2H, d, J=8.8 Hz), 7.11 (2H, d, J=8.8 Hz), 7.33 (1H, dd, J=2.8, 8.8 Hz), 7.58 (1H, d, J=8.8 Hz), 7.61 (1H, d, J=3.2 Hz)

Example 100

3-{4-[(1-cyclopentyl-4-piperidinyl)oxy]phenyl}-2-methylpyrido[2,3-d]pyrimidin-4(3H)-one The title compound was obtained by cyclizing, using 2-methyl-4H-pyrido[2,3-d][1,3]oxadin-4-one and 4-[(1-cyclopentyl-4-piperidinyl)oxy]aniline according to the method of Example 94.
¹HNMR (400 MHz,CDCl₃,δppm): 1.37-1.48 (2H, m), 1.49-1.63 (2H, m), 1.64-1.74 (2H, m), 1.83-1.93 (4H, m),2.00-2.10 (2H, m), 2.34 (3H, s),2.29-2.40 (2H, m),2.49-2.58 (1H, m), 2.78-2.88 (2H, m), 4.33-4.41 (1H, m), 7.04 (2H, d, J=8.8 Hz), 7.12 (2H, d, J=8.8 Hz), 7.39 (1H, dd, J=4.0, 7.6 Hz), 8.56 (1H, dd, J=2.4, 7.6 Hz), 8.96 (1H, dd, J=2.4, 4.8 Hz)

Example 101

3-{4-[(1-cyclopentyl-4-piperidinyl)oxy]phenyl}-2-methylpyrido[4,3-d]pyrimidin-4(3H)-one The title compound was obtained as a white solid (m.p.: 140-143° C.) by cyclizing, using 2-methyl-4H-pyrido[4,3-d][1,3]oxazin-4-one and 4-[(1-cyclopentyl-4-piperidinyl)oxy]aniline according to the method of Example 94, followed by recrystallization (ethyl acetate/diethyl ether).
¹HNMR (400 MHz,CDCl₃,δppm): 1.39-1.49 (2H, m), 1.49-1.63 (2H, m), 1.64-1.78 (2H, m), 1.83-1.95 (4H, m), 2.00-2.12 (2H, m), 2.29 (3H, s), 2.32-2.45 (2H, m), 2.50-2.61 (1H, m), 2.78-2.88 (2H, m), 4.34-4.41 (1H, m), 7.05 (2H, d, J=8.8 Hz), 7.13 (2H, d, J=8.8 Hz), 7.47 (1H, d, J=5.6 Hz), 8.82 (1H, d, J=5.6 Hz), 9.45 (1H, s)

Example 102

6-chloro-3-{4-[(1-cyclopentyl-4-piperidinyl)oxy]phenyl}-2-methylpyrido[3,4-d]pyrimidin-4 (3H)-one The title compound was obtained by cyclizing, using 6-chloro-2-methyl-4H-pyrido[3,4-d][1,3]oxadin-4-one and 4-[(1-cyclopentyl-4-piperidinyl)oxy]aniline according to the method of Example 94.
¹HNMR (400 MHz,CDCl₃,δppm): 1.37-1.48 (2H, m), 1.50-1.62 (2H, m), 1.65-1.76 (2H, m), 1.83-1.94 (4H, m),2.00-2.10 (2H, m), 2.28 (3H, s), 2.32-2.42 (2H, m), 2.48-2.58 (1H, m), 2.78-2.87 (2H, m),4.33-4.41 (1H, m), 7.04 (2H, d, J=8.8 Hz), 7.10 (2H, d, J=8.8 Hz), 8.03 (1H, s), 8.88 (1H, s)

Example 103

3-{4-[(1-cyclopentyl-4-piperidinyl)oxy]phenyl}-2-methylpyrido[3,4-d]pyrimidin-4(3H)-one The title compound was obtained by catalytic reduction of 6-chloro-3-(4-[(1-cyclopentyl-4-piperidinyl)oxy]phenyl)-2-methylpyrido[3,4-d]pyrimidin-4(3H)-one synthesized in Example 102 using palladium charcoal as catalyst in the presence of triethylamine.
¹HNMR (400 MHz,CDCl₃,δppm): 1.40-1.64 (4H, m), 1.65-1.79 (2H, m), 1.84-1.99 (4H, m), 2.01-2.10 (2H, m), 2.29 (3H, s), 2.37-2.45 (2H, m), 2.49-2.64 (1H, m), 2.78-2.87 (2H, m), 4.33-4.47 (1H, m), 7.03 (2H, d, JH, d, J=8.8 Hz), 7.12 (2H, d, J=8.8 Hz), 8.00 (1H, d, J=5.2 Hz), 8.65 (1H, d, J=5.2 Hz), 9.10 (1H, s)

Example 104

3-{4-[(1-cyclobutyl-4-piperidinyl)oxy]phenyl}-2,5-dimethyl-4(3H)-quinazolinone (1) Manufacture of 4-[(1-cyclobutyl-4-piperidinyl)oxy]aniline The target compound was obtained as a light brown solid by the method according to Example 94, using 4-(4-nitrophenoxy)piperidine synthesized in Example 94 and cyclobutanone as starting materials. 4-[(1-cyclobutyl-4-piperidinyl)

oxy]aniline monotosylate can also be prepared by treating the obtained 4-[(1-cyclobutyl-4-piperidinyl)oxy]aniline with one equivalent of p-toluenesulfonic acid.

(2) Manufacture of 3-{4-[(1-cyclobutyl-4-piperidinyl)oxy]phenyl}-2,5-dimethyl-4(3H)-quinazolinone The title compound was synthesized as a white solid (m.p.: 142-143° C.) by the method according to Example 94, using 2-amino-6-methylbenzoic acid, acetic anhydride and 4-[(1-cyclobutyl-4-pyridinyl)oxy]aniline as starting materials, followed by recrystallization (ethyl acetate).
$^1$HNMR (400 MHz,CDCl$_3$,δppm): 1.63-1.75 (2H, m), 1.82-1.96 (4H, m), 1.99-2.10 (4H, m), 2.13-2.22 (2H, m), 2.22 (3H, s), 2.58-2.67 (2H, m), 2.69-2.79 (1H, m), 2.81 (3H, s), 4.33-4.40 (1H, m), 7.02 (2H, d, J=8.8 Hz), 7.11 (2H, d, J=8.8 Hz), 7.19 (1H, d, J=8.0 Hz), 7.48 (1H, d, J=8.0 Hz), 7.57 (1H, t, J=8.0 Hz)

NMR data for 4-[(1-cyclobutyl-4-piperidinyl)oxy]aniline used for manufacturing the compound of this example is shown below.
$^1$HNMR (400 MHZ,CDCl$_3$,δppm): 1.62-2.10 (12H, m), 2.58-2.65 (2H, m), 2.67-2.76 (1H, m), 3.43 (1H,brs), 4.15-4.10 (1H, m), 6.62 (2H, d, J=8.8 Hz), 6.76 (2H, d, J=8.8 Hz)

NMR data for 4-[(1-cyclobutyl-4-piperidinyl)oxy]aniline monotosylate is shown below.
$^1$HNMR (400 MHz,CDCl$_3$/CD$_3$OD=4/1,δppm): 1.68-1.79 (1H, m), 1.81-1.90 (1H, m), 2.09-2.15 (2H, m), 2.19-2.27 (2H, m), 2.34-2.43 (5H, m), 2.52-2.61 (2H, m), 2.86-2.93 (2H, m), 3.34-3.44 (3H, m), 4.52 (1H,brs), 6.70-6.75 (4H, m), 7.21 (2H, d, J=7.8 Hz), 7.79 (2H, d, J=7.8 Hz)

Example 105

3-{4-[(1-cyclobutyl-4-piperidinyl)oxy]phenyl}-5-methoxy-2-methyl-4(3H)-quinazolinone The title compound was synthesized as a light yellow solid (m.p.:153-156° C.) by the method according to Example 94, using 2-amino-6-methoxybenzoic acid, acetic anhydride and 4-(1-cyclobutyl-4-piperidinyl)oxyaniline as starting materials, followed by recrystallization (ethyl acetate/diethyl ether/n-heptane).
$^1$HNMR (400 MHz,CDCl$_3$,δppm): 1.63-1.77 (2H, m), 1.82-1.96 (4H, m), 1.98-2.09 (4H, m), 2.12-2.23 (2H, m), 2.21 (3H, s), 2.58-2.67 (2H, m), 2.69-2.79 (1H, m), 3.94 (3H, s), 4.33-4.40 (1H, m), 6.85 (1H, d, J=8.8 Hz), 6.99 (2H, d, J=8.8 Hz), 7.08 (2H, d, J=8.8 Hz), 7.21 (1H, d, J=8.0 Hz), 7.62 (1H, t, J=8.0 Hz)

Example 106

3-{4-[(1-cyclobutyl-4-piperidinyl)oxy]phenyl}-2-methyl-5-trifluoro methyl-4(3H)-quinazolinone The title compound was synthesized as a white solid (m.p.: 132-134° C.) by the method according to Example 94, using 2-amino-6-trifluoromethylbenzoic acid, acetic anhydride and 4-[(1-cyclobutyl-4-piperidinyl)oxy]aniline as starting materials, followed by recrystallization (ethyl acetate).
$^1$HNMR (400 MHz,CDCl$_3$,δppm): 1.63-1.77 (2H, m), 1.82-1.96 (4H, m), 1.98-2.09 (4H, m), 2.13-2.23 (2H, m), 2.26 (3H, s), 2.58-2.66 (2H, m), 2.70-2.79 (1H, m), 4.33-4.40 (1H, m), 7.01 (2H, d, J=8.8 Hz), 7.12 (2H, d, J=8.8 Hz), 7.77 (1H, d, J=8.0 Hz), 7.82-7.88 (2H, m)

Example 107

5-chloro-3-{4-[(1-cyclobutyl-4-piperidinyl)oxy]phenyl}-2-methyl-4(3H)-quinazolinone The title compound was obtained by the method according to Example 94, using 2-amino-6-chlorobenzoic acid, acetic anhydride and 4-[(1-cyclobutyl-4-piperidinyl)oxy]aniline as starting materials.
$^1$HNMR (400 MHz,CDCl$_3$,δppm): 1.63-1.77 (2H, m), 1.82-1.96 (4H, m), 1.99-2.09 (4H, m), 2.13-2.23 (2H, m), 2.23 (3H, s), 2.58-2.66 (2H, m), 2.69-2.79 (1H, m), 4.33-4.40 (1H, m), 7.00 (2H, d, J=8.8 Hz), 7.12 (2H, d, J=8.8 Hz), 7.43 (1H, dd, J=1.6, 7.2 Hz), 7.52-7.61 (2H, m)

Example 108

3-{4-[(1-cyclobutyl-4-piperidinyl)oxy]phenyl}-2-methylpyrido[4,3-d]pyrimidin-4(3H)-one The title compound was obtained by the method according to Example 94, using 4-aminonicotinic acid, acetic anhydride and 4-[(1-cyclobutyl-4-piperidinyl)oxy]aniline as starting materials.
$^1$HNMR (400 MHz,CDCl$_3$,δppm) 1.63-1.77 (2H, m), 1.82-1.96 (4H, m), 1.99-2.11 (4H, m), 2.14-2.24 (2H, m), 2.29 (3H, s), 2.60-2.68 (2H, m), 2.70-2.80 (1H, m), 4.33-4.41 (1H, m), 7.03 (2H, d, J=8.8 Hz), 7.11 (2H, d, J=8.8 Hz), 7.47 (1H, d, J=5.2 Hz), 8.82 (1H, d, J=5.2 Hz), 9.45 (1H, s)

Example 109

3-{4-[(1-cyclobutyl-4-piperidinyl)oxy]phenyl}-2-ethylpyrido[4,3-d]pyrimidin-4(3H)-one The title compound was synthesized as a white solid (m.p.: 186-189° C.) by the method according to Example 94, using 4-aminonicotinic acid, propionic anhydride and 4-[(1-cyclobutyl-4-piperidinyl)oxy]aniline as starting materials, followed by recrystallization (ethyl acetate/diethyl ether).
$^1$HNMR (400 MHz,CDCl$_3$,δppm): 1.23 (3H, t, J=7.2 Hz), 1.64-1.78 (2H, m), 1.83-1.97 (4H, m), 2.00-2.11 (4H, m), 2.14-2.23 (2H, m), 2.49 (2H, q,J=7.2 Hz), 2.60-2.68 (2H, m), 2.70-2.80 (1H, m), 4.36-4.42 (1H, m), 7.06 (2H, d, J=8.8 Hz), 7.13 (2H, d, J=8.8 Hz), 7.53 (1H, d, J=6.0 Hz), 8.84 (1H, d, J=6.0 Hz), 9.47 (1H, s)

Example 110

3-{4-[(1-cyclobutyl-4-piperidinyl)oxy]phenyl}-2-methylpyrido[2,3-d]pyrimidin-4(3H)-one The title compound was obtained by the method according to Example 94, using 2-aminonicotinic acid, acetic anhydride and 4-[(1-cyclobutyl-4-piperidinyl)oxy]aniline as starting materials.
$^1$HNMR (400 MHz,CDCl$_3$,δppm): 1.63-1.77 (2H, m), 1.82-1.95 (4H, m), 1.99-2.11 (4H, m), 2.15-2.23 (2H, m), 2.34 (3H, s), 2.60-2.68 (2H, m), 2.70-2.80 (1H, m), 4.33-4.41 (1H, m), 7.03 (2H, d, J=8.8 Hz), 7.12 (2H, d, J=8.8 Hz), 7.39 (1H, dd, J=4.4, 8.0 Hz), 8.56 (1H, dd, J=2.0, 7.6 Hz), 8.96 (1H, dd, J=2.4, 4.8 Hz)

Example 111

3-{4-[(1-cyclobutyl-4-piperidinyl)oxy]phenyl}-2-ethylpyrido[2,3-d]pyrimidin-4(3H)-one The title compound was synthesized as a white solid (m.p.: 146-148° C.) by the method according to Example 94, using 2-aminonicotinic acid, propionic anhydride and 4-[(1-cyclobutyl-4-piperidinyl)oxy]aniline, followed by recrystallization (ethyl acetate/diethyl ether).

$^1$HNMR (400 MHZ,CDCl$_3$,δppm): 1.30 (3H, t, J=7.2 Hz), 1.65-1.75 (2H, m), 1.82-1.95 (4H, m), 1.99-2.11 (4H, m), 2.14-2.23 (2H, m), 2.51 (2H, q,J=7.2 Hz),2.60-2.68 (2H, m), 2.70-2.79 (1H, m), 4.34-4.41 (1H, m), 7.02 (2H, d, J=8.8 Hz), 7.10 (2H, d, J=8.8 Hz), 7.39 (1H, dd, J=4.4, 8.8 Hz), 8.57 (1H, dd, J=2.0, 8.0 Hz), 8.96 (1H, dd, J=2.4, 4.8 Hz)

Example 112

6-chloro-3-{4-[(1-cyclobutyl-4-piperidinyl)oxy]phenyl}-2-methylpyrido[3,4-d]pyrimidin-4(3H)-one The title compound was obtained by the method according to Example 94, using 5-amino-2-chloroisonicotinic acid, acetic anhydride and 4-[(1-cyclobutyl-4-piperidinyl)oxy]aniline as starting materials.

$^1$HNMR (400 MHz,CDCl$_3$,δppm) 1.63-1.77 (2H, m), 1.82-1.96 (4H, m), 1.99-2.11 (4H, m), 2.14-2.22 (2H, m), 2.28 (3H, s), 2.60-2.68 (2H, m), 2.70-2.79 (1H, m), 4.33-4.41 (1H, m), 7.02 (2H, d, J=8.8 Hz), 7.10 (2H, d, J=8.8 Hz), 8.03 (1H, s), 8.87 (1H, s)

Example 113

6-chloro-3-{4-[(1-cyclobutyl-4-piperidinyl)oxy]phenyl}-2-ethylpyrido[3,4-d]pyrimidin-4(3H)-one The title compound was obtained by the method according to Example 94, using 5-amino-2-chloroisonicotinic acid, propionic anhydride and 4-[(1-cyclobutyl-4-piperidinyl)oxy]aniline as starting materials.

$^1$HNMR (400 MHz,CDCl$_3$,δppm): 1.23 (3H, t, J=7.6 Hz), 1.62-1.75 (2H, m), 1.82-1.95 (4H, m), 1.99-2.10 (4H, m), 2.10-2.24 (2H, m), 2.46 (2H, q,J=7.2 Hz), 2.60-2.68 (2H, m), 2.70-2.79 (1H, m), 4.34-4.41 (1H, m), 7.02 (2H, d, J=8.8 Hz), 7.08 (2H, d, J=8.8 Hz), 8.03 (1H, s), 8.91 (1H, s)

Example 114

3-{4-[(1-cyclobutyl-4-piperidinyl)oxy]phenyl}-2-methylpyrido[3,4-d]pyrimidin-4(3H)-one The title compound was obtained as a light yellow solid (m.p.:169-171° C.) by catalytic reduction of 6-chloro-3-{4-[(cyclobutyl-4-piperidinyl)oxy]phenyl}-2-methylpyrido[3,4-d]pyrimidine-4(3H)-one synthesized in Example 112 in ethyl acetate using palladium charcoal as catalyst in the presence of triethylamine, followed by recrystallization (ethyl acetate/diethyl ether).

$^1$HNMR (400 MHz,CDCl$_3$,δppm) 1.63-1.77 (2H, m), 1.82-1.95 (4H, m), 1.99-2.11 (4H, m), 2.15-2.23 (2H, m), 2.29 (3H, s), 2.60-2.69 (2H, m), 2.73-2.83 (1H, m), 4.36-4.43 (1H, m), 7.03 (2H, d, J=8.8 Hz), 7.12 (2H, d, J=8.8 Hz), 8.01 (1H, dd, J=0.8, 5.6 Hz), 8.65 (1H, d, J=5.2 Hz), 9.09 (1H, d, J=0.8 Hz)

Example 115

3-{4-[(1-cyclobutyl-4-piperidinyl)oxy]phenyl}-2-ethylpyrido[3,4-d]pyrimidin-4(3H)-one The title compound was obtained by catalytic reduction of 6-chloro-3-{4-[(1-cyclobutyl-4-piperidinyl)oxy]phenyl}-2-ethylpyrido[3,4-d]pyrimidin-4 (3H)-one synthesized in Example 113 using palladium charcoal as catalyst in the presence of triethylamine.

$^1$HNMR (400 MHz,CDCl$_3$,δppm): 1.23 (3H, t, J=7.2 Hz), 1.65-1.75 (2H, m), 1.82-1.96 (4H, m), 2.00-2.11 (4H, m), 2.14-2.23 (2H, m), 2.48 (2H, q,J=7.6 Hz), 2.60-2.68 (2H, m), 2.70-2.79 (1H, m), 4.33-4.42 (1H, m), 7.02 (2H, d, J=8.8 Hz), 7.10 (2H, d, J=8.8 Hz), 8.00 (1H, dd, J=0.8, 5.2 Hz), 8.64 (1H, d, J=5.2 Hz), 9.13 (1H, d, J=0.8 Hz)

Example 116

2-phenyl-3-[4-(3-piperidin-1-ylpropoxy)phenyl]-4(3H)-quinazolinone (1) Manufacture of 2-phenyl-4H-3,1-benzoxazin-4-one Anthranilic acid (1.0 g, 7.29 mmol) was dissolved in pyridine (10 mL), benzoyl chloride (1.13 g, 8.02 mmol) was slowly added on an ice bath, and stirred at 50° C. overnight. The solvent was distilled off under reduced pressure, the residue was dissolved in dry methylene chloride (20 mL), oxalyl chloride (925 mg, 7.29 mmol) and a catalytic amount of dimethylformamide were added on an ice bath, and stirred at room temperature for 4 hours. Saturated sodium hydrogen carbonate aqueous solution was added, the mixture was extracted with methylene chloride, and the organic phase was dried with anhydrous sodium sulfate. The solvent was distilled off under reduced pressure, the residue was washed by diethyl ether/heptane, and the target substance (1.13 g, 69%) was obtained as a light yellow solid.

(2) Manufacture of 2-phenyl-3-[4-(3-piperidin-1-ylpropoxy)phenyl]-4(3H)-quinazolinone The title compound was obtained by cyclizing 2-phenyl-4H-3,1-benzoxazin-4-one and 4-(3-piperidin-1-ylpropoxy) aniline according to Example 18-(2).

$^1$HNMR (400 MHz,CDCl$_3$,δppm): 1.41-1.50 (2H, m), 1.54-1.62 (4H, m), 1.90-1.99 (2H, m), 2.34-2.42 (4H,brs), 2.44 (2H, t, J=7.2 Hz), 3.94 (2H, t, J=6.4 Hz), 6.79 (2H, d, J=8.8 Hz), 7.01 (2H, d, J=8.8 Hz),7.19-7.25 (3H, m), 7.30-7.34 (2H, m), 7.48-7.53 (1H, m), 7.77-7.80 (2H, m), 8.33 (1H, d, J=8.4 Hz)

Example 117 cis-2-methyl-3-(4-{[4-(1-pyrrolidinyl)cyclohexyl]oxy}phenyl)-4(3H)-quinazolinone and trans-2-methyl-3-(4-{[4-(1-pyrrolidinyl)cyclohexyl]oxy}phenyl)-4(3H)-quinazolinone (1) Manufacture of 1,4-dioxaspiro[4.5]decan-8-ol 1,4-dioxaspiro[4.5]decan-8-one (1.0 g, 6.40 mmol) was dissolved in methanol (10 mL), sodium borohydride (242 mg, 6.40 mmol) was slowly added, and stirred at room temperature for 5 minutes. The mixture was cooled on an ice bath, 10% hydrochloric acid aqueous solution and sodium chloride were added, and the mixture extracted with ethyl acetate. The organic phase was washed with saturated brine, and dried by anhydrous sodium sulfate. The sodium sulfate was filtered off, and the product concentrated under reduced pressure to obtain the target compound (614 mg, 61%) as a light yellow oily substance.

(2) Manufacture of 2-methyl-3-{4-[(4-oxocyclohexyl)oxy]phenyl}-4(3H)-quinazolinone 2-methyl-3-(4-hydroxyphenyl)-4-(3H)quinazolinone synthesized according to Example 1-(1) and -(2) (665 mg, 2.63 mmol), 1,4-dioxaspiro[4.5]decan-8-ol (500 mg, 3.16 mmol) and triphenyl phosphine (1.03 g, 3.96 mmol) were dissolvedin dry tetrahydrofuran (5 mL), and cooled on an ice bath. Diisopropyl azodicarboxylate (777 uL, 3.96 mmol) was dripped in at 0° C., and stirred at room temperature for 48 hours. Distilled water was added, and the mixture extracted with ethyl acetate. The organic phase was washed by saturated brine, the residue was purified by silica gel column chromatography (hexane/ethyl acetate=2/8-0/10), the ketal protector of the target compound was obtained, and deprotection was then performed. 10% hydrochloric acid aqueous solution was added to the residue, and stirred at room temperature for 3 hours. 2N sodium hydroxide aqueous solution was added, and the mixture extracted with ethyl acetate. The organic phase was washed by saturated brine solution and dried with anhydrous sodium sulfate. The product was purified by silica gel column chromatography (chloroform/methanol=20/1) to obtain the target substance (511 mg, 49%) as a light orange solid.

(3) Manufacture of cis-2-methyl-3-(4-{[4-(1-pyrrolidinyl)cyclohexyl]oxy}phenyl)-4(3H)-quinazolinone and trans-2-methyl-3-(4-{[4-(1-pyrrolidinyl)cyclohexyl]oxy}phenyl)-4(3H)-quinazolinone 2-methyl-3-{4-[(4-oxocyclohexyl)oxy]phenyl}-4(3H)-quinazolinone (484 mg, 1.39 mmol) and pyrrolidine (99 mg, 1.39 mmol) were dissolved in 0.5M zinc(II) chloride/sodium cyanoborohydride methanol aqueous solution (1.7 mL), and stirred at room temperature for 3 hours. 2N sodium hydroxide aqueous solution was added, and the mixture was extracted with ethyl acetate. The organic phase was washed by saturated brine and dried with anhydrous sodium sulfate. The product was purified by silica gel column chromatography (hexane/ethyl acetate=8/2-5/5), and the cis-isomer (260 mg) and trans-isomer (180 mg) of the title compound were respectively obtained as colorless solids. cis-2-methyl-3-(4-{[4-(1-pyrrolidinyl)cyclohexyl]oxy}phenyl)-4(3H)-quinazolinone $^1$HNMR (400 MHz,CDCl$_3$,δppm): 1.58-1.66 (2H, m), 1.73-1.81 (8H, m), 2.10-2.13 (2H, m), 2.26 (3H, s), 2.61 (4H,brs), 4.53 (1H, m), 7.01 (2H, d, J=8.8 Hz), 7.11 (2H, d, J=8.8 Hz), 7.44 (1H, t, J=8.1 Hz), 7.65 (1H, d, J=8.1 Hz), 7.74 (1H, t, J=8.1 Hz), 8.24 (1H, d, J=8.1 Hz) trans-2-methyl-3-(4-{[4-(1-pyrrolidinyl)cyclohexyl]oxy}phenyl)-4(3H)-quinazolinone $^1$HNMR (400 MHz,CDCl$_3$,δppm): 1.07-1.66 (4H, m), 1.77-1.81 (4H, m), 2.16-2.06 (4H, m), 2.25 (3H, s), 2.61 (4H,brs), 4.19-4.26 (1H, m), 7.00 (2H, d, J=8.8 Hz), 7.11 (2H, d, J=8.8 Hz), 7.44 (1H, t, J=8.1 Hz), 7.65 (1H, d, J=8.1 Hz), 7.74 (1H, t, J=8.1 Hz), 8.25 (1H, d, J=8.1 Hz Example 118

3-{4-[(1-cyclopentyl-3-pyrrolidinyl)oxy]phenyl}-2-methyl-4(3H)-quinazolinone (racemic mixture)

(1) Manufacture of 1-benzyl-3-pyrrolidinol 1-benzyl-3-pyrrolidinone was reduced with sodium borohydride according to Example 117-(1), and the target compound was obtained.

(2) Manufacture of 3-{4-[(1-benzyl-3-pyrrolidinyl)oxy]phenyl}-2-methyl-4(3H)-quinazolinone 1-benzyl-3-pyrrolidinol and 2-methyl-3-(4-hydroxyphenyl)-4-(3H) quinazolinone synthesized according to Example 1-(1) and -(2) were etherated by the Mitsunobu reaction according to Example 117-(2), and the target compound was thus obtained.

(3) Manufacture of 3-{4-[(3-pyrrolidinyl)oxy]phenyl}-2-methyl-4(3H)-quinazolinone The target compound was obtained by catalytic reduction of 3-{4-[(1-benzyl-3-pyrrolidinyl)oxy]phenyl}-2-methyl-4(3H)-quinazolinone using palladium hydroxide as catalyst in methanol.

(4) Manufacture of 3-{4-[(1-cyclopentyl-3-pyrrolidinyl)oxy]phenyl}-2-methyl-4(3H)-quinazolinone (Racemic Mixture)

The title compound was obtained by reduction amination according to Example 88-(3), using 3-{4-[(3-pyrrolidinyl)oxy]phenyl}-2-methyl-4(3H)-quinazolinone and cyclopentanone.

$^1$HNMR (400 MHz,CDCl$_3$,δppm): 1.45-1.57 (2H, m), 1.70-1.73 (4H, m), 1.72-1.85 (2H, m), 1.83-2.04 (1H, m), 2.25 (3H, s), 2.31-2.36 (1H, m), 2.46-2.52 (1H, m),2.52-2.61 (1H, m), 2.79-2.84 (2H, m), 3.00-2.97 (1H, m), 4.82-4.87 (1H, m), 6.96 (2H, d, J=8.8 Hz), 7.12 (2H, d, J=8.8 Hz), 7.44 (1H, t, J=8.1 Hz), 7.64 (1H, d, J=8.1 Hz), 7.74 (1H, t, J=8.1 Hz), 8.24 (1H, d, J=8.1 Hz)

Example 119

3-{4-[(1-cyclobutyl-3-pyrrolidinyl)oxy]phenyl}-2-methyl-4(3H)-quinazolinone (racemic mixture)

The title compound was obtained by reductive amination according to the method of Example 118, using 3-{4-[(3-pyrrolidinyl)oxy]phenyl}-2-methyl-4(3H)-quinazolinone and cyclobutanone.

$^1$HNMR (400 MHz,CDCl$_3$,δppm): 1.68-1.78 (2H, m), 1.94-2.07 (5H, m), 2.25 (3H, s), 2.30-2.35 (1H, m), 2.46-2.52 (1H, m), 2.71-2.76 (2H, m), 2.86-2.91 (1H, m), 2.93-3.00 (1H, m), 4.83-4.87 (1H, m), 6.96 (2H, d, J=8.8 Hz), 7.12 (2H, d, J=8.8 Hz), 7.44 (1H, t, J=8.1 Hz), 7.64 (1H, d, J=8.1 Hz), 7.74 (1H, t, J=8.1 Hz), 8.24 (1H, d, J=8.1 Hz)

Example 120

3-{4-[(1-cyclopentyl-4-azepanyl)oxy]phenyl}-2-methyl-4 (3H)-quinazolinone (Racemic Mixture)

(1) Manufacture of 3-{4-[(4-azepanyl)oxy]phenyl}-2-methyl-4(3H)-quinazolinone 2-methyl-3-(4-hydroxyphenyl)-4(3H)quinazolinone synthesized as in Example 1-(2) and 1-(t-butoxycarbonyl)-4-hydroxy azepan were etherated by the Mitsunobu reaction according to the method of Example 117-(2), and the target compound was obtained by deprotection with trifluoroacetic acid.

(2) Manufacture of 3-{4-[(1-cyclopentyl-4-azepanyl)oxy]phenyl}-2-methyl-4(3H)-quinazolinone (Racemic Mixture)

The title compound was obtained by reductive amination according to Example 117-(3), using 3-{4-[(4-azepanyl)oxy]phenyl}-2-methyl-4(3H)-quinazolinone and cyclopentanone.

$^1$HNMR (400 MHz,CDCl$_3$,δppm): 1.47-1.59 (4H, m), 1.63-1.75 (2H, m), 1.83-1.97 (4H, m), 2.02-2.16 (2H, m), 2.17-2.28 (5H, m), 2.73-2.87 (2H, m),2.88-2.97 (2H, m), 2.98-3.07 (1H, m), 4.57-4.64 (1H, m), 6.97 (2H, d, J=8.8 Hz), 7.11 (2H, d, J=8.8 Hz), 7.43 (1H, t, J=8.0 Hz), 7.64 (1H, d, J=7.2 Hz), 7.73 (1H, t, J=7.2 Hz), 8.23 (1H, d, J=8.0 Hz)

Example 121

3-{4-[(1-cyclobutyl-4-azepanyl)oxy]phenyl}-2-methyl-4(3H)-quinazolinone (Racemic Mixture)

The title compound was obtained by reductive amination according to Example 120, using 3-{4-[(4-azepanyl)oxy]phenyl}-2-methyl-4(3H)-quinazolinone and cyclobutanone.

$^1$HNMR (400 MHz,CDCl$_3$,δppm) 1.56-1.69 (4H, m), 1.80-1.89 (4H, m), 1.98-2.06 (2H, m), 2.08-2.19 (2H, m), 2.24 (3H, s), 2.39-2.50 (2H, m), 2.53-2.62 (2H, m), 2.85-2.95 (1H, m), 4.54-4.61 (1H, m), 6.96 (2H, d, J=8.8 Hz), 7.10 (2H, d, J=8.8 Hz), 7.43 (1H, t, J=8.0 Hz), 7.63 (1H, d, J=7.2 Hz), 7.72 (1H, t, J=7.2 Hz), 8.23 (1H, d, J=8.0 Hz)

Example 122

3-methyl-2-{4-[3-(1-piperidinyl)propoxy]phenyl}-1(2H)-isoquinolinone

(1) Manufacture of 3-(1-hydroxyethyl)-2-benzofuran-1(3H)-one

A dry tetrahydrofuran solution (100 mL) of lithium diisopropyl amide (26.9 mmol) was cooled to −78 degree in a current of nitrogen, and a tetrahydrofuran solution (100 mL) of phthalide (3.0 g, 22.4 mmol) was dripped in. After stirring at −78° C. for 30 minutes, acetaldehyde (1.19 g, 26.9 mmol) was slowly added and stirred at −50° C. for 4 hours. After the temperature had risen to room temperature, distilled water was added and the mixture extracted with ethyl acetate. The organic phase was washed with distilled water and saturated brine, and dried with anhydrous sodium sulfate. The residue was purified by silica gel column chromatography (hexane/ethyl acetate=4/6), and the target compound (1.96 g, 49%) was obtained as a yellow oily residue.

(2) Manufacture of 3-methyl-1H-isochroman-1-one 3-(1-hydroxyethyl)-2-benzofuran-1(3H)-one (1.3 g, 7.30 mmol) and p-toluenesulfonic acid monohydrate (3.46 g, 18.2 mmol) were dissolved in toluene (50 mL), and refluxed for 4 hours. Saturated sodium hydrogen carbonate aqueous solution was added, and the mixture extracted with ethyl acetate. The organic phase was washed with saturated sodium hydrogen carbonate aqueous solution and saturated brine, and dried with anhydrous sodium sulfate. The residue was purified by silica gel column chromatography (hexane/ethyl acetate=10/0-5/5), and the target compound (0.64 g, 55%) was obtained as an orange solid.

(3) Manufacture of 2-(2-oxopropyl)benzoic acid 3-methyl-1H-isochroman-1-one (320 mg, 2.0 mmol) was dissolved in ethanol (5 mL), 2N sodium hydroxide aqueous solution (3 mL) was added, and stirred at 80° C. for 5 hours. Ethanol was distilled off under reduced pressure, 8N hydrochloric acid aqueous solution was added, and the mixture extracted with ethyl acetate. The organic phase was dried with anhydrous sodium sulfate, concentrated and dried to obtain the target compound (280 mg, 79%) as a yellow solid.

(4) Manufacture of 2-(4-methoxyphenyl)-3-methyl-1(2H)-isoquinolinone 2-(2-oxopropyl)benzoic acid (100 mg, 0.56 mmol), 4-methoxyaniline (76 mg, 0.56 mmol), 1-ethyl-3-(3-dimethylaminopropyl)carbodiimide hydrochloride (0.84 mmol) and pyridine (0.5 mL) were dissolved in chloroform (5 mL) and stirred at room temperature overnight. Chloroform was added, the organic phase was washed by aqueous citric acid solution, sodium hydrogen carbonate aqueous solution and saturated brine in that order, and dried with anhydrous sodium sulfate. The product was purified by silica gel column chromatography (hexane/ethyl acetate=10/0-3/7) to obtain the target compound (66 mg, 44%) as a light brown solid.

(5) Manufacture of 2-(4-hydroxyphenyl)-3-methyl-1(2H)-isoquinolinone 2-(4-methoxyphenyl)-3-methyl-1(2H)-isoquinolinone (56 mg, 0.21 mmol) was dissolved in dry methylene chloride, a 1M methylene chloride solution (0.63 mL) of boron tribromide was slowly added at −10° C., and stirred at room temperature for 2 hours. A saturated sodium hydrogen carbonate aqueous solution was added to the reaction mixture, and the methylene chloride distilled off under reduced pressure. 8N hydrochloric acid aqueous solution was added, and the solid precipitate was filtered off and dried to obtain the target compound (48 mg, 91%) as a colorless solid.

(6) Manufacture of 3-methyl-2-{4-[3-(1-piperidinyl)propoxy]phenyl}-1(2H)-isoquinolinone 2-(4-hydroxyphenyl)-3-methyl-1(2H)-isoquinolinone (30 mg, 0.12 mmol), 1-(3-bromopropyl)piperidine hydrobromide (51 mg, 0.18 mmol) and potassium carbonate (49 mg, 0.36 mmol) were mixed in dimethylformamide (3 mL) and stirred at 80° C. for 3 hours. The solvent was distilled off under reduced pressure, distilled water was added. and the mixture extracted with ethyl acetate. The organic phase was dried with anhydrous sodium sulfate, and the product purified by silica gel column chromatography (chloroform/methanol=20/1) to obtain the title compound (18 mg, 40%) as a colorless solid.

¹HNMR (400 MHz,CDCl₃,δppm): 1.41-1.49 (2H, m), 1.56-1.63 (4H, m), 1.97-2.04 (5H, m), 2.38-2.48 (4H,brs), 2.51 (2H, t, J=7.0 Hz), 4.06 (2H, t, J=6.4 Hz), 6.42 (1H, s), 7.01 (2H, d, J=8.8 Hz), 7.13 (2H, d, J=8.8 Hz), 7.39-7.47 (2H, m), 7.63 (1H, t, J=8.0 Hz), 8.37 (1H, d, J=8.0 Hz)

Example 123

2-{4-[(1-cyclobutyl-4-piperidinyl)oxy-one]phenyl}-3-methyl-1(2H)-isoquinolinone

A Mitsunobu reaction and a reductive amination reaction were performed in that order according to the method of Example 88, using the 2-(4-hydroxyphenyl)-3-methyl-1 (2H)-isoquinolinone synthesized in Example 122-(5), N-(t-butoxycarbonyl)-4-piperidinol and cyclobutanone as starting materials, and the title compound was thus obtained as a colorless solid.

¹HNMR (400 MHz, CDCl₃,δppm): 1.62-1.77 (2H, m), 1.82-1.98 (4H, m), 2.02 (3H, s), 2.02-2.10 (4H, m), 2.16-2.26 (2H, m), 2.60-2.69 (2H, m), 2.72-2.80 (1H, m), 4.35-4.42 (1H, m), 6.42 (1H, s), 7.01 (2H, d, J=8.8 Hz), 7.13 (2H, d, J=8.8 Hz), 7.40-7.44 (2H, m), 7.63 (1H, t, J=8.0 Hz), 8.37 (1H, d, J=8.0 Hz)

Example 124

2-methyl-3-[4-{[3-(1-pyrrolidinyl)cyclopentyl]oxy}phenyl]-4(3H)-quinazolinone (trans isomer)

(1) Manufacture of (1)3-{4-[(3-hydroxycyclopentyl)oxy]phenyl}-2-methyl-4(3H)-quinazolinone 3-(4-hydroxyphenyl)-2-methyl-4(3H)-quinazolinone (300 mg, 1.19 mmol), 1,3-cyclopentane diol (242 mg, 2.37 mmol) and triphenylphosphine (468 mg, 1.78 mmol) were dissolved in tetrahydrofuran (3 mL), and diisopropyl azodicarboxylate (0.35 mL, 1.78 mmol) was dripped in at 0° C. and stirred at room temperature for 2 hours. Distilled water was added to reaction mixture, and the mixture extracted with ethyl acetate. The organic phase was washed by saturated brine and dried by anhydrous magnesium sulfate. The product was purified by silica gel column chromatography (hexane/ethyl acetate=40/60-0/100), and the target compound (520 mg) was obtained as a light brown oily residue.

(2) Manufacture of 3-[4-({3-[(methylsulfonyl)oxy]cyclopentyl}oxy)phenyl]-2-methyl-4(3H)-quinazolinone 3-{4-[(3-hydroxycyclopentyl)oxy]phenyl}-2-methyl-4 (3H)-quinazolinone (520 mg, 1.19 mmol) and triethylamine (0.33 mL, 2.32 mmol) were mixed in methylene chloride and cooled on an ice bath. Mesyl chloride (0.12 mL, 1.55 mmol) was dripped in and stirred for 10 minutes at room temperature. Distilled water was added to the reaction mixture, and the mixture extracted with ethyl acetate. The organic phase was washed with distilled water, and dried by anhydrous magnesium sulfate. The residue was concentrated to dryness, and the target compound (553 mg) was thus obtained.

(3) Manufacture of 2-methyl-3-[4-{[3-(1-pyrrolidinyl)cyclopentyl]oxy}phenyl]-4(3H)-quinazollnone (trans isomer)

3-[4-({3-[(methylsulfonyl)oxy]cyclopentyl}oxy)phenyl]-2-methyl-4(3H)-quinazolinone (550 mg, 1.33 mmol), pyrrolidine (474 mg, 6.7 mmol) and potassium carbonate (277 mg, 2.0 mmol) were mixed in dimethylformamide (10 mL) and stirred at 80° C. overnight. Distilled water was added, and the mixture extracted with ethyl acetate. The organic phase was dried by anhydrous magnesium sulfate, and the obtained residue was purified by silica gel column chromatography (chloroform/methanol=20/1) to obtain the title compound (143 mg) as a colorless solid.

2-methyl-3-[4-{[(3-(1-pyrrolidinyl)cyclopentyl]oxy}phenyl]-4(3H)-quinazolinone (trans isomer)

¹HNMR (400 MHz,CDCl₃,δppm): 1.57-1.67 (1H, m), 1.78-1.81 (4H, m), 1.85-1.92 (2H, m), 2.03-2.08 (1H, m), 2.14-2.19 (1H, m), 2.22-2.23 (1H, m), 2.24 (3H, s), 2.76-2.83 (1H, m), 4.81-4.86 (1H, m), 6.96 (2H, d, J=8.8 Hz), 7.11 (2H, d, J=8.8 Hz), 7.44 (1H, t, J=8.1 Hz), 7.66 (1H, d, J=8.1 Hz), 7.73 (1H, t, J=8.1 Hz), 8.23 (1H, d, J=8.1 Hz)

Example 125

3-{4-[3-(7-azabicyclo[2.2.1]hepto-7-yl)propoxy]phenyl}-2-methyl-4(3H)-quinazolinone The title compound was obtained by the method according to Example 1, using anthranilic acid, acetic anhydride, 4-aminophenol, 1,3-bromochloropropane and 7-azabicyclo[2.2.1]heptane hydrochloride as starting materials. 7-azabicyclo[2.2.1]heptane hydrochloride was manufactured by the method described in the literature (J. Am. Chem. Soc., 2003, Vol. 125, p. 15191).

¹HNMR (400 MHz,CDCl₃,δppm): 1.34-1.35 (4H, m), 1.76-1.84 (4H, m), 2.02-2.09 (2H, m), 2.28 (3H, s), 2.59-2.63 (2H, m), 3.37 (2H, brs), 4.12 (2H, t, J=6.2 Hz), 7.04 (2H, d, J=9.0 Hz), 7.16 (2H, d, J=8.4 Hz), 7.46-7.50 (1H, m), 7.67 (1H, d, J=7.8 Hz), 7.76-7.80 (1H, m), 8.28 (1H, dd, J=8.6, 1.6 Hz)

Example 126

3-{4-[3-(8-azabicyclo[3.2.1]octo-8-yl)propoxy]phenyl}-2-methyl-4(3H)-quinazolinone (1) Manufacture of 8-azabicyclo[3.2.1]octane hydrochloride Tropane (11.0 mL, 7.44 mmol) was dissolved in toluene (10 mL), chloroethyl carbonate (2.2 mL, 23 mmol) was added slowly, and the mixture stirred at 80° C. for 24 hours. Distilled water was added to the reaction mixture, and the mixture extracted with ethyl acetate. The organic phase was dried and concentrated by anhydrous magnesium sulfate. The obtained oily residue was dissolved in concentrated hydrochloric acid (10 mL), and heated with stirring at 100° C. for 2 hours. The solvent was distilled off under reduced pressure, toluene was added to the residue, and the mixture distilled under reduced pressure to obtain the target substance (820 mg, 72%) as a colorless solid.

(2) Manufacture of 3-{4-[3-(8-azabicyclo[3.2.1]octo-8-yl)propoxy]phenyl}-2-methyl-4(3H)-quinazolinone The title compound was obtained by the method according to Example 1, using anthranilic-acid, acetic anhydride, 4-aminophenol, 1,3-bromochloropropane and 8-azabicyclo [3.2.1]octane hydrochloride as starting materials.

Example 127

3-{4-[3-(3,3-difluoropyrrolidin-1-yl)propoxy]phenyl}-2-methyl-5-(trifluoromethyl)-4(3H)-quinazolinone trifluoroacetate The title compound was obtained by the method according to Example 1, using anthranilic acid, acetic anhydride, 4-aminophenol, 1,3-bromochloropropane and 3,3-difluoropyrrolidine hydrochloride as starting materials.

$^1$HNMR (400 MHZ,CDCl$_3$,δppm): 2.27 (3H, s), 2.29 (2H, m), 2.70 (2H, m), 3.58 (2H, dd, J=8.8, 8.8 Hz), 3.81 (2H,brs), 4.02 (2H, m), 4.23 (2H, t, J=5.6 Hz), 7.17 (2H, d, J=8.8 Hz), 7.33 (2H, d, J=8.8 Hz), 7.95 (3H, m)

Example 128

3-(4-{3-[(3R)-3-fluoropyrrolidin-1-yl]propoxy}phenyl)-2-methyl-5-(trifluoromethyl)-4(3H)-quinazolinone trifluoroacetate The title compound was obtained by the method according to Example 1, using 2-amino-6-(trifluoromethyl)benzoic acid, acetic anhydride, 4-aminophenol, 1,3-bromochloropropane and (3R)-3-fluoropyrrolidine hydrochloride as starting materials.

$^1$HNMR (400 MHZ,CDCl$_3$,δppm): 2.20-2.80 (2H, m), 2.28 (3H, s), 2.31 (2H, m), 3.20-3.60 (2H, m), 3.53 (2H, m), 3.80-4.20 (2H, m), 4.22 (2H, t, J=5.6 Hz), 5.49 (1H, d, J=60 Hz), 7.17 (2H, d, J=9.2 Hz), 7.32 (2H, d, J=9.2 Hz), 7.95 (3H, m)

Example 129

3-{4-[3-(4,4-difluoropiperidin-1-yl)propoxy]phenyl}-2-methyl-5-(trifluoromethyl)-4(3H)-quinazolinone trifluoroacetate The title compound was obtained by the method according to Example 1, using 2-amino-6-(trifluoromethyl)benzoic acid, acetic anhydride, 4-aminophenol, 1,3-bromochloropropane and 4,4-difluoropiperidine hydrochloride as starting materials.

$^1$HNMR (400 MHz,CDCl$_3$,δppm): 2.20-2.60 (6H, m), 2.27 (3H, s), 3.20-3.50 (2H, m), 3.49 (2H, t, J=8.0 Hz), 3.78 (2H, m), 4.23 (2H, t, J=5.6 Hz), 7.17 (2H, d, J=6.6 Hz), 7.32 (2H, d, J=6.6 Hz), 7.95 (3H, m)

Example 130

3-{4-[3-(4-fluoropiperidin-1-yl)propoxy]phenyl}-2-methyl-5-(trifluoromethyl)-4(3H)-quinazolinone trifluoroacetate The title compound was obtained by the method according to Example 1, using 2-amino-6-(trifluoromethyl) benzoic acid, acetic anhydride, 4-aminophenol, 1,3-bromochloropropane and 4-fluoropiperidine hydrochloride as starting materials.

$^1$HNMR (400 MHz,CDCl$_3$,δppm) 2.18-2.43 (9H, m), 3.11 (2H, m), 3.29 (2H, t, J=7.8 Hz), 3.60 (2H, m), 4.13 (2H, t, J=5.6 Hz), 5.02 (1H, m), 7.03 (2H, d, J=9.0 Hz), 7.19 (2H, d, J=9.0 Hz), 7.82-7.83 (1H, m), 7.89-7.90 (2H, m)

Example 131

3-{4-[3-(3,3-difluoropiperidin-1-yl)propoxy]phenyl}-2-methyl-5-(trifluoromethyl)-4(3H)-quinazolinone trifluoroacetate The title compound was obtained by the method according to Example 1, using 2-amino-6-(trifluoromethyl)benzoic acid, acetic anhydride, 4-aminophenol, 1,3-bromochloropropane and 3,3-difluoropiperidine hydrochloride as starting materials.

$^1$HNMR (400 MHz,DMSO-d6,δppm): 2.15-2.18 (5H, m), 3.32-3.34 (2H, m), 3.74-3.76 (8H, m), 4.14 (2H, t, J=5.9 Hz), 7.11 (2H, d, J=9.0 Hz), 7.39 (2H, d, J=9.0 Hz), 7.92-7.99 (3H, m)

Example 132

3-{4-[3-(3-fluoropiperidin-1-yl)propoxy]phenyl}-2-methyl-5-(trifluoromethyl)-4(3H)-quinazolinone trifluoroacetate (Racemic Mixture)

The title compound was obtained by the method according to Example 1, using 2-amino-6-(trifluoromethyl)benzoic acid, acetic anhydride, 4-aminophenol, 1,3-bromochloropropane and 3-fluoropiperidine hydrochloride as starting materials.

$^1$HNMR (400 MHz,DMSO-d6,δppm): 1.66-2.01 (4H, m), 2.15-2.17 (5H, m), 3.15-3.38 (4H, m), 3.83-4.09 (4H, m), 5.17 (1H, m), 7.11 (2H, d, J=9.0 Hz), 7.39 (2H, d, J=9.0 Hz), 7.94-7.98 (3H, m)

Example 133

2-methyl-3-(4-{3-[(3R)-3-methyl-piperidin-1-yl]propoxy}phenyl)-4(3H)-quinazolinone The title compound was obtained by the method according to Example 1, using anthranilic acid, acetic anhydride, 4-aminophenol, 1,3-bromochloropropane and (3R)-3-methylpiperidine (R)-(−)-mandelate as starting materials. (3R)-3-methylpiperidine (R)-(−)-mandelate was manufactured by the method described in the literature (J. Org. Chem., 1987, Vol. 52, p. 5466).

$^1$HNMR (400 MHZ,CDCl$_3$,δppm): 0.87 (4H, m), 1.50-1.95 (6H, m), 2.00 (2H, m), 2.26 (3H, s), 2.50 (2H, t, J=6.8 Hz), 2.87 (2H, m), 4.07 (2H, t, J=6.4 Hz), 7.05 (2H, d, J=8.6 Hz), 7.15 (2H, d, J=8.6 Hz), 7.46 (1H, t, J=8.0 Hz), 7.67 (1H, d, J=8.0 Hz), 7.76 (1H, t, J=8.4 Hz), 8.27 (1H, d, J=8.0 Hz)

Example 134

3-(4-{3-[(2R,5R)-2,5-dimethylpyrrolidin-1-yl]propoxy}phenyl)-2-methyl-4(3H)-quinazolinone The title compound was obtained by the method according to Example 1, using anthranilic acid, acetic anhydride, 4-aminophenol, 1,3-bromochloropropane and (2R,5R)-2,5-dimethylpyrrolidine as starting materials.

$^1$HNMR (400 MHz,CDCl$_3$,δppm): 1.00 (6H, d, J=6.0 Hz), 1.40 (2H, m), 2.05 (4H, m), 2.26 (3H, s), 2.60 (1H, m), 2.80 (1H, m), 3.10 (2H, m), 4.10 (2H, m), 7.05 (2H, d, J=8.8 Hz),

---

Previous entry (top of column 97):

$^1$HNMR (400 MHz,CDCl$_3$,δppm): 1.37-2.06 (12H, m), 2.60 (2H, t, J=7.2 Hz), 3.29 (2H,brs), 4.13 (2H, t, J=6.2 Hz), 7.07 (2H, d, J=6.1 Hz), 7.17 (2H, d, J=6.1H-z), 7.46-7.50 (1H, m), 7.69 (1H, d, J=7.8 Hz), 7.76-7.80 (1H, m), 8.29 (1H,.dd, .J=7.8, 1.2 Hz)

7.15 (2H, d, J=8.8 Hz), 7.46 (1H, t, J=8.0 Hz), 7.67 (1H, d, J=8.0 Hz), 7.76 (1H, t, J=7.6 Hz), 8.27 (1H, d, J=8.0 Hz)

Example 135

2-methyl-3-(4-{3-[3-methylpyrrolidin-1-yl]propoxy}phenyl)-4(3H)-quinazolinone (racemic Mixture)

The title compound was obtained by the method according to Example 1, using anthranilic acid, acetic anhydride, 4-aminophenol, 1,3-bromochloropropane and 3-methylpyrrolidine as starting materials. 3-methylpyrrolidine was manufactured by the method described in the literature (J. Med. Chem., 2000, Vol. 43, p. 4388).
$^1$HNMR (400 MHz,CDCl$_3$,δppm) 1.05 (3H, d, J=6.8 Hz), 1.38-1.42 (1H, m), 2.02-2.09 (4H, m), 2.26 (3H, s), 2.28-2.30 (1H, m), 2.54-2.56 (1H, m), 2.63-2.72 (2H, m), 2.78-2.80 (1H, m), 2.92 (1H, t, J=8.3 Hz), 4.09 (2H, t, J=6.3 Hz), 7.04 (2H,td, J=6.0, 3.6 Hz), 7.15 (2H, td, J=6.0, 3.6 Hz), 7.46 (1H, t, J=8.0 Hz), 7.67 (1H, d, J=7.8 Hz), 7.74-7.78 (1H, m), 8.27 (1H, dd, J=7.8, 1.5 Hz)

Example 136

5-methoxy-3-[4-(3-piperidin-1-yl-propoxy)phenyl]-2-propyl-4(3H)-quinazolinone

The title compound was obtained by the method according to Example 18, using 2-amino-6-methoxybenzoic acid, butyric anhydride and 4-(3-piperidin-1-yl propoxy)aniline as starting materials.
$^1$HNMR (400 MHz,CDCl$_3$,δppm): 0.87 (3H, t, J=7.6 Hz), 1.41-1.50 (2H, m), 1.52-1.63 (4H, m), 1.66-1.73 (2H, m), 1.97-2.04 (2H, m), 2.36-2.46 (6H, m), 2.51 (2H, t, J=7.6 Hz), 3.94 (3H, s), 4.06 (2H, t, J=6.4 Hz), 6.86 (1H, d, J=7.6 Hz), 7.01 (2H, d, J=9.2 Hz), 7.09 (2H, d, J=9.2 Hz), 7.25 (1H, d, J=8.4 Hz), 7.64 (1H, t, J=8.4 Hz)

Example 137

5-methoxy-2-propyl-3-[4-(3-pyrrolidin-1-yl-propoxy)phenyl]-4(3H)-quinazolinone

The title compound was obtained by the method according to Example 18, using 2-amino-6-methoxybenzoic acid, butyric anhydride and 4-(3-pyrrolidin-1-yl-propoxy)aniline as starting materials.
$^1$HNMR (400 MHZ,CDCl$_3$,δppm): 0.87 (3H, t, J=7.6 Hz), 1.64-1.84 (2H, m), 1.78-1.82 (4H, m), 2.02-2.08 (2H, m), 2.37 (2H, t, J=8.0 Hz), 2.52-2.56 (4H, m), 2.65 (2H, t, J=7.6 Hz), 3.94 (3H, s), 4.08 (2H, t, J=6.4 Hz), 6.86 (1H, dd, J=0.8, 8.4 Hz), 7.02 (2H, d, J=9.2 Hz), 7.10 (2H, d, J=9.2 Hz), 7.25 (1H, dd, J=0.8, 8.4 Hz), 7.64 (1H, t, J=8.4 Hz)

Example 138

2-methyl-3-(4-{3-[(2S)-2-methylpyrrolidin-1-yl]propoxy}phenyl)-4(3H)-quinazolinone (1) Manufacture of 3-[(2S)-2-methylpyrrolidin-1-yl]propan-1-ol (2S)-2-methylpyrrolidine hydrobromide (2.70 g, 16.3 mmol), 3-bromopropanol (2.49 g, 17.9 mmol) and potassium carbonate (6.75 g, 48.9 mmol) were mixed in tetrahydrofuran (20 mL), and stirred at 60° C. for 18 hours. The precipitate was filtered off, and the filtrate was concentrated. The residue was distilled under reduced pressure, and the target compound (1.88 g, 80%) was thus obtained as a colorless oily substance. (2S)-2-methyl-pyrrolidine hydrobromide was manufactured by the method described in the literature (J. Org. Chem., 1989, Vol. 54, p. 209) using D-prolinol as starting material.

(2) Manufacture of (2S)-2-methyl-1-[3-(4-nitrophenoxy)propyl]pyrrolidine

The target compound was obtained by the method according to Example 18, using 3-[(2S)-2-methylpyrrolidin-1-yl]propanol and 4-nitrophenol as starting materials.

(3) Manufacture of 4-{3-[(2S)-2-methylpyrrolidin-1-yl]propoxy}aniline

The target compound was obtained by catalytic reduction of (2S)-2-methyl-1-[3-(4-nitrophenoxy)propyl]pyrrolidine in methanol, using a palladium charcoal catalyst.

(4) Manufacture of 2-methyl-3-(4-{3-[(2S)-2-methylpyrrolidin-1-yl]propoxy}phenyl)-4(3H)-quinazolinone The title compound was obtained by the method according to Example 18, using anthranilic acid, acetic anhydride and 4-{3-[(2S)-2-methylpyrrolidin-1-yl]propoxy}aniline as starting materials.
$^1$HNMR (400 MHz,CDCl$_3$,δppm): 1.12 (3H, d, J=6.0 Hz), 1.40-1.50 (1H, m), 1.60-2.37 (11H, m), 2.97-3.03 (1H, m), 3.18-3.23 (1H, m), 4.07-4.11 (2H, m), 7.05 (2H, d, J=9.2 Hz), 7.15 (2H, d, J=9.2 Hz), 7.46 (1H, t, J=7.6 Hz), 7.67 (1H, d, J=7.6 Hz), 7.76 (1H, t, J=7.6 Hz), 8.27 (1H, d, J=7.6 Hz)
NMR data for 4-{3-[(2S)-2-methylpyrrolidin-1-yl]propoxy}aniline used for manufacturing the compound of this example is shown below.
$^1$HNMR (400 MHz,CDCl$_3$,δppm): 1.60 (3H, d, J=6.4 Hz), 1.93-2.12 (2H, m), 2.18-2.30 (3H, m), 2.41-2.49 (1H, m), 2.95-3.34 (5H, m), 3.46-3.53 (1H, m), 3.86-3.92 (1H, m), 4.07 (2H, t, J=6.4 Hz), 6.89 (2H, d, J=9.2 Hz), 7.31 (2H, d, J=9.2 Hz)

Example 139

2,5-dimethyl-3-(4-{3-[(2S)-2-methylpyrrolidin-1-yl]propoxy}phenyl)-4(3H)-quinazolinone The title compound was obtained by the method according to Example 18, using 2-amino-6-methyl benzoic acid, acetic anhydride and 4-{3-[(2S)-2-methyl-pyrrolidin-1-yl]propoxy}aniline as starting materials.
$^1$HNMR (400 MHZ,CDCl$_3$,δppm): 1.11 (3H, d, J=6.0 Hz), 1;38-1.48 (1H, m), 1.59-2.33 (11H, m), 2.82 (3H, s), 2.97-3.03 (1H, m), 3.17-3.22 (1H, m), 4.06-4.10 (2H, m), 7.04 (2H, d, J=9.2 Hz), 7.15 (2H, d, J=9.2 Hz), 7.21 (1H, d, J=7.2 Hz), 7.50 (1H, d, J=7.2 Hz), 7.59 (1H, t, J=7.2 Hz)

Example 140

2,6-dimethyl-3-(4-{3-[(2S)-2-methylpyrrolidin-1-yl]propoxy}phenyl)-4(3H)-quinazolinone The title compound was obtained by the method according to Example 18, using 2-amino-5-methyl benzoic acid, acetic anhydride and 4-{3-[(2S)-2-methyl-pyrrolidin-1-yl]propoxy}aniline as starting materials.

¹HNMR (400 MHz,CDCl₃,δppm): 1.12 (3H, d, J=6.0 Hz), 1.38-1.48 (1H, m), 1.59-2.37 (11H, m), 2.48 (3H, s), 2.97-3.03 (1H, m), 3.17-3.23 (1H, m), 4.07-4.11 (2H, m), 7.04 (2H, d, J=9.2 Hz), 7.14 (2H, d, J=9.2 Hz), 7.57-7.58 (2H, m), 8.05 (1H, s)

Example 141

2-ethyl-3-(4-{3-[(2S)-2-methylpyrrolidin-1-yl]propoxy}phenyl)-4(3H)-quinazolinone The title compound was obtained by the method according to Example 18, using anthranilic acid, propionic anhydride and 4-{3-[(2S)-2-methylpyrrolidin-1-yl]propoxy}aniline as starting materials.

¹HNMR (400 MHz,CDCl₃,δppm): 1.12 (3H, d, J=6.0 Hz), 1.22 (3H, t, J=7.2 Hz), 1.40-1.50 (1H, m), 1.60-2.37 (8H, m), 2.47 (2H, q, J=7.2 HZ), 2.97-3.04 (1H, m), 3.18-3.23 (1H, m), 4.07-4.11 (2H, m), 7.05 (2H, d, J=9.2 Hz), 7.15 (2H, d, J=9.2 Hz), 7.45 (1H, t, J=7.6 Hz), 7.71 (1H, d, J=7.6 Hz), 7.76 (1H, t, J=7.6 Hz), 8.27 (1H, d, J=7.6 Hz)

Example 142

6-chloro-2-ethyl-3-(4-{3-[(2S)-2-methylpyrrolidin-1-yl]propoxy}phenyl)pyrido[3,4-d]pyrimidin-4(3H)-one The title compound was obtained by the method according to Example 18, using 5-amino-2-chloroisonicotinic acid, propionic anhydride and 4-{3-[(2S)-2-methylpyrrolidin-1-yl]propoxy}aniline as starting materials.

¹HNMR (400 MHz,CDCl₃,δppm) 1.11 (3H, d, J=6.0 Hz), 1.23 (3H, t, J=7.2 Hz), 1.40-1.50 (1H, m), 1.60-2.37 (8H, m), 2.46 (2H, q,J=7.2 Hz), 2.97-3.04 (1H, m), 3.18-3.23 (1H, m), 4.08-4.11 (2H, m), 7.06 (2H, d, J=9.2 Hz), 7.12 (2H, d, J=9.2 Hz), 8.06 (1H, d, J=0.8 Hz), 8.94 (1H, d, J=0.8 Hz)

Example 143

6-methoxy-2-methyl-3-[4-(3-pyrrolidin-1-yl-propoxy)phenyl]-4(3H)-quinazolinone

The title compound was obtained by the method according to Example 18, using a 2-amino-5-methoxybenzoic acid, acetic anhydride and 4-(3-pyrrolidin-1-yl-propoxy)aniline as starting materials.

¹HNMR (400 MHz,CDCl₃,δppm): 1.79-1.83 (4H, m), 2.03-2.09 (2H, m), 2.23 (3H, s), 2.52-2.58 (4H, m), 2.66 (2H, t, J=7.2 Hz), 3.91 (3H, s), 4.10 (2H, t, J=6.4 Hz), 7.05 (2H, d, J=9.2 Hz), 7.14 (2H, d, J=9.2 Hz), 7.36 (1H, dd, J=2.8, 8.8 Hz), 7.61 (1H, d, J=8.8 Hz), 7.63 (1H, d, J=3.2 Hz)

Example 144

6-methoxy-2-methyl-3-(4-{3-[(2S)-2-methylpyrrolidin-1-yl]propoxy}phenyl)-4(3H)-quinazolinone The title compound was synthesized as a white solid (m.p.: 102-106° C.) by the method according to Example 18, using 2-amino-5-methoxybenzoic acid, acetic anhydride and 4-{3-[(2S)-2-methylpyrrolidin-1-yl]propoxy}aniline as starting materials, followed by recrystallization (ethyl acetate/diethyl ether).

¹HNMR (400 MHz,CDCl₃,δppm): 1.12 (3H, d, J=6.0 Hz), 1.38-1.48 (1H, m), 1.59-2.37 (11H, m), 2.97-3.03 (1H, m), 3.17-3.23 (1H, m), 3.91 (3H, s), 4.08-4.11 (2H, m), 7.05 (2H, d, J=9.2 Hz), 7.15 (2H, d, J=9.2 Hz), 7.35 (1H, dd, J=2.8, 8.8 Hz), 7.61 (1H, d, J=9.2 Hz), 7.63 (1H, d, J=3.2 Hz)

Example 145

2-methyl-3-(4-{3-[(3S)-3-methylpiperidin-1-yl]propoxy}phenyl)-4(3H)-quinazolinone (1) Manufacture of 3-[(3S)-3-methylpiperidin-1-yl]propan-1-ol (3S)-3-methyl-piperidine/(S)-(+)-mandelate (19.9 g, 79.1 mmol), 3-bromo-1-propanol (10 g, 71.9 mmol) and potassium carbonate (14.9 g, 108 mmol) were mixed in tetrahydrofuran (200 mL), and heated under reflux for 30 hours. The insoluble matter was filtered off, the filtrate was concentrated, and ethyl acetate and hexane were added to the residue. The insoluble matter produced was filtered off, the filtrate was concentrated and the target substance (9.6 g, 85%) was obtained as a colorless oily material by distillation under reduced pressure. (3S)-3-methyl-piperidine (S)-(+)-mandelate was manufactured by the method described in the literature (J. Org. Chem., 1987, Vol. 52, p. 5466).

(2) Manufacture of 4-{3-[(3S)-3-methylpiperidin-1-yl]propoxy}aniline monotosylate 4-{3-[(3S)-3-methylpiperidin-1-yl]propoxy}aniline was obtained as a light brown oily substance by the method according to Example 18, using 4-nitrophenol and 3-[(3S)-3-methylpiperidin-1-yl]propan-1-ol as starting materials. The obtained oily substance was dissolved in ethyl acetate, 1 Eq of a methanol solution of p-toluenesulfonic acid monohydrate was added, and the target compound was obtained as a light peach-colored solid by filtering off the solid produced.

(3) Manufacture of 2-methyl-3-(4-{3-[(3S)-3-methylpiperidin-1-yl]propoxy}phenyl)-4(3H)-quinazolinone The title compound was obtained by the method according to Example 18, using anthranilic acid, acetic anhydride and 4-{3-[(3S)-3-methylpiperidin-1-yl]propoxy}aniline monotosylate as starting materials.

¹HNMR (400 MHz,CDCl₃,δppm): 0.87-0.89 (4H, m), 1.56-1.76 (5H, m), 1.84-1.91 (1H, m), 2.02-2.06 (2H, m), 2.26 (3H, s), 2.53 (2H, t, J=7.2 Hz), 2.85-2.93 (2H, m), 4.07 (2H, t, J=6.3 Hz), 7.04 (2H, d, J=9.0 Hz), 7.15 (2H, d, J=9.0 Hz), 7.46 (1H, t, J=7.6 Hz), 7.67 (1H, d, J=7.6 Hz), 7.76 (1H, t, J=7.6 Hz), 8.27 (1H, d, J=7.6 Hz)

NMR data for 4-{3-[(3S)-3-methyl piperidin-1-yl]propoxy}aniline monotosylate used for manufacturing the compound of this example is shown below.

¹HNMR (400 MHz,CDCl₃/CD₃OD=10/1,5 ppm): 0.95-1.10 (4H, m), 1.87-1.92 (2H, m), 2.02-2.32 (7H, m), 2.36 (3H, s), 2.51-2.58 (1H, m), 3.22-3.26 (2H, m), 3.52-3.56 (1H, m), 3.66-3.69 (1H, m), 3.95 (2H, t, J=5.6 Hz), 6.64-6.70 (4H, m), 7.19 (2H, d, J=8.3 Hz), 7.76 (2H, d, J=8.3 Hz)

Example 146

5-bromo-2-methyl-3-[4-(3-pyrrolidin-1-yl-propoxy)phenyl]-4(3H)-quinazolinone (1) Manufacture of 2-amino-6-bromobenzoic acid The target compound was obtained by reducing 2-bromo-6-nitrobenzoic acid with iron in a mixed solvent of methanol and ammonium chloride aqueous solution. 2-bromo-6-nitrobenzoic acid was manufactured by the method described in the literature (J. Chem. Soc. Perkin Trans. 1, 1991, p. 1565) using 2-bromo-6-nitrotoluene as starting material.

(2) Manufacture of 5-bromo-2-methyl-3-[4-(3-pyrrolidin-1-yl-propoxy)phenyl]-4(3H)-quinazolinone The title compound was obtained by the method according to Example 18, using 2-amino-6-bromobenzoic acid, acetic anhydride and 4-(3-pyrrolidin-1-yl-propoxy)aniline as starting materials.

$^1$HNMR (400 MHz,CDCl$_3$,δppm): 1.80-1.84 (4H, m), 2.03-2.09 (2H, m), 2.23 (3H, s), 2.60-2.56 (4H, m), 2.68 (2H, t, J=7.6 Hz), 4.08 (2H, t, J=6.3 Hz), 7.04 (2H, d, J=9.3 Hz), 7.14 (2H, d, J=8.8 Hz), 7.51 (1H, t, J=8.0 Hz), 7.62 (1H, dd, J=8.3, 1.5 Hz), 7.70 (1H,dd, J=7.8, 1.5 Hz)

Example 147

5-fluoro-2-methyl-3-(4-{3-[(3S)-3-methylpiperidin-1-yl]propoxy}phenyl)-4(3H)-quinazolinone The title compound was obtained by the method according to Example 18, using 2-amino-6-fluorobenzoic acid, acetic anhydride and 4-{3-[(3S)-3-methylpiperidin-1-yl]propoxy}aniline monotosylate as starting materials.

$^1$HNMR (400 MHz,CDCl$_3$,δppm): 0.83-0.91 (4H, m), 1.54-1.73 (5H, m), 1.83-1.89 (1H, m), 1.98-2.05 (2H, m), 2.24 (3H, s), 2.50 (2H, t, J=7.3 Hz), 2.83-2.90 (2H, m), 4.07 (2H, t, J=6.3 Hz), 7.04 (2H, d, J=9.3 Hz), 7.07-7.12 (1H, m), 7.13 (2H, d, J=9.3 Hz), 7.46 (1H, d, J=8.3 Hz), 7.70-7.65 (1H, m)

Example 148

2-ethyl-5-fluoro-3-(4-{3-[(3S)-3-methyl-piperidin-1-yl]propoxy}phenyl)-4(3H)-quinazolinone The title compound was obtained by the method according to Example 18, using 2-amino-6-fluorobenzoic acid, propionic anhydride and 4-{3-[(3S)-3-methylpiperidin-1-yl]propoxy}aniline monotosylate as starting materials.

$^1$HNMR (400 MHz,CDCl$_3$,δppm): 0.85-0.90 (4H, m), 1.21 (3H, t, J=7.3 Hz) 1.54-1.73 (5H, m), 1.83-1.90 (1H, m), 1.99-2.05 (2H, m), 2.44 (2H, q,J=7.5 Hz), 2.50 (2H, t, J=7.3 Hz), 2.83-2.91 (2H, m), 4.07 (2H, t, J=6.3 Hz), 7.02-7.14 (5H, m), 7.50 (1H, d, J=8.3 Hz), 7.70-7.64 (1H, m)

Example 149

6-fluoro-2-methyl-3-(4-{3-[(3S)-3-methylpiperidin-1-yl]propoxy}phenyl)pyrido[3,4-d]pyrimidin-4(3H)-one The title compound was obtained by the method according to Example 18, using 5-amino-2-fluoroisonicotinic acid, acetic anhydride and 4-{3-[(3S)-3-methylpiperidin-1-yl]propoxy}aniline monotosylate as starting materials. 5-amino-2-fluoroisonicotinic acid was manufactured by the method described in the literature (J. Chem. Soc. Perkin Trans. 1, 1996, p. 2221).

$^1$HNMR (400 MHz, CDCl$_3$,δppm): 0.83-0.93 (4H, m), 1.61-1.75 (5H, m), 1.86-1.92 (1H, m), 2.01-2.08 (2H, m), 2.28 (3H, s), 2.53 (2H, t, J=7.3 Hz), 2.94-2.85 (2H, m), 4.08 (2H, t, J=6.3 Hz), 7.06 (2H, d, J=9.3 Hz), 7.14 (2H, d, J=9.3 Hz), 7.65 (1H, d, J=3.9 Hz), 8.77 (1H, s)

Example 150

2-ethyl6-fluoro3-(4-{3-[(3S)-3-methyl-piperidin-1-yl]propoxy}phenyl)pyrido[3,4-d]pyrimidin-4(3H)-one The title compound was obtained by the method according to Example 18, using 5-amino-2-fluoroisonicotinic acid, propionic anhydride and 4-{3-[(3S)-3-methylpiperidin-1-yl]propoxy}aniline monotosylate as starting materials.

$^1$HNMR (400 MHz,CDCl$_3$,δppm): 0.83-0.92 (4H, m), 1.23 (3H, t, J=7.3 Hz), 1.56-1.74 (5H, m), 1.84-1.90 (1H, m), 2.00-2.07 (2H, m), 2.44-2.53 (4H, m), 2.83-2.91 (2H, m), 4.08 (2H, t, J=6.3 Hz), 7.06 (2H, d, J=9.3 Hz), 7.13 (2H, d, J=8.8 Hz), 7.65 (1H, d, J=3.9 Hz), 8.80 (1H, s)

Example 151

6-chloro-2-methyl-3-(4-{3-[(3S)-3-methylpiperidin-1-yl]propoxy}phenyl)pyrido[3,4-d]-pyrimidin-4(3H)-one The title compound was obtained by the method according to Example 18, using 5-amino-2-chloroisonicotinic acid, acetic anhydride and 4-{3-[(3S)-3-methylpiperidin-1-yl]propoxy}aniline monotosylate as starting materials.

$^1$HNMR (400 MHz,CDCl$_3$,δppm): 0.83-0.92 (4H, m), 1.23 (3H, t, J=7.3 Hz), 1.58-1.74 (5H, m), 1.84-1.90 (1H, m), 2.00-2.07 (2H, m), 2.44-2.53 (4H, m), 2.91-2.84 (2H, m), 4.08 (2H, t, J=6.3 Hz), 7.06 (2H, d, J=9.3 Hz), 7.13 (2H, d, J=9.3 Hz), 7.65 (1H, d, J=3.9 Hz), 8.80 (1H, s)

Example 152

6-chloro-2-ethyl-3-(4-{3-[(3S)-3-methyl-piperidin-1-yl]propoxy}phenyl)pyrido[3,4-d]pyrimidin-4(3H)-one The title compound was obtained by the method according to Example 18, using 5-amino-2-chloroisonicotinic acid, propionic anhydride and 4-{3-[(3S)-3-methylpiperidin-1-yl]propoxy}aniline monotosylate as starting materials.

$^1$HNMR (400 MHz,CDCl$_3$,δppm): 0.83-0.93 (4H, m), 1.23 (3H, t, J=7.3 Hz) 1.58-1.74 (5H, m), 1.86-1.92 (1H, m), 2.01-2.07 (2H, m), 2.47 (2H, q,J=7.3 Hz), 2.52 (2H, t, J=7.6 Hz), 2.92-2.85 (2H, m), 4.08 (2H, t, J=6.3 Hz), 7.06 (2H, d, J=8.8 Hz), 7.12 (2H, d, J=8.8 Hz), 8.06 (1H, d, J=1.0 Hz), 8.94 (1H, d, J=1.0 Hz)

Example 153

2-methyl-3-(4-{3-[(3S)-3-methylpiperidin-1-yl]propoxy}phenyl)pyrido[2,3-d]pyrimidin-4(3H)-one monohydrochloride The title compound was synthesized as a white solid (m.p.: 255-262° C.) by the method according to Example 18, using 2-aminonicotinic acid, acetic anhydride and 4-{3-[(3S)-3-methylpyridin-1-yl]propoxy}aniline monotosylate as starting materials and treating with 1 Eq of a base (4N ethyl acetate solution), followed by recrystallization (ethanol/ethyl acetate).

1H-NMR (400 MHz,CDCl$_3$/CD$_3$OD=10/1,δppm) 1.01 (3H, d, J=6.3 Hz), 1.05-1.15 (1H, m), 1.90-1.99 (2H, m), 2.25-2.51 (8H, m), 2.57-2.64 (1H, m), 3.21-3.25 (2H, m), 3.51-3.54 (1H, m), 3.63-3.67 (1H, m), 4.18 (2H, t, J=5.6 Hz), 7.06 (2H, d, J=8.8 Hz), 7.19 (2H, d, J=8.8 Hz), 7.51 (1H, dd, J=7.8, 4.9 Hz), 8.66 (1H, dd, J=7.8, 2.0 Hz), 9.03 (1H, dd, J=4.9, 2.0 Hz)

Example 154

2-ethyl-3-(4-{3-[(3S)-3-methyl-piperidin-1-yl]propoxy}phenyl)pyrido[2,3-d]pyrimidin-4(3H)-one monohydrochloride The title compound was synthesized as a white solid (m.p.: 245-252° C.) by the method according to Example 18, using 2-aminonicotinic acid, propionic anhydride and 4-{3-[(3S)-3-methylpyridin-1-yl]propoxy}aniline monotosylate as starting materials and treating with 1 Eq of a base (4N ethyl acetate solution), followed by recrystallization (ethanol/ethyl acetate).

$^1$HNMR (400 MHz,CDCl$_3$/CD$_3$OD=10/1,δppm): 0.99 (3H, d, J=6.3 Hz), 1.07-1.14 (1H, m), 1.31 (3H, t, J=7.3 Hz), 1.88-1.99 (2H, m), 2.22-2.30 (1H, m), 2.38-2.58 (7H, m), 3.16-3.22 (2H, m), 3.47-3.52 (1H, m), 3.60-3.64 (1H, m), 4.17 (2H, t, J=5.4 Hz), 7.04 (2H, d, J=8.8 Hz), 7.17 (2H, d, J=8.8 Hz), 7.43 (1H, dd, J=7.8, 4.1 Hz), 8.60 (1H, dd, J=7.8, 2.0 Hz), 9.00 (1H, dd, J=4.1, 2.0 Hz)

Example 155

2-methyl-3-(4-{3-[(3S)-3-methylpiperidin-1-yl]propoxy}phenyl)pyrido[4,3-d]pyrimidin-4(3H)-one monotosylate The title compound was synthesized as a light yellow solid (m.p.:185-188° C.) by the method according to Example 18, using 4-aminonicotinic acid, acetic anhydride and 4-{3-[(3S)-3-methylpyridin-1-yl]propoxy}aniline monotosylate as starting materials and treating with 1 Eq of p-toluene sulfonic acid, followed by recrystallization (ethanol/ethyl acetate).

$^1$HNMR (400 MHz,CDCl$_3$/CD$_3$OD=10/1,δppm): 0.99 (3H, d, J=6.8 Hz), 1.04-1.12 (1H, m), 1.90-1.94 (2H, m), 2.06-2.21 (2H, m), 2.28-2.44 (10H, m), 3.27-3.32 (2H, m), 3.56-3.60 (1H, m), 3.70-3.74 (1H, m), 4.15 (2H, t, J=5.6 Hz), 7.04-7.07 (2H, m), 7.15-7.18 (2H, m), 7.21 (2H, d, J=7.8 Hz), 7.59 (1H, d, J=5.9 Hz), 7.77 (2H, d, J=8.3 Hz), 8.85 (1H, d, J=5.9 Hz), 9.45 (1H, s)

Example 156

2-ethyl-5-methoxy-3-(4-{3-[(3S)-3-methylpiperidin-1-yl]propoxy}phenyl)-4(3H)-quinazolinone hydrochloride The title compound was obtained by the method according to Example 18, using 2-amino-6-methoxybenzoic acid, propionic anhydride and 4-{3-[(3S)-3-methyl-piperidin-1-yl]propoxy}aniline monotosylate as starting materials.

$^1$HNMR (400 MHz,CDCl$_3$, δppm): 0.99 (3H, d, J=6.8 Hz), 1.04-1.15 (1H, m), 1.33 (3H, t, J=7.3 Hz), 1.88-1.98 (2H, m), 2.22-2.31 (1H, m), 2.34-2.43 (1H, m), 2.47-2.61 (4H, m), 2.98-3.05 (2H, m), 3.16-3.22 (2H, m), 3.50 (1H, d, J=10.2 Hz), 3.63 (1H, d, J=11.2 Hz), 3.99 (3H, s), 4.19 (2H, t, J=5.1 Hz), 7.04-7.07 (3H, m), 7.18 (2H, d, J=8.3 Hz), 7.82 (1H, t, J=8.3 Hz), 7.98 (1H, d, J=8.3 Hz)

Example 157

2-methyl-3-(4-{3-[(3S)-3-methyl-piperidin-1-yl]propoxy}phenyl)pyrido[3,4-d]pyrimidin-4(3H)-one The title compound was obtained by catalytic reduction of 6-chloro-2-methyl-3-(4-{3-[(3S)-3-methyl-piperidin-1-yl]propoxy}phenyl)pyrido[3,4-d]pyrimidin-4(3H)-one synthesized in Example 151 using a palladium charcoal catalyst in the presence of triethylamine.

$^1$HNMR (400 MHz,CDCl$_3$,δppm): 0.85-0.93 (4H, m), 1.58-1.75 (5H, m), 1.86-1.93 (1H, m), 2.01-2.08 (2H, m), 2.30 (3H, s), 2.53 (2H, t, J=7.6 Hz), 2.93-2.86 (2H, m), 4.08 (2H, t, J=6.3 Hz), 7.06 (2H, d, J=8.8 Hz), 7.14 (2H, d, J=8.8 Hz), 8.03 (1H, d, J=5.9 Hz), 8.68 (1H, d, J=5.4 Hz), 9.12 (1H, s)

Example 158

2-ethyl-3-(4-{3-[(3S)-3-methylpiperidin-1-yl]propoxy}phenyl)pyrido[3,4-d]pyrimidin-4(3H)-one The title compound was obtained by catalytic reduction of 6-chloro-2-ethyl-3-(4-{3-[(3S)-3-methylpiperidin-1-yl]propoxy}phenyl)pyrido[3,4-d]pyrimidin-4(3H)-one synthesized in Example 152 using a palladium charcoal catalyst in the presence of triethylamine.

$^1$HNMR (400 MHz,CDCl$_3$,δppm): 0.83-0.92 (4H, m), 1.24 (3H, t, J=7.3 Hz) 1.56-1.76 (5H, m), 1.85-1.92 (1H, m), 2.01-2.07 (2H, m), 2.46-2.54 (4H, m), 2.85-2.92 (2H, m), 4.08 (2H, t, J=6.3 Hz), 7.06 (2H, d, J=9.3 Hz), 7.13 (2H, d, J=8.8 Hz), 8.03 (1H, d, J=4.9 Hz), 8.67 (1H, d, J=4.9 Hz), 9.16 (1H, s)

Example 159

8-fluoro-2-methyl-3-(4-{3-[(3S)-3-methyl-piperidin-1-yl]propoxy}phenyl)-4(3H)-quinazolinone hydrochloride The title compound was obtained by the method according to Example 18, using 2-amino-3-fluorobenzoic acid, acetic anhydride and 4-{(3-[(3S)-3-methyl-piperidin-1-yl]propoxy}aniline monotosylate as starting materials.

$^1$HNMR (400 MHz,CDCl$_3$/CD$_3$OD=10/1,δppm): 0.99 (3H, d, J=6.8 Hz), 1.05-1.14 (1H, m), 1.88-1.98 (2H, m), 2.17-2.31 (3H, m), 2.39 (3H, s), 2.45-2.61 (3H, m), 3.17-3.22 (2H, m), 3.50 (1H, d, J=11.7 Hz), 3.63 (1H, d, J=10.7 Hz), 4.17 (2H, t, J=5.4 Hz), 7.04 (2H, d, J=8.3 Hz), 7.19 (2H, d, J=8.3 Hz), 7.41-7.46 (1H, m), 7.50-7.55 (1H, m), 8.05 (1H, d, J=7.8 Hz)

Example 160

8-fluoro-2-methyl-3-{4-[3-(1-pyrrolidinyl)propoxy]phenyl}-4(3H)-quinazolinone hydrochloride The title compound was obtained by the method according to Example 18, using 2-amino 3-fluorobenzoic acid, acetic anhydride and 4-(3-pyrrolidin-1-yl propoxy)aniline as starting materials.

¹HNMR (400 MHz,CDCl₃/CD₃OD=10/1,δppm) 2.09-2.18 (2H, m), 2.21-2.29 (2H, m), 2.39-2.47 (5H, m), 2.86-2.95 (2H, m), 3.37-3.32 (2H, m), 3.83-3.89 (2H, m), 4.18 (2H, t, J=5.4 Hz), 7.07 (2H, d, J=8.3 Hz), 7.22 (2H, d, J=8.8 Hz), 7.46-7.52 (1H, m), 7.57 (1H, t, J=9.0 Hz), 8.06 (1H, d, J=8.3 Hz)

Example 161

6-(2-fluoroethoxy)-2-methyl-3-[4-(3-piperidin-1-ylpropoxy)phenyl]-4(3H)-quinazolinone The title compound was obtained by demethylation and alkylation of 6-methoxy-2-methyl-3-[4-(3-piperidin-1-yl propoxy)phenyl]-4(3H)-quinazolinone synthesized in Example 36 and 2-fluoroethyl tosylate as starting materials by the method according to Example 192.

¹HNMR (400 MHz,CDCl₃,δppm): 1.42-1.48 (2H, m), 1.58-1.63 (4H, m), 2.00-2.05 (2H, m), 2.23 (3H, s), 2.39-2.45 (4H, m), 2.51 (2H, t, J=7.2 Hz), 4.07 (2H, t, J=6.4 Hz) 4.27-4.29 (1H, m), 4.34-4.36 (1H, m), 4.73-4.75 (1H, m), 4.84.4.87 (1H, m), 7.04 (2H, d, J=9.2 Hz), 7.15 (2H, d, J=9.2 Hz), 7.41 (1H, dd, J=2.8, 8.8 Hz), 7.61-7.64 (2H, m)

Example 162

6-(2-fluoroethoxy)-2-methyl-3-[4-(3-pyrrolidin-1-yl-propoxy)phenyl]-4(3H)-quinazolinone The title compound was obtained by demethylation and alkylation of 6-methoxy-2-methyl-3-[4-(3-pyrrolidin-1-yl-propoxy)phenyl]-4(3H)-quinazolinone synthesized in Example 143 by the method according to Example 192.

¹HNMR (400 MHz,CDCl₃,δppm): 1.81-1.84 (4H, m), 2.03-2.12 (2H, m), 2.23 (3H, s), 2.57-2.63 (4H, m), 2.70 (2H, t, J=7.2 Hz), 4.10 (2H, t, J=6.4 Hz), 4.27-4.29 (1H, m), 4.34-4.36 (1H, m), 4.73-4.75 (1H, m), 4.85-4.87 (1H, m), 7.04 (2H, d, J=9.2 Hz), 7.14 (2H, d, J=9.2 Hz), 7.41 (1H, dd, J=2.8, 8.8 Hz), 7.61-7.64 (2H, m)

Example 163

5-methoxy-2-methyl-3-[4-(3-pyrrolidin-1-yl propoxy) phenyl]-4(3H)-quinazolinone

The title compound was obtained by the method according to Example 18, using 2-amino-6-methoxybenzoic acid, acetic anhydride and 4-(3-pyrrolidin-1-yl propoxy)aniline as starting materials.

¹HNMR (400 MHz,CDCl₃,δppm): 1.80-1.85 (4H, m), 2.03-2.10 (2H, m), 2.21 (3H, s), 2.55-2.61 (4H, m), 2.66-2.70 (2H, m), 3.95 (3H, s), 4.08 (2H, t, J=6.1 Hz), 6.87 (1H, d, J=8.3 Hz), 7.01 (2H, d, J=8.8 Hz), 7.11 (2H, d, J=9.3 Hz), 7.23 (1H, d, J=8.3 Hz), 7.65 (1H, t, J=8.3 Hz)

Example 164

5-methoxy-2-methyl-3-(4-{3-[(3S)-3-methylpiperidin-1-yl]propoxy}phenyl)-4(3H)-quinazolinone The title compound was synthesized as a white solid (m.p.: 144-146° C.) by the method according to Example 18, using 2-amino-6-methoxybenzoic acid, acetic anhydride and 4-{3-[(3S)-3-methylpyridin-1-yl]propoxy}aniline monotosylate as starting materials, followed by recrystallization (ethyl acetate/diethyl ether/n-heptane).

¹HNMR (400 MHz,CDCl₃,δppm): 0.85-0.90 (4H, m), 1.58-1.74 (5H, m), 1.83-1.91 (1H, m), 1.98-2.06 (2H, m), 2.21 (3H, s), 2.49-2.54 (2H, m), 2.84-2.92 (3H, m), 3.95 (3H, s), 4.06 (2H, t, J=7.0 Hz), 6.87 (1H, d, J=8.3 Hz), 7.01 (2H, d, J=8.8 Hz), 7.11 (2H, d, J=8.8 Hz), 7.23 (1H, d, J=8.3 Hz), 7.65 (1H, t, J=8.3 Hz)

Example 165

6-methoxy-2-methyl-3-(4-{3-[(3S)-3-methyl-piperidin-1-yl]propoxy}phenyl)-4(3H)-quinazolinone (1) Manufacture of 6-methoxy-2-methyl-4H-3,1-benzoxazin-4-one The target compound was obtained by the method according to Example 1-(1), using 2-amino-5-methoxybenzoic acid and acetic anhydride as starting materials.

(2) Manufacture of 6-methoxy-2-methyl-3-[4-(3-pyrrolidin-1-yl propoxy)phenyl]-4(3H)-quinazolinone 6-methoxy-2-methyl-4H-3,1-benzoxazon-4-one (80 mg, 0.42 mmol) and 4-{3-[(3S)-3-methylpiperidin-1-yl]propoxy}aniline monotosylate (176 mg, 0.42 mmol) were dissolved in acetic acid (2 mL), and stirred at room temperature for 20 hours. Acetic acid was distilled off under reduced pressure, ethyl acetate and 1N sodium hydroxide aqueous solution were added, the mixture extracted with ethyl acetate and dried with anhydrous sodium sulfate. After purifying by silica gel column chromatography (chloroform/methanol=20/1), the title compound (110 mg, 62%) was obtained as colorless crystals by recrystallization (ethyl acetate/diethyl ether).

¹HNMR (400 MHz,CDCl₃,δppm): 0.84-0.91 (4H, m), 1.57-1.75 (5H, m), 1.85-1.93 (1H, m), 2.01-2.08 (2H, m), 2.23 (3H, s), 2.51-2.56 (2H, m), 2.85-2.94 (2H, m), 3.91 (3H, s), 4.08 (2H, t, J=6.3 Hz), 7.04 (2H, d, J=8.8 Hz), 7.15 (2H, d, J=9.3 Hz), 7.36 (1H, dd, J=9.0, 3.2 Hz), 7.61 (1H, d, J=8.8 Hz), 7.63 (1H, d, J=2.9 Hz)

Example 166

6-(difluoromethoxy)-2-methyl-3-(4-{3-[(3S)-3-methyl-piperidin-1-yl]propoxy}phenyl)-4(3H)-quinazolinone The title compound was obtained by the method according to Example 253, using 3-(4-{3-[(3S)-3-methylpiperidin-1-yl]propoxy}phenyl)-4(3H)-quinazolinone synthesized in Example 165 and sodium chlorodifluoroacetate as starting materials.

¹HNMR (400 MHz,CDCl₃,δppm): 0.84-0.92 (4H, m), 1.54-1.74 (5H, m), 1.84-1.90 (1H, m), 1.99-2.06 (2H, m), 2.25 (3H, s), 2.51 (2H, t, J=7.3 Hz), 2.92-2.84 (2H, m), 4.07 (2H, t, J=6.3 Hz), 6.61 (1H, t, J=73.4 Hz), 7.05 (2H, d, J=8.8 Hz), 7.14 (2H, d, J=8.8 Hz), 7.53 (1H, dd, J=8.8, 2.9 Hz), 7.69 (1H, d, J=8.8 Hz), 7.94 (1H, d, J=4 Hz)

Example 167

5-(difluoromethoxy)-2-methyl-3-(4-{3-[(3S)-3-methyl-piperidin-1-yl]propoxy}phenyl)-4(3H)-quinazolinone The title compound was obtained by the method according to Example 253, using 5-methoxy-2-methyl-3-(4-{3-[(3S)-3-methyl-piperidin-1-yl]propoxy}phenyl)-4(3H)-quinazolinone synthesized in Example 164 and sodium chlorodifluoroacetate as starting materials.

$^1$HNMR (400 MHz,CDCl$_3$,δppm) 0.83-0.92 (4H, m), 1.54-1.73 (5H, m), 1.83-1.90 (1H, m), 1.99-2.06 (2H, m), 2.25 (3H, s), 2.50 (2H, t, J=7.6 Hz), 2.84-2.91 (2H, m), 4.06 (2H, t, J=6.3 Hz), 6.67 (1H, t, J=75.9 Hz), 7.04 (2H, d, J=8.8 Hz), 7.13 (2H, d, J=9.3 Hz), 7.24 (1H, d, J=7.3 Hz), 7.58 (1H, dd, J=8.3, 1.0 Hz), 7.71 (1H, t, J=8.3 Hz)

Example 168

7-methoxy-2-methyl-3-[4-(3-pyrrolidin-1-ylpropoxy)phenyl]-4(3H)-quinazolinone

The title compound was obtained by the method according to Example 165, using 2-amino-4-methoxybenzoic acid, acetic anhydride and 4-(3-pyrrolidin-1-yl-propoxy)aniline as starting materials. 2-amino-4-methoxybenzoic acid was manufactured by the method described in the literature (J. Chem. Soc. Perkin Trans. 1, 1997, p. 3261).

$^1$HNMR (400 MHz,CDCl$_3$,δppm): 1.79-1.82 (4H, m), 2.01-2.08 (2H, m), 2.24 (3H, s), 2.53-2.56 (4H, m), 2.65 (2H, t, J=7.6 Hz), 3.93 (3H, s), 4.09 (2H, t, J=6.3 Hz), 7.06-7.01 (4H, m), 7.14 (2H, d, J=8.8 Hz), 8.16 (1H, d, J=8.8 Hz)

Example 169

7-methoxy-2-methyl-3-[4-(3-piperidin-1-yl-propoxy)phenyl]-4(3H)-quinazolinone

The title compound was obtained by the method according to Example 165, using 2-amino-4-methoxybenzoic acid, acetic anhydride and 4-(3-piperidin-1-ylpropoxy)aniline monohydrochloride as starting materials.

$^1$HNMR (400 MHz,CDCl$_3$,δppm): 1.43-1.48 (2H, m), 1.58-1.64 (4H, m), 1.98-2.05 (2H, m), 2.24 (3H, s), 2.39-2.46 (4H, m), 2.51 (2H, t, J=7.6 Hz), 3.93 (3H, s), 4.07 (2H, t, J=6.3 Hz), 7.07-7.01 (4H, m), 7.14 (2H, d, J=8.8 Hz), 8.16 (1H, d, J=8.8 Hz)

Example 170

7-methoxy-2-methyl-3-(4-{3-[(3S)-3-methyl-piperidin-1-yl]propoxy}phenyl)-4(3H)-quinazolinone The title compound was synthesized as a light yellow solid (m.p.:94-96° C.) by the method according to Example 165, using 2-amino-4-methoxybenzoic acid, acetic anhydride and 4-{3-[(3S)-3-methylpyridin-1-yl]propoxy}aniline monotosylate as starting materials, followed by recrystallization (ethyl acetate/diethyl ether).

$^1$HNMR (400 MHz,CDCl$_3$,δppm): 0.83-0.92 (4H, m), 1.54-1.73 (5H, m), 1.83-1.89 (1H, m), 1.98-2.06 (2H, m), 2.24 (3H, s), 2.50 (2H, t, J=7.6 Hz), 2.83-2.91 (2H, m), 3.93 (3H, s), 4.07 (2H, t, J=6.3 Hz), 7.06-7.01 (4H, m), 7.14 (2H, d, J=8.8 Hz), 8.16 (1H, d, J=8.8 Hz)

Example 171

5-methoxy-2-methyl-3-(4-{3-[(2R)-2-methyl-pyrrolidin-1-yl]propoxy}phenyl)-4(3H)-quinazolinone (1) Manufacture of 4-{3-[(2R)-2-methylpyrrolidin-1-yl]propoxy}aniline monotosylate 4-{3-[(2R)-2-methylpyrrolidin-1-yl]propoxy}aniline was obtained as a light brown oily substance by the method according to Example 138, using (2R)-2-methylpyrrolidine hydrobromide, 3-bromopropanol and 4-nitrophenol as starting materials. The obtained oily substance was dissolved in ethyl acetate, 1 Eq of a methanol solution of p-toluenesulfonic acid monohydrate was added, and the target compound was obtained as a colorless solid by filtering off the solid produced. (2R)-2-methylpyrrolidine hydrobromide was manufactured by the method described in the literature (J. Org. Chem., 1989, Vol. 54, p. 209)

(2) Manufacture of 5-methoxy-2-methyl-3-(4-{3-[(2R)-2-methylpyrrolidin-1-yl]propoxy}phenyl)-4(3H)-quinazolinone The title compound was obtained by the method according to Example 165, using 2-amino-6-methoxybenzoic acid, acetic anhydride and 4-{3-[(2R)-2-methylpyrrolidin-1-yl]propoxy}aniline monotosylate as starting materials.

$^1$HNMR (400 MHz,CDCl$_3$,δppm): 1.11 (3H, d, J=5.9 Hz), 1.38-1.48 (1H, m), 1.59-1.82 (2H, m), 1.89-2.33 (9H, m), 2.97-3.03 (1H, m), 3.17-3.22 (1H, m), 3.95 (3H, s), 4.05-4.10 (2H, m), 6.87 (1H, d, J=8.3 Hz), 7.02 (2H, d, J=9.3 Hz), 7.11 (2H, d, J=9.3 Hz), 7.24 (1H, d, J=8.3 Hz), 7.65 (1H, t, J=8.0 Hz)

NMR data for 4-{3-[(2R)-2-methylpyrrolidin-1-yl]propoxy}aniline monotosylate used for manufacturing the compound of this example is shown below.

$^1$HNMR (400 MHz,CDCl$_3$/CD$_3$OD=5/1,δppm): 1.54 (3H, d, J=5.4 Hz), 1.89-2.06 (2H, m), 2.18-2.43 (6H, m), 2.61 (4H,brs), 2.90-3.08 (1H, m), 3.21-3.26 (1H, m), 3.44-3.52 (1H, m), 3.91-4.02 (3H, m), 6.67-6.72 (4H, m), 7.19 (2H, d, J=8.3 Hz), 7.75 (2H, d, J=8.3 Hz)

Example 172

6-methoxy-2-methyl-3-(4-{3-[(2R)-2-methylpyrrolidin-1-yl]propoxy}phenyl)-4(3H)-quinazolinone The title compound was synthesized as a white solid (m.p.: 106-108° C.) by the method according to Example 165, using 2-amino-5-methoxybenzoic acid, acetic anhydride and 4-{3-[(2R)-3-methylpyridin-1-yl]propoxy}aniline monotosylate as starting materials, followed by recrystallization (ethyl acetate/diethyl ether).

$^1$HNMR (400 MHz,CDCl$_3$,δppm): 1.11 (3H, d, J=5.9 Hz), 1.39-1.48 (1H, m), 1.59-1.83 (2H, m), 1.89-2.07 (3H, m), 2.10-2.34 (6H, m), 2.97-3.04 (1H, m), 3.17-3.22 (1H, m), 3.91 (3H, s), 4.07-4.12 (2H, m), 7.05 (2H, d, J=8.8 Hz), 7.15 (2H, d, J=8.8 Hz), 7.36 (1H, dd, J=8.8, 2.9 Hz), 7.61 (1H, d, J=8.8 Hz), 7.63 (1H, d, J=2.9 Hz)

Example 173

7-methoxy-2-methyl-3-(4-{3-[(2R)-2-methyl-pyrrolidin-1-yl]propoxy}phenyl)-4(3H)-quinazolinone The title compound was obtained by the method according to Example 165, using 2-amino-4-methoxybenzoic acid, acetic anhydride and 4-{3-[(2R)-2-methyl-pyrrolidin-1-yl]propoxy}aniline monotosylate as starting materials.

$^1$HNMR (400 MHz,CDCl$_3$,δppm): 1.11 (3H, d, J=6.3 Hz), 1.39-1.48 (1H, m), 1.58-1.83 (2H, m), 1.89-2.07 (3H, m), 2.10-2.51 (6H, m), 2.97-3.04 (1H, m), 3.17-3.22 (1H, m), 3.93 (3H, s), 4.10-4.06 (2H, m), 7.01-7.06 (4H, m), 7.15 (2H, d, J=8.8 Hz), 8.16 (1H, d, J=8.8 Hz)

Example 174

3-[4-(3-azepan-1-ylpropoxy)phenyl-]-2,6-dimethyl-4 (3H)-quinazolinone (1) Manufacture of 4-(3-azepan-1-ylpropoxy)aniline The target compound was obtained by the method according to Example 138, using azepane, 3-bromopropanol and 4-nitrophenol as starting materials.

(2) Manufacture of 3-[4-(3-azepan-1-ylpropoxy) phenyl]-2,6-dimethyl-4(3H)-quinazolinone The title compound was obtained by the method according to Example 165, using 2-amino-5-methyl-benzoic acid, acetic anhydride and 4-(3-azepan-1-yl-propoxy)aniline as starting materials.

$^1$HNMR (400 MHz,CDCl$_3$,δppm): 1.62-1.64 (8H, m), 1.96-2.02 (2H, m), 2.24 (3H, t, J=11.7 Hz), 2.48 (3H, t, J=11.7 Hz), 2.68 (6H, t, J=7.3 Hz), 4.07-4.09 (2H, m), 7.04 (2HH, dd, J=6.0, 3.6 Hz), 7.14 (2HH, dd, J=12.2, 6.1 Hz), 7.57 (2H, d, J=1.0 Hz), 8.05 (1H, s)

Example 175

3-[4-(3-azepan-1-ylpropoxy)phenyl]-5-fluoro2-methyl-4(3H)-quinazolinone

The title compound was obtained by the method according to Example 165, using 2-amino-6-fluorobenzoic acid, acetic anhydride and 4-(3-azepan-1-yl-propoxy)aniline as starting materials. $^1$HNMR (400 MHz,CDCl$_3$,δppm): 1.61-1.63 (8H, m), 1.95-2.02 (2H, m), 2.22 (3H, t, J=10.0 Hz), 2.67-2.68 (6H, m), 4.08 (2H, t, J=6.3 Hz), 7.03-7.15 (5H, m), 7.46 (1H, d, J=8.3 Hz), 7.68 (1H, td, J=8.3, 5.4 Hz)

Example 176

3-[4-(3-azepan-1-ylpropoxy)phenyl]-7-fluoro2-methyl-4(3H)-quinazolinone

The title compound was obtained by the method according to Example 165, using 2-amino 4-fluorobenzoic acid, acetic anhydride and 4-(3-azepan-1-yl-propoxy)aniline as starting materials.

$^1$HNMR (400 MHz,CDCl$_3$,δppm): 1.62-1.65 (8H, m), 1.95-2.02 (2H, m), 2.23 (3H, t, J=14.6 Hz), 2.67-2.68 (6H, m), 4.08 (2H, t, J=6.3 Hz), 7.04-7.06 (2H, m), 7.12-7.20 (3H, m), 7.31 (1H, dd, J=9.8, 2.4 Hz), 8.28 (1H, dd, J=8.8, 5.9 Hz)

Example 177

3-[4-(3-azepan-1-ylpropoxy)phenyl]-5-methoxy-2-methyl-4 (3H)-quinazolinone

The title compound was obtained by the method according to Example 165, using 2-amino-6-methoxybenzoic acid, acetic anhydride and 4-(3-azepan-1-ylpropoxy)aniline as starting materials.

$^1$HNMR (400 MHz,CDCl$_3$,δppm): 1.63-1.66 (8H, m), 1.96-2.03 (2H, m), 2.20 (3H, s), 2.68 (6H, d, J=6.8 Hz), 3.96 (3H, s), 4.08 (2H, t, J=6.3 Hz), 6.88 (1H, d, J=7.8 Hz), 7.01-7.04 (2H, m), 7.10-7.13 (2H, m), 7.24 (1H, d, J=4.1 Hz), 7.65 (1H, t, J=8.0 Hz)

Example 178

3-[4-(3-azepan-1-ylpropoxy)phenyl]-6-methoxy-2-methyl-4(3H)-quinazolinone

The title compound was obtained by the method according to Example 165, using 2-amino-5-methoxybenzoic acid, acetic anhydride and 4-(3-azepan-1-yl-propoxy)aniline as starting materials.

$^1$HNMR (400 MHz,CDCl$_3$,δppm): 1.62-1.66 (8H, m), 1.96-2.03 (2H, m), 2.20 (3H, s), 2.68-2.70 (6H, m), 3.91 (3H, s), 4.09 (2H, t, J=6.3 Hz), 7.05 (2H, td, J=6.0, 3.6 Hz), 7.13-7.16 (2H, m), 7.36 (1H, dd, J=9.0, 3.2 Hz), 7.60 (1H, s), 7.63 (1H, t, J=3.4 Hz)

Example 179

The title compound was obtained as white crystals, after treating with 1 Eq of a ethyl acetate solution of 4N hydrochloric acid, and recrystallizing (from ethanol/ethyl acetate), what had been synthesized by the method according to Example 165, using 2-amino-6-methoxybenzoic acid, acetic anhydride and 4-{3-[(3S)-2-methylpyrrolidin-1-yl]propoxy}aniline monotosylate as starting materials.

$^1$HNMR (400 MHz,CDCl$_3$/CD$_3$OD=10/1,δppm): 1.01 (3H, d, J=6.3 Hz), 1.07-1.12 (1H, m), 1.90-1.99 (2H, m), 2.25-2.52 (11H, m), 2.56-2.63 (1H, m), 3.20-3.24 (2H, m), 3.51-3.54 (1H, m), 3.63-3.67 (1H, m), 4.15-4.18 (2H, m), 7.04 (2H, d, J=8.3 Hz), 7.18 (2H, d, J=8.3 Hz), 7.60-7.64 (2H, m), 8.04 (1H, s)

Example 180

3-[4-(3-azepan-1-ylpropoxy)phenyl]-2-methylpyrido [4,3-d]pyrimidin-4(3H)-one

The title compound was obtained by the method according to Example 165, using 4-aminonicotinic acid, acetic anhydride and 4-(3-azepan-1-yl-propoxy)aniline as starting materials.

$^1$HNMR (400 MHz,CDCl$_3$,δppm): 1.63 (4H,brs), 1.72 (4H,brs), 2.06-2.08 (2H, m), 2.30 (3H, s), 2.76 (6H,brs), 4.10 (2H, t, J=6.3 Hz), 7.05-7.08 (2H, m), 7.13-7.16 (2H, m), 7.49 (1H, d, J=2.9 Hz), 8.85 (1H, d, J=5.9 Hz), 9.47 (1H, s)

Example 181

2-methyl-3-(4-{3-[(2R)-2-methyl-pyrrolidin-1-yl]propoxy}phenyl)-4(3H)-quinazolinone The title compound was obtained by the method according to Example 165, using anthranilic acid, acetic anhydride and 4-{3-[(2R)-2-methyl-pyrrolidin-1-yl]propoxy}aniline monotosylate as starting materials.

$^1$HNMR (400 MHz,CDCl$_3$,δppm): 1.14 (3H, d, J=5.9 Hz), 1.43-1.55 (1H, m), 1.69-1.85 (2H, m), 1.93-2.54 (9H, m), 2.99-3.07 (1H, m), 3.21-3.26 (1H, m), 4.06-4.11 (2H, m), 7.05 (2H, d, J=8.8 Hz), 7.15 (2H, d, J=8.8 Hz), 7.46 (1H, t, J=7.6 Hz), 7.67 (1H, d, J=7.8 Hz), 7.78-7.74 (1H, m), 8.27 (1H, dd, J=8.0, 1.2 Hz)

Example 182

2,5-dimethyl-3-[2-methoxy-4-[3-(1-piperidinyl)propoxy]phenyl]-4(3H)-quinazolinone The title compound was obtained by the method according to Example 63, using 2-amino-6-methylbenzoic acid, acetic anhydride, 4-amino-3-methoxyphenol and 1-(3-bromopropyl) piperidine hydrobromide as starting materials. 4-amino-3-methoxyphenol was manufactured by the method described in the literature (J. Med. Chem., 1995, Vol. 38, p. 2748).

$^1$HNMR (400 MHZ,CDCl$_3$,δppm): 1.42-1.48 (2H, m), 1.58-1.64 (4H, m), 1.97-2.04 (2H, m), 2.19 (3H, s), 2.39-2.44 (4H, m), 2.50 (2H, t, J=7.2 Hz), 2.82 (3H, s), 3.77 (3H, s), 4.06 (2H, t, J=6.4 Hz), 6.59-6.62 (2H, m), 7.08 (1H, d, J=8.8 Hz), 7.19 (1H, d, J=8.0 Hz), 7.49 (1H, d, J=8.0 Hz), 7.58 (1H, t, J=8.0 Hz)

Example 183

2,5-dimethyl-3-{2-methoxy-4-[3-(1-pyrrolidinyl)propoxy]phenyl}-4(3H)-quinazolinone The title compound was obtained by the method according to Example 63, using 2-amino-6-methyl benzoic acid, acetic anhydride, 4-amino-3-methoxyphenol and 1-(3-bromopropyl)pyrrolidine hydrobromide as starting materials.

$^1$HNMR (400 MHz, CDCl$_3$,δppm): 1.80-1.83 (4H, m), 2.01-2.07 (2H, m), 2.19 (3H, s), 2.54-2.58 (4H, m), 2.66 (2H, t, J=7.2 Hz), 2.82 (3H, s), 3.77 (3H, s), 4.08 (2H, t, J=6.4 Hz), 6.59-6.62 (2H, m), 7.08 (1H, d, J=8.8 Hz), 7.19 (1H, d, J=8.0 Hz), 7.49 (1H, d, J=8.0 Hz), 7.58 (1H, t, J=8.0 Hz)

Example 184

6-chloro-3-[2-methoxy-4-(3-piperidin-1-ylpropoxy)phenyl]-2-methylpyrido[3,4-d]pyrimidin-4(3H)-one The title compound was obtained by the method according to Example 63, using 5-amino-2-chloroisonicotinic acid, acetic anhydride, 4-amino-3-methoxyphenol and 1-(3-bromopropyl)piperidine hydrobromide as starting materials.

$^1$HNMR (400 MHz,CDCl$_3$,δppm): 1.42-1.48 (2H, m), 1.58-1.64 (4H, m), 2.00-2.05 (2H, m), 2.25 (3H, s), 2.40-2.45 (4H, m), 2.51 (2H, t, J=7.2 Hz), 3.77 (3H, s), 4.07 (2H, t, J=6.4 Hz), 6.61-6.64 (2H, m), 7.07 (1H, d, J=9.2 Hz), 8.06 (1H, d, J=0.8 Hz), 8.90 (1H, d, J=0.8 Hz)

Example 185

6-chloro-3-{2-methoxy-4-[3-(1-pyrrolidinyl)propoxy]phenyl}-2-methylpyrido[3,4-d]pyrimidin-4(3H)-one The title compound was obtained by the method according to Example 63, using 5-amino-2-chloroisonicotinic acid, acetic anhydride, 4-amino-3-methoxyphenol and 1-(3-bromopropyl)pyrrolidine hydrobromide as starting materials.

$^1$HNMR (400 MHz,CDCl$_3$,δppm): 1.80-1.84 (4H, m), 2.02-2.09 (2H, m), 2.25 (3H, s), 2.55-2.60 (4H, m), 2.68 (2H, t, J=7.2 Hz), 3.77 (3H, s), 4.10 (2H, t, J=6.4 Hz), 6.61-6.64 (2H, m), 7.06 (1H, d, J=9.2 Hz), 8.06 (1H, d, J=0.8 Hz), 8.89 (1H, d, J=0.8 Hz)

Example 186

6-fluoro-3-[2-methoxy-4-(3-piperidin-1-ylpropoxy)phenyl]-2-methylpyrido[3,4-d]pyrimidin-4(3H)-one The title compound was obtained by the method according to Example 63, using 5-amino-2-fluoroisonicotinic acid, acetic anhydride, 4-amino-3-methoxyphenol and 1-(3-bromopropyl)piperidine hydrobromide as starting materials.

$^1$HNMR (400 MHz,CDCl$_3$,δppm): 1.42-1.51 (2H, m), 1.58-1.64 (4H, m), 1.98-2.06 (2H, m), 2.25 (3H, s), 2.40-2.45 (4H, m), 2.51 (2H, t, J=7.2 Hz), 3.78 (3H, s), 4.07 (2H, t, J=6.4 Hz), 6.61-6.64 (2H, m), 7.07 (1H, d, J=9.2 Hz), 7.64-7.65 (1H, m), 8.76 (1H, s)

Example 187

6-fluoro-3-{2-methoxy-4-[3-(1-pyrrolidinyl)propoxy]phenyl}-2-methylpyrido[3,4-d]pyrimidin-4(3H)-one The title compound was obtained by the method according to Example 63, using 5-amino-2-fluoroisonicotinic acid, acetic anhydride, 4-amino-3-methoxyphenol and 1-(3-bromopropyl)pyrrolidine hydrobromide as starting materials.

$^1$HNMR (400 MHz,CDCl$_3$,δppm): 1.80-1.84 (4H, m), 2.02-2.09 (2H, m), 2.24 (3H, s), 2.55-2.60 (4H, m), 2.67 (2H, t, J=7.2 Hz), 3.77 (3H, s), 4.10 (2H, t, J=6.4 Hz), 6.61-6.64 (2H, m), 7.07 (1H, d, J=9.2 Hz), 7.64-7.66 (1H, m), 8.76 (1H, s)

Example 188

3-[2-methoxy-4-(3-piperidin-1-ylpropoxy)phenyl]-2-methylpyrido[3,4-d]-pyrimidin-4(3H)-one The title compound was obtained by catalytic reduction of 6-chloro-3-[2-methoxy-4-(3-piperidin-1-ylpropoxy)phenyl]-2-methylpyrido[3,4-d]pyrimidin-4(3H)-one synthesized in Example 184 using a palladium charcoal catalyst in the presence of triethylamine.

$^1$HNMR (400 MHZ,CDCl$_3$,δppm): 1.42-1.48 (2H, m), 1.58-1.63 (4H, m), 1.98-2.06 (2H, m), 2.27 (3H, s), 2.40-2.45 (4H, m), 2.51 (2H, t, J=7.2 Hz), 3.77 (3H, s), 4.07 (2H, t, J=6.4 Hz), 6.61-6.64 (2H, m), 7.07 (1H, d, J=9.2 Hz), 8.03 (1H, dd, J=0.8, 5.2 Hz), 8.66 (1H, d, J=5.2 Hz), 9.12 (1H, d, J=0.8 Hz)

Example 189

3-{2-methoxy-4-[3-(1-pyrrolidinyl)propoxy]phenyl}-2-methylpyrido[3,4-d]-pyrimidin-4(3H)-one The title compound was obtained by catalytic reduction of 6-chloro-3-{2-methoxy-4-[3-(1-pyrrolidinyl)propoxy]phenyl}-2-methylpyrido[3,4-d]pyrimidin-4(3H)-one synthesized in Example 185 using a palladium charcoal catalyst in the presence of triethylamine.

$^1$HNMR (400 MHz,CDCl$_3$,δppm): 1.82-1.86 (4H, m), 2.04-2.11 (2H, m), 2.27 (3H, s), 2.59-2.63 (4H, m), 2.70 (2H, t, J=7.2 Hz), 3.77 (3H, s), 4.10 (2H, t, J=6.4 Hz), 6.61-6.64 (2H, m), 7.07 (1H, d, J=9.2 Hz), 8.03 (1H, dd, J=0.8, 5.2 Hz), 8.66 (1H, d, J=5.2 Hz), 9.12 (1H, d, J=0.8 Hz)

Example 190

3-[2-methoxy-4-(3-piperidin-1-ylpropoxy)phenyl]-2-methylpyrido[4,3-d]pyrimidin-4(3H)-one The title compound was obtained by the method according to Example 63, using 4-aminonicotinic acid, acetic anhydride, 4-amino-3-methoxyphenol and 1-(3-bromopropyl)piperidine hydrobromide as starting materials.
$^1$HNMR (400 MHz,CDCl$_3$,δppm): 1.42-1.48 (2H, m), 1.58-1.63 (4H, m), 1.98-2.06 (2H, m), 2.26 (3H, s), 2.40-2.45 (4H, m), 2.50 (2H, t, J=7.2 Hz), 3.78 (3H, s), 4.07 (2H, t, J=6.4 Hz), 6.61-6.64 (2H, m), 7.08 (1H, d, J=8.8 Hz), 7.48 (1H, dd, J=0.8, 5.6 Hz), 8.83 (1H, d, J=5.6 Hz), 9.47 (1H, d, J=0.8 Hz)

Example 191

3-{3-bromo-4-[3-(1-pyrrolidinyl)propoxy]phenyl}-2-methyl 5-(trifluoromethyl)-4(3H)-quinazolinone (1) Manufacture of 4-amino-2-bromophenol The target compound was obtained by reducing 2-bromo-4-nitrophenol with iron in a mixed solution of methanol and ammonium chloride aqueous solution. 2-bromo-4-nitrophenol was manufactured by the method described in the literature (J. Org. Chem., Vol. 62, 1997, p. 4504).

(2) Manufacture of 3-{3-bromo-4-[3-(1-pyrrolidinyl) propoxy]phenyl}-2-methyl-5-(trifluoromethyl)-4 (3H)-quinazolinone The title compound was obtained by the method according to Example 63, using 2-amino-6-(trifluoromethyl)benzoic acid, acetic anhydride, 4-amino-2-bromophenol and 1-(3-bromopropyl)pyrrolidine hydrobromide as starting materials.
$^1$HNMR (400 MHz,CDCl$_3$,δppm): 1.81 (4H, m), 2.10 (2H, m), 2.28 (3H, s), 2.57 (4H, m), 2.70 (2H, m), 4.13 (2H, m), 7.05 (1H, d, J=8.8 Hz), 7.17 (1H, d, J=8.8 Hz), 7.46 (1H, s), 7.83 (1H, d, J=8.0 Hz), 7.88 (2H, d, J=8.0 Hz)

Example 192

6-chloro-3-[2-fluoroethoxy-4-(3-piperidin-1-ylpropoxy) phenyl]-2-methylpyrido[3,4-d]pyrimidin-4 (3H)-one (1) Manufacture of 6-chloro-3-[2-hydroxy-4-(3-piperidin-1-ylpropoxy)phenyl]-2-methylpyrido[3,4-d] pyrimidine-4(3H)-one 6-chloro-3-[2-methoxy-4-(3-piperidin-1-ylpropoxy)phenyl]-2-methylpyrido[3,4-d]pyrimidin-4(3H)-one synthesized in Example 184 (143 mg, 0.32 mmol) was dissolved in methylene chloride (3 mL), boron tribromide (1M methylene chloride solution, 3.2 mmol) was added on an ice bath, stirred at room temperature for 15 hours, and stirred at 40° C. for 3 hours. Saturated carbonated water was added to stop the reaction, the mixture was extracted with ethyl acetate, and dried with anhydrous sodium sulfate. The product was purified by silica gel column chromatography (chloroform/methanol=20/1), and the target compound (49 mg, 35%) was obtained as a light yellow solid.
$^1$HNMR (400 MHz,CDCl$_3$,δppm): 1.38-1.43 (2H, m), 1.52-1.59 (4H, m), 2.01-2.07 (2H, m), 2.32 (3H, s), 2.51-2.57 (4H, m), 2.64-2.80 (2H, m), 3.99 (2H, t, J=6.4 Hz), 6.41-6.45 (2H, m), 6.99 (1H, d, J=8.4 Hz), 8.05 (1H, d, J=0.8 Hz), 8.90 (1H, d, J=0.8 Hz)

(2) Manufacture of 6-chloro-3-[2-fluoroethoxy-4-(3-piperidin-1-ylpropoxy)phenyl]-2-methylpyrido[3,4-d]pyrimidin-4(3H)-one 6-chloro-3-[2-hydroxy-4-(3-piperidin-1-ylpropoxy)phenyl]-2-methylpyrido[3,4-d]-pyrimidin-4(3H)-one (10 mg), 2-fluoroethyl tosylate (7.6 mg) and potassium carbonate (16 mg) were mixed in dimethylformamide (2 mL) and stirred at 80° C. for 10 hours. Distilled water was added, the mixture extracted with ethyl acetate, and dried with anhydrous sodium sulfate. The product was purified by silica gel thin layer chromatography (chloroform/methanol=10/1), and the title compound (8.5 mg, 77%) was obtained as a colorless solid.
$^1$HNMR (40 MHz,CDCl$_3$,δppm): 1.42-1.48 (2H, m), 1.58-1.64 (4H, m), 1.98-2.05 (2H, m), 2.28 (3H, s), 2.40-2.45 (4H, m), 2.50 (2H, t, J=7.2 Hz), 4.07 (2H, t, J=6.4 Hz) 4.10-4.36 (2H, m), 4.49-4.52 (1H, m), 4.61-4.64 (1H, m), 6.64 (1H, d, J=2.4 Hz), 6.67 (1H, dd, J=2.4, 8.4 Hz), 7.09 (1H, d, J=8.4 Hz), 8.05 (1H, s), 8.90 (1H, s)

Example 193

2,5-dimethyl-3-[2-hydroxy-4-(3-piperidin-1-ylpropoxy)phenyl]-4(3H)-quinazolinone 2,5-dimethyl-3-{2-methoxy-4-[3-(1-pyrrolidinyl)propoxy]phenyl}-4(3H)-quinazolinone synthesized in Example 182 was demethylated using the method according to Example 192-(1), and the title compound was thus obtained.
$^1$HNMR (400 MHz,CDCl$_3$,δppm): 1.38-1.45 (2H, m), 1.55-1.61 (4H, m), 1.97-2.04 (2H, m), 2.27 (3H, s), 2.43-2.52 (4H, m), 2.55-2.64 (2H, m), 2.80 (3H, s), 3.92-3.98 (2H, m), 6.44-6.48 (2H, m), 6.99 (1H, d, J=8.0 Hz), 7.16 (1H, d, J=8.0 Hz), 7.49 (1H, d, J=8.0 Hz), 7.56 (1H, t, J=8.0 Hz)

Example 194

2,5-dimethyl-3-{2-fluoroethoxy-4-[3-(1-piperidinyl) propoxy]phenyl}-4(3H)-quinazolinone The title compound was obtained by the method according to Example 192-(2) using 2,5-dimethyl-3-{2-hydroxy-4-[3-(1-pyrrolidinyl)propoxy]phenyl}-4(3H)-quinazolinone synthesized in Example 193, and 2-fluoroethyl tosylate as starting materials.
$^1$HNMR (400 MHZ,CDCl$_3$,δppm): 1.42-1.49 (2H, m), 1.59-1.65 (4H, m), 1.98-2.06 (2H, m), 2.22 (3H, s), 2.40-2.49 (4H, m), 2.52 (2H, t, J=7.2 Hz), 2.82 (3H, s), 4.05 (2H, t, J=6.4 Hz), 4.10-4.33 (2H, m), 4.50-4.54 (1H, m), 4.62-4.66 (1H, m), 6.62 (1H, d, J=2.4 Hz), 6.65 (1H, dd, J=2.4, 8.4 Hz), 7.10 (1H, d, J=8.4 Hz), 7.20 (1H, d, J=8.0 Hz), 7.51 (1H, d, J=8.0 Hz), 7.58 (1H, t, J=8.0 Hz)

Example 195

3-{2-fluoroethoxy-4-[3-(1-piperidinyl)propoxy]phenyl}-2-methylpyrido[3,4-d]-pyrimidin-4(3H)-one The title compound was obtained by catalytic reduction of 6-chloro-3-{2-fluoroethoxy-[3-(1-piperidinyl)propoxy]phenyl}-2-methylpyrido[3,4-]pyrimidin-(3H)-one synthesized in Example 192 using a palladium charcoal catalyst in the presence of triethylamine.

$^1$HNMR (400 MHz,CDCl$_3$,δppm): 1.42-1.49 (2H, m), 1.58-1.64 (4H, m), 1.98-2.06 (2H, m), 2.29 (3H, s), 2.40-2.47 (4H, m), 2.51 (2H, t, J=7.2 Hz), 4.07 (2H, t, J=6.4 Hz), 4.10-4.36 (2H, m), 4.49-4.52 (1H, m), 4.61-4.64 (1H, m), 6.64 (1H, d, J=2.4 Hz), 6.67 (1H, dd, J=2.4, 8.4 Hz), 7.10 (1H, d, J=8.4 Hz), 8.02 (1H, dd, J=0.8, 5.2 Hz), 8.66 (1H, d, J=5.2 Hz), 9.12 (1H, d, J=0.8 Hz)

Example 196

3-{2-fluoroethoxy-4-[3-(1-piperidinyl)propoxy]phenyl}-2-methylpyrido[4,3-d]pyrimidin-(3H)-one The title compound was obtained by the method according to Example 192, using 3-{2-methoxy-4-[3-(1-piperidinyl)propoxy]phenyl}-2-methylpyrido[4,3-d]pyrimidin-4(3H)-one synthesized in Example 190 and 2-fluoroethyl tosylate as starting materials.

$^1$HNMR (400 MHz,CDCl$_3$,δppm) 1.42-1.49 (2H, m), 1.58-1.64 (4H, m), 2.01-2.05 (2H, m), 2.29 (3H, s), 2.41-2.47 (4H, m), 2.52 (2H, t, J=7.2 Hz), 4.07 (2H, t, J=6.4 Hz), 4.10-4.38 (2H, m), 4.50-4.53 (1H, m), 4.62-4.64 (1H, m), 6.64 (1H, d, J=2.4 Hz), 6.67 (1H, dd, J=2.4, 8.4 Hz), 7.11 (1H, d, J=8.4 Hz), 7.49 (1H, dd, J=0.8, 5.6 Hz), 8.84 (1H, d, J=5.6 Hz), 9.46 (1H, d, J=0.8 Hz)

Example 197

3-(4-hydroxyphenyl)-6-methoxy-2-methylpyrido[3,4-d]pyrimidin-4(3H)-one (1) Manufacture of 6-chloro-3-(4-hydroxyphenyl)-2-methylpyrido[3,4-d]pyrimidin-4(3H)-one The target compound was obtained by the method according to Example 1-(1) and -(2), using 5-amino-2-chloroisonicotinic acid, acetic anhydride and 4-aminophenol as starting materials.

(2) Manufacture of 3-(4-hydroxyphenyl)-6-methoxy-2-methylpyrido[3,4-d]pyrimidin-4(3H)-one 6-chloro-3-(4-hydroxyphenyl)-2-methylpyrido[3,4-d]pyrimidin-4(3H)-one (300 mg, 1.04 mmol) was dissolved in dry methanol (15 mL) in a current of nitrogen, sodium methoxide (7 mmol) was added and the mixture was heated under reflux for 20 hours. After leaving to cool, acetic acid was added and the solvent was distilled off under reduced pressure. Distilled water was added to the residue, the solid precipitate was filtered off, and the title compound (259 mg, 88%) was thus obtained as a lavender color solid.

$^1$HNMR (400 MHZ,CDCl$_3$/CD$_3$OD=5/1,δppm) 2.21 (3H, s), 3.99 (3H, s), 6.94 (2H, d, J=8.8 Hz), 7.01 (2H, d, J=8.8 Hz), 7.40 (1H, s), 8.71 (1H, s)

Example 198

2-ethyl-3-(4-hydroxyphenyl)-6-methoxypyrido[3,4-d]pyrimidin-4(3H)-one

The title compound was obtained by the method according to Example 197, using 5-amino-2-chloroisonicotinic acid, propionic anhydride, 4-aminophenol and sodium methoxide as starting materials.

$^1$HNMR (400 MHz,CDCl$_3$/CD$_3$OD=5/1,δppm) 1.21 (3H, t, J=7.6 Hz), 2.47 (2H, q,J=7.6 Hz), 4.03 (3H, s), 6.98 (2H, d, J=8.8 Hz), 7.04 (2H, d, J=8.8 Hz), 7.44 (1H, s), 8.79 (1H, s)

Example 199

6-methoxy-2-methyl-3-[4-(3-piperidin-1-ylpropoxy)phenyl]pyrido[3,4-d]pyrimidin-4(3H)-one The title compound was synthesized as a white solid (m.p.: 145-147° C.) by the method according to Example 63, using 3-(4-hydroxyphenyl)-6-methoxy-2-methylpyrido[3,4-d]pyrimidin-4(3H)-one synthesized in Example 197 and 1-(3-bromopropyl)pyridine hydrobromide as starting materials, followed by recrystallization (ethyl acetate/diethyl ether).

$^1$HNMR (400 MHz,CDCl$_3$,δppm): 1.43-1.49 (2H, m), 1.58-1.64 (4H, m), 2.00-2.06 (2H, m), 2.24 (3H, s), 2.40-2.47 (4H, m), 2.52 (2H, t, J=7.2 Hz), 4.03 (3H, s), 4.07 (2H, t, J=6.4 Hz), 7.05 (2H, d, J=9.2 Hz), 7.13 (2H, d, J=9.2 Hz), 7.45 (1H, d, J=0.8 Hz), 8.75 (1H, d, J=0.8 Hz)

Example 200

6-methoxy-2-methyl-3-[4-(3-pyrrolidin-1-ylpropoxy)phenyl]pyrido[3,4-d]-pyrimidin-4(3H)-one The title compound was synthesized as a white solid (m.p.: 123-126° C.) by the method according to Example 63, using 3-(4-hydroxyphenyl)-6-methoxy-2-methylpyrido[3,4-d]pyrimidin-4(3H)-one synthesized in Example 197 and 1-(3-bromopropyl)pyrrolidine hydrobromide as starting materials, followed by recrystallization (ethyl acetate/diethyl ether).

$^1$HNMR (400 MHz,CDCl$_3$,δppm): 1.80-1.84 (4H, m), 2.02-2.08 (2H, m), 2.23 (3H, s), 2.55-2.61 (4H, m), 2.68 (2H, t, J=7.2 Hz), 4.03 (3H, s), 4.10 (2H, t, J=6.4 Hz), 7.05 (2H, d, J=9.2 Hz), 7.13 (2H, d, J=9.2 Hz), 7.45 (1H, d, J=0.8 Hz), 8.75 (1H, d, J=0.8 Hz)

Example 201

2-ethyl-6-methoxy-3-{4-[3-(1-piperidinyl)propoxy]phenyl}pyrido[3,4-d]pyrimidin-4(3H)-one The title compound was obtained by the method according to Example 63, using 2-ethyl-3-(4-hydroxyphenyl)-6-methoxypyrido[3,4-d]pyrimidin-4(3H)-one synthesized in Example 198 and 1-(3-bromopropyl)piperidine hydrobromide as starting materials.

$^1$HNMR (400 MHz, CDCl$_3$,δppm): 1.21 (3H, t, J=7.6 Hz), 1.43-1.49 (2H, m), 1.58-1.64 (4H, m), 2.00-2.06 (2H, m), 2.40-2.58 (8H,m), 4.01-4.08 (5H, m), 7.05 (2H, d, J=9.2 Hz), 7.13 (2H, d, J=9.2 Hz), 7.45 (1H, s), 8.77 (1H, s)

Example 202

2-ethyl-6-methoxy-3-{4-[3-(1-pyrrolidinyl)propoxy]phenyl}-pyrido[3,4-d]pyrimidin-4(3H)-one The title compound was obtained by the method according to Example 63, using 2-ethyl 3-(4-hydroxyphenyl)-6-methoxypyrido[3,4-d]pyrimidin-4(3H)-one synthesized in Example 198 and 1-(3-bromopropyl)pyrrolidine hydrobromide as starting materials.

$^1$HNMR (400 MHz,CDCl$_3$,δppm): 1.22 (3H, t, J=7.6 Hz), 1.82-1.86 (4H, m), 2.04-2.11 (2H, m), 2.44 (2H, q,J=7.2 Hz), 2.58-2.63 (4H, m), 2.70 (2H, t, J=7.2 Hz), 4.04 (3H, s), 4.10

(2H, t, J=6.4 Hz), 7.05 (2H, d, J=9.2 Hz), 7.13 (2H, d, J=9.2 Hz), 7.45 (1H, s), 8.79 (1H, s)

Example 203

6-methoxy-3-{2-methoxy-4-[3-(1-pyrrolidinyl)propoxy]phenyl}-2-methylpyrido[3,4-d]pyrimidin-4(3H)-one (1) Manufacture of 3-(4-hydroxy-2-methoxyphenyl)-6-methoxy-2-methylpyrido[3,4-d]pyrimidin-4(3H)-one The target compound was obtained by the method according to Example 197, using 5-amino-2-chloroisonicotinic acid, acetic anhydride, 4-amino-3-methoxyphenol and sodium methoxide as starting materials.

(2) Manufacture of 6-methoxy-3-{2-methoxy-4-[3-(1-pyrrolidinyl)propoxy]phenyl}-2-methylpyrido[3,4-d]pyrimidin-4(3H)-one The title compound was obtained by the method according to Example 63, using 3-(4-hydroxy-2-methoxyphenyl)-6-methoxy-2-methylpyrido[3,4-d]pyrimidin-4(3H)-one and 1-(3-bromopropyl)pyrrolidine hydrobromide as starting materials.

$^1$HNMR (400 MHz,CDCl$_3$,δppm): 1.80-1.84 (4H, m), 2.02-2.07 (2H, m), 2.20 (3H, s), 2.55-2.60 (4H, m), 2.68 (2H, t, J=7.2 Hz), 3.77 (3H, s), 4.02 (3H, s), 4.09 (2H, t, J=6.4 Hz), 6.60-6.63 (2H, m), 7.07 (1H, d, J=8.8 Hz), 7.45 (1H, s), 8.75 (1H, s)

Example 204

6-bromo-3-{2-fluoroethoxy-4-[3-(1-pyrrolidinyl)propoxy]phenyl}-2-methyl-4(3H)-quinazolinone (1) Manufacture of 6-bromo-3-{2-methoxy-4-[3-(1-pyrrolidinyl)propoxy]phenyl}-2-methyl-4(3H)-quinazolinone The target compound was obtained by the method according to Example 63, using 2-amino-5-bromobenzoic acid, acetic anhydride, 4-amino-3-methoxyphenol and 1-(3-bromopropyl)pyrrolidine hydrobromide as starting materials.

(2) Manufacture of 6-bromo-3-{2-fluoroethoxy-4-[3-(1-pyrrolidinyl)propoxy]phenyl}-2-methyl-4(3H)-quinazolinone The title compound was obtained by the method according to Example 192 using 6-bromo-3-{2-methoxy-4-[3-(1-pyrrolidinyl)propoxy]phenyl}-2-methyl-4(3H)-quinazolinone and 2-fluoroethyl tosylate as starting materials.

$^1$HNMR (400 MHz,CDCl$_3$,δppm): 1.82-1.86 (4H, m), 2.05-2.12 (2H, m), 2.23 (3H, s), 2.62-2.66 (4H, m), 2.72 (2H, t, J=7.2 Hz), 4.10 (2H, t, J=6.4 Hz), 4.12-4.34 (2H, m), 4.50 (1H, t, J=4.0 Hz), 4.62 (1H, t, J=4.0 Hz), 6.64-6.68 (2H, m), 7.09 (1H, d, J=8.8 Hz), 7.55 (1H, d, J=8.4 Hz), 7.82 (1H, dd, J=8.8, 2.4 Hz), 8.37 (1H, d, J=2.4 Hz

Example 205

6-ethoxycarbonyl-3-{2-fluoroethoxy-4-[3-(1-pyrrolidinyl)propoxy]phenyl}-2-methyl-4(3H)-quinazolinone 6-bromo-3-{2-fluoroethoxy-4-[3-(1-pyrrolidinyl)propoxy]phenyl}-2-methyl-4(3H)-quinazolinone synthesized in Example 204 (37 mg), palladium(II) acetate (2 mg), dppf (1,1'-bis(diphenylphosphino)ferrocene) (8.2 mg) and triethylamine (22 mg) were mixed in ethanol (5 mL), and the atmosphere in the system was replaced by carbon monoxide. The mixture was then heated under reflux in the carbon monoxide atmosphere for 2 days. Ethyl acetate was added to the reaction liquid, and the solid precipitate was filtered off. The filtrate was concentrated, purified by silica gel thin layer chromatography (chloroform/methanol=10/1), and the title compound (23 mg, 63%) was thus obtained as a light gray solid.

$^1$HNMR (400 MHz,CDCl$_3$,δppm): 1.41 (3H, t, J=7.2 Hz), 1.60-1.81 (4H, m), 2.17-2.21 (4H, m), 2.27 (3H, s), 2.43-2.50 (2H, m), 3.23-3.32 (2H, m), 4.13-4.38 (4H, m), 4.41 (2H, q, J=7.2 Hz), 4.50-4.53 (1H, m), 4.62-4.64 (1H, m), 6.65 (1H, dd, J=2.4, 8.8 Hz), 6.70 (1H, d, J=2.4 Hz), 7.13 (1H, d, J=8.8 Hz), 7.71 (1H, d, J=8.8 Hz), 8.38 (1H, dd, J=2.4, 8.8 Hz), 8.93 (1H, d, J=2.4 Hz)

Example 206

3-{2-fluoroethoxy-4-[3-(1-pyrrolidinyl)propoxy]phenyl}-6-methoxycarbonyl-2-methyl 4(3H)-quinazolinone 6-ethoxycarbonyl-3-{2-fluoroethoxy-4-[3-(1-pyrrolidinyl)propoxy]-phenyl}-2-methyl-4(3H)-quinazolinone synthesized in Example 205 was treated by sodium methoxide in dry methanol, and the title compound was thus obtained.

$^1$HNMR (400 MHz, CDCl$_3$,δppm): 1.82-1.88 (4H, m), 2.05-2.12 (2H, m), 2.27 (3H, s), 2.62-2.66 (4H, m), 2.72 (2H, t, J=7.3 Hz), 3.95 (3H, s), 4.10 (2H, t, J=6.3 Hz), 4.17-4.34 (2H, m), 4.50 (1H, t, J=4.1 Hz), 4.62 (1H, t, J=4.1 Hz), 6.65-6.68 (2H, m), 7.11 (1H, d, J=8.3 Hz), 7.70 (1H, d, J=8.3 Hz), 8.37 (1H, dd, J=8.5, 2.2 Hz), 8.93 (1H, d, J=2.0 Hz)

Example 207

3-{3-fluoro-4-[3-(1-piperidinyl)propoxy]phenyl}-2-methyl-4(3H)-quinazolinone

The title compound was obtained by the method according to Example 63, using anthranilic acid, acetic anhydride, 4-amino-2-fluorophenol and 1-(3-bromopropyl) piperidine hydrobromide as starting materials.

$^1$HNMR (400 MHz,CDCl$_3$,δppm): 1.43-1.48 (2H, m), 1.57-1.63 (4H, m), 2.02-2.09 (2H, m), 2.28 (3H, s), 2.39-2.45 (4H, m), 2.52 (2H, t, J=7.1 Hz), 4.16 (2H, t, J=6.3 Hz), 6.96-7.06 (2H, m), 7.13 (1H, t, J=8.8 Hz), 7.49-7.45 (1H, m), 7.67 (1H, d, J=8.3 Hz), 7.75-7.79 (1H, m), 8.27 (1H, dd, J=7.8, 1.5 Hz)

Example 208

3-{2-fluoro-4-[3-(1-piperidinyl)propoxy]phenyl}-2-methyl 4(3H)-quinazolinone

The title compound was obtained by the method according to Example 63, using anthranilic acid, acetic anhydride, 4-amino-3-fluorophenol and 1-(3-bromopropyl)piperidine hydrobromide as starting materials.
¹HNMR (400 MHz,CDCl₃,δppm): 1.42-1.49 (2H, m), 1.58-1.63 (4H, m), 1.98-2.04 (2H, m), 2.29 (3H, s), 2.38-2.44 (4H, m), 2.49 (2H, t, J=7.3 Hz), 4.06 (2H, t, J=6.3 Hz), 6.82-6.86 (2H, m), 7.17 (1H, t, J=8.5 Hz), 7.45-7.49 (1H, m), 7.68 (1H, d, J=7.3 Hz), 7.75-7.79 (1H, m), 8.27 (1H, dd, J=8.0, 1.2 Hz)

Example 209

2-methyl-3-{3-methyl-4-[3-(1-piperidinyl)propoxy]phenyl}-4(3H)-quinazolinone

The title compound was obtained by the method according to Example 63, using anthranilic acid, acetic anhydride, 4-amino-2-methylphenol and 1-(3-bromopropyl) piperidine hydrobromide as starting materials.
¹HNMR (400 MHz,CDCl₃,δppm): 1.43-1.49 (2H, m), 1.59-1.64 (4H, m), 2.01-2.08 (2H, m), 2.26 (3H, s), 2.27 (3H, s), 2.40-2.46 (4H, m), 2.51-2.55 (2H, m), 4.03-4.11 (2H, m), 6.94 (1H, d, J=8.8 Hz), 7.00-7.03 (2H, m), 7.45 (1H, td, J=7.6, 1.3 Hz), 7.67 (1H, d, J=7.3 Hz), 7.73-7.78 (1H, m), 8.27 (1H, dd, J=7.8, 1.0 Hz)

Example 210

2-methyl-3-{2-methyl-4-[3-(1-piperidinyl)propoxy]phenyl}-4(3H)-quinazolinone

The title compound was obtained by the method according to Example 63, using anthranilic acid, acetic anhydride, 4-amino-3-methyl phenol and 1-(3-bromopropyl)piperidine hydrobromide as starting materials.
¹HNMR (400 MHz,CDCl₃,δppm): 1.43-1.48 (2H, m), 1.58-1.64 (4H, m), 1.98-2.05 (2H, m), 2.08 (3H, s), 2.20 (3H, s), 2.39-2.46 (4H, m), 2.50 (2H, t, J=7.4 Hz), 4.05 (2H, t, J=6.3 Hz), 6.92-6.86 (2H, m), 7.04 (1H, d, J=8.3 Hz), 7.45-7.49 (1H, m), 7.68 (1H, d, J=7.8 Hz), 7.75-7.79 (1H, m), 8.28 (1H, dd, J=8.0, 1.7 Hz)

Example 211

3-{4-[(1-cyclobutyl-piperidin-4-yl)oxy]-2-methoxyphenyl}-2,5-dimethyl-4(3H)-quinazolinone The title compound was obtained by the method according to Example 88, using 2-amino-6-methylbenzoic-acid, acetic anhydride, 4-amino-3-methoxyphenol, t-butyl-4-hydroxypiperidine-1-carboxylate and cyclobutanone as starting materials.
¹HNMR (400 MHz,CDCl₃,δppm): 1.65-1.77 (2H, m), 1.84-1.95 (4H, m), 2.01-2.10 (4H, m), 2.17-2.25 (5H, m), 2.59-2.68 (2H, m), 2.73-2.81 (1H, m), 2.83 (3H, s), 3.77 (3H, s), 4.33-4.41 (1H, m), 6.58-6.63 (2H, m), 7.07 (1H, d, J=8.4 Hz), 7.20 (1H, d, J=8.4 Hz), 7.50 (1H, d, J=8.4 Hz), 7.58 (1H, t, J=8.4 Hz)

Example 212

3-{4-[(1-cyclobutyl-piperidin-4-yl)oxy]phenyl}-6-methoxy-2-methylpyrido[3,4-d]-pyrimidin-4(3H)-one The title compound was obtained by the method according to Example 88, using 3-(4-hydroxyphenyl)-6-methoxy-2-methylpyrido[3,4-d]pyrimidin-4(3H)-one synthesized in Example 197, t-butyl-4-hydroxy piperidine-1-carboxylate and cyclobutanone as starting materials.
¹HNMR (400 MHz,CDCl₃,δppm): 1.65-1.77 (2H, m), 1.84-1.95 (4H, m), 2.01-2.10 (4H, m), 2.17-2.24 (2H, m), 2.25 (3H, s), 2.61-2.69 (2H, m), 2.73-2.81 (1H, m), 4.04 (3H, s), 4.37-4.43 (1H, m), 7.05 (2H, d, J=8.8 Hz), 7.14 (2H, d, J=8.8 Hz), 7.46 (1H, s), 8.77 (1H, s)

Example 213

3-{4-[(1-cyclopentyl-piperidin-4-yl)oxy]phenyl}-6-methoxy-2-methylpyrido[3,4-d]pyrimidin-4(3H)-one The title compound was obtained by the method according to Example 88, using 3-(4-hydroxyphenyl)-6-methoxy-2-methylpyrido[3,4-d]pyrimidin-4(3H)-one synthesized in Example 197, t-butyl-4-hydroxy piperidine-1-carboxylate and cyclopentanone as starting materials.
¹HNMR (400 MHz,CDCl₃,δppm) 1.40-1.49 (2H, m), 1.52-1.62 (2H, m), 1.67-1.75 (2H, m), 1.85-1.95 (4H, m), 2.03-2.13 (2H, m), 2.24 (3H, s), 2.34-2.42 (2H, m), 2.53-2.58 (1H, m), 2.80-2.86 (2H, m), 4.03 (3H, s), 4.36-4.41 (1H, m), 7.05 (2H, d, J=8.8 Hz), 7.14 (2H, d, J=8.8 Hz), 7.45 (1H, s), 8.75 (1H, s)

Example 214

6-chloro-3-{4-[(1-cyclobutylpiperidin-4-yl)oxy]-2-methoxyphenyl}-2-methylpyrido[3,4-d]pyrimidin-4(3H)-one The title compound was obtained by the method according to Example 88, using 5-amino-2-chloroisonicotinic-acid, acetic anhydride, 4-amino-3-methoxyphenol and t-butyl-4-hydroxypiperidine-1-carboxylate and cyclobutanone as starting materials.
¹HNMR (40 MHz,CDCl₃,δppm): 1.64-1.77 (2H, m), 1.84-1.95 (4H, m), 2.01-2.10 (4H, m), 2.17-2.25 (5H, m), 2.59-2.68 (2H, m), 2.73-2.82 (1H, m), 3.77 (3H, s), 4.36-4.42 (1H, m), 6.586.63 (2H, m), 7.07 (1H, d, J=8.4 Hz), 8.06 (1H, s), 8.90 (1H, s)

Example 215

3-{4-[(1-cyclobutyl-piperidin-4-yl)oxy]-2-methoxyphenyl}-2-methylpyrido[4,3-d]pyrimidin-4(3H)-one The title compound was obtained by the method according to Example 88, using 4-aminonicotinic acid, acetic anhydride, 4-amino-3-methoxyphenol, t-butyl-4-hydroxypiperidine-1-carboxylate and cyclobutanone as starting materials.
¹HNMR (400 MHz,CDCl₃,δppm): 1.65-1.74 (2H, m), 1.82-1.95 (4H, m), 2.01-2.10 (4H, m), 2.17-2.24 (2H, m), 2.26 (3H, s), 2.62-2.69 (2H, m), 2.73-2.80 (1H, m), 3.77 (3H, s), 4.36-4.41 (1H, m), 6.59-6.63 (2H, m), 7.07 (1H, d, J=8.4 Hz), 7.48 (1H, d, J=5.6 Hz), 8.83 (1H, d, J=5.6 Hz), 9.46 (1H, s)

Example 216

3-{4-[(1-cyclobutyl-piperidin-4-yl)oxy]-3-fluorophenyl}-2-methyl-4(3H)-quinazolinone The title compound was obtained by the method according to Example 88, using anthranilic acid, acetic anhydride, 4-amino-2-fluorophenol, t-butyl-4-hydroxypiperidine-1-carboxylate and cyclobutanone as starting materials.

¹HNMR (400 MHZ,CDCl₃,δppm): 1.64-1.75 (2H, m), 1.85-1.96 (4H, m), 1.99-2.10 (4H, m), 2.16-2.26 (2H, m), 2.28 (3H, s), 2.59-2.70 (2H, m), 2.72-2.81 (1H, m), 4.37-4.45 (1H, m), 6.95-6.98 (1H, m), 7.03 (1H, dd, J=10.7, 2.4 Hz), 7.12 (1H, t, J=8.8 Hz), 7.46-7.50 (1H, m), 7.67 (1H, d, J=7.3 Hz), 7.78 (1H, td, J=7.7, 1.6 Hz), 8.26 (1H, dd, J=7.8, 1.5 Hz)

Example 217

3-{4-[(1-cyclopentyl-piperidin-4-yl)oxy]-3-fluorophenyl}-2-methyl 4(3H)-quinazolinone The title compound was obtained by the method according to Example 88, using anthranilic acid, acetic anhydride, 4-amino-2-fluorophenol, t-butyl-4-hydroxypiperidine-1-carboxylate and cyclopentanone as starting materials.

¹HNMR (400 MHz,CDCl₃,δppm): 1.39-1.49 (2H, m), 1.53-1.61 (2H, m), 1.68-1.74 (2H, m), 1.86-1.98 (4H, m), 2.03-2.11 (2H, m), 2.28 (3H, s), 2.35-2.46 (2H, m), 2.52-2.59 (1H, m), 2.87-2.79 (2H, m), 4.39-4.44 (1H, m), 6.95-6.98 (1H, m), 7.03 (1H, dd, J=10.7, 2.4 Hz), 7.13 (1H, t, J=8.5 Hz), 7.48 (1H, t, J=8.0 Hz), 7.67 (1H, d, J=7.8 Hz), 7.76-7.80 (1H, m), 8.27 (1H, dd, J=7.8, 1.5 Hz)

Example 218

3-{4-[(1-cyclobutyl-piperidin-4-yl)oxy]-2-fluorophenyl}-2-methyl-4(3H)-quinazolinone The title compound was obtained by the method according to Example 88, using anthranilic acid, acetic anhydride, 4-amino-3-fluorophenol, t-butyl-4-hydroxypiperidine-1-carboxylate and cyclobutanone as starting materials.

¹HNMR (400 MHz,CDCl₃,δppm): 1.65-1.75 (2H, m), 1.84-1.95 (4H, m), 2.01-2.10 (4H, m), 2.17-2.27 (2H, m), 2.29 (3H, s), 2.59-2.67 (2H, m), 2.73-2.81 (1H, m), 4.39-4.34 (1H, m), 6.80-6.85 (2H, m), 7.17 (1H, t, J=8.8 Hz), 7.46-7.49 (1H, m), 7.68 (1H, d, J=8.3 Hz), 7.75-7.79 (1H, m), 8.27 (1H, dd, J=8.0, 1.2 Hz)

Example 219

3-{4-[(1-cyclopentyl-piperidin-4-yl)oxy]-2-fluorophenyl}-2-methyl-4(3H)-quinazolinone The title compound was obtained by the method according to Example 88, using anthranilic acid, acetic anhydride, 4-amino-3-fluorophenol, t-butyl-4-hydroxypiperidine-1-carboxylate and cyclopentanone as starting materials.

¹HNMR (400 MHz,CDCl₃,δppm): 1.41-1.49 (2H, m), 1.53-1.60 (2H, m), 1.68-1.75 (2H, m), 1.86-1.94 (4H, m), 2.03-2.11 (2H, m), 2.29 (3H, s), 2.37-2.45 (2H, m), 2.53-2.60 (1H, m), 2.79-2.85 (2H, m), 4.40-4.34 (1H, m), 6.80-6.85 (2H, m), 7.17 (1H, t, J=8.8 Hz), 7.45-7.49 (1H, m), 7.68 (1H, d, J=7.8 Hz), 7.75-7.79 (1H, m), 8.27 (1H, dd, J=8.3, 1.5 Hz)

Example 220

2-methyl-3-{4-[(1-cyclobutyl-piperidin-4-yl)oxy]-2-methylphenyl}-4(3H)-quinazolinone hydrochloride The title compound was obtained by the method according to Example 88, using anthranilic acid, acetic anhydride, 4-amino-3-methylphenol, t-butyl-4-hydroxypiperidine-1-carboxylate and cyclobutanone as starting materials.

¹HNMR (400 MHz,CDCl₃,δppm): 1.73-1.85 (2H, m), 2.12 (3H, s), 2.17-2.30 (4H, m), 2.69-2.90 (7H, m), 3.34-3.45 (4H, m), 4.78-4.83 (1H, m), 6.93-7.00 (2H, m), 7.23-7.15 (1H, m), 7.70 (1H, t, J=7.6 Hz), 7.95 (1H, t, J=7.3 Hz), 8.32 (1H, d, J=7.8 Hz), 8.41 (1H, d, J=7.3 Hz)

Example 221

2-methyl-3-{4-[(1-cyclopentyl-piperidin-4-yl)oxy]-2-methylphenyl}-4(3H)-quinazolinone The title compound was obtained by the method according to Example 88, using anthranilic acid, acetic anhydride, 4-amino-3-methylphenol, t-butyl-4-hydroxypiperidine-1-carboxylate and cyclopentanone as starting materials.

¹HNMR (400 MHz,CDCl₃,δppm): 1.40-1.49 (2H, m), 1.53-1.59 (2H, m), 1.67-1.74 (2H, m), 1.85-1.93 (4H, m), 2.02-2.09 (5H, m), 2.20 (3H, s), 2.35-2.43 (2H, m), 2.51-2.58 (1H, m), 2.79-2.86 (2H, m), 4.34-4.40 (1H, m), 6.87 (1H, dd, J=8.8, 2.9 Hz), 6.92 (1H, d, J=2.4 Hz), 7.04 (1H, d, J=8.3 Hz), 7.45-7.49 (1H, m), 7.68 (1H, d, J=7.3 Hz), 7.75-7.80 (1H, m), 8.29 (1H, dd, J=8.0, 1.2 Hz)

Example 222

3-{4-[(1-cyclopentyl-piperidin-4-yl)oxy]-2-(2-fluoroethoxy)phenyl}-2-methylpyrido[4,3-d]pyrimidin-4(3H)-one The title compound was obtained by the method according to Example 192, using 3-{4-[(1-cyclobutyl-piperidin-4-yl)oxy]-2-methoxyphenyl}-2-methylpyrido[4,3-d]pyrimidin-4(3H)-one synthesized in Example 221 and 2-fluoroethyl tosylate which were used as starting materials.

¹HNMR (400 MHz,CDCl₃,δppm): 1.65-1.77 (2H, m), 1.84-1.95 (4H, m), 2.01-2.11 (4H, m), 2.15-2.23 (2H, m), 2.29 (3H, s), 2.61-2.69 (2H, m), 2.71-2.80 (1H, m), 4.10-4.34 (2H, m), 4.35-4.41 (1H, m), 4.50-4.52 (1H, m), 4.62-4.64 (1H, m), 6.64-6.67 (2H, m), 7.10 (1H, d, J=8.4 Hz), 7.48 (1H, d, J=5.6 Hz), 8.84 (1H, d, J=5.6 Hz), 9.46 (1H, s)

Example 223

3-{4-[(1-cyclobutylpiperidin-4-yl)oxy]phenyl}-5-fluoroethoxy-2-methyl-4(3H)-quinazolinone The title compound was obtained by the method according to Example 192, using 3-{4-[(1-cyclobutyl-piperidin-4-yl)oxy]phenyl}-5-methoxy-2-methyl-4(3H)-quinazolinone synthesized in Example 105 and 2-fluoroethyl tosylate as starting materials. ¹HNMR (400 MHz,CDCl₃,δppm): 1.65-1.76 (2H m), 1.84-1.96 (4H, m), 2.01-2.10 (4H, m), 2.18-2.25 (5H, m), 2.61-2.69 (2H, m), 2.73-2.81 (1H, m), 4.28-4.31 (1H, m), 4.36-4.40 (2H, m), 4.75-4.77 (1H, m), 4.87-4.89 (1H, m), 6.89 (1H, d, J=8.4 Hz), 7.01 (2H, d, J=8.8 Hz), 7.12 (2H, d, J=8.8 Hz), 8.29 (1H, d, J=8.0 Hz), 7.64 (1H, t, J=8.0 Hz)

Example 224

6-chloro-3-{4-[(1-cyclobutylpiperidin-4-yl)oxy]-2-(2-fluoroethoxy)phenyl}-2-methylpyrido[3,4-d]pyrimidin-4(3H)-one The title compound was obtained by the method according to Example 192, using 6-chloro-3-{4-[(1-cyclobutylpiperidin-4-yl) oxy]-2-methoxyphenyl}-2-methylpyrido[3.,4-d]

pyrimidin-4(3H)-one synthesized in Example 220 and 2-fluoroethyl tosylate as starting materials.

$^1$HNMR (400 MHz,CDCl$_3$,δppm) 1.67-1.75 (2H, m), 1.84-1.95 (4H, m), 2.01-2.10 (4H, m), 2.15-2.24 (2H, m), 2.28 (3H, s), 2.61-2.69 (2H, m), 2.73-2.81 (1H, m), 4.10-4.32 (2H, m), 4.34-4.40 (1H, m), 4.49-4.51 (1H, m), 4.61-4.63 (1H, m), 6.64-6.66 (2H, m), 7.08 (1H, d, J=8.4 Hz), 8.05 (1H, s), 8.90 (1H, s)

Example 225

3-{4-[(1-cyclobutyl-piperidin-4-yl)oxy]-2-(2-fluoro-ethoxyphenyl}-2-methylpyrido[3,4-d]pyrimidin-4 (3H)-one The title compound was obtained by catalytic reduction of 6-chloro-3-{4-[(1-cyclobutylpiperidin-4-yl)oxy]-2-(2-fluoroethoxy)phenyl}-2-methylpyrido[3,4-d]pyrimidin-4(3H)-one synthesized in Example 230, using palladium charcoal as catalyst in the presence of triethylamine.

$^1$HNMR (400 MHz,CDCl$_3$,δppm): 1.66-1.77 (2H, m), 1.84-1.95 (4H, m), 2.01-2.10 (4H, m), 2.15-2.24 (2H, m), 2.29 (3H, s), 2.61-2.69 (2H, m), 2.72-2.81 (1H, m), 4.10-4.33 (2H, m), 4.35-4.41 (1H, m), 4.49-4.51 (1H, m), 4.61-4.63 (1H, m), 6.64-6.67 (2H, m), 7.10 (1H, d, J=8.4 Hz), 8.02 (1H, dd, J=1.2, 5.6 Hz), 8.66 (1H, d, J=5.6 Hz), 9.12 (1H, d, J=1.2 Hz)

Example 226

3-{(2-[(1-cyclobutylpiperidin-4-yl)oxy]-pyrimidin-5-yl}-2-methyl-5-(trifluoromethyl)-4(3H)-quinazolinone (1) Manufacture of t-butyl-4-[(5-nitroglycerine-pyrimidin-2-yl)oxy]piperidine-1-carboxylate 2-chloro-5-nitroglycerine-pyrimidine (80 mg, 0.5 mmol), t-butyl-4-hydroxypiperidine-1-carboxylate (100 mg, 0.5 mmol) and cesium fluoride (114 mg, 0.75 mmol) were mixed in dimethylformamide, and stirred at room temperature for 12 hours. The solvent was distilled off under reduced pressure, the product was purified by silica gel column chromatography (hexane/ethyl acetate =10/0-3/7), and the target compound (61 mg, 38%) was thus obtained as a light yellow solid.

(2) Manufacture of t-butyl-4-[(5-aminopyrimidin-2-yl)oxy]piperidine-1-carboxylate t-butyl-4-[(5-nitroglycerine-pyrimidin-2-yl)oxy]piperidine-1-carboxylate (500 mg, 1.54 mmol) was dissolved in a mixed solvent of methanol (10 mL) and tetrahydrofuran (10 mL), and palladium charcoal (10%, 200 mg) was added in a current of nitrogen. The atmosphere in the system was replaced by hydrogen, and the mixture stirred at room temperature for 3 hours. The reaction liquid was filtered through cerite, the filtrate was concentrated, dried, and the target compound (439 mg, 97%) was thus obtained.

(3) 2-methyl-3-[2-(piperidin-4-yl-oxy)pyrimidine 5-yl]-5-(trifluoromethyl)-4(3H)-quinazolinone 2-methyl-5-(trifluoromethyl)-4H-3,1-benzoxadin-4-one (78 mg, 0.34 mmol) and t-butyl-4-[(5-amino-pyrimidin-2-yl)oxy]piperidine-1-carboxylate (100 mg, 0.34 mmol) were dissolved in acetic acid (2 mL), and stirred at 130° C. for 6 hours. Acetic acid was distilled off under reduced pressure, 1N sodium hydroxide aqueous solution was added, and the mixture extracted with ethyl acetate. The product was dried with anhydrous sodium sulfate, and concentrated to obtain the target compound (112 mg, 81%) as a brown amorphous solid.

(4) Manufacture of 3-{2-[(1-cyclobutylpiperidin-4-yl)oxy]pyrimidin-5-yl}-2-methyl-5-trifluoromethyl-4 (3H)-quinazolinone The title compound was obtained by the method according to Example 88-(3), using 2-methyl-3-[2-(piperidin-4-yl-oxy) pyrimidin-5-yl]-5-(trifluoromethyl)-4(3H)-quinazolinone and cyclobutanone as starting materials.

$^1$HNMR (400 MHz,CDCl$_3$,δppm): 1.64-1.75 (2H, m), 1.86-2.01 (4H, m), 2.01-2.15 (4H, m), 2.17-2.28 (2H, m), 2.32 (3H, s), 2.64-2.74 (2H, m), 2.74-2.81 (1H, m), 5.10-5.18 (1H,brs), 7.83-7.93 (3H, m), 8.46 (2H, s)

Example 227

3-{4-[(1-cyclobutyl-piperidin-4-yl)oxy]phenyl}-5-methoxy-2-propyl-4(3H)-quinazolinone The title compound was obtained by the method according to Example 94, using 2-amino-6-methoxybenzoic acid, butyric anhydride and 4-[(1-cyclobutylpiperidin-4-yl)oxy] aniline as starting materials.

$^1$HNMR (400 MHZ,CDCl$_3$,δppm): 0.86 (3H, t, J=7.2 Hz), 1.64-1.75 (4H, m), 1.83-1.95 (4H, m), 2.01-2.11 (4H, m), 2.14-2.22 (2H, m), 2.36-2.40 (2H, m), 2.60-2.70 (2H, m), 2.72-2.80 (1H, m), 3.94 (3H, s), 4.35-4.42 (1H, m), 6.86 (1H, dd, J=0.8, 8.4 Hz), 7.00 (2H, d, J=8.8 Hz), 7.10 (2H, d, J=8.8 Hz), 7.26 (1H, dd, J=0.8, 8.0 Hz), 7.64 (1H, t, J=8.0 Hz)

Example 228

3-{4-[(1-cyclobutylpiperidin-4-yl)oxy]phenyl}-6-methoxy-2-methyl-4(3H)-quinazolinone The title compound was synthesized as a white solid (m.p.: 171-173° C.) by the method according to Example 94, using 2-amino-5-methoxybenzoic acid, acetic anhydride and 4-[(1-cyclobutylpiperidin-4-yl)oxy]aniline monotosylate as starting materials, followed by recrystallization (ethyl acetate/diethyl ether).

$^1$HNMR (400 MHz,CDCl$_3$,δppm): 1.64-1.74 (2H, m), 1.85-1.96 (4H, m), 2.01-2.13 (4H, m), 2.15-2.24 (2H, m), 2.23 (3H, s), 2.60-2.72 (2H, m), 2.72-2.81 (1H, m), 3.91 (3H, s), 4.35-4.42 (1H,brs), 7.04 (2H, d, J=6.8 Hz), 7.13 (2H, d, J=6.8 Hz), 7.36 (1H, dd, J=3.2, 9.2 Hz), 7.61 (1H, d, J=9.2 Hz), 7.63 (1H, d, J=3.2 Hz)

Example 229

3-{4-[(1-cyclobutylpiperidin-4-yl)oxy]phenyl}-2-ethyl-6-fluoropyrido[3,4-d]pyrimidin-4(3H)-one The title compound was obtained by the method according to Example 94, using 5-amino-2-fluoroisonicotinic acid, propionic anhydride and 4-[(1-cyclobutylpiperidin-4-yl)oxy] aniline as starting materials.

$^1$HNMR (400 MHz,CDCl$_3$,δppm): 1.23 (3H, t, J=7.2 Hz), 1.65-1.76 (2H, m), 1.85-1.96 (4H, m), 2.03-2.15 (4H, m), 2.16-2.28 (2H, m), 2.46 (2H, q,J=7.2 Hz) 2.62-2.72 (2H, m), 2.73-2.82 (1H, m), 4.38-4.44 (1H, m), 7.06 (2H, d, J=8.8 Hz), 7.13 (2H, d, J=6.8 Hz), 7.65 (1H, d, J=3.2 Hz), 8.81 (1H, s)

Example 230

3-{4-[(1-cyclobutyl-piperidin-4-yl)oxy]phenyl}-6-fluoro-2-methylpyrido[3,4-d]pyrimidin-4(3H)-one The title compound was synthesized as a white solid (m.p.: 161-163° C.) by the method according to Example 94, using 5-amino-2-fluoroisonicotinic acid, acetic anhydride and 4-[(1-cyclobutylpiperidin-4-yl)oxy]aniline as starting materials, followed by recrystallization (ethyl acetate/diethyl ether/n-heptane).

$^1$HNMR (400 MHz,CDCl$_3$,δppm): 1.65-1.75 (2H, m), 1.80-1.93 (4H, m), 2.00-2.11 (4H, m), 2.12-2.24 (2H, m), 2.28 (3H, s), 2.60-2.70 (2H, m), 2.72-2.78 (1H, m), 4.36-4.42 (1H, m), 7.05 (2H, d, J=6.8 Hz), 7.13 (2H, d, J=6.8 Hz), 7.65 (1H, d, J=4.0 Hz), 8.77 (1H, s)

Example 231

3-{4-[(1-cyclobutylpiperidin-4-yl)oxy]phenyl}-5-fluoro-2-methyl-4(3H)-quinazolinone The title compound was synthesized as a white solid (m.p.: 190-192° C.) by the method according to Example 94, using 2-amino-6-fluorobenzoic acid, acetic anhydride and 4-[(1-cyclobutylpiperidin-4-yl)oxy]aniline monotosylate as starting materials, followed by recrystallization (ethyl acetate).

$^1$HNMR (400 MHz,CDCl$_3$,δppm): 1.65-1.75 (2H, m), 1.83-1.93 (4H, m), 2.00-2.11 (4H, m), 2.13-2.24 (2H, m), 2.24 (3H, s), 2.60-2.68 (2H, m), 2.72-2.79 (1H, m), 4.36-4.41 (1H, m), 7.04 (2H, d, J=8.8 Hz), 7.08-7.14 (3H, m), 7.46 (1H, d, J=8.0 Hz), 7.65-7.71 (1H, m)

Example 232

3-{4-[(1-cyclobutylpiperidin-4-yl)oxy]phenyl}-6-fluoro-2-methyl-4(3H)-quinazolinone The title compound was synthesized as a light yellow solid (m.p.:122-125° C.) by the method according to Example 94, using 2-amino-5-fluorobenzoic acid, acetic anhydride and 4-[(1-cyclobutylpiperidin-4-yl)oxy]aniline monotosylate as starting materials, followed by recrystallization (ethyl acetate/diethyl ether).

$^1$HNMR (400 MHz,CDCl$_3$,δppm): 1.63-1.75 (2H, m), 1.84-1.92 (4H, m), 2.01-2.12 (4H, m), 2.16-2.24 (2H, m), 2.25 (3H, s), 2.61-2.70 (2H, m), 2.72-2.81 (1H, m), 4.36-4.42 (1H, m), 7.04 (2H, d, J=8.8 Hz), 7.14 (2H, d, J=8.8 Hz), 7.45-7.51 (1H, m), 7.68 (1H, dd, J=4.8, 8.8 Hz), 7.89 (1H, dd, J=3.2, 8.0 Hz)

Example 233

3-{4-[(1-cyclobutylpiperidin-4-yl)oxy]phenyl}-7-fluoro-2-methyl-4(3H)-quinazolinone The title compound was synthesized as a white solid (m.p.: 163-166° C.) by the method according to Example 94, using 2-amino-4-fluorobenzoic acid, acetic anhydride and 4-[(1-cyclobutylpiperidin-4-yl)oxy]aniline monotosylate as starting materials, followed by recrystallization (ethyl acetate/diethyl ether).

$^1$HNMR (400 MHz,CDCl$_3$,δppm): 1.65-1.75 (2H, m), 1.82-1.96 (4H, m), 2.00-2.11 (4H, m), 2.14-2.24 (2H, m), 2.25 (3H, s), 2.60-2.68 (2H, m), 2.72-2.79 (1H, m), 4.36-4.41 (1H, m), 7.04 (2H, d, J=8.4 Hz), 7.12-7.20 (3H, m), 7.31 (1H, dd, J=2.0, 9.6 Hz), 8.27 (1H, dd, J=6.0, 8.4 Hz)

Example 234

3-{4-[(1-cyclobutylpiperidin-4-yl)oxy]phenyl}-6,7-difluoro-2-methyl-4(3H)-quinazolinone The title compound was obtained by the method according to Example 94, using 2-amino-4,5-difluorobenzoic acid, acetic anhydride and 4-[(1-cyclobutylpiperidin-4-yl)oxy]aniline and monotosylate as starting materials.

$^1$HNMR (400 MHz,CDCl$_3$,δppm): 1.66-1.75 (2H, m), 1.83-1.95 (4H, m), 2.00-2.11 (4H, m), 2.16-2.24 (2H, m), 2.24 (3H, s), 2.60-2.68 (2H, m), 2.72-2.79 (1H, m), 4.35-4.42 (1H, m), 7.04 (2H, d, J=8.4 Hz), 7.13 (2H, d, J=8.4 Hz), 7.44 (1H, dd, J=6.8, 10.4 Hz), 8.01 (1H, dd, J=8.4, 9.6 Hz)

Example 235

3-{4-[(1-cyclobutylpiperidin-4-yl)oxy]phenyl}-2-ethyl-5-methyl-4(3H)-quinazolinone The title compound was obtained by the method according to Example 94, using 2-amino-6-methyl benzoic acid, propionic anhydride and 4-[(1-cyclobutylpiperidin-4-yl)oxy]aniline monotosylate as starting materials.

$^1$HNMR (400 MHz,CDCl$_3$,δppm): 1.20 (3H, t, J=7.0 Hz), 1.69 (2H, m), 1.88 (4H, m), 2.05 (4H, m), 2.19 (2H, m), 2.44 (2H, q, J=7.0 Hz), 2.63 (2H, m), 2.75 (1H, m), 2.82 (3H, s), 4.37 (1H, m), 7.04 (2H, d, J=8.4 Hz), 7.13 (2H, d, J=8.4 Hz), 7.21 (1H, d, J=7.2 Hz), 7.54 (1H, d, J=8.0 Hz), 7.59 (1H, dd, J=7.2, 8.0 Hz)

Example 236

3-{4-[(1-cyclobutylpiperidin-4-yl)oxy]phenyl}-2-ethyl-5-fluoro-4(3H)-quinazolinone The title compound was obtained by the method according to Example 94, using 2-amino-6-fluorobenzoic acid, propionic anhydride and 4-[(1-cyclobutylpiperidine 4-yl)oxy]aniline monotosylate as starting materials.

$^1$HNMR (400 MHz,CDCl$_3$,δppm): 1.20 (3H, t, J=7.2 Hz), 1.64-1.76 (2H, m), 1.83-1.96 (4H, m), 2.00-2.10 (4H, m), 2.14-2.23 (2H, m), 2.44 (2H, q, J=7.2 Hz) 2.60-2.68 (2H, m), 2.71-2.79 (1H, m), 4.35-4.40 (1H, m), 7.04 (2H, d, J=8.8 Hz), 7.06-7.08 (1H, m), 7.12 (2H, d, J=8.8 Hz), 7.49 (1H, d, J=8.0 Hz), 7.64-7.70 (1H, m)

Example 237

3-{4-[(1-cyclobutylpiperidin-4-yl)oxy]phenyl}-2-ethyl-5-methoxy-4(3H)-quinazolinone The title compound was obtained by the method according to Example 94, using 2-amino-6-methoxybenzoic acid, propionic anhydride and 4-[(1-cyclobutylpiperidine 4-yl)oxy]aniline monotosylate as starting materials.

$^1$HNMR (400 MHz,CDCl$_3$,δppm): 1.20 (3H, t, J=7.2 Hz), 1.64-1.76 (2H, m), 1.83-1.96 (4H, m), 2.00-2.10 (4H, m), 2.14-2.22 (2H, m), 2.43 (2H, q, J=7.2 Hz) 2.60-2.68 (2H, m), 2.71-2.79 (1H, m), 3.95 (3H, s), 4.35-4.40 (1H, m), 6.86 (1H, d, J=8.0 Hz), 7.01 (2H, d, J=8.8 Hz), 7.10 (2H, d, J=8.8 Hz), 7.28 (1H, d, J=8.0 Hz), 7.64 (1H, t, J=8.0 Hz)

Example 238

5-chloro-3-{4-[(1-cyclobutylpiperidin-4-yl)oxy]phenyl}-2-ethyl-4(3H)-quinazolinone

The title compound was obtained by the method according to Example 94, using 2-amino-6-chlorobenzoic acid, propionic anhydride and 4-[(1-cyclobutylpiperidin-4-yl)oxy] aniline monotosylate as starting materials.

$^1$HNMR (400 MHz,CDCl$_3$,δppm): 1.20 (3H, t, J=7.2 Hz), 1.62-1.78 (2H, m), 1.83-1.96 (4H, m), 2.00-2.10 (4H, m), 2.14-2.22 (2H, m), 2.44 (2H, q,J=7.2 Hz), 2.60-2.68 (2H, m), 2.71-2.79 (1H, m), 4.35-4.40 (1H, m), 7.03 (2H, d, J=8.8 Hz), 7.12 (2H, d, J=8.8 Hz), 7.45 (1H, dd, J=2.8, 6.4 Hz), 7.57-7.62 (2H, m)

Example 239

3-{3-bromo-4-[(1-cyclobutylpiperidin-4-yl)oxy]phenyl}-5-fluoro-2-methyl-4(3H)-quinazolinone

(1) Manufacture of 3-bromo-4-[(1-cyclobutylpiperidin-4-yl)oxy]aniline monotosylate 3-bromo-4-[(1-cyclobutylpiperidin-4-yl)oxy]aniline was obtained according to the method of Example 94, using 2-bromo-4-nitrophenol, N-Boc-4-piperidinol and cyclobutanone as starting materials. By treating this with 1 Eq of p-toluenesulfonic acid monohydrate, the target compound was obtained as a colorless solid. 2-bromo-4-nitrophenol was manufactured by the method described in the literature (J. Org. Chem., Vol. 62, 1997, p. 4504).

(2) Manufacture of 3-{3-bromo-4-[(1-cyclobutylpiperidin-4-yl)oxy]phenyl}-5-fluoro-2-methyl-4(3H)-quinazolinone The title compound was obtained by the method according to Example 94, using 2-amino-6-fluorobenzoic acid, acetic anhydride and 3-bromo-4-[(1-cyclobutylpiperidin-4-yl)oxy] aniline monotosylate as starting materials.

$^1$HNMR (400 MHz,CDCl$_3$,δppm): 1.67-1.75 (2H, m), 1.86-2.10 (8H, m), 2.26 (3H, s), 2.28-2.38 (2H, m), 2.52-2.63 (2H, m), 2.74-2.83 (1H, m), 4.50-4.54 (1H, m), 7.03 (1H, d, J=8.8 Hz), 7.08-7.15 (2H, m), 7.45-7.47 (2H, m), 7.72-7.66 (1H, m)

Example 240

3-{3-bromo-4-[(1-cyclobutylpiperidin-4-yl)oxy]phenyl}-2,5-dimethyl-4(3H)-quinazolinone

The title compound was obtained by the method according to Example 94, using 2-amino-6-methylbenzoic acid, acetic anhydride and 3-bromo-4-[(1-cyclobutylpiperidin-4-yl)oxy] aniline as starting materials.

$^1$HNMR (400 MHz,CDCl$_3$,δppm): 1.72 (2H, m), 1.80-2.15 (8H, m), 2.24 (3H, s), 2.34 (2H, m), 2.44 (2H, m), 2.78 (1H, m), 2.81 (3H, s), 4.52 (1H,brs), 7.04 (1H, d, J=8.8 Hz), 7.14 (1H, dd, J=2.4, 8.8 Hz), 7.23 (1H, d, J=7.8 Hz), 7.46 (1H, d, J=2.4 Hz), 7.50 (1H, d, J=7.8 Hz), 7.60 (1H, t, J=7.8 Hz)

Example 241

3-{4-[(1-cyclobutylpiperidin-4-yl)oxy]phenyl}-2-ethyl-5-(trifluoromethyl)-4(3H)-quinazolinone hydrochloride

The title compound was obtained by the method according to Example 94, using 2-amino-6-(trifluoromethyl)benzoic acid, propionic anhydride, 4-[(1-cyclobutylpiperidin-4-yl) oxy] aniline and monotosylate as starting materials.

$^1$HNMR (400 MHz,CDCl$_3$,δppm): 1.32 (3H, t, J=6.8 Hz), 1.75-1.83 (1H, m), 1.98-2.07 (1H, m), 2.17-2.29 (4H, m), 2.72-2.91 (8H, m), 3.35-3.43 (3H, m), 4.78-4.81 (1H, m), 7.08 (2H, d, J=8.0 Hz), 7.24 (2H, d, J=8.4 Hz), 7.92-8.00 (2H, m), 8.40 (1H, d, J=7.8 Hz)

Example 242

3-{4-[(1-cyclobutylpiperidin-4-yl)oxy]phenyl}-8-fluoro-2-methyl-4(3H)-quinazolinone

The title compound was synthesized as a light brown solid (m.p.:177-179° C.) by the method according to Example 94, using 2-amino-4-fluorobenzoic acid, acetic anhydride and 4-[(1-cyclobutylpiperidin-4-yl)oxy]aniline monotosylate as starting materials, followed by recrystallization (ethyl acetate/diethyl ether).

$^1$HNMR (400 MHz,CDCl$_3$,δppm): 1.66-1.75 (2H, m), 1.84-1.95 (4H, m), 2.02-2.11 (4H, m), 2.17-2.28 (2H, m), 2.31 (3H, s), 2.61-2.68 (2H, m), 2.75-2.80 (1H, m), 4.37-4.43 (1H, m), 7.05 (2H, d, J=9.3 Hz), 7.14 (2H, d, J=9.3 Hz), 7.42-7.37 (1H, m), 7.47-7.52 (1H, m), 8.05 (1H, d, J=7.8 Hz)

Example 243

2-[3-(benzyloxy)propyl]-3-{4-[(1-cyclopentylpiperidin-4-yl)oxy]phenyl}pyrido[2,3-d]pyrimidin-4(3H)-one

(1) Manufacture of 2-{[4-(benzyloxy)butanoyl]amino}nicotinic acid 4-(benzyloxy)butyric acid (154 mg, 0.79 mmol) was dissolved in chloroform, thionyl chloride (158 mg) was added, and the mixture stirred at room temperature for 1 Hour. The solvent and excess thionyl chloride were distilled off under reduced pressure, the residue was dissolved in chloroform, triethylamine (0.46 mL) and 2-aminonicotinic acid ethyl ester (110 mg, 0.66 mmol) were added, and the mixture stirred at room temperature for 2 hours. Saturated sodium hydrogen carbonate aqueous solution was added to the reaction liquid, the mixture extracted with chloroform, and dried with anhydrous sodium sulfate. The obtained residue was dissolved in methanol, 2N sodium hydroxide aqueous solution (0.66 mL) was added, and the mixture stirred at room temperature for 2 hours. After adding hydrochloric acid aqueous solution to the reaction liquid to render it weakly acid, the solvent was distilled off under reduced pressure. Ethyl acetate and a small amount of ethanol were added to the residue, the solid precipitate was filtered off, and the target compound (166 mg, 80%) was thus obtained as a colorless solid.

(2) Manufacture of 2-[3-(benzyloxy)propyl]-4H-pyrido[2,3-d][1,3]oxadin-4-one 2-{[4-(benzyloxy)butanoyl]amino}nicotinic acid (100 mg, 0.32 mmol) was dissolved in chloroform (4 mL) in a current of nitrogen, oxalyl chloride (50 microL) was added, and the mixture stirred at room temperature for 2 hours. Triethylamine (0.2 mL) was added to the reaction liquid, and stirred for 1 Hour. Saturated sodium hydrogen carbonate aqueous solution was added, and the mixture extracted with chloroform. This was dried with anhydrous sodium sulfate, concentrated, and the target compound (42 mg, 45%) was thus obtained as a brown oily residue.

(3) Manufacture of 2-[3-(benzyloxy)propyl]-3-{4-[(1-cyclopentylpiperidin-4-yl)oxy]phenyl}pyrido[2,3-d]pyrimidin-4(3H)-one The title compound was obtained by the method according to Example 94, using 2-[3-(benzyloxy)propyl]-4H-pyrido[2,3-d][1,3]oxazin-4-one and 4-[(1-cyclopentylpiperidin-4-yl)oxy]aniline as starting materials.

$^1$HNMR (400 MHz, CDCl$_3$, δppm): 1.43-1.53 (2H, m), 1.53-1.62 (2H, m), 1.68-1.76 (2H, m), 1.86-1.94 (4H, m), 2.03-2.12 (2H, m), 2.13-2.19 (2H, m), 2.35-2.46 (2H, m), 2.55-2.61 (1H, m), 2.62 (2H, t, J=7.2 Hz), 2.82-2.88 (2H, m), 3.54 (2H, t, J=5.6 Hz), 4.37-4.42 (1H, m), 4.40 (2H, s) 7.02 (2H, d, J=8.8 Hz), 7.12 (2H, d, J=8.8 Hz), 7.17 (2H, d, J=8.0 Hz), 7.22-7.28 (3H, m), 7.41 (1H, dd, J=4.8, 8.0 Hz), 8.58 (1H, dd, J=2.0, 8.0 Hz), 8.98 (1H, dd, J=2.0, 4.4 Hz)

Example 244

2-[2-(allyloxy)ethyl]-6-chloro-3-{4-[(1-cyclobutylpiperidin-4-yl)oxy]phenyl}pyrido[3,4-d]pyrimidin-4(3H)-one (1) Manufacture of 2-[2-(allyloxy)ethyl]-6-chloro-4H-pyrido[3,4-d][1,3]oxadin-4-one The target compound was obtained by the method according to Example 243, using 5-amino-2-chloroisonicotinic acid ethyl ester and 3-(allyloxy)propionic acid as starting materials.

(2) Manufacture of 2-[2-(allyloxy)ethyl]-6-chloro-3-{4-[(1-cyclobutylpiperidin-yl)oxy]phenyl}pyrido[3,4-d]pyrimidin-4(3H)-one The title compound was obtained by the method according to Example 94, using 2-[2-(allyloxy)ethyl]-6-chloro-4H-pyrido[3,4-d][1,3]oxadin-4-one and 4-[(1-cyclobutylpiperidin-4-yl)oxy]aniline as starting materials.

$^1$HNMR (400 MHz, CDCl$_3$, δppm): 1.65-1.75 (2H, m), 1.83-1.94 (4H, m), 2.00-2.11 (4H, m), 2.16-2.23 (2H, m), 2.60-2.69 (2H, m), 2.76 (2H, t, J=6.4 Hz), 3.86 (2H, t, J=6.4 Hz), 3.97 (2HH, dd, J=1.2, 6.0 Hz), 4.35-4.42 (1H, m), 5.17 (2H, dd, J=1.2, 10.4 Hz), 5.22-5.28 (2H, m), 5.81-5.90 (1H, m), 7.03 (2H, d, J=8.8 Hz), 7.10 (2H, d, J=8.8 Hz), 8.06 (1H, s), 8.91 (1H, s)

Example 245

6-chloro-3-{4-[(1-cyclopropylpiperidin-4-yl)oxy]phenyl}-2-methylpyrido[3,4-d]pyrimidin-4(3H)-one (1) Manufacture of 1-cyclopropyl-4-(4-nitrophenoxy)piperidine 4-(4-nitrophenoxy)piperidine (1.92 g, 8.63 mmol) and [(1-ethoxycyclopropyl)oxy](trimethyl)silane (2.27 g, 12.9 mmol) were dissolved in a mixed solvent of acetic acid (20 mL) and methanol (20 mL), sodium cyanoborohydride (1.08 g, 17.3 mmol) was added, and the mixture stirred at 65° C. for 18 hours. The solvent was distilled off under reduced pressure, ethyl acetate and 1N sodium hydroxide aqueous solution were added, the mixture was extracted with ethyl acetate, and the organic phase was washed with distilled water. After drying with anhydrous sodium sulfate, the product was concentrated, and the target compound (1.94 g, 86%) was thus obtained as a light brown oily substance. 4-(4-nitrophenoxy)piperidine was that manufactured in Example 94.

(2) Manufacture of 4-[(1-cyclopropyl piperidin-4-yl)oxy]aniline

The target compound was obtained by catalytic reduction of 1-cyclopropyl-4-(4-nitrophenoxy)piperidine in a mixed solvent of methanol and ethyl acetate, using a palladium charcoal catalyst.

(3) Manufacture of 6-chloro-3-{4-[(1-cyclopropylpiperidin-4-yl)oxy]phenyl}-2-methylpyrido[3,4-d]pyrimidin-4(3H)-one The title compound was obtained by the method according to Example 94, using 5-amino-2-chloroisonicotinic acid, acetic anhydride and 4-[(1-cyclopropylpiperidin-4-yl) oxy]aniline as starting materials.

$^1$HNMR (400 MHz, CDCl$_3$, δppm): 0.41-0.50 (4H, m), 1.62-1.65 (1H, m), 1.80-1.88 (2H, m), 1.97-2.04 (2H, m), 2.29 (3H, s), 2.48-2.57 (2H, m), 2.90-2.96 (2H, m), 4.37-4.42 (1H, m), 7.06 (2H, d, J=8.8 Hz), 7.13 (2H, d, J=8.8 Hz), 8.06 (1H, s), 8.90 (1H, s)

Example 246

3-{4-[(1-cyclopropylpiperidin-4-yl)oxy]phenyl}-2-methylpyrido[3,4-d]pyrimidin-4(3H)-one The title compound was obtained by catalytic reduction of 6-chloro-3-{4-[(1-cyclopropyl-piperidin-4-yl)oxy]phenyl}-2-methylpyrido[3,4-d]pyrimidin-4(3H)-one synthesized in Example 251 using a palladium charcoal catalyst in the presence of triethylamine.

$^1$HNMR (400 MHz, CDCl$_3$, δppm): 0.41-0.50 (4H, m), 1.62-1.66 (1H, m), 1.79-1.88 (2H, m), 1.97-2.04 (2H, m), 2.30 (3H, s), 2.49-2.56 (2H, m), 2.90-2.96 (2H, m), 4.37-4.42 (1H, m), 7.06 (2H, d, J=8.8 Hz), 7.13 (2H, d, J=8.8 Hz), 8.03 (1H, d, J=5.2 Hz), 8.68 (1H, d, J=5.2 Hz), 9.13 (1H, s)

Example 247

3-{4-[(1-cyclobutylpiperidin-4-yl)oxy]phenyl}-6-(difluoromethoxy)-2-methyl-(3H)-quinazolinone (1) Manufacture of 3-{4-[(1-cyclobutylpiperidin-yl)oxy]phenyl}-6-hydroxy-methyl-(3H)-quinazolinone The target compound was obtained by demethylating 3-{4-[(1-cyclobutylpiperidin-4-yl)oxy]phenyl}-6-methoxy-2-methyl-4(3H)-quinazolinone synthesized in Example 234 by the method according to Example 192 (1).

(2) Manufacture of 3-{4-[1-cyclobutylpiperidin-4-yl)oxy]phenyl}-6-(difluoromethoxy)-2-methyl-4(3H)-quinazolinone 3-{4-[(1-cyclobutylpiperidin-4-yl)oxy]phenyl}-6-hydroxy-2-methyl-4(3H)-quinazolinone (37 mg), sodium chlorodifluoroacetate (17 mg) and potassium carbonate (25 mg) were mixed in dimethylformamide, and stirred at 120° C. for 2 hours. Distilled water was added to the reaction liquid, the mixture was extracted with chloroform, and dried with anhydrous sodium sulfate. The product was purified by silica gel column chromatography (chloroform/methanol=15/1), and the title compound (19 mg, 46%) was thus obtained as a light yellow oily residue.

$^1$HNMR (400 MHz, CDCl$_3$, δppm): 1.65-1.77 (2H, m), 1.84-1.97 (4H, m), 2.01-2.10 (4H, m), 2.17-2.27 (5H, m), 2.61-2.68 (2H, m), 2.74-2.81 (1H, m), 4.42-4.36 (1H, m), 6.61 (1H, t, J=73.2 Hz), 7.04 (2H, d, J=9.3 Hz), 7.14 (2H, d, J=8.8 Hz), 7.53 (1H, dd, J=9.0, 2.7 Hz), 7.69 (1H, d, J=8.8 Hz), 7.94 (1H, d, J=2.9 Hz)

Example 248

3-{4-[(1-cyclobutylpiperidin-4-yl)oxy]phenyl}-7-methoxy-2-methyl-4(3H)-quinazolinone The title compound was obtained by the method according to Example 94, using 2-amino 4-methoxybenzoic acid, acetic anhydride and 4-[(1-cyclobutylpiperidin-4-yl)oxy]aniline as starting materials.

$^1$HNMR (400 MHz, CDCl$_3$, δppm): 1.65-1.76 (2H, m), 1.83-1.95 (4H, m), 2.00-2.09 (4H, m), 2.15-2.23 (2H, m), 2.24 (3H, s), 2.60-2.68 (2H, m), 2.71-2.79 (1H, m), 3.93 (3H, s), 4.35-4.41 (1H, m), 7.06-7.01 (4H, m), 7.14 (2H, d, J=9.3 Hz), 8.16 (1H, d, J=8.8 Hz

Example 249

6-chloro-3-(2-methoxy-4-{3-[(3S)-3-methylpiperidin-1-yl]propoxy}phenyl)-2-methylpyrido[3, 4-d]pyrimidin-4 (3H)-one (1) Manufacture of 6-chloro-3-(4-hydroxy-2-methoxyphenyl)-2-methylpyrido[3, 4-d]pyrimidin-4(3H)-one The title compound was obtained by the method according to Example 1-(1) and -(2), using 5-amino-2-chloroisonicotinic acid, acetic anhydride and 4-amino-3-methoxyphenol as starting materials.

(2) Manufacture of 6-chloro-3-(2-methoxy-4-{3-[(3S)-3-methylpiperidin-1-yl]propoxy}phenyl)-2-methylpyrido[3, 4-d]pyrimidin-4(3H)-one 6-chloro-3-(4-hydroxy-2-methoxyphenyl)-2-methylpyrido[3, 4-d]pyrimidin-4(3H)-one (250 mg, 0.79 mmol, 3-[(3S)-3-methylpiperidin-1-yl]propan-1-ol (186 mg, 1.2 mmol) and triphenylphosphine (310 mg, 1.2 mmol)-were dissolved in dry tetrahydrofuran (6 mL) in a current of nitrogen, and cooled on an ice bath. Diisopropyl azodicarboxylate (0.23 mL, 1.2 mmol) was dripped in, and stirred for 2 days at room temperature. The mixture was concentrated under reduced pressure, diethyl ether was added, and the solid precipitate was filtered off. The filtrate was concentrated, the product was purified by silica gel column chromatography (chloroform/methanol=100/0-95/5), and the title compound (200 mg, 56%) was thus obtained as colorless crystals.

$^1$HNMR (400 MHz, CDCl$_3$, δppm): 0.83-0.93 (4H, m), 1.55-1.74 (5H, m), 1.84-1.89 (1H, m), 1.99-2.06 (2H, m), 2.25 (3H, s), 2.50 (2H, t, J=7.3 Hz), 2.83-2.91 (2H, m), 3.77 (3H, s), 4.07 (2H, t, J=6.3 Hz), 6.61-6.64 (2H, m), 7.05-7.07 (1H, m), 8.05 (1H, s), 8.89 (1H, s)

Example 250

6-chloro-3-(2-hydroxy-4-{3-[(3S)-3-methylpiperidin-1-yl]propoxy}phenyl)-2-methylpyrido[3, 4-d]pyrimidin-4 (3H)-one 6-chloro-3-(2-methoxy-4-{3-[(3S)-3-methylpiperidin-1-yl]propoxy}phenyl)-2-methylpyrido[3, 4-d]pyrimidin-4 (3H)-one synthesized in Example 249 was demethoxylated by the method according to Example 192 (1), and the title compound was thus obtained.

$^1$HNMR (400 MHz, CDCl$_3$, δppm): 0.77-0.89 (4H, m), 1.52-1.74 (5H, m), 1.97-2.07 (3H, m), 2.32 (3H, s), 2.64-2.81 (2H, m), 2.96-3.07 (2H, m), 3.97 (2H, t, J=5.6 Hz), 6.41-6.39 (1H, m), 6.44 (1H, dd, J=8.8, 2.4 Hz), 6.98 (1H, d, J=8.3 Hz), 8.04 (1H, s), 8.89 (1H, s)

Example 251

6-chloro-3-(2-(2-fluoroethoxy)-4-{3-[(3S)-3-methylpiperidin-1-yl]propoxy}phenyl)-2-methylpyrido[3, 4-d]pyrimidin-4(3H)-one The title compound was obtained by the method according to Example 192 (1), using 6-chloro-3-(2-hydroxy-4-{3-[(3S)-3-methylpiperidin-1-yl]propoxy}phenyl)-2-methylpyrido[3, 4-d]pyrimidin-4(3H)-one synthesized in Example 250 and 2-fluoroethyl tosylate as starting materials.

$^1$HNMR (400 MHz, CDCl$_3$, δppm): 0.83-0.93 (4H, m), 1.53-1.74 (5H, m), 1.84-1.91 (1H, m), 1.99-2.06 (2H, m), 2.27 (3H, s), 2.51 (2H, t, J=7.3 Hz), 2.83-2.92 (2H, m), 4.07 (2H, t, J=6.3 Hz), 4.10-4.34 (2H, m), 4.49-4.51 (1H, m), 4.63-4.61 (1H, m), 6.64 (1H, d, J=2.4 Hz), 6.67 (1H, dd, J=8.8, 2.4 Hz), 7.09 (1H, d, J=8.8 Hz), 8.05 (1H, s), 8.90 (1H, s)

Example 252

2-ethyl-6-methoxy-3-(4-{3-[(2S)-2-methylpyrrolidin-1-yl]propoxy}phenyl)pyrido[3, 4-d]pyrimidin-4 (3H)-one The title compound was obtained by the method according to Example 249, using 2-ethyl-6-methoxy-3-(4-hydroxyphenyl)pyrido[3, 4-d]pyrimidin-4(3H)-one synthesized in Example 198 and 3-[(2S)-2-methylpyrrolidin-1-yl]propan-1-ol as starting materials.

$^1$HNMR (400 MHz, CDCl$_3$, δppm): 1.11 (3H, d, J=6.0 Hz), 1.23 (3H, t, J=7.2 Hz), 1.40-1.50 (1H, m), 1.60-2.37 (8H, m), 2.44 (2H,q,J=7.2 Hz), 2.97-3.03 (1H, m), 3.18-3.23 (1H, m), 4.03 (3H, s), 4.07-4.11 (2H, m), 7.05 (2H, d, J=9.2 Hz), 7.12 (2H, d, J=9.2 Hz), 7.45 (1H, s), 8.78 (1H,s)

Example 253

2-ethyl-6-methoxy-3-(4-{3-[(3S)-3-methylpiperidin-1-yl]propoxy}phenyl)pyrido[3, 4-d]pyrimidin-(3H)-one hydrochloride The title compound was obtained by the method according to Example 249, using 2-ethyl-6-methoxy-3-(4-hydroxyphenyl)pyrido[3, 4-d]pyrimidin-4(3H)-one synthesized in Example 198 and 3-[(3S)-3-methylpiperidin-1-yl]propan-1-ol as starting materials.

$^1$HNMR (400 MHz, CDCl$_3$, δppm): 1.00 (3H, d, J=6.8 Hz), 1.07-1.13 (1H, m), 1.22 (3H, t, J=7.6 Hz), 1.82-1.98 (6H, m), 2.40-2.54 (4H, m), 3.17-3.23 (2H, m), 3.47-3.65 (2H, m), 4.03 (3H, s), 4.16 (2H, t, J=5.4 Hz), 7.02 (2H, d, J=8.8 Hz), 7.15 (2H, d, J=8.8 Hz), 7.44 (1H, s), 8.79 (1H, s)

Example 254

6-methoxy-3-(2-methoxy-4-{3-[(3S)-3-methylpiperidin-1-yl]propoxy}phenyl)-2-methylpyrido[3, 4-d]pyrimidin-(3H)-one The title compound was obtained by the method according to Example 249, using 6-methoxy-3-(4-hydroxy-2-methoxyphenyl)-2-methylpyrido[3, 4-d]pyrimidin-4(3H)-one synthesized in Example 203 (1) and 3-[(3S)-3-methylpiperidin-1-yl]propan-1-ol as starting materials.

$^1$HNMR (400 MHz, CDCl$_3$, δppm): 0.82-0.93 (4H, m), 1.57-1.74 (5H, m), 1.84-1.91 (1H, m), 1.99-2.06 (2H, m), 2.20 (3H, s), 2.52 (2H, t, J=7.3 Hz), 2.85-2.92 (2H, m), 3.76 (3H, s), 4.02 (3H, s), 4.07 (2H, t, J=6.3 Hz), 6.59-6.62 (2H, m), 7.07 (1H, d, J=8.8 Hz), 7.45 (1H, s), 8.75 (1H, s)

Example 255

6-methoxy-2-methyl-3-(4-{3-[(3S)-3-methylpiperidin-1-yl]propoxy}phenyl)pyrido[3, 4-d]pyrimidin-4(3H)-one The title compound was obtained by the method according to Example 249, using 3-(4-hydroxyphenyl)-6-methoxy-2-methylpyrido[3, 4-d]pyrimidin-4(3H)-one synthesized in Example 197 and 3-[(3S)-3-methyl-piperidin-1-yl]propan-1-ol as starting materials.

$^1$HNMR (400 MHz, CDCl$_3$, δppm): 0.86-0.91 (4H, m), 1.56-1.75 (5H, m), 1.85-1.93 (1H, m), 2.00-2.08 (2H, m), 2.24 (3H, s), 2.50-2.56 (2H, m), 2.85-2.95 (2H, m), 4.03 (3H, s), 4.07 (2H, t, J=6.0 Hz), 7.05 (2H, d, J=8.8 Hz), 7.14 (2H, d, J=8.8 Hz), 7.45 (1H, s), 8.75 (1H, s)

Example 256

6-methoxy-2-methyl-3-(4-{3-[(2R)-2-methylpyrrolidin-1-yl]propoxy}phenyl)pyrido[3, 4-d]pyrimidin-4(3H)-one The title compound was obtained by the method according to Example 249, using 3-(4-hydroxyphenyl)-6-methoxy-2-methylpyrido[3, 4-d]pyrimidin-4(3H)-one synthesized in Example 197 and 3-[(2R)-2-methylpyrrolidin-1-yl]propan-1-ol as starting materials.

$^1$HNMR (400 MHz, CDCl$_3$, δppm): 1.17 (3H, d, J=4.9 Hz), 1.47-2.50 (12H, m), 3.01-3.10 (1H, m), 3.23-3.31 (1H, m), 4.03 (3H, s), 4.12-4.08 (2H, m), 7.05 (2H, d, J=8.8 Hz), 7.14 (2H, d, J=8.8 Hz), 7.45 (1H, s), 8.75 (1H, s)

Example 257

2,5-dimethyl-3-(4-{3-[(2R)-2-methylpyrrolidin-1-yl]propoxy}phenyl)-4(3H)-quinazolinone The title compound was obtained by the method according to Example 165, using 2-amino-6-methylbenzoic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.13 (3H, d, J=5.9 Hz), 1.42-1.51 (1H, m), 1.61-2.09 (5H, m), 2.17-2.54 (6H, m), 2.82 (3H, s), 2.99-3.04 (1H, m), 3.20-3.25 (1H, m), 4.05-4.11 (2H, m), 7.03-7.07 (2H, m), 7.13-7.16 (2H, m), 7.21 (1H, d, J=7.3 Hz), 7.50 (1H, d, J=7.8 Hz), 7.59 (1H, t, J=7.8 Hz)

Example 258

2-methyl-3-(4-{3-[(2R)-2-methylpyrrolidin-1-yl]propoxy}phenyl)-5-(trifluoromethyl)-4(3H)-quinazolinone The title compound was obtained by the method according to Example 165, using 2-amino-6-(trifluoromethyl)benzoic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.14 (3H, d, J=6.3 Hz), 1.42-1.51 (1H, m), 1.61-1.86 (2H, m), 1.91-2.10 (3H, m), 2.15-2.43 (6H, m), 2.98-3.06 (1H, m), 3.20-3.25 (1H, m), 4.04-4.11 (2H, m), 7.03-7.06 (2H, m), 7.14-7.18 (2H, m), 7.80 (1H, t, J=7.8 Hz), 7.86-7.89 (2H, m)

Example 259

5-chloro-2-methyl-3-(4-{3-[(2R)-2-methylpyrrolidin-1-yl]propoxy}phenyl)-4(3H)-quinazolinone The title compound was obtained by the method according to Example 165, using 2-amino-6-chlorobenzoic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.13 (3H, d, J=5.9 Hz), 1.41-1.51 (1H, m), 1.59-2.08 (5H, m), 2.14-2.54 (6H, m), 2.99-3.04 (1H, m), 3.20-3.25 (1H, m), 4.04-4.13 (2H, m), 7.03-7.06 (2H, m), 7.12-7.16 (2H, m), 7.45 (1H, dd, J=7.3, 1.5 Hz), 7.55-7.62 (2H, m)

Example 260

5-fluoro-2-methyl-3-(4-{3-[(2R)-2-methylpyrrolidin-1-yl]propoxy}phenyl)-4(3H)-quinazolinone The title compound was synthesized as a white solid (m.p.: 125-127° C.) by the method according to Example 165, using 2-amino-6-fluorobenzoic acid, acetic anhydride and 4-{3-[(2R)-2-methylpyrrolidin-1-yl)propoxy]aniline monotosylate as starting materials, followed by recrystallization (ethyl acetate/diethyl ether).

$^1$HNMR (400 MHz, CDCl$_3$, δppm): 1.13 (3H, d, J=6.3 Hz), 1.41-1.51 (1H, m), 1.60-1.85 (2H, m), 1.91-2.09 (3H, m), 2.14-2.54 (6H, m), 2.99-3.06 (1H, m), 3.20-3.25 (1H, m), 4.05-4.13 (2H, m), 7.03-7.15 (6H, m), 7.46 (1H, d, J=8.3 Hz), 7.65-7.70 (1H, m)

Example 261

6-fluoro-2-methyl-3-(4-{3-[(2R)-2-methylpyrrolidin-1-yl]propoxy}phenyl)-4(3H)-quinazolinone The title compound was obtained by the method according to Example 165, using 2-amino-5-fluorobenzoic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.13 (3H, d, J=5.9 Hz), 1.42-1.51 (1H, m), 1.59-1.86 (2H, m), 1.91-2.09 (3H, m), 2.15-2.54 (6H, m), 2.99-3.06 (1H, m), 3.20-3.25 (1H, m), 4.06-4.12 (2H, m), 7.04-7.07 (2H, m), 7.13-7.16 (2H, m), 7.45-7.50 (1H, m), 7.66-7.69 (1H, m), 7.88-7.91 (1H, m)

Example 262

7-fluoro-2-methyl-3-(4-{3-[(2R)-2-methylpyrrolidin-1-yl]propoxy}phenyl)-4(3H)-quinazolinone The title compound was obtained by the method according to Example 165, using 2-amino-4-fluorobenzoic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.15 (3H, d, J=5.9 Hz), 1.44-1.53 (1H, m), 1.60-1.87 (2H, m), 1.92-2.11 (3H, m), 2.20-2.56 (6H, m), 3.01-3.08 (1H, m), 3.23-3.27 (1H, m), 4.06-4.14 (2H, m), 7.04-7.07 (2H, m), 7.13-7.20 (3H, m), 7.31 (1H, dd, J=9.3, 2.4 Hz), 8.27 (1H, dd, J=8.8, 6.3 Hz)

Example 263

8-fluoro-2-methyl-3-(4-{3-[(2R)-2-methylpyrrolidin-1-yl]propoxy}phenyl)-4(3H)-quinazolinone The title compound was obtained by the method according to Example 165, using 2-amino-3-fluorobenzoic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.16 (3H, d, J=6.3 Hz), 1.44-1.54 (1H, m), 1.62-1.85 (2H, m), 1.93-2.12 (3H, m), 2.21-2.41 (6H, m), 3.01-3.08 (1H, m), 3.23-3.28 (1H, m), 4.06-4.14 (2H, m), 7.05-7.08 (2H, m), 1.13-7.17 (2H, m), 7.37-7.42 (1H, m), 7.47-7.51 (1H, m), 8.05 (1H, d, J=7.8 Hz)

Example 264

2,6-dimethyl-3-(4-{3-[(2R)-2-methylpyrrolidin-1-yl]propoxy}phenyl)-4(3H)-quinazolinone The title compound was obtained by the method according to Example 165, using 2-amino-5-methyl benzoic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.15 (3H, d, J=6.3 Hz), 1.47-1.53 (1H, m), 1.62-1.84 (2H, m), 1.92-2.11 (3H, m), 2.20-2.54 (9H, m), 3.01-3.08 (1H, m), 3.23-3.27 (1H, m), 4.06-4.12 (2H, m), 7.03-7.06 (2H, m), 7.13-7.16 (2H, m), 7.57-7.57 (2H, m), 8.05 (1H, s)

Example 265

2-methyl-3-(4-{3-[(2R)-2-methylpyrrolidin-1-yl]propoxy}phenyl)pyrido[2,3-d]pyrimidin-4(3H)-one The title compound was obtained by the method according to Example 165, using 2-aminonicotinic acid, acetic anhydride and 4-{3-[(2R)-2-methylpyrrolidin-1-yl]propoxy}aniline monotosylate as starting materials.

$^1$HNMR (400 MHz, CDCl$_3$, δppm): 1.15 (3H, d, J=6.3 Hz), 1.44-1.53 (1H, m), 1.63-1.87 (2H, m), 1.92-2.11 (3H, m), 2.18-2.40 (6H, m), 3.01-3.08 (1H, m), 3.22-3.27 (1H, m), 4.06-4.14 (2H, m), 7.05-7.08 (2H, m), 7.14-7.17 (2H, m), 7.40-7.43 (1H, m), 8.59 (1H, dd, J=7.8, 2.0 Hz), 8.98-8.99 (1H, m)

Example 266

2-methyl-3-(4-{3-[(2R)-2-methylpyrrolidin-1-yl]propoxy}phenyl)pyrido[4,3-d]pyrimidin-4(3H)-one The title compound was synthesized as a light yellow solid (m.p.:238-250° C.) by the method according to Example 165, using 4-aminonicotinic acid, acetic anhydride and 4-{3-[(2R)-2-methylpyrrolidin-1-yl]propoxy}aniline monotosylate as starting materials, followed by recrystallization (ethyl acetate/diethyl ether/n-heptane).

$^1$HNMR (400 MHz, CDCl$_3$, δppm): 1.14 (3H, d, J=6.3 Hz), 1.42-1.51 (1H, m), 1.61-1.85 (2H, m), 1.91-2.10 (3H, m), 2.15-2.38 (6H, m), 3.00-3.07 (1H, m), 3.21-3.25 (1H, m), 4.08-4.12 (2H, m), 7.05-7.09 (2H, m), 7.13-7.16 (2H, m), 7.48-7.50 (1H, m), 8.85 (1H, d, J=5.9 Hz), 9.47 (1H, d, J=1.0 Hz)

Example 267

2-methyl-3-(4-{3-[(2R)-2-methylpyrrolidin-1-yl]propoxy}phenyl)pyrido[3, 4-d]pyrimidin-4(3H)-one (1) Manufacture of 6-chloro-2-methyl-3-(4-{3-[(2R)-2-methylpyrrolidin-1-yl]propoxy}phenyl)pyrido[3, 4-d]pyrimidin-4(3H)-one The target compound was obtained by the method according to Example 165, using 5-amino-2-chloroisonicotinic acid, acetic anhydride and 4-{3-[(2R)-2-methylpyrrolidin-1-yl]propoxy}aniline monotosylate as starting materials.

(2) Manufacture of 2-methyl-3-(4-{3-[(2R)-2-methylpyrrolidin-1-yl]propoxy}phenyl)pyrido[3, 4-d]pyrimidin-4(3H)-one The title compound was obtained by dissolving 6-chloro-2-methyl-3-(4-{3-[(2R)-2-methylpyrrolidin-1-yl]propoxy}phenyl)pyrido[3, 4-d]pyrimidin-4(3H)-one in ethyl acetate, and performing catalytic reduction with a palladium charcoal catalyst in the presence of triethylamine.

$^1$HNMR (400 MHz, CDCl$_3$, δppm): 1.11 (3H, d, J=5.9 Hz), 1.39-1.48 (1H, m), 1.59-1.85 (2H, m), 1.89-2.08 (3H, m), 2.10-2.41 (6H, m), 2.97-3.04 (1H, m), 3.17-3.22 (1H, m), 4.08-4.12 (2H, m), 7.06-7.09 (2H, m), 7.13-7.16 (2H, m), 8.03 (1H, dd, J=5.4, 1.0 Hz), 8.67 (1H, d, J=5.4 Hz), 9.12 (1H, d, J=1.0 Hz)

Example 268

2-methyl-3-[4-(3-piperidin-1-yl-propoxy)phenyl]pyrido[3,2-d]pyrimidin-4(3H)-one (1) Manufacture of 3-nitropyridine-2-carboxylic acid This was manufactured by the method described in the literature (Tetrahedron, 1998, Vol. 54, p. 6311; and J. Am. Chem. Soc., 1954, Vol. 76, p. 3167) using 2-chloro-3-nitropyridine as starting material.

(2) Manufacture of 3-aminopyridine-2-carboxylic acid 3-nitropyridine-2-carboxylic acid (2.72 g, 16.2 mmol) and sodium hydrogencarbonate (1.34 g, 16.2 mmol) were dissolved in distilled water (20 mL), and the atmosphere in the system was replaced by nitrogen. After adding 10% palladium charcoal (1.72 g), the atmosphere in the system was replaced by hydrogen, and the mixture stirred at room temperature for 50 hours. 1N hydrochloric acid aqueous solution was added, and the pH of the reaction solution was adjusted to weak acidity. The solvent was distilled off under reduced pressure, a small amount of ethanol and ethyl acetate were added to the residue, and the precipitate produced was filtered off. The filtrate was concentrated, and the target substance (1.50 g, 67%) was thus obtained as a light yellow solid.

(3) Manufacture of 3-[4-(3-piperidin-1-yl-propoxy)phenyl]-2-methylpyrido[3,2-d]pyrimidin-4(3H)-one The title compound was obtained by the method according to Example 165, using 3-aminopyridine-2-carboxylic acid, acetic anhydride and 4-(3-piperidin-1-yl-propoxy)aniline as starting materials.

$^1$HNMR (400 MHz, CDCl$_3$, δppm): 1.49-1.43 (2H, m), 1.58-1.63 (4H, m), 2.02 (2H, dt, J=14.6, 6.3 Hz), 2.27 (3H, s), 2.37-2.45 (4H, m), 2.50 (2H, t, J=7.6 Hz), 4.07 (2H, t, J=6.3 Hz), 7.06 (2H, td, J=2.4, 9.3 Hz), 7.17 (2H, td, J=2.4, 9.3 Hz), 7.68 (1H, dd, J=8.3, 4.4 Hz), 8.01 (1H, dd, J=8.3, 1.5 Hz), 8.86 (1H, dd, J=4.4, 1.5 Hz)

Example 269

2-methyl-3-(4-{3-[(2R)-2-methylpyrrolidin-1-yl]propoxy}phenyl)pyrido[3,2-d]pyrimidin-4(3H)-one The title compound was obtained by the method according to Example 165, using 3-aminopyridine-2-carboxylic acid synthesized in Example 268, acetic anhydride and 4-{3-[(2R)-2-methylpyrrolidin-1-yl]propoxy}aniline monotosylate as starting materials.

$^1$HNMR (400 MHz, CDCl$_3$, δppm): 1.13 (3H, d, J=5.9 Hz), 1.51-1.42 (1H, m), 1.68-1.87 (2H, m), 1.93-2.00 (1H, m), 2.01-2.10 (2H, m), 2.16-2.30 (4H, m), 2.27 (3H, s), 2.32-2.42 (1H, m), 3.03 (1H, dt, J=12.2, 7.8 Hz), 3.23 (1H, td, J=8.3, 2.9 Hz), 4.09 (2H, td, J=5.9, 2.4 Hz), 7.06 (2H, d, J=8.8 Hz), 7.17 (2H, d, J=8.8 Hz), 7.68 (1H, dd, J=8.3, 4.4 Hz), 8.01 (1H, dd, J=8.3, 1.5 Hz), 8.86 (1H, dd, J=4.4, 1.5 Hz)

Example 270

2-methyl-3-[4-(3-pyrrolidin-1-yl-propoxy)phenyl]pyrido[3,2-d]pyrimidin-4(3H)-one The title compound was obtained by the method according to Example 165, using 3-aminopyridine-2-carboxylic acid synthesized in Example 268, acetic anhydride and 4-(3-pyrrolidin-1-yl-propoxy)aniline as starting materials.

$^1$HNMR (400 MHz, CDCl$_3$, δppm): 1.79-1.86 (4H, m), 2.03-2.10 (2H, m), 2.27 (3H, s), 2.56-2.62 (4H, m), 2.69 (2H, t, J=7.3 Hz), 4.09 (2H, t, J=6.3 Hz), 7.06 (2H, td, J=2.4, 8.8 Hz), 7.17 (2H, td, J=2.4, 8.8 Hz), 7.68 (1H, dd, J=8.3, 4.4 Hz), 8.01 (1H, dd, J=8.3, 1.5 Hz), 8.85 (1H, dd, J=4.4, 1.5 Hz)

Example 271

2-methyl-3-(4-{3-[(3S)-3-methylpiperidin-1-yl]propoxy}phenyl)pyrido[3,2-d]pyrimidin-4(3H)-one The title compound was obtained by the method according to Example 165, using 3-amino pyridine-2-carboxylic acid synthesized in Example 268, acetic anhydride and 4-{3-[(3S)-3-methylpiperidin-1-yl]propoxy}aniline monotosylate as starting materials.

$^1$HNMR (400 MHz, CDCl$_3$, δppm): 0.94-0.82 (1H, m), 0.88 (3H, d, J=6.8 Hz), 1.57-1.74 (5H, m), 1.89 (1H, td, J=11.2, 2.9 Hz), 2.04 (2H, q, J=6.3 Hz), 2.27 (3H, s), 2.53 (2H, t, J=7.6 Hz), 2.86-2.93 (2H, m), 4.07 (2H, t, J=6.3 Hz), 7.05 (2H, d, J=8.8 Hz), 7.17 (2H, d, J=8.8 Hz), 7.67 (1H, dd, J=8.3, 4.4 Hz), 8.00 (1H, dd, J=8.3, 1.5 Hz), 8.84 (1H, dd, J=4.4, 1.5 Hz).

Example 272

3-{4-[(1-cyclobutyl-piperidin-4-yl)oxy]phenyl}-2-methylpyrido[3,2-d]pyrimidin-4(3H)-one The title compound was obtained by the method according to Example 165, using 3-amino pyridine-2-carboxylic acid synthesized in Example 268, acetic anhydride and 4-[(1-cyclobutylpiperidin-4-yl)oxy]aniline monotosylate as starting materials.

$^1$HNMR (400 MHz, CDCl$_3$, δppm): 1.67-1.74 (2H, m), 1.96-1.84 (4H, m), 2.03-2.10 (4H, m), 2.17-2.25 (2H, m), 2.27 (3H, s), 2.59-2.71 (2H, m), 2.73-2.79 (1H, m), 4.36-4.42 (1H, m), 7.05 (2H, td, J=2.0, 8.8 Hz), 7.17 (2H, td, J=2.0, 8.8 Hz), 7.67 (1H, dd, J=8.3, 4.4 Hz), 8.00 (1H, dd, J=8.3, 1.5 Hz), 8.84 (1H, dd, J=4.4, 1.5 Hz)

Example 273

3-{4-[(1-cyclobutyl-piperidin-4-yl)oxy]phenyl}-2-ethylpyrido[3,2-d]pyrimidin-4(3H)-one The title compound was obtained by the method according to Example 165, using 3-aminopyridine-2-carboxylic acid synthesized in Example 268, propionic anhydride and 4-[(1-cyclobutylpiperidin-4-yl)oxy]aniline monotosylate as starting materials.

$^1$HNMR (400 MHz, CDCl$_3$, δppm): 1.22 (3H, t, J=7.3 Hz), 1.64-1.76 (2H, m), 1.84-1.95 (4H, m), 2.00-2.10 (4H, m), 2.15-2.23 (2H, m), 2.46 (2H, q, J=7.3 Hz), 2.60-2.69 (2H, m), 2.73-2.79 (1H, m), 4.34-4.42 (1H, m), 7.04 (2H, d, J=8.8 Hz), 7.15 (2H, d, J=8.8 Hz), 7.67 (1H, dd, J=8.3, 4.4 Hz), 8.05 (1H, dd, J=8.3, 1.5 Hz), 8.85 (1H, dd, J=4.4, 1.5 Hz)

Example 274

3-[4-(3-azepan-1-yl-propoxy)phenyl]-2-methylpyrido[3, 4-d]pyrimidin-4(3H)-one (1) Manufacture of 3-[4-(3-azepan-1-yl-propoxy)phenyl]-6-chloro-2-methylpyrido[3, 4-d]pyrimidin-4(3H)-one The target compound was obtained by the method according to Example 165, using 5-amino-2-chloroisonicotinic acid, acetic anhydride and 4-(3-azepan-1-yl-propoxy)aniline as starting materials.

(2) Manufacture of 3-[4-(3-azepan-1-yl-propoxy)phenyl]-6-chloro-2-methylpyrido[3, 4-d]pyrimidin-4(3H)-one The title compound was obtained by catalytic reduction of 3-[4-(3-azepan-1-yl-propoxy)phenyl]-6-chloro-2-methylpyrido[3, 4-d]pyrimidin-4(3H)-one in ethyl acetate using a palladium charcoal catalyst in the presence of triethylamine.

¹HNMR (400 MHz, CDCl₃, δppm): 1.64-1.73 (8H, m), 2.08-2.10 (2H, m), 2.30 (3H, s), 2.77-2.79 (6H, m), 4.11 (2H, t, J=6.1 Hz), 7.07 (2H, d, J=9.5 Hz), 7.15 (2H, d, J=11.7 Hz), 8.03 (1H, dd, J=5.4, 1.0 Hz), 8.68 (1H, d, J=4.9 Hz), 9.13 (1H, s).

Example 275

3-[4-(3-azepan-1-yl-propoxy)phenyl]-6-methoxy-2-methylpyrido[3, 4-d]pyrimidin-4(3H)-one The title compound was obtained by the method according to Example 249, using 3-(4-hydroxyphenyl)-6-methoxy-2-methylpyrido[3, 4-d]pyrimidin-4(3H)-one synthesized in Example 268 and 3-(azepan-1-yl)propan-1-ol as starting materials.

¹HNMR (400 MHz, CDCl₃, δppm): 1.63-1.69 (8H, m), 2.01-2.04 (2H, m), 2.24 (3H, s), 2.71-2.74 (6H, m), 4.03 (3H, s), 4.09 (2H, t, J=6.1 Hz), 7.05 (2H, d, J=8.8 Hz), 7.14 (2H, d, J=6.6 Hz), 7.45 (1H, d, J=1.0 Hz), 8.76 (1H, s)

Example 276

3-[4-(3-azepan-1-yl-propoxy)phenyl]-2-methylpyrido[3, 4-d]pyrimidin-4(3H)-one

The target compound was obtained by the method according to Example 165, using 2-aminonicotinic acid, acetic anhydride and 4-(3-azepan-1-yl-propoxy)aniline as starting materials.

¹HNMR (400 MHz, CDCl₃, δppm): 1.62-1.65 (8H, m), 1.95-2.02 (2H, m), 2.35 (3H, s), 2.65-2.69 (6H, m), 4.09 (2H, t, J=6.3 Hz), 7.07 (2H, d, J=11.7 Hz), 7.15 (2H, d, J=12.2 Hz), 7.42 (1H, dd, J=7.8, 4.9 Hz), 8.59 (1H, dd, J=7.8, 2.0 Hz), 8.99 (1H, q, J=2.3 Hz)

Example 277

5-fluoro-2-methyl-3-[4-(3-pyrrolidin-1-ylbutoxy)phenyl]-4(3H)-quinazolinone (racemic mixture)

(1) Manufacture of 4-(3-pyrrolidin-1-yl-butoxy)aniline (Racemic Mixture)

The target compound was obtained by the method according to Example 18, using 3-pyrrolidin-1-yl-butan-1-ol (racemic mixture) manufactured by the method described in the literature (J. Org. Chem., 1949, Vol. 14, p. 862) and 4-nitrofluorobenzene as starting materials.

¹HNMR (400 MHz, CDCl₃, δppm): 1.14 (3H, d, J=6.3 Hz), 1.82-1.65 (5H, m), 2.10 (1H, m), 2.61-2.53 (5H, m), 3.41 (1H, brs), 3.97 (2H, m), 6.64 (2H, d, J=9.0 Hz), 6.75 (2H, d, J=9.0 Hz)

(2) Manufacture of 5-fluoro-2-methyl-3-[4-(3-pyrrolidin-1-yl-butoxy)phenyl]-4(3H)-quinazolinone (Racemic Mixture)

The title compound was obtained by the method according to Example 18, using 2-amino-6-fluorobenzoic acid, acetic anhydride and 4-(3-pyrrolidin-1-yl-butoxy)aniline as starting materials.

¹HNMR (400 MHz, CDCl₃, δppm): 1.17 (3H, d, J=6.8 Hz), 1.79 (4H, m), 1.88 (1H, m), 2.15 (1H, m), 2.24 (3H, s), 2.61 (5H, m), 4.10 (2H, m), 7.05 (2H, d, J=9.0 Hz), 7.08 (1H, m), 7.14 (2H, d, J=9.0 Hz), 7.46 (1H, d, J=8.3 Hz), 7.68 (1H, m)

Example 278

2-methyl-3-[4-(3-pyrrolidin-1-yl-butoxy)phenyl]-5-(trifluoromethyl)-4(3H)-quinazolinone (Racemic Mixture)

The title compound was obtained by the method according to Example 18, using 2-amino-6-(trifluoromethyl)benzoic acid, acetic anhydride and 4-(3-pyrrolidin-1-yl-butoxy)aniline as starting materials.

¹HNMR (400 MHz, CDCl₃, δppm): 1.17 (3H, d, J=6.8 Hz), 1.80 (4H, m), 1.88 (1H, m), 2.15 (1H, m), 2.27 (3H, s), 4.09 (2H, m), 2.62 (5H, m), 7.05 (2H, d, J=9.0 Hz), 7.16 (2H, d, J=9.0 Hz), 7.80 (1H, t, J=7.8 Hz), 7.87 (1H, d, J=7.8 Hz), 7.88 (1H, d, J=7.8 Hz)

Example 279

2,5-dimethyl-3-[4-(3-pyrrolidin-1-yl-butoxy)phenyl]-4(3H)-quinazolinone (Racemic Mixutre)

The title compound was obtained by the method according to Example 18, using 2-amino-6-methylbenzoic acid, acetic anhydride and 4-(3-pyrrolidin-1-yl-butoxy)aniline as starting materials.

¹HNMR (400 MHz, CDCl₃, δppm): 1.17 (3H, d, J=6.3 Hz), 1.80 (4H, m), 1.88 (1H, m), 2.15 (1H, m), 2.22 (3H, s), 2.62 (5H, m), 2.82 (3H, s), 4.09 (2H, m), 7.05 (2H, d, J=8.8 Hz), 7.15 (2H, d, J=8.8 Hz), 7.21 (1H, d, J=7.6 Hz), 7.50 (1H, d, J=7.6 Hz), 7.59 (1H, t, J=7.6 Hz)

Pharmacological test examples, in which 2-ethyl-3-{4-[3-(1-piperidinyl)propoxy]phenyl}-4(3H)-quinazolinone (the compound of Example 1) was used as a test compound, are shown below.

Pharmacological Test Example 1: Histamine Analog Coupling Inhibition Test

A cDNA sequence [International Patent Application WO00/3916 Specification No. 4] which encodes human histamine H3 receptor was cloned using the expression vectors pCR2.1, pEF1x (product of Invitrogen), and pCI-neo (product of Promega Inc.). The expression vector obtained was transfected to the host cells, HEK293 and CHO-K1 (American type culture collection), using the cationic lipid method [Proceedings of the National Academy of Sciences of the United States of America, Vol. 84, p. 7413 (1987), and histamine H3 receptor expression cells were thus obtained.

A film preparation made from the cells which represented the histamine H3 receptor, the test compound (the compound of Exaple 1) and 20,000 cpm of [3H]N-α-methylhistamine (product of NEN) were incubated in an assay buffer solution (50 mM Tris buffer solution, pH 7.4) at 25° C. for 2 hours, and filtered on a glass filter GF/C. After washing by 50 mM Tris buffer solution, pH7.4, the radioactivity on the glass filter was found. Non-specific linkages were measured in the presence of 10 microM thioperamide (product of SIGAM), and the 50% inhibition concentration (IC₅₀ value) of the test compound with respect to specific N-α-methylhistamine linkages was found (Molecular Pharmacology, Vol. 55, p. 1101 (1999)). As a result, the IC₅₀ value of the test compound was 15 nM.

As described above, the compound of Exaple 1 strongly prevented binding of N-α-methylhistamine to the histamine H3 receptor (histamine analog).

Pharmacological Test Example 2: Antagonism Test of Drinking Behavior Induced by R-α-Methylhistamine, a Histamine H3 Receptor Selective Agonist Under ketamine/xylazine anaesthesia (74 mg/kg and 11 mg/kg intraperitoneal single-dose administration), a chronic guide cannula (26 gauge, length 11 mm) was inserted in the ventriculus tertius of a male SD rat (7-10 weeks old, 200-300 g) using a brain stereotaxis apparatus, and fixed by dental resin. The position of the tip of the guide cannula was 2.2 mm back from the bregma, and at a depth of 8 mm from the skull surface on the median line. After about 1 week convalescence, R-α-methylhistamine (0.3 μg/1 μL/head, 30% propylene glycol solution) was administered to the ventriculus tertius. The test compound (the compound of Exaple 1) suspended in 0.5% methylcellulose aqueous solution was administered orally 2 hours before the R-α-methylhistamine administration, and the drinking water amount was measured 1 hour after R-α-methylhistamine administration. As a result, the test compound (10 mg/kg) significantly suppressed the increase in drinking water amount due to R-α-methylhistamine administered to the ventriculus tertius.

Pharmacological Test Example 3: In Vitro Kinetic Test

The test compound (the compound of Exaple 1) was administered orally or intravenously to SD type male rats (7-10 weeks old, 200-400 g) which had abstained from food overnight, and about 100 μL of blood was collected from a caudal vein using a heparinized capillary tube at a predetermined time. The blood was centrifuged (4° C., 6000 rpm, 10 minutes), and plasma was obtained. Three times the amount of ethanol (containing an internal reference) was added to the plasma, stirred, left for 20 minutes at −20° C., and centrifuged (4° C., 10,000 rpm, 10 minutes). The supernatant liquid was analyzed by LC/MS/MS, and the plasma concentration was measured by the relative calibration curve method. As a result, the test compound had 60% bioavailability, and a half-life of 6.3 hours in blood.

Pharmacological Test Example 4: Brain/Cerebrospinal Fluid Activity Test

The test compound (the compound of Exaple 1) was administered orally or intravenously to SD type male rats (7-10 weeks old, 200-400 g), and exsanguination was performed from the abdominal aorta under ether anesthesia using a heparin treatment syringe at a predetermined time. The skin at the back of the head was cut open, pierced with a 30G dental needle between the cervical vertebrae, and inserted into the subarachnoid space. 50-100 μL of cerebrospinal fluid was extracted by a 1 mL syringe via a tube connected to the 30G needle, and the brain was extracted. A blood sample was centrifuged (4° C., 6000 rpm, 10 minutes), and three times the amount of ethanol (containing an internal reference) was added to the plasma and stirred. 2 mL of water was added to a brain sample, homogenized, a part was removed, and three times the amount of ethanol (containing an internal reference) was added and stirred. The cerebrospinal fluid was taken, three times the amount of ethanol (containing an internal reference) was added, and stirred. The above sample was left at −20° C. for 0.20 minutes, centrifuged (4° C., 12,000 g, 10 minutes), the supernatant liquid was analyzed by LC/MS/MS, and the concentration in plasma, brain and cerebrospinal fluid was measured by the relative calibration curve method. As a result, the test compound had an intracerebral concentration of 3.16 nmol/g, cerebrospinal fluid concentration of 0.142 μM, and plasma concentration of 2.32 μM at 2 hours after oral administration (10 mg/kg).

The novel fused ring 4-oxopyrimidine derivative represented by formula (I), or a pharmaceutically acceptable salt thereof, has a powerful histamine antagonistic or inverse agonistic activity, and is therefore useful in the prophylaxis or therapy of metabolic diseases such as obesity, diabetes mellitus, hormone secretion disorders, hyperlipidemia, gout and fatty liver; circulatory diseases such as angina pectoris, acute or congestive heart failure, myocardial infarction, annular arteriosclerosis, hypertension, kidney disease and electrolyte imbalance; or central or peripheral nervous system diseases such as sleep disorders or diseases accompanied by sleep disorders (e.g., idiopathic hypersomnia, repeatability hypersomnia, intrinsic hypersomnia, narcolepsy, periodic limb movement during sleep, sleep apnea syndrome, circadian rhythm hindrance, chronic fatigue syndrome, REM sleep hindrance, sleep loss in the elderly, night shift worker sleep insanitation, idiopathic insomnia, repeatability insomnia, intrinsic insomnia, depression, insecurity and schizophrenia), bulimia, emotional disorders, epilepsy, delirium, dementia, attention deficit/hyperactivity disorder, memory impairment, Alzheimer's disease, Parkinson's disease, cognitive disorder, movement disorder, dysesthesia, dysosmia, morphine resistance, narcotics dependence, alcohol dependence and tremor.

What is claimed is:

1. A compound of the formula:

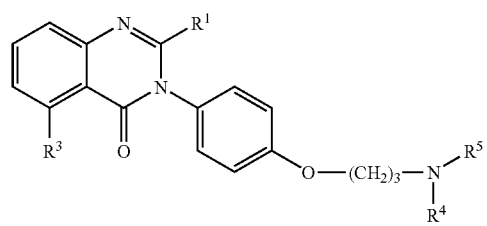

wherein:
R$^1$ is selected from the group consisting of:
methyl, ethyl, n-propyl, isopropyl and trifluoromethyl;
R$^3$ is selected from the group consisting of:
hydroxy, chloro, bromo, fluoro, methyl, trifluoromethyl and methoxy;
R$^4$, R$^5$ and the nitrogen atom to which they are attached together form an unsubstituted pyrrolidine ring or an unsubstituted piperidine ring;
or a pharmaceutically acceptable salt thereof.
2. The compound of claim 1 wherein R$^1$ is methyl.
3. The compound of claim 1 wherein R$^1$ is ethyl.
4. The compound of claim 1 wherein R$^3$ is hydroxy.
5. The compound of claim 1 wherein R$^3$ is chloro.
6. The compound of claim 1 wherein R$^3$ is fluoro.
7. The compound of claim 1 wherein R$^3$ is methyl.
8. The compound of claim 1 wherein R$^3$ is trifluoromethyl.
9. The compound of claim 1 wherein R$^3$ is methoxy.
10. The compound of claim 1 wherein R$^4$, R$^5$ and the nitrogen atom to which they are attached together form an unsubstituted pyrrolidine ring.

11. The compound of claim 1 wherein $R^4$, $R^5$ and the nitrogen atom to which they are attached together form an unsubstituted piperidine ring.

12. The compound of claim 1 which is selected from the group consisting of:
- 2,5-dimethyl-3-{4-[3-(1-piperidinyl)propoxy]phenyl}4(3H)-quinazolinone,
- 2-ethyl-5-methyl-3-{4-[3-(1-piperidinyl)propoxy]phenyl}-4(3H)-quinazolinone,
- 5-fluoro-2-methyl-3-{4-[3-(1-piperidinyl)propoxy]phenyl}-4(3H)-quinazolinone,
- 5-chloro-2-methyl-3-{4-[3-(1-piperidinyl)propoxy]phenyl}-4(3H)-quinazolinone,
- 5-methoxy-2-methyl-3-{4-[3-(1-piperidinyl)propoxy]phenyl}-4(3H)-quinazolinone,
- 2-methyl-3-{4-[3-(1-piperidinyl)propoxy]phenyl}-5-trifluoromethyl-4(3H)-quinazolinone,
- 2-ethyl-5-methyl-3-{4-[3-(1-pyrrolidinyl)propoxy]phenyl}-4(3H)-quinazolinone,
- 5-fluoro-2-methyl-3-{4-[3-(1-pyrrolidinyl)propoxy]phenyl}-4(3H)-quinazolinone,
- 2-methyl-3-{4-[3-(1-pyrrolidinyl)propoxy]phenyl}-5-trifluoromethyl-4(3H)-quinazolinone,
- 5-chloro-2-methyl-3-{4-[3-(1-pyrrolidinyl)propoxy]phenyl}-4(3H)-quinazolinone,
- 2,5-dimethyl-3-{4-[3-(1-pyrrolidinyl)propoxy]phenyl}-4(3H)-quinazolinone,
- 5-hydroxy-2-methyl-3-{4-[3-(1-piperidinyl)propoxy]phenyl}-4(3H)-quinazolinone, or a pharmaceutically acceptable salt thereof.

13. A compound which is 2,5-dimethyl-3-{4-[3-(1-pyrrolidinyl)propoxy]phenyl}-4(3H)-quinazolinone, or a pharmaceutically acceptable salt thereof.

14. The compound of claim 13 which is 2,5-dimethyl-3-{4-[3-(1-pyrrolidinyl)propoxy]phenyl}-4(3H)-quinazolinone.

15. A compound which is 2-methyl-3-{4-[3-(1-pyrrolidinyl)propoxy]phenyl}-5-trifluoromethyl-4(3H)-quinazolinone, or a pharmaceutically acceptable salt thereof.

16. The compound of claim 15 which is 2-methyl-3-{4-[3-(1-pyrrolidinyl)propoxy]phenyl}-5-trifluoromethyl-4(3H)-quinazolinone.

17. A compound which is 5-fluoro-2-methyl-3-{4-[3-(1-piperidinyl)propoxy]phenyl}-4(3H)-quinazolinone, or a pharmaceutically acceptable salt thereof.

18. The compound of claim 17 which is 5-fluoro-2-methyl-3-{4-[3-(1-piperidinyl)propoxy]phenyl}-4(3H)-quinazolinone.

19. A pharmaceutical composition comprising the compound of claim 1 or a pharmaceutically acceptable salt thereof and a pharmaceutically acceptable carrier.

20. A pharmaceutical composition comprising the compound of claim 12 or a pharmaceutically acceptable salt thereof and a pharmaceutically acceptable carrier.

21. A pharmaceutical composition comprising the compound of claim 13 or a pharmaceutically acceptable salt thereof and a pharmaceutically acceptable carrier.

22. A pharmaceutical composition comprising the compound of claim 14 and a pharmaceutically acceptable carrier.

23. A pharmaceutical composition comprising the compound of claim 15 or a pharmaceutically acceptable salt thereof and a pharmaceutically acceptable carrier.

24. A pharmaceutical composition comprising the compound of claim 16 and a pharmaceutically acceptable carrier.

25. A pharmaceutical composition comprising the compound of claim 17 or a pharmaceutically acceptable salt thereof and a pharmaceutically acceptable carrier.

26. A pharmaceutical composition comprising the compound of claim 18 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,521,455 B2 | Page 1 of 1 |
| APPLICATION NO. | : 11/058444 | |
| DATED | : April 21, 2009 | |
| INVENTOR(S) | : Nagase et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 816 days.

Signed and Sealed this
Fourth Day of October, 2011

David J. Kappos
*Director of the United States Patent and Trademark Office*